(12) United States Patent
Alimardanov et al.

(10) Patent No.: US 10,017,516 B2
(45) Date of Patent: Jul. 10, 2018

(54) BMP INHIBITORS AND METHODS OF USE THEREOF

(71) Applicants: The Brigham and Women's Hospital, Inc., Boston, MA (US); The United States of America, as represented by the Secretary, Department of Health and Human Services, National Institute of Health, Washington, DC (US)

(72) Inventors: Asaf Alimardanov, North Bethesda, MD (US); Gregory D. Cuny, Houston, TX (US); Gurmit S. Grewal, Lexington, MA (US); Arthur Lee, San Jose, CA (US); John C. McKew, Boyds, MD (US); Agustin H. Mohedas, Somerville, MA (US); Min Shen, Boyds, MD (US); Xin Xu, Potomac, MD (US); Paul B. Yu, Boston, MA (US)

(73) Assignees: The Brigham and Women's Hospital, Inc., Boston, MA (US); The United States of America, as Represented by the Secretary, Department of Health and Human Services, National Institutes of Health, Washington, DC (US)

( * ) Notice: Subject to any disclaimer, the term of this patent is extended or adjusted under 35 U.S.C. 154(b) by 0 days.

(21) Appl. No.: 15/598,540

(22) Filed: May 18, 2017

(65) Prior Publication Data
US 2017/0334918 A1    Nov. 23, 2017

Related U.S. Application Data

(63) Continuation of application No. 14/776,302, filed as application No. PCT/US2014/026042 on Mar. 13, 2014, now Pat. No. 9,682,983.

(60) Provisional application No. 61/783,695, filed on Mar. 14, 2013.

(51) Int. Cl.
*C07D 487/04* (2006.01)
*C07D 519/00* (2006.01)

(52) U.S. Cl.
CPC ......... *C07D 487/04* (2013.01); *C07D 519/00* (2013.01)

(58) Field of Classification Search
CPC .......................... C07D 487/04; C07D 519/00
See application file for complete search history.

(56) References Cited

U.S. PATENT DOCUMENTS

| 6,235,741 | B1 | 5/2001 | Bilodeau et al. |
| 6,245,759 | B1 | 6/2001 | Bilodeau et al. |
| 7,276,525 | B2 | 10/2007 | Miyazono et al. |
| 8,507,501 | B2 | 8/2013 | Yu et al. |
| 9,045,484 | B2 | 6/2015 | Yu et al. |
| 9,708,295 | B2 | 7/2017 | Xiao et al. |
| 2002/0041880 | A1 | 4/2002 | DeFeo-Jones et al. |
| 2006/0063208 | A1 | 3/2006 | Woolf et al. |
| 2006/0135537 | A1 | 6/2006 | Knegtel et al. |
| 2009/0197862 | A1 | 8/2009 | Steinig et al. |
| 2010/0062527 | A1 | 3/2010 | Pera et al. |
| 2010/0249104 | A1 | 9/2010 | Liu et al. |
| 2012/0022857 | A1 | 1/2012 | Baldwin et al. |
| 2014/0038953 | A1 | 2/2014 | Yu et al. |

FOREIGN PATENT DOCUMENTS

| RU | 99101118 A | 1/2001 |
| RU | 2285532 C2 | 10/2006 |
| WO | WO-1998/052038 A1 | 11/1998 |
| WO | WO-1998/054093 A1 | 12/1998 |
| WO | WO-00/43393 A1 | 7/2000 |
| WO | WO-2004/052286 A2 | 6/2004 |
| WO | WO-2005/092345 A1 | 10/2005 |
| WO | WO-2006/052913 A1 | 5/2006 |
| WO | WO-2007/041712 A1 | 4/2007 |
| WO | WO-2007/085873 A1 | 8/2007 |
| WO | WO-2007/111904 A2 | 10/2007 |
| WO | WO-2007/111904 A3 | 12/2007 |
| WO | WO-2008/006583 A1 | 1/2008 |
| WO | WO-2008/025820 A1 | 3/2008 |

(Continued)

OTHER PUBLICATIONS

Alesiani, et al., "Inhibition of Mek 1/2 kinase activity and stimulation of melanogenesis by 5,7-dimethoxycoumarin treatment of melanoma cells," Int J Oncol, 34(6): 1727-1735 (2009).
Anderson et al., "Small-molecule dissection of BMP signaling," Nature Chemical Biology, 4(1):15-16 (2008).
Banker, et al., (1996), Modern Pharmaceuticals, p. 596.
Cabrera et al., "Structure-activity relationship studies of orally active antimalarial 3, 5-substituted 2-aminopyridines," J Med Chem, 55(24): 1102-11030 (2012).
Cuny et al., "Structure-activity relationship study of bone morphogenetic protein (BMP) signaling inhibitors," *Bioorganic and Medicinal Chemistry Letters*, 18(15):4388-4392 (2008).
Daly et al., "Transforming growth factor beta-induced Smad1/5 phosphorylation in epithelial cells is mediated by novel receptor complexes and is essential for anchorage-independent growth," *Molecular and Cellular Biology*, 28(22):6889-6902 (2008).

(Continued)

*Primary Examiner* — Kahsay Habte
(74) *Attorney, Agent, or Firm* — David P. Halstead; Foley Hoag LLP

(57) ABSTRACT

The present invention provides small molecule inhibitors of BMP signaling. These compounds may be used to modulate cell growth, differentiation, proliferation, and apoptosis, and thus may be useful for treating diseases or conditions associated with BMP signaling, including inflammation, cardiovascular disease, hematological disease, cancer, and bone disorders, as well as for modulating cellular differentiation and/or proliferation. These compounds may also be used to reduce circulating levels of ApoB-100 or LDL and treat or prevent acquired or congenital hypercholesterolemia or hyperlipoproteinemia; diseases, disorders, or syndromes associated with defects in lipid absorption or metabolism; or diseases, disorders, or syndromes caused by hyperlipidemia.

5 Claims, 24 Drawing Sheets

(56) References Cited

FOREIGN PATENT DOCUMENTS

| WO | WO-2008/033408 A2 | 3/2008 |
|---|---|---|
| WO | WO-2008/074997 A1 | 6/2008 |
| WO | WO-2009/023059 A2 | 2/2009 |
| WO | WO-2008/074997 A8 | 4/2009 |
| WO | WO-2009/053737 A2 | 4/2009 |
| WO | WO-2009/053737 A3 | 7/2009 |
| WO | WO-2009/087224 A1 | 7/2009 |
| WO | WO-2009/087225 A2 | 7/2009 |
| WO | WO-2009/099982 A1 | 8/2009 |
| WO | WO-2009/114180 A1 | 9/2009 |
| WO | WO-2009/087225 A3 | 11/2009 |
| WO | WO-2010/088735 A1 | 8/2010 |
| WO | WO-2011/008640 A1 | 1/2011 |
| WO | WO-2012/100229 A2 | 7/2012 |
| WO | WO-2013/016452 A2 | 1/2013 |
| WO | WO-2013/037779 A1 | 3/2013 |
| WO | WO-2013/073859 A1 | 5/2013 |
| WO | WO-2014/138088 A1 | 9/2014 |
| WO | WO-2014/151761 A1 | 9/2014 |
| WO | WO-2014/160203 A2 | 10/2014 |
| WO | WO-2015/148654 A1 | 10/2015 |
| WO | WO-2016/011019 A1 | 1/2016 |
| WO | WO-2016/054406 A1 | 4/2016 |

OTHER PUBLICATIONS

Database accession No. CID58170108, Database PubChem Compound [Online] NCBI; Aug. 19, 2012 (Aug. 19, 2012), XP002759316, abstract.
Database accession No. CID60182388, Database PubChem Compound [Online] NCBI; Sep. 28, 2012 (Sep. 28, 2012), XP002759315, abstract.
Derwall et al., "Inhibition of Bone Morphogenetic Protein Signaling Reduces Vascular Calcification and Atherosclerosis," Arterioscl Throm Vas, Lippincott Williams & Wilkins, US, 32(3): 613-622 (Mar. 1, 2012).
Duarte, et al., "Cardiovascular effects of visnagin on rats," Planta Med, 66(1): 35-39 (2000).
Engers et al., Synthesis and structure-activity relationships of a novel and selective bone morphogenetic protein receptor (BMP) inhibitor derived from the pyrazolo[1.5-a]pyrimidine scaffold of Dorsomorphin: The discovery of ML347 as ALK2 versus ALK3 selective MLPCN probe, Bioorganic & Medicinal Chemistry Letters, pp. 3248-3252 (2013).
European Search Report for European Application No. EP 10 17 2229 dated Oct. 8, 2010.
Extended European Search Report for European Application No. EP 09 72 0039 dated Jul. 17, 2011.
Extended European Search Report issued by the European Patent Office in corresponding Application No. PCT/US2015/022470, dated Jul. 11, 2017.
Fraley et al., "Database Biosis [Online] Biosciences Information Service, "Synthesis and initial SAR studies of 3, 6-disubstituted pyrazolo(1,5-a)pyrimidines: A new class of KDR kinase inhibitors, Database accession No. PREV200200560660 *abstract* & Bioorganic and Medicinal Chemistry Letters, 12(19):2767-2770 (2002).
Fraley et al., "Optimization of a Pyrazolo[1,5-a]pyrimidine Class of KDR Kinase Inhibitors: Improvements in Physical Properties Enhance Cellular Activity and Pharmacokinetics," Bioorganice & Medicinal Chemistry Letters, 12(24):3537-3541 (2002).
Fraley, et al., "Synthesis and initial SAR studies of 3,6-disubstituted pyrazolo(1,5-a)pyrimidines: A new class of KDR kinase inhibitors," Bioorg Med Chem Lett, 12(19): 2767-2770 (2002).
Fukuda et al, "A unique mutation of ALK2, G356D, found in a patient with fibrodysplasia ossificans progressiva is a moderately activated BMP type I receptor," Biochemical and Biophysical Research Communications, 377(3):905-909 (2008).
Fukuda et al., "Constitutively activated ALK2 and increased SMAD1/5 cooperatively induce bone morphogenetic protein signaling in fibrodysplasia ossificans progressiva," Journal of Biological Chemistry, 284(11):7149-7156 (2009).
Hao et al., "Dorsomorphin, a selective small molecule inhibitor of BMP signaling, promotes cardiomyogenesis in embryonic stem cells," PLoS One, 3(8):e2904 (2008).
Hong et al., "Applications of small molecule BMP inhibitors in physiology and disease," Cytokine Growth Factor Rev., 20(5-6):409-418 (2009).
Hong et al., "KRC-408, a novel c-Met inhibitor, suppresses cell proliferation and angiogenesis of gastric cancer," Cancer Lett, 332(1): 74-82 (2013).
Hong, "Large-scale small-molecule screen using zebrafish embryos," Methods in Molecular Biology, 486:43-55 (2009).
International Search Report dated Oct. 16, 2014 and Written Opinion dated Jun. 22, 2014 for PCT/US2014/026042.
International Search Report and Written Opinion for International Application No. PCT/US2015/053545 dated Feb. 10, 2016.
International Search Report and Written Opinion dated Jul. 28, 2009 for PCT/US2009/001606.
International Search Report and Written Opinion dated Oct. 17, 2008 for PCT/US07/19831.
International Search Report for PCT/US2014/020360 dated Aug. 21, 2014 and Written Opinion dated May 27, 2014.
International Search Report dated Oct. 4, 2012 for PCT/US2012/022119.
Lim et al., "Noggin Antagonizes BMP Signaling to Create a Niche for Adult Neurogenesis", Neuron, vol. 28, 713-726, (2000).
Liu et al., "TGFbeta-stimulated Smad1/5 phosphorylation requires the ALK5 L45 loop and mediates the pro-migratory TGFbeta switch," EMBO Journal, 28(2):88-98 (2009).
Machrouhi, et al., "The rational design of a novel potent analogue of the 5?-AMP-activated protein kinase inhibitor compound C with improved selectivity and cellular activity," Bioorg Med Chem Lett, 20(22): 6394-6399 (2010).
Manchester et al., "Discovery of a novel azaindole class of antibacterial agents targeting the ATPase domains of DNA gyrase and Topoisomerase IV," Bioorg Med Chem Lett, 22(15): 5150-5156 (2012).
Mashkovskiy, "Lekarstvennye sredstva," Moska, Novaya Volna, 212-214, 407.
Miriyala et al., "Bone Morphogenic Protein-4 Induces Hypertension in Mice: Role of Noggin, Vascular NADPH Oxidases, and Impaired Vasorelaxation," Circulation, 113:2818-25 (2006).
Mohedas et al., "Development of an ALK2-Biased BMP Type I Receptor Kinase Inhibitor", ACS Chemical Biology, 8.6: 1291-1302 (2013).
Mohedas et al., "Structure-Activity Relationship of 3, 5-Diaryl-2-aminopyridine ALK2 Inhibitors Reveals Unaltered Binding Affinity for Fibrodysplasia Ossificans Progressiva Causing Mutants," J Med Chem, 57.19: 7900-7915 (2014).
Moreno-Miralles et al.., "New insights into bone morphogenetic protein signaling: focus on angiogenesis," Current Opinion in Hematology, 16(3):195-201 (2009).
Nam et al., "Compound C inhibits clonal expansion of preadipocytes by increasing p21 level irrespectively of AMPK inhibition," Archives of Biochemistry and Biophysics, 479:74-81 (2008).
Niehrs et al., "Dickkofp1 and the Spemann-Mangold Head Organizer," International Journal of Developmental Biology, 45(1):237-240 (2001).
Nishimatsu et al., "Ventral mesoderm induction and patterning by bone morphogenetic protein heterodimers in Xenopus embryos," Mechanism of Development, 74(1-2):75-88 (1998).
Piccolo et al., "Dorsoventral Patterning in Xenopus: Inhibition of Ventral Signals by Direct Binding of Chordin to BMP-4," Cell, 86(23):589-598 (1996).
Racane et al., "Synthesis and antiproliferative evaluation of some new amidino-substituted bis-benzothiazolyl-pyridines and pyrazine," Eur J Med Chem, 55: 108-116 (2012).

(56) References Cited

OTHER PUBLICATIONS

Re'em-Kalma et al, Competition between noggin and bone morphogenetic protein 4 activities may regulate dorsalization during Xenopus development, Proc. Natl. Acad. Sci. USA, Dec. 1995, vol. 92, pp. 12141-12145, see entire document.

Ross et al., "Twisted gastrulation is a conserved extracellular BMP antagonist," Nature, 410(6827):479-483 (2001).

Saeed et al., "Pharmacological Supression of Hepcidin Increases Macrophage Cholesterol Efflux and Reduces Foam Cell Formation and Atherosclerosis", Arteriosclerosis, Thrombosis , and Vascular Biology, vol. 32. No. 2, pp. 299-307 (2012).

Sanvitale, et al., "A new class of small molecule inhibitor of BMP signaling," PLoS One, 8(4): e62721 (2013).

Sasai et al., "Regulation of Neural Induction by the CHD and BMP-4 Antagonistic Patterning Signals in Xenopus," 376:333-335 (1995).

Seib et al., "Endogenous bone morphogenetic proteins in human bone marrow-derived multipotent mesenchymal stromal cells," *European Journal of Cell Biology*, 88(5):257-271 (2009).

Steinbeisser H. et al, The role of gsc and BMP-4 in dorsal-ventral patterning of the marginal zone in Xenopus: a loss-of-function study using antisense RNA, EMBO Journal, 1995, vol. 14, No. 21, pp. 5230-5243, see entire document.

Stella, "Prodrugs: Some thoughts and current issues," J Pharm Sci, 99(12): 4755-4765 (2010).

Su et al., The transforming growth factor beta 1/SMAD signaling pathway involved in human chronic myeloid leukemia, Tumori, 96:659-666 (2010).

Supplementary Partial European Search Report dated Oct. 22, 2009 for EP 07 83 8105.

Thomsen, G.H., "Antagonism within and around the organizer: BMP inhibitors in vertebrate body patterning," Trends in Genetics, 13(6):209-211 (1997).

Vogt et al., "The specificities of small molecule inhibitors of the TGFb and BMP pathways," Cellular Signalling, 23:1831-1842 (2011).

Vucicevic et al., "AMP-activated protein kinase-dependent and -independent mechanisms underlying in vitro antiglioma action of compound C," *Biochemical Pharmacology*, 77(11):1684-1693 (2009).

Wei et al., "Efficient orange-red phosphorescent organic light-emitting diodes using an in situ synthesized copper(I) complex as the emitterf," J Mater Chem C, 2(31): 6333-6341 (2014).

Wolff et al., "Burger's Medicinal Chemistry and Drug Discovery," 5th Ed. Part 1, pp. 975-977 (1995).

Wrighton et al., "Transforming Growth Factor {beta} Can Stimulate Smad1 Phosphorylation Independently of Bone Morphogenic Protein Receptors," *Journal of Biological Chemistry*, 284(15):9755-9763 (2009).

Written Opinion for PCT/US2012/022119 dated Sep. 29, 2012.

Xu, R.H et al, Involvement of Ras/Ra6'AP-1 in BMP-4 signaling during Xenopus embryonic devlopment, Proc. Natl. Acad..Sci. USA, Jan. 1996, vol. 93, pp. 834-838, sec entire document.

Yu et al., "BMP type I receptor inhibition reduces heterotopic [corrected] ossification," Nature Medicine, 14(12):1363-1369 (2008).

Yu et al., "Dorsomorphin inhibits BMP signals required for embryogenesis and iron metabolism," Nature Chemical Biology,4(1):33-41 (2007).

Yu et al., "Structure-activity relationship of 3,5-diaryl-2-aminopyridine ALK2 inhibitors reveals unaltered binding affinity for fibrodysplasia ossificans progressiva causing mutants," J Med Chem, 57(19): 7900-7915 (2014).

Zhou et al., "Role of AMP-activated protein kinase in mechanism of metformin action," Journal of Clinical Investigation, 108(8):1167-1174 (2001).

Zimmerman et al., "The Spemann Organizer Signal Noggin Binds and Inactivates Bone Morphogenetic Protein 4," Cell, 86(23):599-606 (1996).

Adams et al., "Quantification of the Effect of Conformational Restriction on Supramolecular Effective Molarities," J Am Chem Soc, 135(5): 1853-1863 (2013).

Aher et al., "QSAR and Pharmacophore Modeling of Diverse Aminothiazoles and Aminopyridines for Antimalarial Potency Against Multidrug-resistant Plasmodium Falciparum," Med Chem Res, 23(9): 4238-4249 (2014).

Cleveland Clinic, "Juvenile Polyposis Syndrome," (2017). [https://my.clevelandclinic.org/health/articles/juvenile-polyposis-syndrome?view=print].

Ettmayer et al., "Lessons learned from marketed and investigational prodrugs," J Med Chem, 47(10):2393-2404 (2004).

Gazzard et al., "Discovery of the 1,7-diazacarbazole Class of Inhibitors of Checkpoint Kinase 1," Bioorg Med Chem Lett, 24(24): 5704-5709 (2014).

Han et al., "Targeted prodrug design to optimize drug delivery," AAPS PharmaSci, 2(1):article 6, pp. 1-11 (2000).

Laliberte, "20 Ways to Never Get Cancer," Prevention (2017). [https://www.prevention.com/health/health-concerns/everyday-cancer-prevention-tips].

Mayo Clinic, "Anemia," (2017). [https://www.mayoclinic.org/diseases-conditions/anemia/symptoms-causes/syc-20351360?p=1].

Mayo Clinic, "Congenital heart defects in children," (2017). [https://www.mayoclinic.org/diseases-conditions/congenital-heart-defects-children/diagnosis-treatment/drc-20350080?p=1].

Mayo Clinic, "Pulmonary hypertension," (2017). [https://www.mayoclinic.org/diseases-conditions/pulmonary-hypertension/diagnosis-treatment/drc-20350702?p=1].

National Organization for Rare Disorders, "Hereditary Hemorrhagic Telangiectasia," (2017). [https://rarediseases.org/rare-diseases/hereditary-hemorrhagic-telangiectasia/].

Testa, "Prodrug research: futile or fertile?" Biochem Pharmacol, 68(11):2097-2106 (2004).

*: alternative site of oxidation

BMP INHIBITORS AND METHODS OF USE THEREOF

RELATED APPLICATIONS

This application is a continuation of U.S. patent application Ser. No. 14/776,302, filed Sep. 14, 2015, which is the U.S. national phase of International Patent Application No. PCT/US2014/026042, filed Mar. 13, 2014, which claims the benefit of U.S. Provisional Patent Application Ser. No. 61/783,695, filed Mar. 14, 2013, all of which are hereby incorporated by reference herein in their entirety.

STATEMENT REGARDING FEDERALLY SPONSORED RESEARCH OR DEVELOPMENT

This invention was created in the performance of a Cooperative Research and Development Agreement with the National Institutes of Health, an Agency of the Department of Health and Human Services. This invention was further supported by National Institutes of Health Grants 3R01AR057374 and 3R01AR057374-0351. The Government of the United States has certain rights in this invention.

BACKGROUND OF THE INVENTION

Signaling involving the Transforming Growth Factor β (TGF-β) superfamily of ligands is central to a wide range of cellular processes, including cell growth, differentiation, and apoptosis. TGF-β signaling involves binding of a TGF-β ligand to a type II receptor (a serine/threonine kinase), which recruits and phosphorylates a type I receptor. The type I receptor then phosphorylates a receptor-regulated SMAD (R-SMAD; e.g., SMAD1, SMAD2, SMAD3, SMAD5, SMAD8 or SMAD9), which binds to SMAD4, and the SMAD complex then enters the nucleus where it plays a role in transcriptional regulation. The TGF superfamily of ligands includes two major branches, characterized by TGF-β/activin/nodal and Bone Morphogenetic Proteins (BMPs).

Signals mediated by bone morphogenetic protein (BMP) ligands serve diverse roles throughout the life of vertebrates. During embryogenesis, the dorsoventral axis is established by BMP signaling gradients formed by the coordinated expression of ligands, receptors, co-receptors, and soluble inhibitors (Massague et al. *Nat. Rev. Mol. Cell. Biol.* 1:169-178, 2000). Excess BMP signaling causes ventralization, an expansion of ventral at the expense of dorsal structures, while diminished BMP signaling causes dorsalization, an expansion of dorsal at the expense of ventral structures (Nguyen et al. *Dev. Biol.* 199: 93-110, 1998; Furthauer et al. *Dev. Biol.* 214:181-196, 1999; Mintzer et al. *Development* 128:859-869, 2001; Schmid et al. *Development* 127:957-967, 2000). BMPs are key regulators of gastrulation, mesoderm induction, organogenesis, and endochondral bone formation, and regulate the fates of multipotent cell populations (Zhao, *Genesis* 35:43-56, 2003). BMP signals also play critical roles in physiology and disease, and are implicated in primary pulmonary hypertension, hereditary hemorrhagic telangiectasia syndrome, fibrodysplasia ossificans progressiva, and juvenile polyposis syndrome (Waite et al. *Nat. Rev. Genet.* 4:763-773, 2003; Papanikolaou et al. *Nat. Genet.* 36:77-82, 2004; Shore et al. *Nat. Genet.* 38:525-527, 2006).

The BMP signaling family is a diverse subset of the TGF-β superfamily (Sebald et al. *Biol. Chem.* 385:697-710, 2004). Over twenty known BMP ligands are recognized by three distinct type II (BMPRII, ActRIIa, and ActRIIb) and at least four type I (ALK1, ALK2, ALK3, and ALK6) receptors. Dimeric ligands facilitate assembly of receptor heteromers, allowing the constitutively-active type II receptor serine/threonine kinases to phosphorylate type I receptor serine/threonine kinases. Activated type I receptors phosphorylate BMP-responsive (BR-) SMAD effectors (SMADs 1, 5, and 8) to facilitate nuclear translocation in complex with SMAD4, a co-SMAD that also facilitates TGF signaling. In addition, BMP signals can activate intracellular effectors such as MAPK p38 in a SMAD-independent manner (Nohe et al. *Cell Signal* 16:291-299, 2004). Soluble BMP inhibitors, such as noggin, chordin, gremlin, and follistatin, limit BMP signaling by ligand sequestration.

A role for BMP signals in regulating expression of hepcidin, a peptide hormone and central regulator of systemic iron balance, has also been suggested (Pigeon et al. *J. Biol. Chem.* 276:7811-7819, 2001; Fraenkel et al. *J. Clin. Invest.* 115:1532-1541, 2005; Nicolas et al. *Proc. Natl. Acad. Sci. U.S.A.* 99:4596-4601, 2002; Nicolas et al. *Nat. Genet.* 34:97-101, 2003). Hepcidin binds and promotes degradation of ferroportin, the sole iron exporter in vertebrates. Loss of ferroportin activity prevents mobilization of iron to the bloodstream from intracellular stores in enterocytes, macrophages, and hepatocytes (Nemeth et al. *Science* 306:2090-2093, 2004). The link between BMP signaling and iron metabolism represents a potential target for therapeutics.

Given the tremendous structural diversity of the BMP and TGF-β superfamily at the level of ligands (>25 distinct ligands at present) and receptors (four type I and three type II receptors that recognize BMPs), and the heterotetrameric manner of receptor binding, traditional approaches for inhibiting BMP signals via soluble receptors, endogenous inhibitors, or neutralizing antibodies are not practical or effective. Endogenous inhibitors such as noggin and follistatin have limited specificity for ligand subclasses. Single receptors have limited affinity for ligand, whereas receptors heterotetramers exhibit more specificity for particular ligands. Neutralizing antibodies which are specific for particular ligands or receptors have been previously described, and are also limited by the structural diversity of this signaling system. Thus, there is a need in the art for pharmacologic agents that specifically antagonize BMP signaling pathways and that can be used to manipulate these pathways in therapeutic or experimental applications, such as those listed above.

SUMMARY OF THE INVENTION

In one aspect, the invention provides compounds that inhibit BMP-induced phosphorylation of SMAD1/5/8 including compounds represented by general formula I or a pharmaceutically acceptable salt, ester, or prodrug thereof,

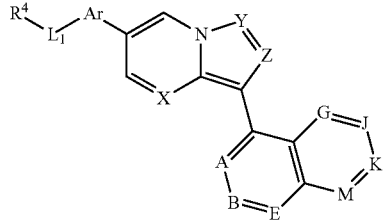

Formula I wherein
X and Y are independently selected from CR$^{15}$ and N, preferably both N;

Z is selected from CR$^3$ and N, preferably CR$^3$, most preferably CH;

Ar is a phenyl ring substituted with at least one non-protium ($^1$H) substituent or a substituted or unsubstituted heteroaryl ring;

L$_1$ is absent or selected from substituted or unsubstituted alkyl and heteroalkyl; and G, J, K, and M are all absent or, independently for each occurrence, are selected from CR$^{16}$ and N;

A, B, and E, independently for each occurrence, are selected from CR$^{16}$ and N;

provided that no more than three (and preferably no more than two) of A, B, E, G, J, K, and M are N, and at least one of E and M is N, and that if G, J, K, and M are absent then the carbon atom adjacent to E and M is optionally substituted with R$^{16}$;

R$^3$ is selected from H, halogen, cyano, and substituted or unsubstituted alkyl, cycloalkyl, acylamino, carbamate, sulfonyl, sulfoxido, sulfamoyl, or sulfonamido;

R$^4$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

R$^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and R$^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, or sulfonamide.

In certain embodiments, B is C—R$^{25}$ when E is N or K is C—R$^{25}$ when M is N or both, such that at least one of B and K is C—R$^{25}$, and R$^{25}$ is selected from deuterium, halogen (preferably fluorine or chlorine), lower alkyl (preferably methyl), lower alkoxy (preferably methoxy), or hydroxyl, such as deuterium, fluorine, chlorine, methyl, ethyl, hydroxy, or methoxy.

In certain embodiments, A, G, and J are each CH.

In another aspect, the invention provides compounds that inhibit BMP-induced phosphorylation of SMAD1/5/8 including compounds represented by general formula II or a pharmaceutically acceptable salt, ester, or prodrug thereof, Formula II wherein
X and Y are independently selected from CR$^{15}$ and N, preferably both N;

Z is selected from CR$^3$ and N, preferably CR$^3$, most preferably CH;

Ar is selected from substituted or unsubstituted aryl and heteroaryl;

L$_1$ is absent or selected from substituted or unsubstituted alkyl and heteroalkyl; and G, J, K, and M are all absent or, independently for each occurrence, are selected from CR$^{16}$ and N;

A, B, and E, independently for each occurrence, are selected from CR$^{16}$ and N;

provided that no more than three (and preferably no more than two) of A, B, E, G, J, K, and M are N, and at least one of E and M is N, and that if G, J, K, and M are absent then the carbon atom adjacent to E and M is optionally substituted with R$^{16}$;

R$^3$ is selected from H, halogen, cyano, and substituted or unsubstituted alkyl, cycloalkyl, acylamino, carbamate, sulfonyl, sulfoxido, sulfamoyl, or sulfonamido;

R$^4$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

R$^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and R$^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, or sulfonamido;

wherein B is C—R$^{25}$ when E is N or K is C—R$^{25}$ when M is N or both such that at least one of B and K is C—R$^{25}$, where R$^{25}$ is selected from deuterium, halogen (preferably fluorine or chlorine), hydroxyl, lower alkyl (preferably methyl), and lower alkoxy (preferably methoxy), such as deuterium, fluorine, chlorine, methyl, ethyl, hydroxy, or methoxy.

In certain embodiments, Ar is a substituted or unsubstituted nitrogen-containing heteroaryl group selected from pyridine, pyrazine, pyrimidine, oxazole, thiazole, and thiadiazole, e.g., selected from substituted or unsubstituted:

-continued

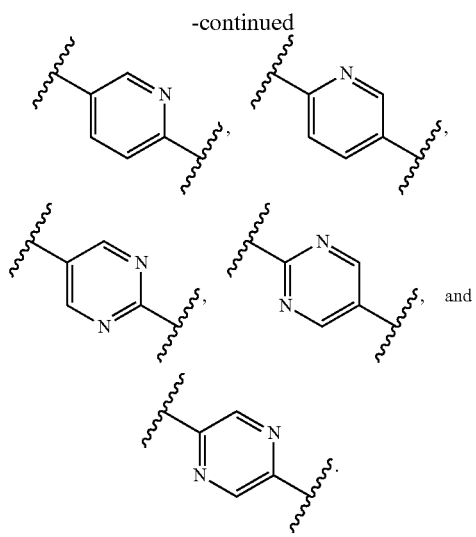

In certain embodiments wherein Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy).

In certain embodiments, Ar is a substituted or unsubstituted six-membered ring. In certain such embodiments, $L_1$ is disposed on the para-position of Ar relative to the bicyclic core bearing X, Y, and Z. In certain embodiments of the foreign wherein Ar is phenyl substituted with a non-protium substituent, either the substituent is halogen (preferably fluoro or chloro) or cyano, or is positioned ortho to $L_1$, or both.

In certain embodiments, $L_1$ is absent. In other embodiments, $L_1$ has a structure

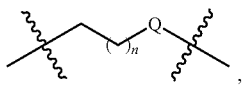

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer from 0-4, wherein any $CH_2$ subunit of $L_1$ is optionally substituted with one or two lower alkyl groups, preferably one or two methyl groups.

In certain embodiments, $R^4$ is selected from

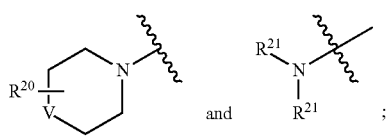

$L_1$ is absent or selected from substituted or unsubstituted alkyl and heteroalkyl, preferably absent; V is absent or is $C(R^{21})_2$, O, or $NR^{21}$; $R^{20}$ is absent or represents from 1-4 substituents selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamido.

In certain embodiments, $R^4$ is

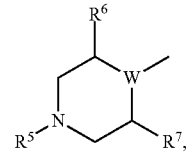

wherein W is N, CH, or $CCH_3$, preferably N or CH; $R^5$ is selected from H and substituted or unsubstituted alkyl, acyl, or ester (thereby forming a carbamate); and $R^6$ and $R^7$ are each independently selected from H or alkyl, preferably from H or methyl, or $R^6$ forms a one- or two-carbon (e.g., $CH_2$ or $CH_2CH_2$) bridge to the carbon atom adjacent to $R^7$ and $NR^5$.

In certain embodiments, A, G, and J are each CH.

In yet another aspect, the invention provides compounds that inhibit BMP-induced phosphorylation of SMAD1/5/8 including compounds represented by general formula III or a pharmaceutically acceptable salt, ester, or prodrug thereof, Formula III

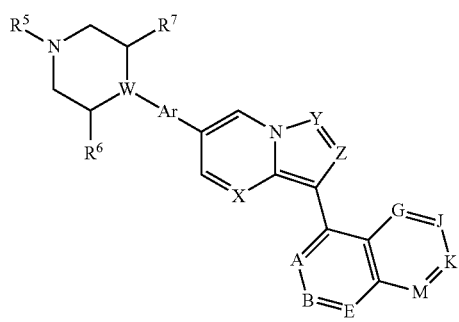

wherein
X and Y are independently selected from $CR^{15}$ and N, preferably both N;
Z is selected from $CR^3$ and N, preferably $CR^3$, most preferably CH;
Ar is selected from substituted or unsubstituted aryl and heteroaryl;
$R^5$ is selected from H and substituted or unsubstituted alkyl, acyl, or ester (thereby forming a carbamate);
$R^6$ and $R^7$ are each independently selected from H or alkyl, preferably from H or methyl, or $R^6$ forms a one- or two-carbon (e.g., $CH_2$ or $CH_2CH_2$) bridge to the carbon atom adjacent to $R^7$ and $NR^5$;
W is N, CH, or $CCH_3$, preferably N or CH; and
G, J, K, and M are all absent or, independently for each occurrence, are selected from $CR^{16}$ and N;
A, B, and E, independently for each occurrence, are selected from $CR^{16}$ and N;

provided that no more than three (and preferably no more than two) of A, B, E, G, J, K, and M are N, and at least one of E and M is N, and that if G, J, K, and M are absent then the carbon atom adjacent to E and M is optionally substituted with $R^{16}$;

$R^3$ is selected from H and substituted or unsubstituted alkyl, cycloalkyl, halogen, acylamino, carbamate, cyano, sulfonyl, sulfoxido, sulfamoyl, or sulfonamido;

$R^4$ is selected from H and substituted or unsubstituted alkenyl, alkynyl, cycloalkyl, heterocyclyl, aryl, heteroaryl, acyl, carboxyl, ester, hydroxyl, alkoxyl, alkylthio, acyloxy, amino, acylamino, carbamate, amido, amidino, sulfonyl, sulfoxido, sulfamoyl, or sulfonamido;

$R^3$ is selected from H, halogen, cyano, and substituted or unsubstituted alkyl, cycloalkyl, acylamino, carbamate, sulfonyl, sulfoxido, sulfamoyl, or sulfonamido;

$R^4$ is selected from H, hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, or sulfonamido;

$R^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, or sulfonamido; and $R^{16}$, independently for each occurrence, is absent or is selected from H (including, and in certain embodiments preferably, D), OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, or sulfonamide.

wherein either W is CH or $CCH_3$, or $R^6$ and $R^7$ are not both H.

In certain embodiments, $R^6$ and $R^7$ are both methyl, optionally disposed in a syn relationship to each other. In certain embodiments, $R^6$ represents a one-carbon bridge, thereby forming a diazanorbornane bicycle.

In certain embodiments, B is C—$R^{25}$ when E is N or K is C—$R^{25}$ when M is N or both, such that at least one of B and K is C—$R^{25}$, and $R^{25}$ is selected from deuterium, halogen (preferably fluorine or chlorine), lower alkyl (preferably methyl), lower alkoxy (preferably methoxy), or hydroxy, such as deuterium, fluorine, chlorine, methyl, ethyl, hydroxy, or methoxy.

In certain embodiments, Ar is a substituted or unsubstituted nitrogen-containing heteroaryl group selected from pyridine, pyrazine, pyrimidine, oxazole, thiazole, and thiadiazole, e.g., selected from substituted or unsubstituted:

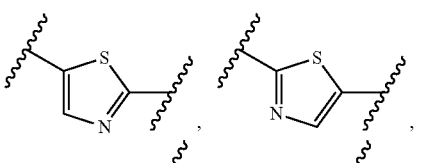

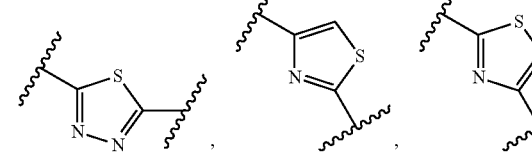

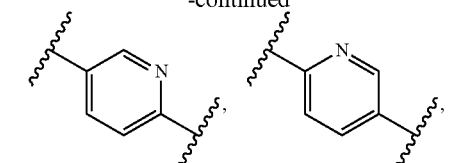

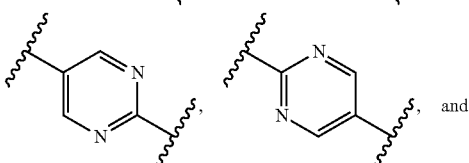

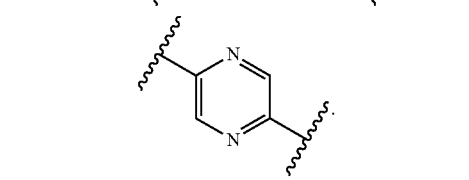

In certain embodiments wherein Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy).

In certain embodiments, Ar is a substituted or unsubstituted six-membered ring. In certain such embodiments, W is disposed on the para-position of Ar relative to the bicyclic core bearing X, Y, and Z. In certain embodiments of the foregoing wherein Ar is phenyl substituted with a non-protium substituent, either the substituent is halogen (preferably fluoro or chloro) or cyano, or is positioned ortho to W, or both.

In certain embodiments, A, G, and J are each CH.

In certain of the embodiments disclosed above, compounds of formula I have one or more of the following features:

B is C—$R^{25}$ when E is N or K is C—$R^{25}$ when M is N or both, such that at least one of B and K is C—$R^{25}$, and $R^{25}$ is selected from deuterium, halogen (preferably fluorine or chlorine), lower alkyl (preferably methyl), lower alkoxy (preferably methoxy), or hydroxyl;

$R^{25}$ is selected from deuterium, fluorine, chlorine, methyl, ethyl, hydroxy, or methoxy;

Ar is a substituted or unsubstituted nitrogen-containing heteroaryl group selected from pyridine, pyrazine, pyrimidine, oxazole, thiazole, and thiadiazole, e.g., selected from substituted or unsubstituted:

-continued

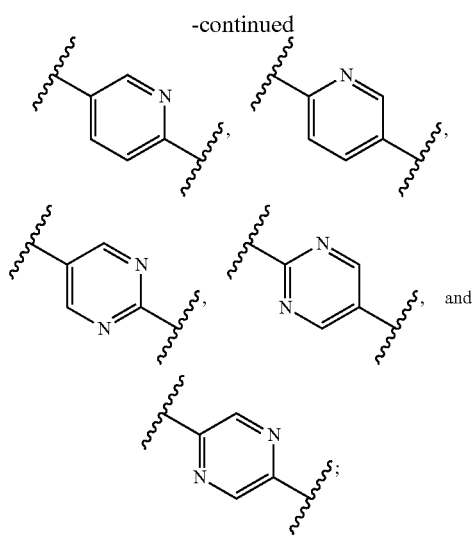

when Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy);

Ar is a substituted or unsubstituted six-membered ring;

$L_1$ is disposed on the para-position of Ar relative to the bicyclic core bearing X, Y, and Z;

when Ar is phenyl substituted with a non-protium substituent, either the substituent is halogen (preferably fluoro or chloro) or cyano, or is positioned ortho to $L_1$, or both;

$L_1$ is absent;

$L_1$ has a structure

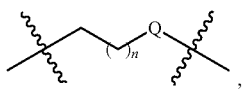

wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer from 0-4, wherein any $CH_2$ subunit of $L_1$ is optionally substituted with one or two lower alkyl groups, preferably one or two methyl groups;

$R^4$ is selected from

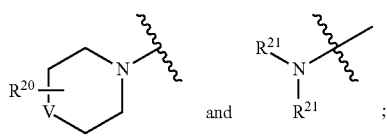

$L_1$ is absent or selected from substituted or unsubstituted alkyl and heteroalkyl, preferably absent; V is absent or is $C(R^{21})_2$, O, or $NR^{21}$; $R^{20}$ is absent or represents from 1-4 substituents selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide;

$R^4$ is

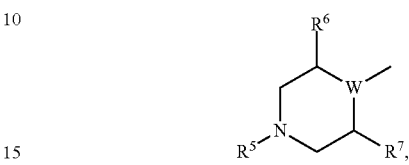

wherein W is N, CH, or $CCH_3$, preferably N or CH; $R^5$ is selected from H and substituted or unsubstituted alkyl, acyl, or ester (thereby forming a carbamate); and $R^6$ and $R^7$ are each independently selected from H or alkyl, preferably from H or methyl, or $R^6$ forms a one- or two-carbon (e.g., $CH_2$ or $CH_2CH_2$) bridge to the carbon atom adjacent to $R^7$ and $NR^5$;

A, G, and J are each CH.

In certain of the embodiments disclosed above, compounds of formula II have one or more of the following features:

$R^{25}$ is selected from deuterium, fluorine, chlorine, methyl, ethyl, hydroxy, or methoxy;

Ar is a substituted or unsubstituted nitrogen-containing heteroaryl group selected from pyridine, pyrazine, pyrimidine, oxazole, thiazole, and thiadiazole, e.g., selected from substituted or unsubstituted:

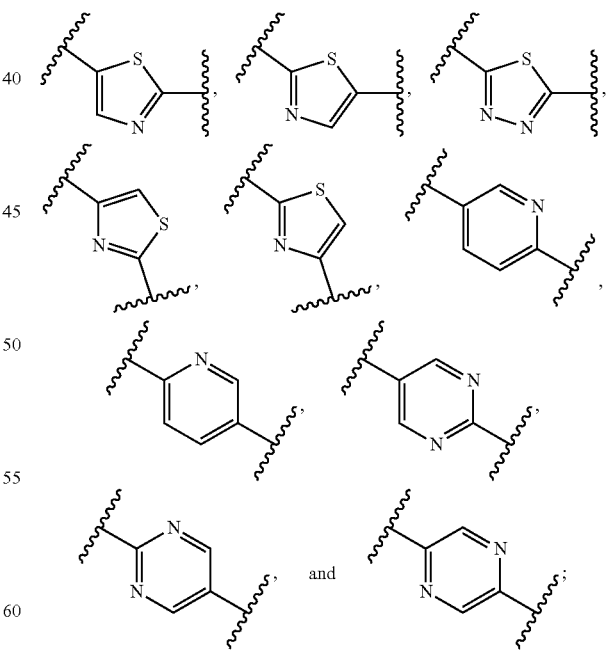

when Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy);

Ar is a substituted or unsubstituted six-membered ring;

$L_1$ is disposed on the para-position of Ar relative to the bicyclic core bearing X, Y, and Z;

when Ar is phenyl substituted with a non-protium substituent, either the substituent is halogen (preferably fluoro or chloro) or cyano, or is positioned ortho to $L_1$, or both;

$L_1$ is absent;

$L_1$ has a structure

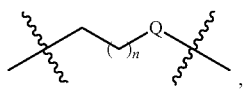

, wherein Q is selected from $CR^{10}R^{11}$, $NR^{12}$, O, S, S(O), and $SO_2$; $R^{10}$ and $R^{11}$, independently for each occurrence, are selected from H and substituted or unsubstituted alkyl, cycloalkyl, heterocyclyl, cycloalkylalkyl, heterocyclylalkyl, amino, acylamino, carbamate, amido, amidino, cyano, sulfonyl, sulfoxido, sulfamoyl, or sulfonamido; $R^{12}$ selected from H and substituted or unsubstituted alkyl, cycloalkyl, heterocyclyl, heterocyclylalkyl, amino, acylamino, carbamate, amido, amidino, sulfonyl, sulfamoyl, or sulfonamide; and n is an integer from 0-4, wherein any $CH_2$ subunit of $L_1$ is optionally substituted with one or two lower alkyl groups, preferably one or two methyl groups;

$R^4$ is selected from

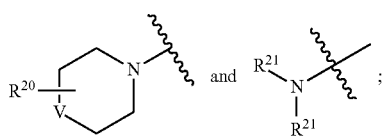

;

$L_1$ is absent or selected from substituted or unsubstituted alkyl and heteroalkyl, preferably absent; V is absent or is $C(R^{21})_2$, O, or $NR^{21}$; $R^{20}$ is absent or represents from 1-4 substituents selected from substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfoxido, sulfamoyl, and sulfonamido; and $R^{21}$, independently for each occurrence, is selected from H and substituted or unsubstituted alkyl, aralkyl, cycloalkyl, heterocyclyl, aryl, heteroaryl, heteroaralkyl, cycloalkylalkyl, heterocyclylalkyl, acyl, sulfonyl, sulfamoyl, or sulfonamide;

$R^4$ is

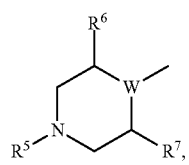

, wherein W is N, CH, or $CCH_3$, preferably N or CH; $R^5$ is selected from H and substituted or unsubstituted alkyl, acyl, or ester (thereby forming a carbamate); and $R^6$ and $R^7$ are each independently selected from H or alkyl, preferably from H or methyl, or $R^6$ forms a one- or two-carbon (e.g., $CH_2$ or $CH_2CH_2$) bridge to the carbon atom adjacent to $R^7$ and $NR^5$;

A, G, and J are each CH.

In certain of the embodiments disclosed above, compounds of formula III have one or more of the following features:

$R^6$ and $R^7$ are both methyl, optionally disposed in a syn relationship to each other;

$R^6$ represents a one-carbon bridge, thereby forming a diazanorbornane bicycle;

B is C—$R^{25}$ when E is N or K is C—$R^{25}$ when M is N or both, such that at least one of B and K is C—$R^{25}$, and $R^{25}$ is selected from deuterium, halogen (preferably fluorine or chlorine), lower alkyl (preferably methyl), lower alkoxy (preferably methoxy), or hydroxyl;

$R^{25}$ is selected from deuterium, fluorine, chlorine, methyl, ethyl, hydroxy, or methoxy;

Ar is a substituted or unsubstituted nitrogen-containing heteroaryl group selected from pyridine, pyrazine, pyrimidine, oxazole, thiazole, and thiadiazole, e.g., selected from substituted or unsubstituted:

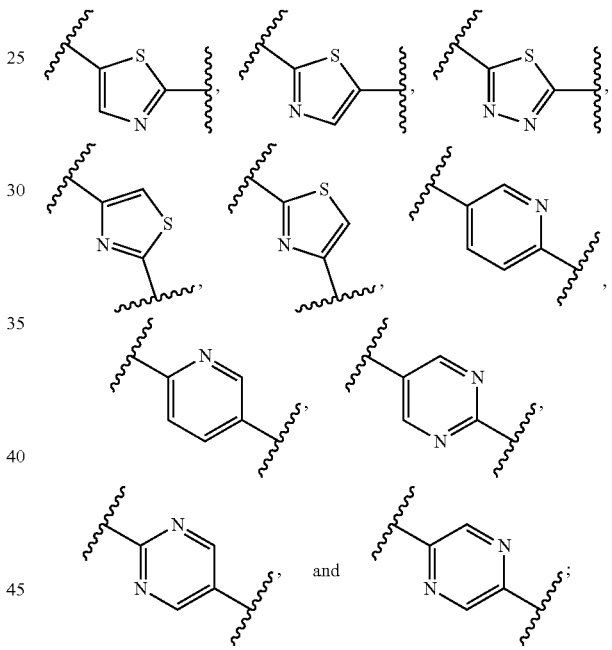

when Ar is substituted, the substituent is selected from deuterium, halogen (preferably fluoro or chloro), hydroxy, cyano, lower alkyl (preferably methyl or ethyl, most preferably methyl), or lower alkoxy (preferably methoxy);

Ar is a substituted or unsubstituted six-membered ring;

W is disposed on the para-position of Ar relative to the bicyclic core bearing X, Y, and Z;

when Ar is phenyl substituted with a non-protium substituent, either the substituent is halogen (preferably fluoro or chloro) or cyano, or is positioned ortho to W, or both; and A, G, and J are each CH.

Exemplary compounds of Formulae I, II and III include the compounds shown in Table 1 and their salts (including pharmaceutically acceptable salts).

In one aspect, the invention provides a pharmaceutical composition comprising a compound as disclosed herein and a pharmaceutically acceptable excipient or solvent. In certain embodiments, a pharmaceutical composition may comprise a prodrug of a compound as disclosed herein.

In another aspect, the invention provides a method of inhibiting BMP-induced phosphorylation of SMAD1/5/8, comprising contacting a cell with a compound or composition as disclosed herein.

In certain embodiments, the method treats or prevents a disease or condition in a subject that would benefit by inhibition of Bone Morphogenetic Protein (BMP) signaling. In certain embodiments, the disease or condition is selected from pulmonary hypertension, hereditary hemorrhagic telangectasia syndrome, cardiac valvular malformations, cardiac structural malformations, fibrodysplasia ossificans progressiva, juvenile familial polyposis syndrome, parathyroid disease, cancer (e.g., breast carcinoma, prostate carcinoma, renal cell carcinoma, bone metastasis, lung metastasis, osteosarcoma, and multiple myeloma), anemia, vascular calcification, atherosclerosis, valve calcification, renal osteodystrophy, inflammatory disorders (e.g., ankylosing spondylitis), infections with viruses, bacteria, fungi, tuberculosis, and parasites.

In certain embodiments, the method reduces the circulating levels of ApoB-100 and/or LDL and/or total cholesterol in a subject that has levels of ApoB-100 and/or LDL and/or total cholesterol that are abnormally high or that increase a patient's risk of developing a disease or unwanted medical condition. In certain embodiments, the method of reducing circulating levels of ApoB-100 and/or LDL and/or total cholesterol in a subject reduces the risk of primary or secondary cardiovascular events. In certain embodiments, the method treats or prevents a disease or condition in a subject that would benefit by inhibition of Bone Morphogenetic Protein (BMP) signaling. In certain embodiments, the disease or condition is selected from pulmonary hypertension; hereditary hemorrhagic telangectasia syndrome; cardiac valvular malformations; cardiac structural malformations; fibrodysplasia ossificans progressive; juvenile familial polyposis syndrome; parathyroid disease; cancer (e.g., breast carcinoma, prostate carcinoma, renal cell carcinoma, bone metastasis, lung metastasis, osteosarcoma, and multiple myeloma); anemia; vascular calcification; vascular inflammation; atherosclerosis; acquired or congenital hypercholesterolemia or hyperlipoproteinemia; diseases, disorders, or syndromes associated with defects in lipid absorption or metabolism; diseases, disorders, or syndromes caused by hyperlipidemia; valve calcification; renal osteodystrophy; inflammatory disorders (e.g., ankylosing spondylitis); infections with viruses; bacteria; fungi; tuberculosis; and parasites.

In another aspect, the invention provides a method of treating hypercholesterolemia, hyperlipidemia, hyperlipoproteinemia or hepatic steatosis in a subject comprising administering an effective amount of a compound as disclosed herein. In certain embodiments, the hypercholesterolemia, hyperlipidemia, or hyperlipoproteinemia is congenital hypercholesterolemia, hyperlipidemia, or hyperlipoproteinemia. In certain embodiments, the hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B). In certain such embodiments, the hypercholesterolemia, hyperlipidemia, hyperlipoproteinemia or hepatic steatosis is acquired hypercholesterolemia, hyperlipidemia, hyperlipoproteinemia or hepatic steatosis. In certain such embodiments, the hypercholesterolemia, hyperlipidemia, hyperlipoproteinemia, or hepatic steatosis is associated with diabetes mellitus, hyperlipidemic diet and/or sedentary lifestyle, obesity, metabolic syndrome, intrinsic or secondary liver disease, biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids.

In another aspect, the invention provides a method of treating a disease, disorder, or syndrome associated with defects in lipid absorption or metabolism or caused by hyperlipidemia in a subject, comprising administering an effective amount of a compound as disclosed herein.

In another aspect, the invention provides a method of reducing primary and secondary cardiovascular events arising from coronary, cerebral, or peripheral vascular disease in a subject, comprising administering an effective amount of a compound as disclosed herein.

In another aspect, the invention provides a method of preventing cardiovascular disease in a subject with elevated markers of cardiovascular risk, comprising administering an effective amount of a compound as disclosed herein.

In another aspect, the invention provides a method of preventing and treating hepatic dysfunction in a subject associated with nonalcoholic fatty liver disease (NAFLD), steatosis-induced liver injury, fibrosis, cirrhosis, or nonalcoholic steatohepatitis (NASH) in a subject comprising administering an effective amount of a compound as disclosed herein.

In another aspect, the invention provides a method of inducing expansion or differentiation of a cell, comprising contacting the cell with a compound as disclosed herein. In certain embodiments, the cell is selected from an embryonic stem cell and an adult stem cell. In certain embodiments, the cell is in vitro.

In certain embodiments, a method of the invention may comprise contacting a cell with a prodrug of a compound as disclosed herein.

DETAILED DESCRIPTION OF THE INVENTION

Figure 1:
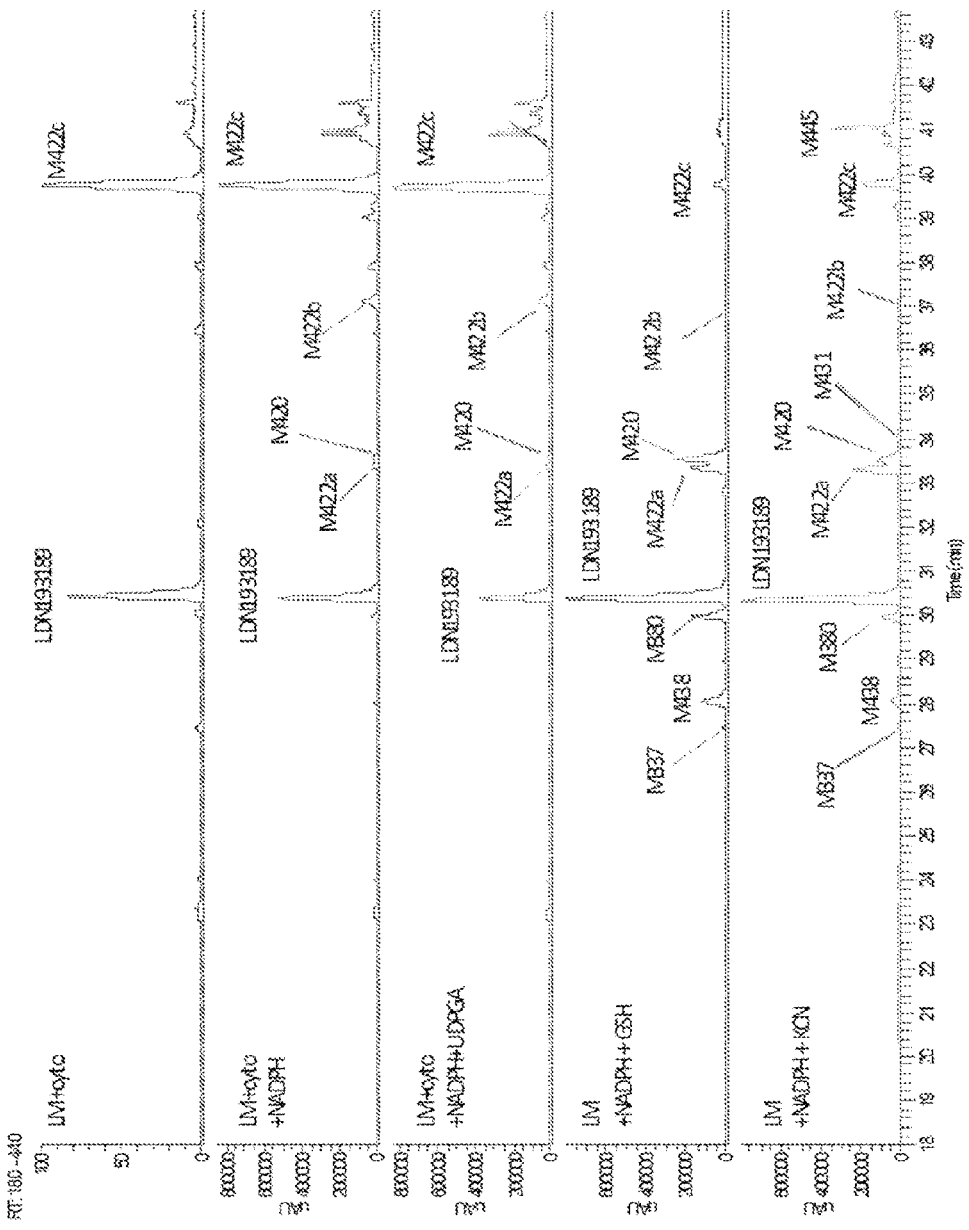
FIG. 1 shows the metabolite profiles (LC/UV) of LDN-193189 following incubations with mouse liver microsomes (LM) and cytosol (cyto) in the presence of NADPH, UDPGA, GSH, and KCN.
Figure 2:
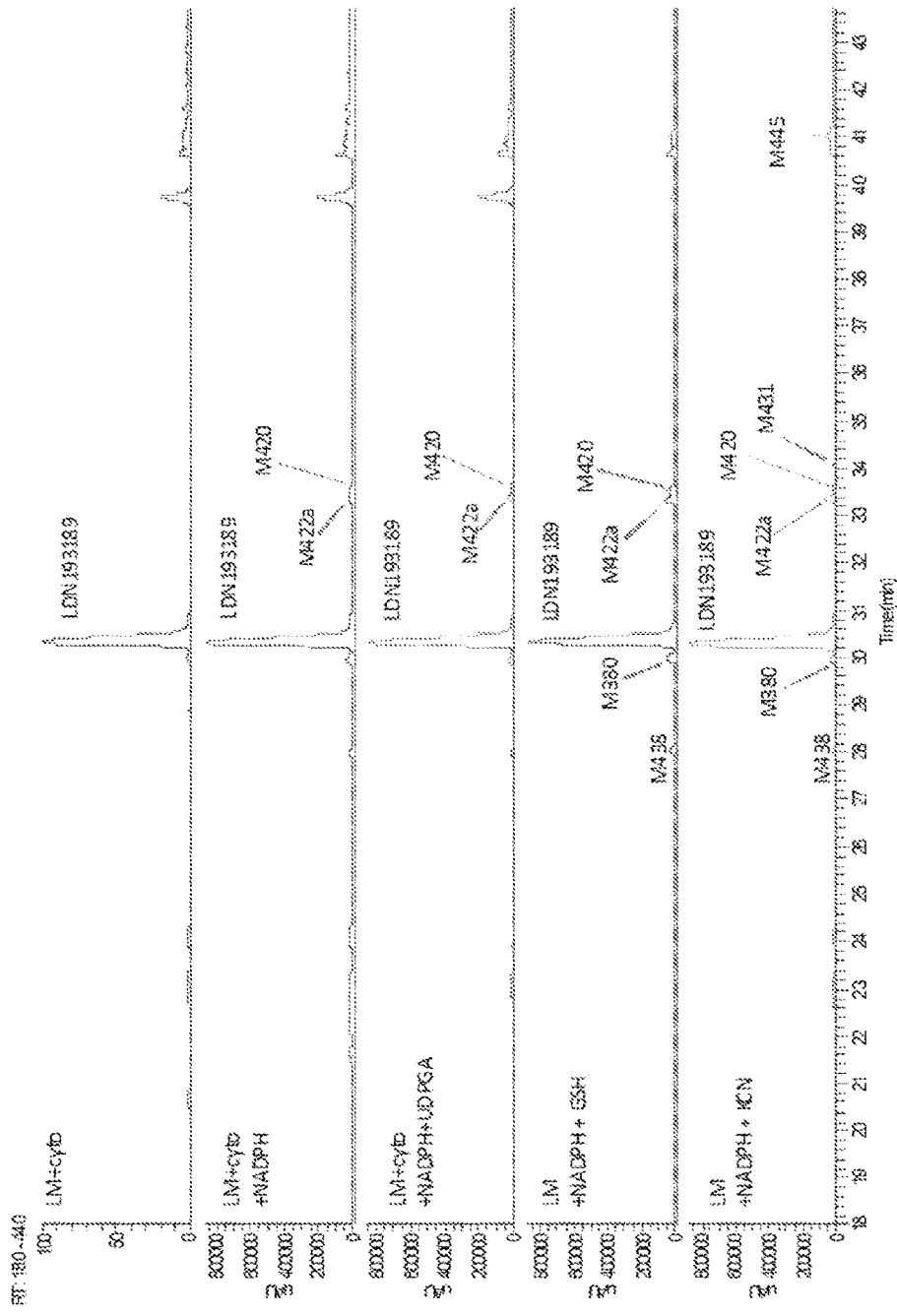
FIG. 2 shows the metabolite profiles (LC/UV) of LDN-193189 following incubations with rat liver microsomes (LM) and (cyto) cytosol in the presence of NADPH, UDPGA, GSH, and KCN.
Figure 3:
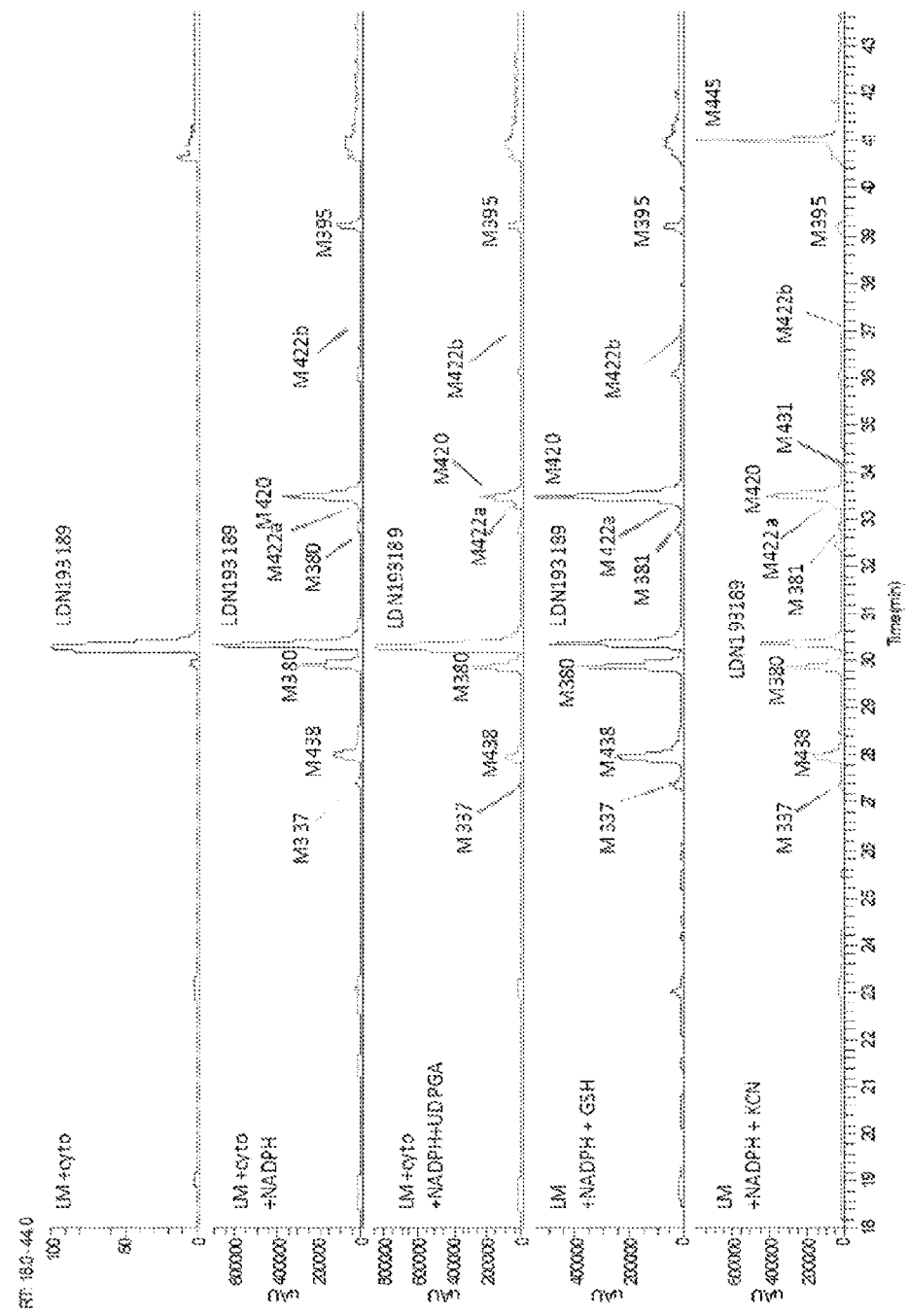
FIG. 3 shows the metabolite profiles (LC/UV) of LDN-193189 following incubations with dog liver microsomes (LM) and cytosol (cyto) in the presence of NADPH, UDPGA, GSH, and KCN.
Figure 4:
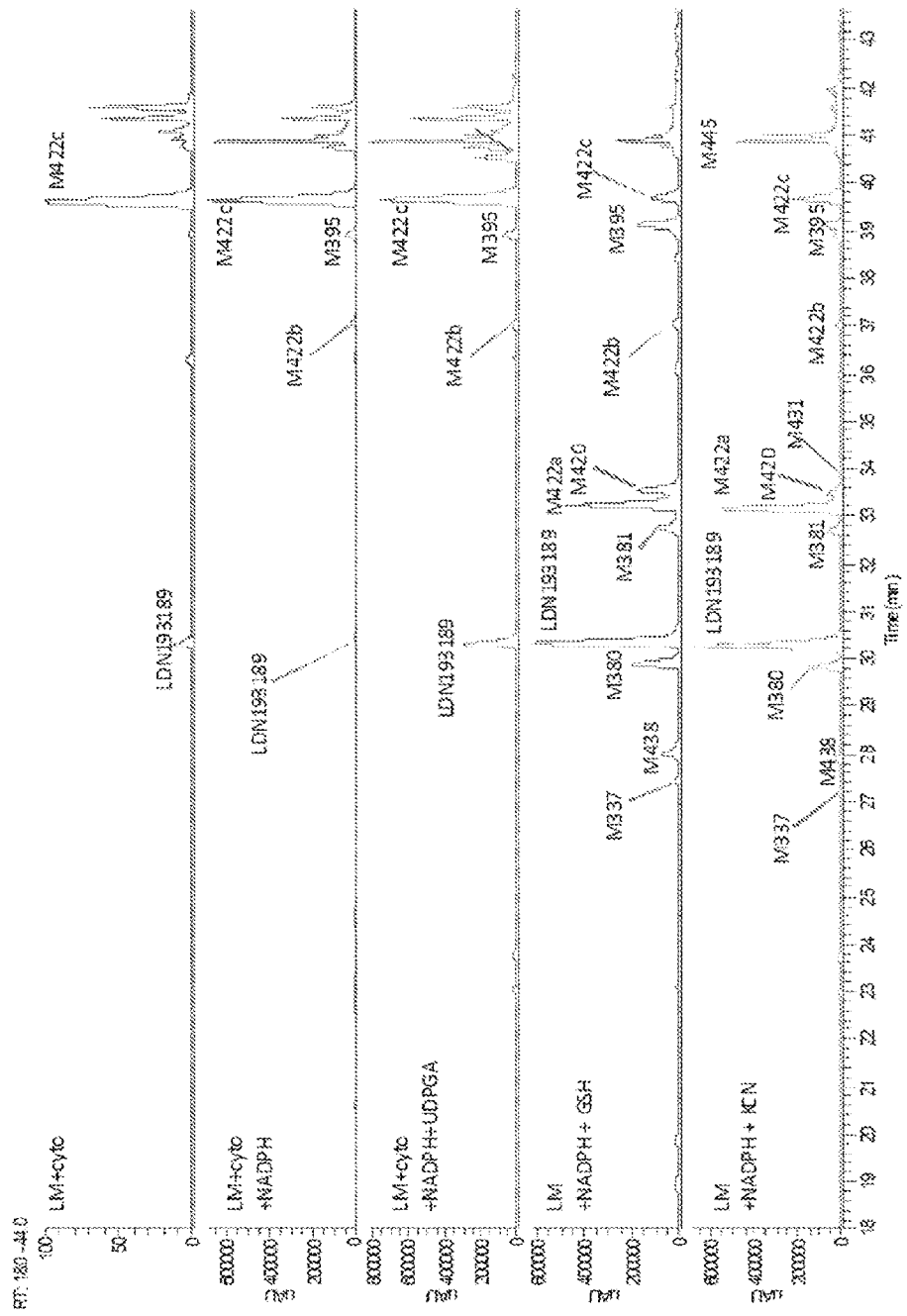
FIG. 4 shows the metabolite profiles (LC/UV) of LDN-193189 following incubations with rabbit liver microsomes (LM) and cytosol (cyto) in the presence of NADPH, UDPGA, GSH, and KCN.
Figure 5:
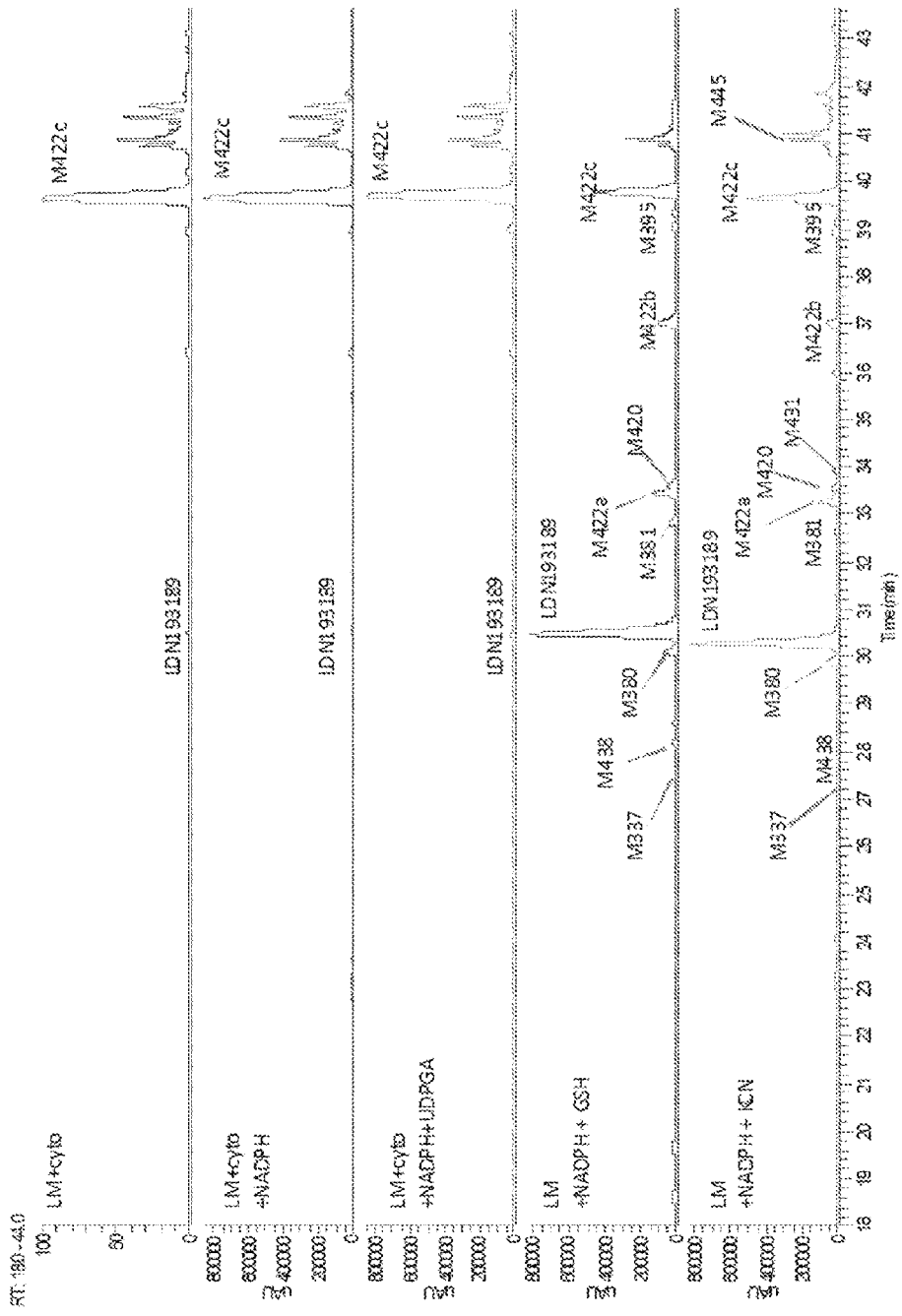
FIG. 5 shows the metabolite profiles (LC/UV) of LDN-193189 following incubations with monkey liver microsomes (LM) and cytosol (cyto) in the presence of NADPH, UDPGA, GSH, and KCN.
Figure 6:
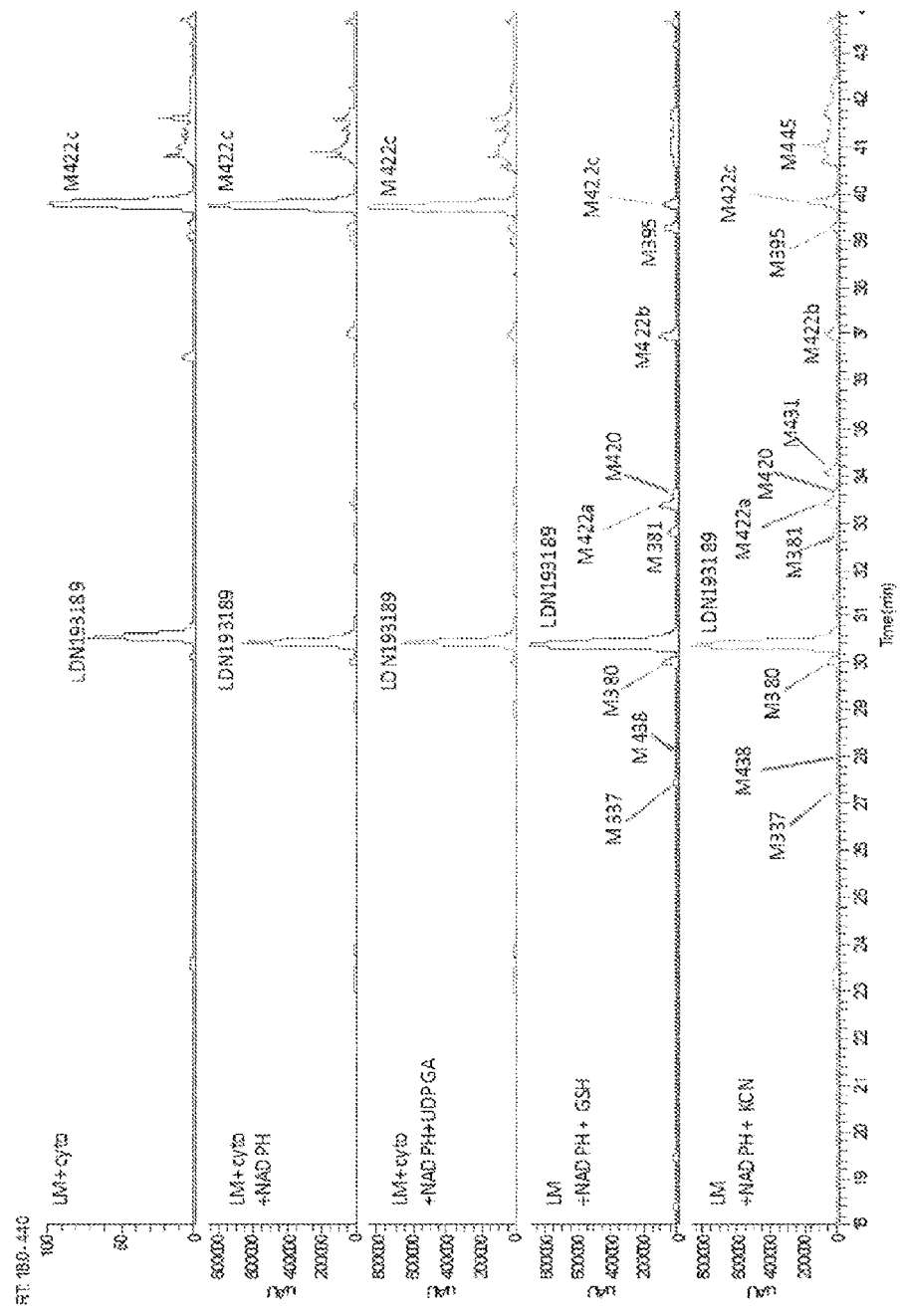
FIG. 6 shows the metabolite profiles (LC/UV) of LDN-193189 following incubations with human liver microsomes (LM) and cytosol (cyto) in the presence of NADPH, UDPGA, GSH, and KCN.

The invention provides for compounds that inhibit the BMP signaling pathway, as well as methods to treat or prevent a disease or condition in a subject that would benefit by inhibition of BMP signaling.

I. Compounds

Compounds of the invention include compounds of Formulae I, II or III as disclosed above and their salts (including pharmaceutically acceptable salts). Such compounds are suitable for the compositions and methods disclosed herein.

Compounds disclosed in International Application WO 2009/114180 and U.S. Provisional Application 61/772,465, filed Mar. 4, 2013, inhibit the BMP signaling pathway, and are suitable compounds for use in methods of treating and preventing a disease or condition in a subject that would benefit by inhibition of BMP signaling. Metabolic studies were performed on structure types represented by compounds disclosed in International Application WO 2009/114180 and U.S. Provisional Application 61/772,465, filed Mar. 4, 2013, to identify dominant metabolic degradation pathways, to provide guidance for mitigating reactive metabolite formation, and to identify metabolically active sites that could be blocked or inhibited in modified compounds. Studies related to metabolite formation and identification of metabolically active sites allow for the investigation of compounds that may overcome the difficulties associated with the identified metabolism, thereby improving in vivo efficacy, simplifying dosage regimens, and ultimately improving patient outcomes.

Specifically, as an initial study, the metabolism of LDN-193189 was examined. As shown in Example 4, LDN-193189 was incubated with liver microsomes from 6 species (mouse, rat, rabbit, monkey, dog and human). In all species, when the liver microsomes were incubated with NADPH cofactor and KCN, a metabolite, M431, indicated the presence of a reactive iminium species. As shown in Scheme A, the production of this species is the first step in the dealkylation of the piperazine, providing a pathway that could ultimately yield a toxic aniline metabolite.

Scheme A:

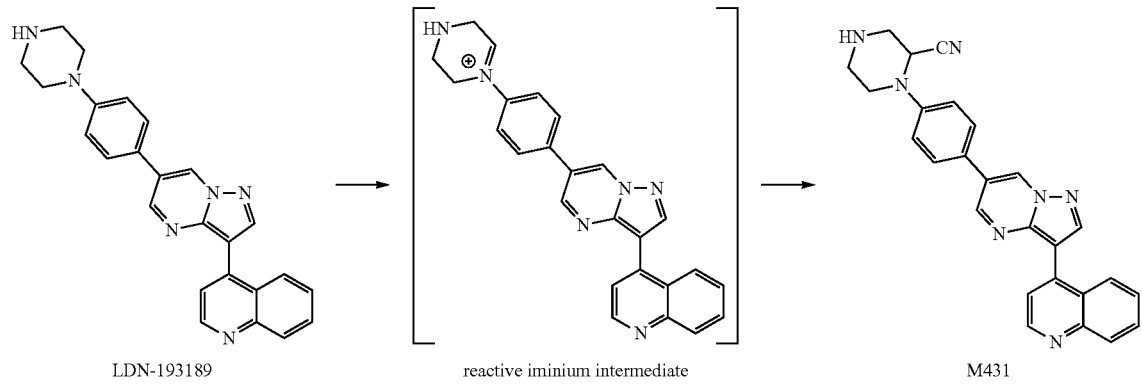

LDN-193189 → reactive iminium intermediate → M431

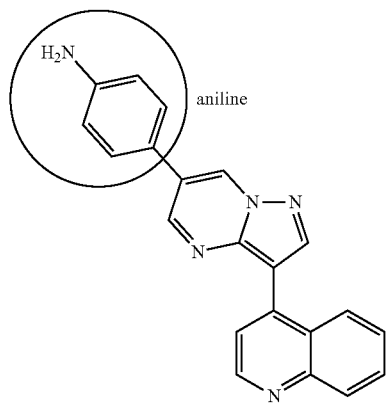

aniline

The proposed reactive iminum intermediate was not trapped with glutathione (GSH), a "soft" nucleophile, but was trapped with cyanide (KCN), a "hard" nucleoophile. The iminium ion itself is a "hard" electrophile and is thus more likely to react with with a "hard" nucleophile. Indeed, there was no glutathione adduct detected in any of these experiments.

The major metabolite was seen in the presence of cytosol. Thus, it was suspected that the cytosolic enzyme aldehyde oxidase (AO) was involved. Evidence for its involvement is supported by the fact that in dogs, a species that lacks AO, metabolite 422c was not observed. In addition, in MLM and HLM where AO is present, M422c was substantially decreased when treated with menadione, an AO inhibitor. The identity of M422c was confirmed with the synthesis of NIH-Q55,

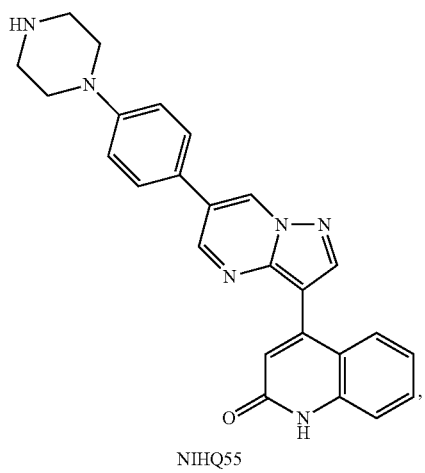

NIHQ55 which gave the identical retention time and MS/MS fragmentation patterns as the metabolite 422c. M422c was shown to be much less potent (800 nM) in our ALK2 LANCE assay compared to LDN-193189 (13 nM).

From this study, two metabolic "hot spots" were identified: 1) formation of an iminium ion that was subsequently tapped by cyanide, and 2) oxidation of the 2-position of the quinoline moeity to give metabolite 422c.

Figure 13:
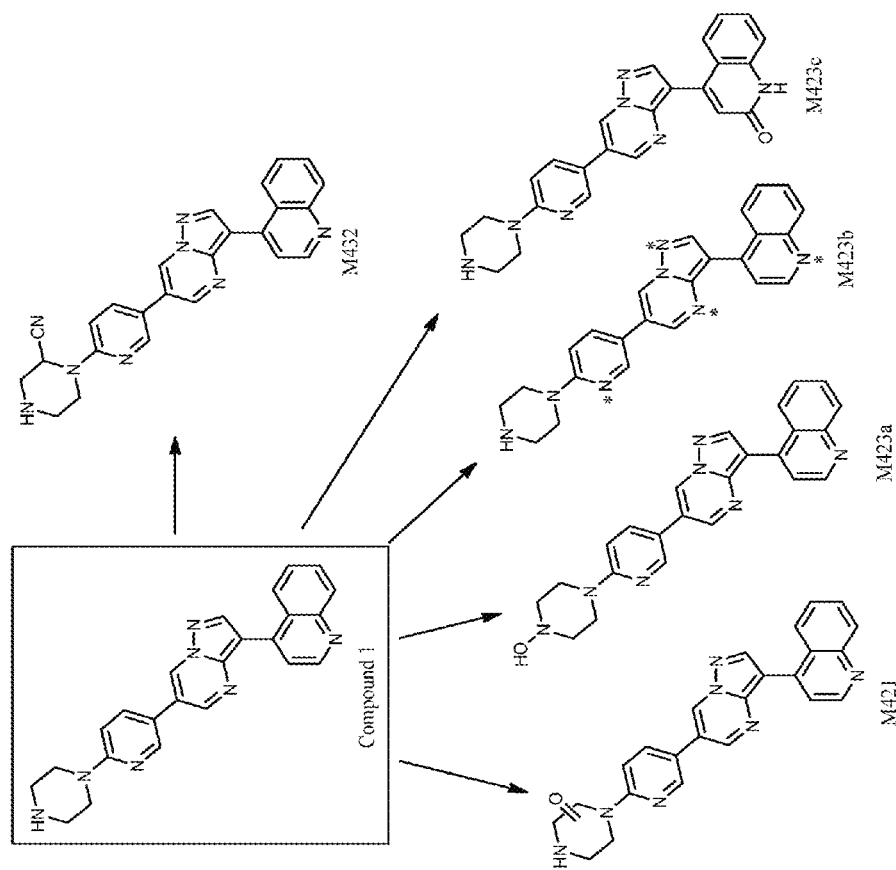
FIG. 13 shows the proposed metabolic pathways of compound 1 in liver microsomes and cytosols from mice and humans.

In a second study, described in Example 5 below, three different chemotypes were studied. These chemotypes can be represented by compound 1, compound 2 and compound 48:

The first chemotype, represented by compound 1, has a pyridine ring instead of a phenyl ring of LDN-193189. The iminium intermediate was evidenced by the trapping with cyanide to yield M432 (FIG. 13). However, 2-aminopyridines do not have the same toxic properties of anilines. The major metabolite in the presence of mouse or human cytosol was M423c (FIG. 13), presumably the oxidation of the 2-position of the quinoline ring as seen in the metabolism of LDN-193189 in the presence of cytosol.

Figure 16:
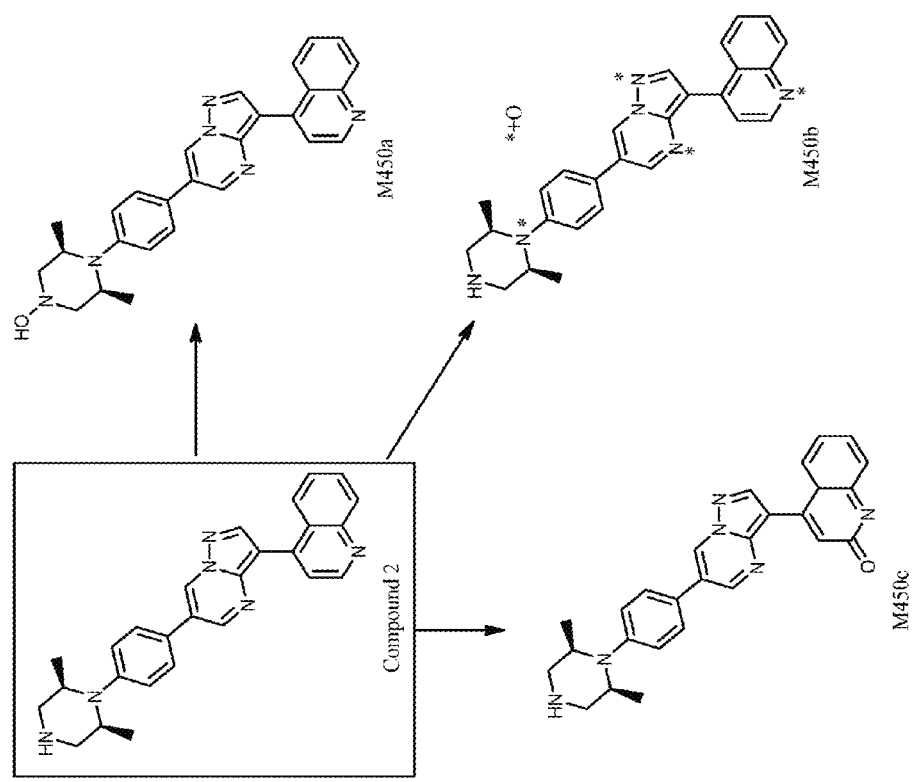
FIG. 16 shows the proposed metabolic pathways of compound 2 in liver microsomes and cytosols from mice and humans.

The second chemotype, represented by compound 2, contains two methyl groups next to the nitrogen of aniline nitrogen. The methyl groups were intended to sterically block and prevent CYP450 enzyme from forming the reactive iminium species, the first step toward dealkylation to form a toxic aniline metabolite. When incubated with either MLM or HLM, there was no trapping of iminium ion by cyanide as seen in previous examples, indicating that the steric effects of the methyl groups successfully block the oxidative pathway that forms the imminium ion. Again, in the presence of cytosol, the major metabolite was presumably oxidation at the 2-position of the quinoline, M450c (FIG. 16).

Figure 19:
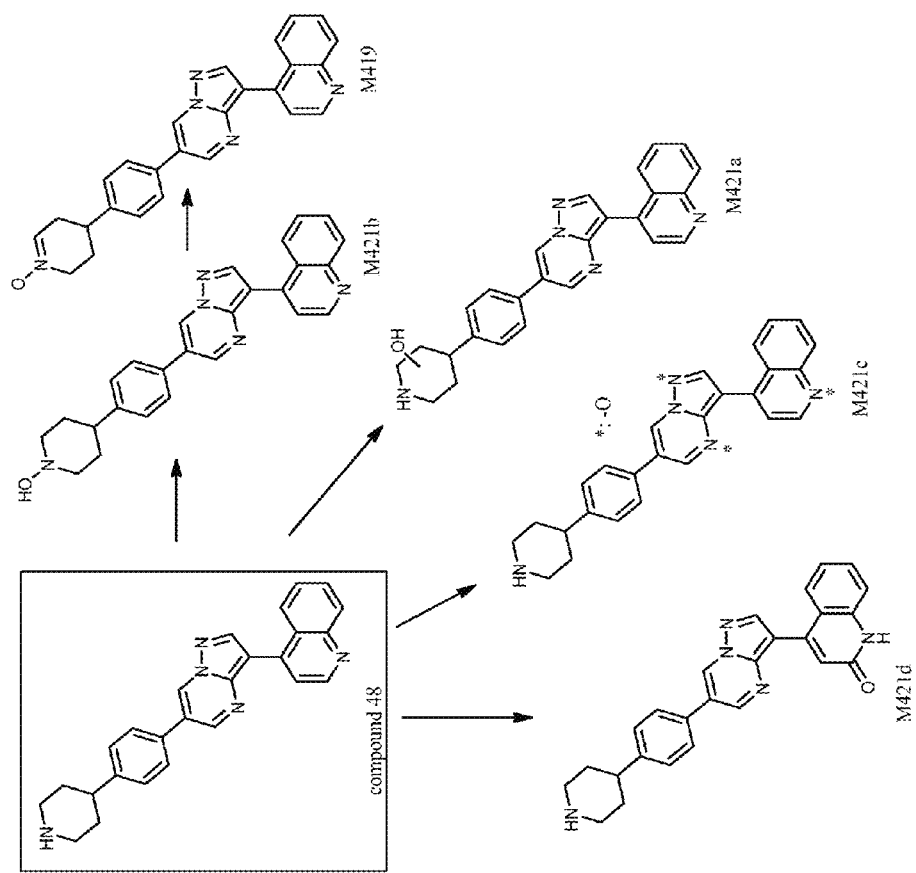
FIG. 19 shows the proposed metabolic pathways of compound 48 in liver microsomes and cytosols from mice and humans.

The last chemotype, represented by compound 48, lacks the aniline nitrogen altogether. Incubation with MLM and HLM again did not produce a cyanide adduct. The major metabolite in the presence of mouse or human cytosol was the oxidation of the 2-position of the quinoline yielding M421d (FIG. 19).

In conclusion, this study showed that one can eliminate oxidative formation of a reactive iminium species, the first step toward piperazine dealkylation by either incorporation steric hindrance at the adjacent positions to the aniline (as in compound 2) or removing the aniline nitrogen (as in compound 48). In the case of compound 1, dealkylation of the piperazine ring would yield a 2-aminopyridine which does not have the toxic properties of aniline.

The final study, described in Example 6 below, was designed to determine whether blocking the 2-position of the quinoline by either a deuterium (D) or a methyl group would eliminate oxidation of the 2-position of the quinoline. Incubation of compound 17,

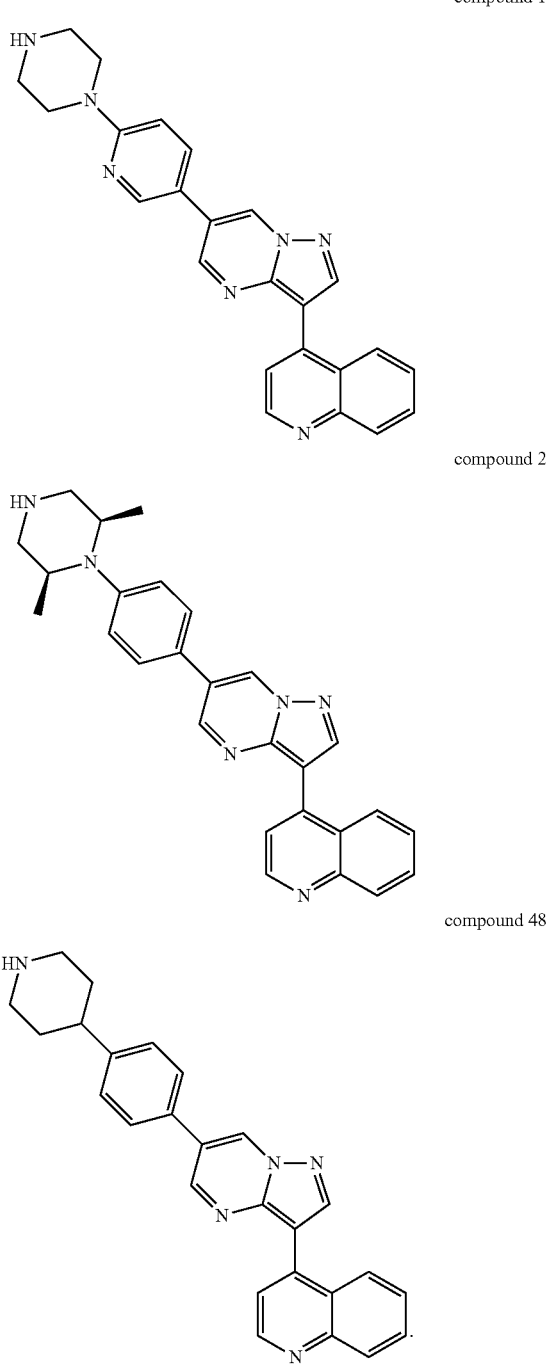

compound 1 compound 2 compound 48

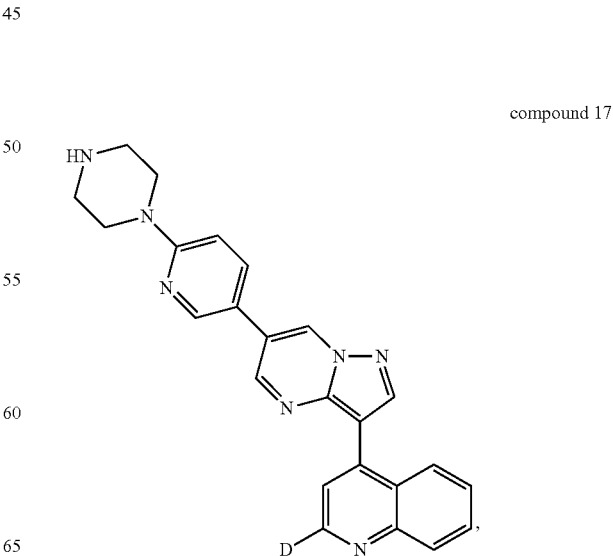

compound 17 and compound 12, compound 12

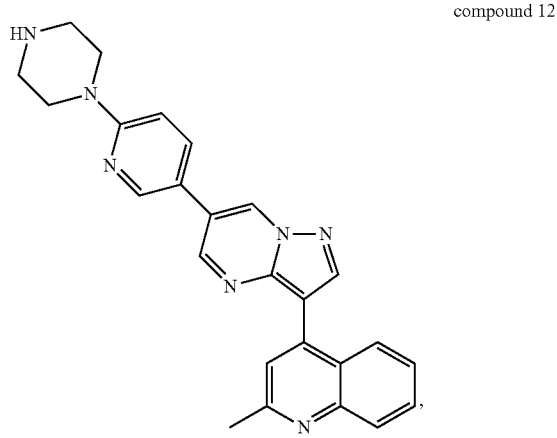 [SMILES: Cc1cc(-c2cnn3cc(-c4ccc(N5CCNCC5)nc4)cnc23)c2ccccc2n1]

with HLM and human cytosol showed no oxidation products without NADPH, a cofactor for CYPP450. Accordingly, the ability of AO to oxidize the 2-position of the quinoline had been successfully thwarted. In both cases, oxidation of the piperazine ring to form the iminium ion was seen by evidence of the cyanide adduct, which can be blocked by other modifications as demonstrated above.

The results of these studies have shown that we have viable strategies to address 1) CYP450 metabolism leading to toxic metabolites, and 2) AO oxidation to form inactive metabolites. Accordingly, the compounds of the invention (e.g., compounds of formula I, II or III) overcome the difficulties associated with the identified metabolism, thereby providing improved in vivo efficacy.

II. Definitions

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—, preferably alkylC(O)NH—.

The term "acyloxy" is art-recognized and refers to a group represented by the general formula hydrocarbylC(O)O—, preferably alkylC(O)O—.

The term "aliphatic", as used herein, includes straight, chained, branched or cyclic hydrocarbons which are completely saturated or contain one or more units of unsaturation. Aliphatic groups may be substituted or unsubstituted.

The term "alkoxy" refers to an oxygen having an alkyl group attached thereto. Representative alkoxy groups include methoxy, ethoxy, propoxy, tert-butoxy and the like.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

Such substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aryl or heteroaryl moiety.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2, 2-trifluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkylS—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "amide", as used herein, refers to a group

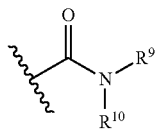

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

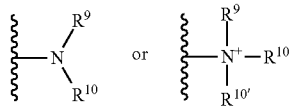

wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, and the like.

The term "carbamate" is art-recognized and refers to a group

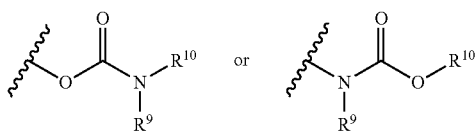

wherein $R^9$ and $R^{10}$ independently represent hydrogen or a hydrocarbyl group, such as an alkyl group.

The terms "carbocycle", "carbocyclyl", and "carbocyclic", as used herein, refers to a non-aromatic saturated or unsaturated ring in which each atom of the ring is carbon. Preferably a carbocycle ring contains from 3 to 10 atoms, more preferably from 5 to 7 atoms.

The term "carbocyclylalkyl", as used herein, refers to an alkyl group substituted with a carbocycle group.

The term "carbonate" is art-recognized and refers to a group —OCO$_2$—R$^9$, wherein R$^9$ represents a hydrocarbyl group, such as an alkyl group.

The term "carboxy", as used herein, refers to a group represented by the formula —CO$_2$H.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The term "ester", as used herein, refers to a group —C(O)OR$^9$ wherein R$^9$ represents a hydrocarbyl group, such as an alkyl group or an aralkyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen", as used herein, means halogen and includes chloro, fluoro, bromo, and iodo.

The term "heteroalkyl", as used herein, refers to a saturated or unsaturated chain of carbon atoms including at least one heteroatom (e.g., O, S, or NR$^{50}$, such as where R$^{50}$ is H or lower alkyl), wherein no two heteroatoms are adjacent.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Heteroaryl groups include, for example, pyrrole, furan, thiophene, imidazole, oxazole, thiazole, pyrazole, pyridine, pyrazine, pyridazine, quinoline, and pyrimidine, and the like.

The term "heteroatom", as used herein, means an atom of any element other than carbon or hydrogen. Preferred heteroatoms are nitrogen, oxygen, and sulfur.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. Heterocyclyl groups include, for example, piperidine, piperazine, pyrrolidine, morpholine, lactones, lactams, and the like.

The term "heterocyclylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. Examples of straight chain or branched chain lower alkyl include methyl, ethyl, isopropyl, propyl, butyl, tertiary-butyl, and the like. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitation aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Preferred polycycles have 2-3 rings. Each of the rings of the polycycle can be substituted or unsubstituted. In certain embodiments, each ring of the polycycle contains from 3 to 10 atoms in the ring, preferably from 5 to 7.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt or ester thereof.

The term "sulfonamide" is art-recognized and refers to the group represented by the general formulae

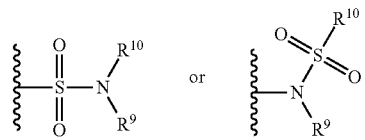

wherein $R^9$ and $R^{10}$ independently represents hydrogen or hydrocarbyl, such as alkyl.

The term "sulfoxide" is art-recognized and refers to the group —S(O)—$R^9$, wherein $R^9$ represents a hydrocarbyl, such as alkyl, aryl, or heteroaryl.

The term "sulfonate" is art-recognized and refers to the group —SO$_3$H, or a pharmaceutically acceptable salt or ester thereof.

The term "sulfone" is art-recognized and refers to the group —S(O)$_2$—$R^9$, wherein $R^9$ represents a hydrocarbyl, such as alkyl, aryl, or heteroaryl.

The term "thioester", as used herein, refers to a group —C(O)S$R^9$ or —SC(O)$R^9$ wherein $R^9$ represents a hydrocarbyl, such as alkyl.

The term "thioether", as used herein, is equivalent to an ether, wherein the oxygen is replaced with a sulfur.

The term "urea" is art-recognized and may be represented by the general formula

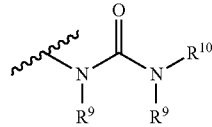

wherein $R^9$ and $R^{10}$ independently represent hydrogen or a hydrocarbyl, such as alkyl.

At various places in the present specification substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, propyl, isopropyl, n-butyl, sec-butyl, isobutyl, etc.

For a number qualified by the term "about", a variance of 2%, 5%, 10% or even 20% is within the ambit of the qualified number As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The term "prodrug" is intended to encompass compounds which, under physiologic conditions, are converted into the therapeutically active agents of the present invention (e.g., a compound of Formula I, II or III). A common method for making a prodrug is to include one or more selected moieties which are hydrolyzed under physiologic conditions to reveal the desired molecule. In other embodiments, the prodrug is converted by an enzymatic activity of the host animal. For example, esters (e.g., esters of alcohols or carboxylic acids) are preferred prodrugs of the present invention. In various embodiments disclosed herein (e.g., the various compounds, compositions, and methods), some or all of the compounds of formula A, compounds of any one of Formula I, II or III, all or a portion of a compound of Formula I, II or III in a formulation represented above can be replaced with a suitable prodrug, e.g., wherein a hydroxyl or carboxylic acid present in the parent compound is presented as an ester.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

The term "small molecule" refers to an organic molecule having a molecular weight less than about 2500 amu, preferably less than about 2000 amu, even more preferably less than about 1500 amu, still more preferably less than about 1000 amu, or most preferably less than about 750 amu. Preferably a small molecule contains one or more heteroatoms.

The phrase "activity of ALK2" means ALK-2 enzymatic activity (e.g., such as kinase activity; the ability of ALK-2 to phosphorylate BMP-responsive SMAD proteins) and/or ALK-2-mediated signaling (e.g., such as the ability of ALK-2 to mediate downstream signal transduction and transcriptional activity following activation of ALK-2 by binding of BMP ligands). In some embodiments, "activity of ALK2" means ALK2-mediated BMP signaling. In some embodiments, "activity of ALK2" means ALK2-mediated BMP-responsive gene transcription (e.g., transcriptional activity mediated by BMP/ALK2 signal transduction). The assays described in Examples 1-3 permit the measurement of ALK2 activity.

The phrase "activity of ALK5" means ALK-5 enzymatic activity (e.g., such as kinase activity; the ability of ALK-5 to phosphorylate TGF-β responsive SMAD proteins; the ability of ALK-5 to phosphorylate SMAD2 or SMAD3) and/or ALK-5-mediated signaling (e.g., such as the ability of ALK-5 to mediate downstream signal transduction and transcriptional activity following activation of ALK-5 by binding of TGF-β ligands). In some embodiments, "activity of ALK5" means ALK5-mediated TGF-β signaling. In some embodiments, "activity of ALK5" means ALK5-mediated TGF-β-responsive gene transcription (e.g, transcriptional activity mediated by TGFβ/ALK5 signal transduction). The assays described in Examples 1-3 permit the measurement of ALK5 activity.

The phrase "activity of ALK1" means ALK-1 enzymatic activity (e.g., such as kinase activity; the ability of ALK-1 to phosphorylate BMP-responsive SMAD proteins) and/or ALK-1-mediated signaling (e.g., such as the ability of ALK-1 to mediate downstream signal transduction and transcriptional activity following activation of ALK-1 by binding of BMP ligands). In some embodiments, "activity of ALK1" means ALK1-mediated BMP signaling. In some embodiments, "activity of ALK1" means ALK1-mediated BMP-responsive gene transcription (e.g., transcriptional activity mediated by BMP/ALK1 signal transduction). The assays described in Examples 1-3 permit the measurement of ALK1 activity.

The phrase "activity of ALK3" means ALK-3 enzymatic activity (e.g., such as kinase activity; the ability of ALK-3 to phosphorylate BMP-responsive SMAD proteins) and/or ALK-3-mediated signaling (e.g., such as the ability of ALK-3 to mediate downstream signal transduction and transcriptional activity following activation of ALK-3 by binding of BMP ligands). In some embodiments, "activity of ALK3" means ALK3-mediated BMP signaling. In some embodiments, "activity of ALK3" means ALK3-mediated BMP-responsive gene transcription (e.g., transcriptional activity mediated by BMP/ALK3 signal transduction). The assays described in Examples 1-3 permit the measurement of ALK3 activity.

The phrase "activity of ALK4" means ALK-4 enzymatic activity (e.g., such as kinase activity; the ability of ALK-4 to phosphorylate activin-responsive SMAD proteins; the ability of ALK-4 to phosphorylate SMAD 2 or SMAD 3) and/or ALK-4-mediated signaling (e.g., such as the ability of ALK-4 to mediate downstream signal transduction and transcriptional activity following activation of ALK-4 by binding of activin ligands). In some embodiments, "activity of ALK4" means ALK4-mediated activin signaling. In some embodiments, "activity of ALK4" means ALK4-mediated activin-responsive gene transcription (e.g., transcriptional activity mediated by activin/ALK4 signal transduction). The assays described in Examples 1-3 permit the measurement of ALK4 activity.

The phrase "activity of ALK6" means ALK-6 enzymatic activity (e.g., such as kinase activity; the ability of ALK-6 to phosphorylate BMP-responsive SMAD proteins) and/or ALK-6-mediated signaling (e.g., such as the ability of ALK-6 to mediate downstream signal transduction and transcriptional activity following activation of ALK-6 by binding of BMP ligands). In some embodiments, "activity of ALK6" means ALK6-mediated BMP signaling. In some embodiments, "activity of ALK6" means ALK6-mediated GDF5 signaling. In some embodiments, "activity of ALK6" means ALK6-mediated BMP-responsive gene transcription (e.g., transcriptional activity mediated by BMP/ALK6 signal transduction). The assays described in Examples 1-3 permit the measurement of ALK6 activity.

Human ALK2 is a 509 amino acid protein. The protein sequence is published, for example, as GenBank accession number NP_001104537.1, (with corresponding nucleotide sequence at NM_001111067.2) UniProt entry Q04771.

Human ALK5 has, at least, two isoforms: a 503 amino acid protein (isoform 1) and a 426 amino acid protein. The protein sequence for human ALK5 isoform 1 is published, for example, as GenBank accession number NP_004603.1 (with corresponding nucleotide sequence at NM_004612.2) The protein sequence for the 426 amino acid isoform is published, for example, as GenBank accession number NP_001124388.1 (with corresponding nucleotide sequence at NM_001130916.1). Information regarding both isoforms is also published as UniProt entry P36897.

Human ALK1 is a 503 amino acid protein. The protein sequence is published, for example, as GenBank accession number NP_001070869.1 (with corresponding nucleotide sequence at NM_001077401.1; transcript variant 2) and NP_000011.2 (with corresponding nucleotide sequence at NM_000020.2; transcript variant 1), UniProt entry P37023.

Human ALK3 is a 532 amino acid protein. The protein sequence is published, for example, as GenBank accession number NP_004320 (with corresponding nucleotide sequence at NM_004329.2), UniProt entry P36894.

Human ALK4 has at least three isoforms. Isoform a is a 505 amino acid protein. The protein sequence is published, for example, as GenBank accession number NP_004293 (with corresponding nucleotide sequence at NM_004302), UniProt entry P36896.

Isoform a of human ALK6 is a 532 amino acid protein and isoform b is a 502 amino acid protein. The protein sequence for human ALK6 isoform a is published, for example, as GenBank accession number NP_001243722 (with corresponding nucleotide sequence at NM_001256793.1). The protein sequence for human ALK6 isoform b is published, for example, as GenBank accession number NP_001194 (with corresponding nucleotide sequence at NM_001203.2).

Note that each of the foregoing proteins is further processed in vivo, such as by the cleaving of a signal sequence, to yield a mature form.

III. Pharmaceutical Compositions

Compounds of the present invention may be used in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with compounds of the invention, or to minimize side effects caused by the compound of the invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The terms "pharmaceutically effective amount" or "therapeutically effective amount", as used herein, means the total amount of each active component of the pharmaceutical composition or method that is sufficient to show a meaningful patient benefit, e.g., treatment, healing, prevention, inhibition or amelioration of a physiological response or condition, such as an inflammatory condition or pain, or an increase in rate of treatment, healing, prevention, inhibition or amelioration of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

Each of the methods of treatment or use of the present invention, as described herein, comprises administering to a mammal in need of such treatment or use a pharmaceutically or therapeutically effective amount of a compound of the present invention, or a pharmaceutically acceptable salt or ester form thereof. Compounds of the present invention may be administered in accordance with the method of the invention either alone or in combination with other therapies.

Administration of compounds of the present invention used in the pharmaceutical composition or to practice the method of the present invention can be carried out in a variety of conventional ways. Exemplary routes of administration that can be used include oral, parenteral, intravenous, intra-arterial, cutaneous, subcutaneous, intramuscular, topical, intracranial, intraorbital, ophthalmic, intravitreal, intraventricular, intracapsular, intraspinal, intracisternal, intraperitoneal, intranasal, aerosol, central nervous system (CNS) administration, or administration by suppository.

When a therapeutically effective amount of a compound(s) of the present invention is administered orally, compounds of the present invention may be in the form of a tablet, capsule, powder, solution or elixir. When administered in tablet form, the pharmaceutical composition of the invention may additionally contain a solid carrier such as a gelatin or an adjuvant. The tablet, capsule, and powder may contain from about 5 to 95% compound of the present invention, and preferably from about 10% to 90% compound of the present invention. When administered in liquid form, a liquid carrier such as water, petroleum, oils of animal or plant origin such as peanut oil, mineral oils, phospholipids, tweens, triglycerides, including medium chain triglycerides, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition typically contains from about 0.5 to 90% by weight of compound of the present invention, and preferably from about 1 to 50% compound of the present invention.

When a therapeutically effective amount of a compound(s) of the present invention is administered by intravenous, cutaneous or subcutaneous injection, compounds of the present invention may be in the form of a pyrogen-free, parenterally acceptable aqueous solution. The preparation of such parenterally acceptable solutions, having due regard to pH, isotonicity, stability, and the like, is within the skill in the art. A preferred pharmaceutical composition for intravenous, cutaneous, or subcutaneous injection should contain, in addition to compounds of the present invention, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additives known to those of skill in the art.

The amount of compound(s) of the present invention in the pharmaceutical composition of the present invention will depend upon the nature and severity of the condition being treated, and on the nature of prior treatments the patient has undergone. Ultimately, the practitioner will decide the amount of compound of the present invention with which to treat each individual patient. Initially, the practitioner may administer low doses of compound of the present invention and observe the patient's response. Larger doses of compounds of the present invention may be administered until the optimal therapeutic effect is obtained for the patient, and at that point the dosage is not increased further. It is contemplated that the various pharmaceutical compositions used to practice the method of the present invention should contain about 0.1 µg to about 100 mg (preferably about 0.1 mg to about 50 mg, more preferably about 1 mg to about 2 mg) of compound of the present invention per kg body weight.

The duration of intravenous therapy using the pharmaceutical composition of the present invention will vary, depending on the severity of the disease being treated and the condition and potential idiosyncratic response of each individual patient. It is contemplated that the duration of each application of the compounds of the present invention will be in the range of 12 to 24 hours of continuous intravenous administration. Ultimately the practitioner will decide on the appropriate duration of intravenous therapy using the pharmaceutical composition of the present invention.

IV. Use with Polymers

The compounds as disclosed herein may be conjugated to a polymer matrix, e.g., for controlled delivery of the compound. The compound may be conjugated via a covalent bond or non-covalent association. In certain embodiments wherein the compound is covalently linked to the polymer matrix, the linkage may comprise a moiety that is cleavable under biological conditions (e.g., ester, amide, carbonate, carbamate, imide, etc.). In certain embodiments, the conjugated compound may be a pharmaceutically acceptable salt, ester, or prodrug of a compound disclosed herein. A compound as disclosed herein may be associated with any type of polymer matrix known in the art for the delivery of therapeutic agents.

V. Synthetic Preparation

The compounds disclosed herein can be prepared in a variety of ways known to one skilled in the art of organic synthesis, and in analogy with the exemplary compounds whose synthesis is described herein. The starting materials used in preparing these compounds may be commercially available or prepared by known methods. Preparation of compounds can involve the protection and deprotection of various chemical groups. The need for protection and deprotection, and the selection of appropriate protecting groups can be readily determined by one skilled in the art. The chemistry of protecting groups can be found, for example, in Greene and Wuts, *Protective Groups in Organic Synthesis*, 44th. Ed., Wiley & Sons, 2006, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected.

VI. Uses

BMPs and TGF-beta signaling pathways are essential to normal organogenesis and pattern formation, as well as the normal and pathological remodeling of mature tissues. Defects in the BMP signaling pathway are implicated in a number of congenital and acquired disease processes, including Hereditary Hemorrhagic Telangectasia syndrome, Primary Pulmonary Hypertension or Pulmonary Arterial Hypertension, Juvenile Familial Polyposis, as well as sporadic renal cell and prostate carcinomas. It has been suggested that in certain disease states associated with defective signaling components, attenuated BMP signaling might be a cause, while our findings have suggested that in some contexts excess BMP signaling might be pathogenic (Waite et al. *Nat. Rev. Genet.* 4:763-773, 2005; Yu et. *J. Biol. Chem.* 280:24443-24450, 2003). The ability to modulate BMP signaling experimentally would provide a means for investigating therapy, and for determining the root causes of these conditions.

A. Treatment of Anemia, Including Iron Deficiency and Anemia of Chronic Disease

For a review, see Weiss et al. *N Engl. J. Med.* 352:1011-1023, 2005. Anemia of inflammation (also called anemia of chronic disease) can be seen in patients with chronic infections, autoimmune diseases (such as systemic lupus erythematosis and rheumatoid arthritis, and Castleman's disease), inflammatory bowel disease, cancers (including multiple myeloma), and renal failure. Anemia of inflammation is often caused by maladaptive expression of the peptide hormone hepcidin. Hepcidin causes degradation of ferroportin, a critical protein that enables transport of iron from intracellular stores in macrophages and from intestinal epithelial cells. Many patients with renal failure have a combination of erythropoietin deficiency and excess hepcidin expression. BMP signaling induces expression of hepcidin and inhibiting hepcidin expression with BMP inhibitors increases iron levels. Compounds as described herein can be used to treat anemia due to chronic disease or inflammation and associated hyperhepcidinemic states.

The inflammatory cytokine IL-6 is thought to be the principal cause of elevated hepcidin expression in inflammatory states, based upon the elevation of IL-6 in anemia of inflammation of diverse etiologies, the effects of chronic IL-6 administration in vivo, and the protection against anemia in rodents deficient in IL-6 (Weiss et al. *N Engl. J. Med.* 352:1011-1023, 2005). It has been shown that stimulating hepatoma cell lines with IL-6 induces hepcidin expression, while treatment with a BMP inhibitor abrogates IL-6-induced hepcidin expression (Yu et al. *Nat. Chem. Biol.* 4:33-41, 2008). Moreover, we have found that BMP inhibitors can inhibit hepcidin expression induced by injection of pathogenic bacteria in vivo. It has also been shown that systemic iron administration in mice and zebrafish rapidly activates BMP-responsive-SMADs and hepcidin expression in the liver, and that BMP antagonism effectively blocks these responses (Yu et al. *Nat. Chem. Biol.* 4:33-41, 2008). The functional importance of BMP signaling in iron regulation is supported by our finding that BMP inhibitors can inhibit hepcidin expression and raise serum iron levels in vivo. Taken together these data suggest that iron- and inflammation-mediated regulation of hepcidin and circulating iron levels require BMP signaling. Compounds as described herein may be used to alter iron availability in diverse circumstances for therapeutic benefit.

Compounds as described herein may be used in anemic states to (i) augment the efficacy of dietary iron or oral iron supplementation (which is safer than intravenous administration of iron) to increase serum iron concentrations; (ii) augment build up of hemoglobin in the blood in anticipation of surgery or to enable blood donation for self in anticipation of surgery; (iii) enhance the efficacy of erythropoietin and its relatives, thereby enabling lower doses of erythropoietin to be administered for anemia while minimizing known toxicities and side effects of erythropoietin (i.e., hypertension, cardiovascular events, and tumor growth), and (iv) inhibit the hepcidin expression to help correct the anemia associated with inflammatory bowel disease (Wang et al., Inflamm. Bowel Dis. 2012 January; 18(1):112-9. Epub 2011 Feb. 23).

B. Treatment of Fibrodysplasia Ossificans Progressiva (FOP)

FOP is caused by the presence of a constitutively-active mutant form of ALK2 in affected individuals (Shore et al. Nat. Genet. 38:525-527, 2006). A specific inhibitor of BMP signaling such as a compound as described herein can be used to prevent excessive bone formation in response to trauma, musculoskeletal stress or inflammation. Such a compound could also be used to aid in regression of pathologic bone. The BMP inhibitor could be administered systemically or locally to concentrate or limit effects to areas of trauma or inflammation.

A BMP inhibitor as described herein may be used as chronic therapy to suppress spontaneous bone formation in individuals who are highly susceptible. Transient therapy may be used to prevent abnormal bone formation in FOP individuals who develop osteomas or pathologic bone most frequently in association with trauma by administration before, during, or even after the traumatic incident. Transient therapy with BMP inhibitors as described herein could be used before, during or immediately after necessary or emergent medical or surgical procedures (and even important immunizations and tooth extractions) in individuals with FOP, to prevent pathologic calcification. Combination therapy with other bone inhibiting agents, immune modulatory or anti-inflammatory drugs (such as NSAIDs, steroids, cyclosporine, cyclophosphamide, azathioprine, methotrexate, rituxumab, etanercept, or similar drugs) may increase the effectiveness of BMP inhibitors in inhibiting heterotopic bone formation in this disorder.

A mouse model of FOP has been developed in which expression of a constitutively-active mutant form of ALK2 is induced by injecting the popliteal fossa of a genetically-modified mouse with an adenovirus directing expression of Crerecombinase. This model reproduces the ectopic calcification and disability seen in FOP patients.

C. Treatment of Cancers

Excessive BMP signaling, which could arise due to overexpression of BMPs, or, paradoxically, as a result of loss of BMP type II receptor expression, may contribute to the oncogenesis, growth or metastasis of certain solid tumors, including breast, prostate carcinomas, bone, lung, and renal cell carcinomas (Yu et al. *J. Biol. Chem.* 280:24443-24450, 2008; Waite et al. *Nat. Rev. Genet.* 4:763-773, 2003; Alarmo et al. *Genes, Chromosomes Cancer* 45:411-419, 2006; Kim et al. *Cancer Res.* 60:2840-2844, 2000; Kim et al. *Clin. Cancer Res.* 9:6046-6051, 2003; Kim et al. *Oncogene* 23:7651-7659, 2004). Inhibition of BMP9 signaling can prevent ovarian cancer cell growth (Herrera et al. Cancer Res. 2009 Dec. 15; 69(24):9254-62). Ovarian cancer growth is promoted by ALK2-SMAD signaling and could be inhibited by selective ALK2 inhibitors (Tsai et al. Cell Rep. 2012 Aug. 30; 2(2):283-93. Epub 2012 Aug. 9), such as with the compounds described herein.

If increased BMP activity associated with BMP overexpression or BMP type II receptor deficiency contributes to the pathogenesis of disease, then inhibiting BMP signaling activity using compounds as described herein at the level of BMP type I receptors (downstream of both ligands and type II receptor) could be an effective means of normalizing BMP signaling activity and potentially inhibiting tumor growth or metastasis.

Compounds as described herein can be used to slow or arrest the growth or metastasis of such tumor cells (as well as other tumor constituent cell types) for clinical benefit, either as adjunctive or primary chemotherapy. Also, BMP inhibitors as described herein may be used to interfere with the bone metastatic properties of certain types of cancers (e.g., adenocarcinoma, such as prostate and breast carcinomas). In addition, compounds as described herein can be used to inhibit osteoblastic activity in tumors that either form bone or are bone-derived, such as osteosarcomas (as adjunctive or primary chemotherapy). Further, compounds as described herein can be used to inhibit osteoclastic activity (also regulated by BMPs through the action of its target gene RANKL), which is pathologically increased in conditions such as multiple myeloma and other bone-targeted tumors. Application of BMP inhibitors in these conditions may reduce the presence of osteolytic lesions and bone fractures due to tumor involvement.

D. Immune Modulation via BMP Inhibitors

BMPs have been reported to attenuate the inflammatory or immune response (Choi et al. *Nat. Immunol.* 7:1057-1065, 2006; Kersten et al. *BMC Immunol.* 6:9, 2005), which can impair an individual's ability to fight infections (i.e., viral, bacterial, fungal, parasitic, or tuberculosis). Inhibitors of BMP signaling as described herein may thus augment the inflammatory or immune response enabling individuals to clear infections more rapidly.

Lymphocytes and other immune cells express BMP receptors on their cell surfaces, and there is growing evidence that BMPs regulate the development and maturation of various humoral and cellular immunologic compartments, and regulate humoral and cellular immune responses in mature organisms. The effects of BMP signals on immune cells are likely to be context-specific, as is commonly known for the effects of numerous cytokines of immunologic importance, and thus whether they augment or diminish the development or function of particular lymphocyte populations must be empirically determined. BMP antagonism using compounds as described herein may be an effective strategy for intentionally biasing the development of cellular, innate, or humoral immune compartments for therapy, or a strategy for the therapeutic deviation of immune responses in mature immune systems. These strategies may target inborn disorders of cellular, innate, or humoral immunity, or target disorders in which immune responses are inappropriately weak (e.g., as an adjuvant to promote successful antigen sensitization when immunization is difficult or ineffective by other means), or target disorders in which immune responses are excessive or inappropriate (e.g., autoimmunity and autosensitization). BMP inhibitors as described herein may also be effective in some contexts for the intentional induction of immune tolerance (i.e., in allotransplantation or autoimmunity) and for indications such as autoimmune diseases and inflammatory bowel disease (IBD) (Wang et al., Inflamm. Bowel Dis. 2012 January; 18(1):112-9. Epub 2011 Feb. 23). BMP inhibitors as described herein may also attenuate macrophage-mediated inflammation in response to *Salmonella typhimurium* in a model of inflammatory colitis (Wang L et al, J Clin Invest. 2009; 119(11):3322).

E. Treatment of Pathologic Bone Formation

Compounds as described herein can be used to ameliorate pathologic bone formation/bone fusion in inflammatory disorders, such as ankylosing spondylitis or other "seronegative" spondyloarthropathies, in which autoimmunity and inflammation in such disorders appear to stimulate bone formation. One application of the compounds would be to prevent excess bone formation after joint surgery, particularly in patients with ankylosing spondylitis or rheumatoid arthritis. Compounds as described herein can also be used to prevent calcinosis (dystrophic soft-tissue calcification) in diseases such as systemic lupus erythematosus, scleroderma, or dermatomyositis.

Blunt traumatic injury to muscles can cause abnormal bone formation within muscle in certain individuals, resulting in a disorder called myositis ossificans traumatica (Cushner et al. *Orthop. Rev.* 21:1319-1326, 1992.). Head trauma and burn injury can also induce heterotopic bone formation markedly impairing patient rehabilitation and recovery. Treatment with a BMP inhibitor as described herein, optionally in addition to anti-inflammatory medications usually prescribed for such a condition (eg. non-steroidal anti-inflammatory drugs such as indomethacin or ibuprofen) may help to prevent the formation of pathologic bone in predisposed individuals, or to help lessen or regress lesions in individuals recently or remotely affected. Very rarely other muscles have been described to develop ossification in the presence of injury or trauma, including heart muscle, and similar treatment with a BMP inhibitor as described herein could be helpful in those circumstances.

F. Treatment of Ectopic or Maladaptive Bone Formation

BMP signals and their transcriptional targets are implicated in intimal and medial vascular remodeling and calcification in Monckeberg's vascular calcification disease and in atheromatous vascular disease (Bostrom et al. *J. Clin. Invest.* 91:1800-1809, 1993; Tyson et al. *Arterioscler. Thromb. Vasc. Biol.* 23:489-494, 2003). BMPs and BMP-induced osteodifferentation are also implicated in cardiac valvular calcification. Native cardiac valves can calcify particularly when they are already abnormal. A classic example is bicuspid aortic valve—these valves typically become calcified leading to stenosis. Patients with calcific aortic valve stenosis often require cardiac surgery for valve replacement. Abnormal calcification can adversely affect the function of prosthetic vascular grafts or cardiac valves. For example, prosthetic heart valves become calcified leading to narrowing and often leakage.

Compounds as described herein can be used to inhibit vascular or valvular calcific disease alone or in combination with atheromatous disease, renal disease, renal osteodystrophy or parathyroid disease.

Compounds as described herein can be used to inhibit calcification of prosthetic vascular or valvular materials by systemic or local administration or direct incorporation into prosthesis materials or other implants (e.g., in admixture with a polymer that coats or constitutes all or part of the implant or prosthesis).

In some instances, it is desired to delay fracture healing following a bone fracture, or to purposely inhibit fracture healing in certain locations to prevent impairment of function by maladaptive bone formation. For example, if a fracture occurs and for medical or practical reasons surgery cannot be performed immediately, fracture healing may be temporarily "suspended" by use of a BMP inhibitor as described herein, until definitive surgery or manipulation can be performed. This could prevent the need for subsequent intentional re-fracture in order to ensure correct apposition of bone fragments, for example. It is expected that upon stopping a BMP inhibitor normal fracture healing processes would ensue if the period of treatment is relatively short. In other cases, any amount of novel bone growth might impair function, such as when fracture affects a joint directly. In these cases, global or local inhibition of BMP activity (by systemic or local delivery of a BMP inhibitor as described herein via diffusion from a local implant or matrix) may be used to inhibit fracture healing or prevent fracture calluses at the critical areas.

G. Treatment of Skin Diseases

Expansion of cultured keratinocytes—In vitro, BMPs inhibit keratinocyte proliferation and promote differentiation (reviewed in Botchkarev et al. *Differentiation* 72:512-526, 2004). In patients in need of skin grafting (eg. after burns), skin grafts are made from cultured keratinocytes. The keratinocytes may be derived from other animals (xenografts), but these are only temporary as they will be rejected by the immune system. Keratinocytes can be derived from the patient themselves and can be grown into sheets of cells in the laboratory (cultured epithelial autografts). The patient will not reject keratinocytes derived from his/her own body. Addition of BMP inhibitors as described herein to keratinocyte cultures can be used to facilitate keratinocyte proliferation enabling patients to receive grafts sooner.

Improved epithelialization—BMP6 is highly expressed in skin injury, and high levels of BMP6 are detected in chronic human wounds of different etiologies (Kaiser et al. *J. Invest. Dermatol.* 111:1145-1152, 1998). In mice overexpressing BMP6 in their skin, reepithelialization and healing skin wounds were significantly delayed (Kaiser et al. *J. Invest. Dermatol.* 111:1145-1152, 1998). Improved epithelialization can reduce scar formation. Topical or systemic administration of BMP inhibitors as described herein can be used to augment epithelialization of skin wounds, for example, in the treatment of pressure ulcers (bed sores) or non-healing or poorly-healing skin ulcers (e.g., in patients with peripheral vascular disease, diabetes mellitus, venous incompetence). Compounds would also be expected to decrease scar formation.

Promotion of hair growth—Growth of hair follicles on the scalp is cyclic with three phases: anagen (the growth phase), catagen (the involutional phase), and telogen (resting phase). Recent evidence suggests that BMP signals delay the transition from telogen to anagen (Plikus et al. *Nature* 451:340-344, 2008). Inhibition of BMP signaling using compounds as described herein can shorten the telogen phase and increase the number of follicles in the anagen phase. Compounds as described herein can be used to treat circumstances wherein hair follicles are insufficient or when hairs are being lost more frequently than they are grown. These circumstances include androgenetic alopecia (male pattern balding), alopecia areata, and telogen effluvium.

Treatment of psoriasis—Psoriasis is an inflammatory skin disorder which sometimes occurs following skin trauma and the ensuing repair and inflammation (Koebner phenomenon). BMPs may participate in repair and inflammatory mechanisms that cause psoriasis, since over-expression of BMP6 in the skin of mice leads to skin lesions similar to those seen in patients with psoriasis (Blessing et al. *J. Cell. Biol.* 135:227-239, 1996). Compounds as described herein may be administered topically or systemically to treat established psoriasis or prevent its development after skin injury.

Treatment of corneal scarring—BMP6 expression is associated with conjunctival scarring (Andreev et al. *Exp. Eye Res.* 83:1162-1170, 2006). Compounds as described herein can be used to prevent or treat corneal scarring and the resulting blindness.

H. Treatment of Systemic Hypertension

Infusion of BMP4 induces systemic hypertension in mice (Miriyala et al. *Circulation* 113:2818-2825, 2006). Vascular smooth muscle cells express a variety of BMP ligands.

BMPs increase the expression of voltage gated potassium channels and thereby increase constriction of vascular smooth muscle (Fantozzi et al. *Am. J. Physiol. Lung Cell. Mol. Physiol.* 291:L993-1004, 2006). Compounds as described herein that inhibit BMP signaling can be used to reduce blood pressure. Sustained reduction of blood pressure in patients with hypertension would be expected to prevent myocardial infarction, congestive heart failure, cerebrovascular accidents, and renal failure. BMP inhibitors as described herein can be used to target the hypertension in specific vascular beds, such as in pulmonary hypertension via local delivery (e.g., via aerosol).

I. Treatment of Pulmonary Hypertension

BMP signaling contributes to the pathogenesis of pulmonary hypertension. For example, mice with decreased BMP4 levels are protected from the pulmonary hypertension and pulmonary vascular remodeling induced by breathing low oxygen concentrations for prolonged periods (Frank et al. *Circ. Res.* 97:496-504, 2005). Moreover, mutations in the gene encoding the type II BMP receptor (BMPRII) are frequently found in patients with sporadic and familial pulmonary arterial hypertension. It might be anticipated that decreased BMP signaling might cause pulmonary hypertension. However, Yu and colleagues (Yu et al. *J. Biol. Chem.* 280:24443-24450, 2008) reported that BMPRII deficiency paradoxically increases BMP signaling by subsets of BMP ligands, and thus increased BMP signaling using compounds as described herein may actually contribute to the development of pulmonary hypertension.

Compounds as described herein can be used to prevent the development of pulmonary arterial hypertension in patients at risk for the disease (e.g., patients with BMPRII mutations) or to treat patients with idiopathic or acquired pulmonary arterial hypertension. Decreased pulmonary hypertension in individuals treated with the compounds described herein would be expected to decrease shortness of breath, right ventricular hypertrophy, and right ventricular failure.

J. Treatment of Ventricular Hypertrophy

BMP-10 levels are increased in the hypertrophied ventricles of rats with hypertension, and this BMP ligand induces hypertrophy in cultured neonatal rat ventricular myocytes (Nakano et al. *Am. J. Physiol. Heart. Circ. Physiol.* 293:H3396-3403, 2007). Sun et al. (Hypertension 2013 February; 61(2):352-60) suggest that small molecule BMP inhibitors can reduce adverse left ventricular remodeling (hypertrophy). Inhibition of BMP-10 signaling with compounds as described herein can to prevent/treat ventricular hypertrophy. Ventricular hypertrophy can lead to congestive heart failure due to diastolic dysfunction. Compounds described herein would be expected to prevent/treat congestive heart failure.

K. Treatment of Neurologic Disorders

Treatment of spinal cord injury and neuropathy—BMPs are potent inhibitors of axonal regeneration in the adult spinal cord after spinal cord injury (Matsuura et al. *J. Neurochem.* 2008). Expression of BMPs is reported to be elevated in oligodendrocytes and astrocytes around the injury site following spinal cord contusion. Intrathecal administration of noggin, a BMP inhibitor, led to enhanced locomotor activity and significant regrowth of the corticospinal tract after spinal cord contusion.

RGMa inhibits axonal growth and recovery after spinal cord injury, as well as synapse re-formation, effects which are blocked by an antibody directed against RGMa (Hata et al. *J. Cell. Biol.* 173:47-58, 2006; Kyoto et al. *Brain Res.* 1186:74-86, 2007). RGMa enhances BMP signaling (Babitt et al. *J. Biol. Chem.* 280:29820-29827, 2005) suggesting that BMP signaling may be responsible for preventing axonal growth and recovery.

Based on these considerations, compounds as described herein would be expected to increase axonal growth and recovery after spinal cord injury. Compounds as described herein would be expected to prevent/treat neuropathies associated with a wide spectrum of disorders including diabetes mellitus. Compounds as described herein would be expected to treat both the pain and motor dysfunction associated with neuropathies.

Treatment of neurologic disorders associated with central nervous system inflammation—BMP4 and 5 have been detected in multiple sclerosis and Creutzfeldt-Jakob disease lesions (Deininger et al. *Acta Neuropathol.* 90:76-79, 1995). BMPs have also been detected in mice with experimental autoimmune encephalomyelitis, an animal model of multiple sclerosis (Ara et al. *J. Neurosci. Res.* 86:125-135, 2008). Compounds as described herein may be used to prevent or treat multiple sclerosis as well as other neurologic disorders associated with central nervous system inflammation, or maladaptive injury repair processes mediated by BMP signals.

Treatment of dementias—Inhibitors of BMP signaling can promote neurogenesis in mouse neural precursor cells (Koike et al. *J. Biol. Chem.* 282:15843-15850, 2007). Compounds as described herein can be used to augment neurogenesis in a variety of neurologic disorders associated with accelerated loss of neurons including cerebrovascular accidents and Alzheimer's Disease, as well as other dementias.

Altering memory and learning—BMP signaling has an important role in the development and maintenance of neurons involved in memory and cognitive behavior. For example, mice deficient in the BMP inhibitor, chordin, have enhanced spatial learning but less exploratory activity in a novel environment (Sun et al. *J. Neurosci.* 27:7740-7750, 2007). Compounds as described herein can be used to alter or prevent memory or learning, for example, inducing amnesia for anesthesia or in other situations likely to cause distress, or to prevent Post-Traumatic Stress Disorder.

L. Treatment of Atherosclerosis

Abundant evidence suggests that BMP ligands are pro-inflammatory and pro-atherogenic in the blood vessel wall (Chang et al. *Circulation* 116:1258-1266, 2007). Knocking-down expression of BMP4 decreased inflammatory signals, whereas knocking-down BMP inhibitors (eg follistatin or noggin) increased inflammatory signals. Compounds as described herein can be used to reduce vascular inflammation associated with atherosclerosis, autoimmune disease, and other vasculitides. By decreasing atherosclerosis, it would be anticipated that compounds as described herein would decrease the incidence and/or severity of acute coronary syndromes (angina pectoris and heart attack), transient ischemic attacks, stroke, peripheral vascular disease, and other vascular ischemic events. Moreover, in so far as atherosclerosis contributes to the pathogenesis of aneurysm formation, compounds as described herein can be used to slow the progression of aneurysm formation decreasing the frequency of aneurismal rupture and the requirement for surgery.

As BMPs and many of the BMP-induced gene products that affect matrix remodeling are overexpressed in early atherosclerotic lesions, BMP signals may promote atherosclerotic plaque formation and progression (Bostrom et al. *J Clin Invest.* 91: 1800-1809. 1993; Dhore et al. *Arterioscler Thromb Vasc Biol.* 21: 1998-2003. 2001). BMP signaling activity in the atheromatous plaque may thus represent a form of maladaptive injury-repair, or may contribute to inflammation. Over time, BMP signals may also induce resident or nascent vascular cell populations to differentiate into osteoblast-like cells, leading to intimal and medial calcification of vessels (Hruska et al. Circ Res. 97: 105-112. 2005). Calcific vascular disease, or arteriosclerosis, is associated with decreased vascular distensibility, and increased risk of cardiovascular events and mortality, and is particularly problematic when associated with underlying atherosclerotic disease (Bostrom et al. Crit Rev Eukaryot Gene Expr. 10: 151-158. 2000). Both atherosclerotic and calcific lesions may be amenable to regression, however, if signals which contribute to their progression can be intercepted (Sano et al. Circulation. 103: 2955-2960. 2001). In certain aspects, inhibitor of BMP type I receptor activity may be used to limit the progression of atheromatous plaques and vascular calcification in vivo (Derwall et al. Arteriosclerosis, Thrombosis, and Vascular Biology. 2012; 32: 613-622).

M. Treatment of Hypercholesterolemia or Hyperlipoproteinemia

Treatment with small molecule or recombinant BMP inhibitors reduces vascular inflammation (via macrophage accumulation and cathepsin activity), atheroma formation, and vascular calcification in mice deficient in low-density lipoprotein receptor (LDLR$^{-/-}$). Without wishing to be bound by theory, as potential explanations for impact on vascular inflammation, oxidized LDL (oxLDL) has been found to increase BMP2 expression and induce the production of reactive oxygen species (ROS) in human aortic endothelial cells. ROS production induced by oxLDL appears to require BMP signaling, based on inhibition by small molecule or recombinant BMP inhibitors. Treatment with small molecule BMP inhibitors reduces plasma low-density lipoprotein levels without inhibiting HMG-CoA reductase activity, suggesting a role of BMP signaling in the regulation of LDL cholesterol biosynthesis. Small molecule BMP inhibitors have also been found to inhibit hepatosteatosis seen in LDLR-deficient mice fed a high-fat diet. Small molecule or recombinant BMP inhibitors inhibit the synthesis of ApoB-100 in hepatoma cells in vitro. These findings implicate BMP signaling in vascular calcification and atherogenesis and provide at least two novel mechanisms by which BMP signaling may contribute to the pathogenesis of atherosclerosis. These studies highlight the BMP signaling pathway as a therapeutic target in the treatment of atherosclerosis while identifying several novel functions of BMP signaling in the regulation of vascular oxidative stress, inflammation and lipid metabolism.

In certain embodiments, BMP inhibitors as described herein may be used for the reduction of circulating levels of ApoB-100 in patients. In certain embodiments, BMP inhibitors as described herein may be used for the reduction of circulating levels of LDL in patients. Accordingly, BMP inhibitors as described herein may be used for the treatment of hypercholesterolemia, hyperlipidemia, or hyperlipoproteinemia, including congenital or acquired hypercholesterolemia, hyperlipidemia, or hyperlipoproteinemia.

In certain embodiments, the congenital hypercholesterolemia, hyperlipidemia, or hyperlipoproteinemia is autosomal dominant hypercholesterolemia (ADH), familial hypercholesterolemia (FH), polygenic hypercholesterolemia, familial combined hyperlipidemia (FCHL), hyperapobetalipoproteinemia, or small dense LDL syndrome (LDL phenotype B).

In certain embodiments, the acquired hypercholesterolemia, hyperlipidemia, or hyperlipoproteinemia is associated with diabetes mellitus, hyperlipidemic diet and/or sedentary lifestyle, obesity, metabolic syndrome, intrinsic or secondary liver disease, primary biliary cirrhosis or other bile stasis disorders, alcoholism, pancreatitis, nephrotic syndrome, endstage renal disease, hypothyroidism, iatrogenesis due to administration of thiazides, beta-blockers, retinoids, highly active antiretroviral agents, estrogen, progestins, or glucocorticoids.

In certain embodiments, BMP inhibitors as described herein may be used for the treatment of diseases, disorders, or syndromes associated with defects in lipid absorption or metabolism, such as sitosterolemia, cerebrotendinous xanthomatosis, or familial hypobetalipoproteinemia.

In certain embodiments, BMP inhibitors as described herein may be used for the treatment of diseases, disorders, or syndromes caused by hyperlipidemia, such as coronary artery disease and its manifestations (e.g., myocardial infarction; angina pectoris; acute coronary artery syndromes, such as unstable angina pectoris; cardiac dysfunction, such as congestive heart failure, caused by myocardial infarction; or cardiac arrhythmia associated with myocardial ischemia/infarction), stroke due to occlusion of arteries supplying portions of the brain, cerebral hemorrhage, peripheral arterial disease (e.g., mesenteric ischemia; renal artery stenosis; limb ischemia and claudication; subclavian steal syndrome; abdominal aortic aneurysm; thoracic aortic aneurysm, pseudoaneurysm, intramural hematoma; or penetrating aortic ulcer, aortic dissection, aortic stenosis, vascular calcification, xanthoma, such as xanthoma affecting tendons or scleral and cutaneous xanthomas, xanthelasma, or hepatosteatosis. In certain embodiments, BMP inhibitors as described herein may be used for the treatment of the foregoing diseases, disorders, or syndromes regardless of circulating lipid levels, such as in individuals exhibiting normal circulating lipid levels or metabolism.

In certain embodiments, BMP inhibitors as described herein may be used for the reduction of secondary cardiovascular events arising from coronary, cerebral, or peripheral vascular disease. In certain such embodiments, BMP inhibitors as described herein may be used to treat individuals regardless of lipid levels, such as used in the treatment of individuals exhibiting normal circulating cholesterol and lipid levels. In certain such embodiments, BMP inhibitors as described herein are administered conjointly with a HMG-CoA reductase inhibitor.

In certain embodiments, BMP inhibitors as described herein may be used for the prevention of cardiovascular disease, such as in individuals with elevated markers of cardiovascular risk (e.g., C-reactive protein) or, for example, an elevated Framingham Risk Score. In certain such embodiments, BMP inhibitors as described herein may be used to prevent cardiovascular disease in individuals exhibiting normal circulating cholesterol and lipid levels.

In certain embodiments wherein one or more BMP inhibitors as described herein are used in the treatment or prevention of the foregoing diseases, disorders, or syndromes, the patient being treated is not diagnosed with and/or is not suffering from one or more of the following conditions: vascular inflammation associated with atherosclerosis, autoimmune disease, and other vasculitides; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

In other embodiments wherein one or more BMP inhibitors as described herein are used in the treatment or prevention of the foregoing diseases, disorders, or syndromes (e.g., for the reduction of circulating levels of ApoB-100 and/or LDL in patients; for the treatment of hypercholesterolemia, hyperlipidemia, or hyperlipoproteinemia, including congenital or acquired hypercholesterolemia, hyperlipidemia, or hyperlipoproteinemia; for the treatment of diseases, disorders, or syndromes associated with defects in lipid absorption or metabolism; for the treatment of diseases, disorders, or syndromes caused by hyperlipidemia; for the reduction of secondary cardiovascular events arising from coronary, cerebral, or peripheral vascular disease; or for the reduction of secondary cardiovascular events arising from coronary, cerebral, or peripheral vascular disease), the patient being treated is also diagnosed with and/or is also suffering from one or more of the following conditions: vascular inflammation associated with atherosclerosis, autoimmune disease, and other vasculitides; atherosclerotic disease, atheromatous plaques, and/or vascular calcification; an aneurysm and/or aneurysm formation; acute coronary syndromes (angina pectoris and heart attack), transient ischemic attacks, stroke, peripheral vascular disease, or other vascular ischemic events.

N. Propagation, Engraftment and Differentiation of Progenitor Cells Including Embryonic and Adult Stem Cells In Vitro and In Vivo BMP signals are crucial for regulating the differentiation and regeneration of precursor and stem cell populations, in some contexts and tissues preventing (while in other contexts directing) differentiation towards a lineage. Compounds as described herein can be used to (i) maintain a pluripotential state in stem cell or multipotent cell populations in vivo or in vitro; (ii) expand stem cell or multipotent cell populations in vivo or in vitro; (iii) direct differentiation of stem cell or multipotent cell populations in vivo or in vitro; (iv) manipulate or direct the differentiation of stem cell or multipotent cell populations in vivo or in vitro, either alone or in combination or in sequence with other treatments; and (v) modulate the de-differentiation of differentiated cell populations into multipotent or progenitor populations.

Numerous stem cell and precursor lineages require BMP signals in order to determine whether they will expand, differentiate towards specific tissue lineages, home in and integrate with particular tissue types, or undergo programmed cell death. Frequently BMP signals interact with signals provided by growth factors (bFGF, PDGF, VEGF, HBEGF, PlGF, and others), Sonic Hedgehog (SHH), notch, and Wnt signaling pathways to effect these changes (Okita et al. *Curr. Stem Cell Res. Ther.* 1:103-111, 2006). Compounds as described herein can be used to direct the differentiation of stem cells (e.g., embryonic stem cells) or tissue progenitor cells towards specific lineages for therapeutic application (Park et al. *Development* 131:2749-2762, 2004; Pashmforoush et al. *Cell* 117:373-386, 2004). Alternatively for certain cell populations, BMP inhibitors as described herein may be effective in preventing differentiation and promoting expansion, in order to produce sufficient numbers of cells to be effective for a clinical application. The exact combination of BMP inhibitor and growth factor or signaling molecule may be highly specific to each cell and tissue type.

For example, certain embryonic stem cell lines require co-culture with leukemia inhibitory factor (LIF) to inhibit differentiation and maintain the pluripotency of certain cultured embryonic stem cell lines (Okita et al. *Curr. Stem Cell Res. Ther.* 1:103-111, 2006). Use of a BMP inhibitor as described herein may be used to maintain pluripotency in the absence of LIF. Other ES cell lines require coculture with a specific feeder cell layer in order to maintain pluripotency. Use of a BMP inhibitor as described herein, alone or in combination with other agents, may be effective in maintaining pluripotency when concerns of contamination with a feeder cell layer, or its DNA or protein components would complicate or prevent use of cells for human therapy.

In another example, in some circumstances antagonizing BMP signals with a protein such as noggin shortly before cessation of LIF in culture is able to induce differentiation into a cardiomyocyte lineage (Yuasa et al. *Nat. Biotechnol.* 23:607-611, 2005). Use of a pharmacologic BMP inhibitor as described herein may achieve similar if not more potent effects. Such differentiated cells could be introduced into diseased myocardium therapeutically. Alternatively, such treatment may actually be more effective on engrafted precursor cells which have already homed in to diseased myocardium. Systemic therapy with a protein inhibitor of BMP such as noggin would be prohibitively expensive and entail complicated dosing. Delivery of a BMP inhibitor as described herein, systemically or locally, could bias the differentiation of such precursor cells into functioning cardiomyocytes in situ.

O. Treatment of Cartilage Defects

The selective inhibition of specific BMP receptors enables cartilage formation by preventing calcification and mineralization of scaffolds produced by mesenchymal stem cells (Hellingman et al. Tissue Eng Part A. 2011 April; 17(7-8): 1157-67. Epub 2011 Jan. 17.) Accordingly, compounds of the invention may be useful to promote cartilage repair/regeneration in patients with cartilage injuries or defects, as well as in the ex vivo or in vitro production of cartilage tissue, e.g., for implantation, from appropriate cells, such as mesenchymal stem cells.

P. Application of Compounds with Varying Degrees of Selectivity: Compounds which Inhibit BMP Signaling Via Particular BMP Type I Receptors, or Compounds which Also Affect Signaling Via TGF-β, Activin, AMP Kinase, or VEGF Receptors ALK-specific inhibitors—Dorsomorphin inhibits the activity of the BMP type I receptors, ALK2, ALK3, and ALK6. Dorsomorphin inhibits ALK2 and ALK3 to a greater extent than it does ALK6 (Yu et al. *Nat. Chem. Biol.* 4:33-41, 2008). Several of the compounds described herein will have relative greater selectivity for particular BMP type I receptors. The pathogenesis of certain diseases might be attributed to the dysfunctional signaling of one particular receptor. For example, fibrodysplasia ossificans progressiva is a disease caused by aberrant (constitutively active) ALK2 function (Yu et al. *Nat. Chem. Biol.* 4:33-41, 2008). In such instances, compounds as described herein which specifically antagonize the function a subset of the BMP type I receptors may have the advantage of reduced toxicity or side effects, or greater effectiveness, or both.

Some compounds as described herein may have a high degree of selectivity for BMP vs. TGF-β, Activin, AMP kinase, and VEGF receptor signaling. Other compounds may be less specific and may target other pathways in addition to BMP signaling. In the treatment of tumors, for example, agents which inhibit BMP signaling as well as one or more of the above pathways can have beneficial effects (e.g. decrease tumor size), when molecular phenotyping of specific patients' tumors reveals dysregulation of multiple pathways.

Some compounds as described herein have a high degree of selectivity for ALK2 versus ALK1 or ALK3 or ALK4 or ALK5 or ALK6. Selective inhibition of ALK2 versus ALK1 or ALK3 or ALK4 or ALK5 or ALK6 may minimize unwanted effects or toxicity. Chronic ALK3 inhibition might impair normal mucosal epithelial turnover due to known importance in intestinal crypt stem cell recycling, and implication of ALK3 function in juvenile familial polyposis. ALK1 inhibition might impair normal vascular remodeling and lead to complications similar to human hereditary telangiectasia syndrome type 2 (HHT2), such as leaky capillaries, AV malformations, and bleeding. Accordingly, compounds that selectively inhibit ALK2 relative to ALK3 and ALK1 may help avoid toxicities of this type that might be encountered through the use of an unselective inhibitor.

In certain embodiments, the invention provides a method of inhibiting the activity of ALK2 in a human, comprising administering to the human a small molecule that selectively inhibits the activity of human ALK2 relative to the activity of human ALK1. In some such embodiments, the small molecule inhibits the activity of human ALK2 with an $IC_{50}$ that is lower by a factor of about 2 than its $IC_{50}$ for inhibiting the activity of human ALK1. In some such embodiments, the small molecule inhibits the activity of human ALK2 with an $IC_{50}$ that is lower by a factor of 5 than its $IC_{50}$ for inhibiting the activity of human ALK1. In some such embodiments, the small molecule inhibits the activity of human ALK2 with an $IC_{50}$ that is lower by a factor of 10 than its $IC_{50}$ for inhibiting the activity of human ALK1. In some such embodiments, the small molecule inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK1. In certain embodiments, the small molecule has a structure of Formula I, II or II as described herein.

In certain embodiments, the invention provides a method of inhibiting the activity of ALK2 in a human, comprising administering to the human a small molecule that selectively inhibits the activity of human ALK2 relative to the activity of human ALK3. In some such embodiments, the small molecule inhibits the activity of human ALK2 with an $IC_{50}$ that is lower by a factor of 15 than its $IC_{50}$ for inhibiting the activity of human ALK3. In some such embodiments, the small molecule inhibits the activity of human ALK2 with an $IC_{50}$ that is lower by a factor of 20 than its $IC_{50}$ for inhibiting the activity of human ALK3. In some such embodiments, the small molecule inhibits the activity of human ALK2 with an $IC_{50}$ that is lower by a factor of 30 than its $IC_{50}$ for inhibiting the activity of human ALK3. In some such embodiments, the small molecule inhibits the activity of human ALK2 with an $IC_{50}$ that is lower by a factor of 50 or 100 or 200 or 300 or 400 or 500 or 600 or 800 or 1000 or 1500 or 2000 or 5000 or 10000 or 15,000 or 20,000 or 40,000 or 60,000 or 70,000 or 80,000 or 90,000 or 100,000 than its $IC_{50}$ for inhibiting the activity of human ALK3. In certain embodiments, the small molecule has a structure of Formula I, II or III as described herein.

In certain embodiments, the invention provides a method of inhibiting the activity of ALK2 in a human, comprising administering to the human a small molecule that selectively inhibits the activity of human ALK2 relative to the activity of human ALK4. In some such embodiments, the small molecule inhibits the activity of human ALK2 with an $IC_{50}$ that is lower by a factor of 1000 than its $IC_{50}$ for inhibiting the activity of human ALK4. In some such embodiments, the small molecule inhibits the activity of human ALK2 with an $IC_{50}$ that is lower by a factor of 2000 than its $IC_{50}$ for inhibiting the activity of human ALK4. In some such embodiments, the small molecule inhibits the activity of human ALK2 with an $IC_{50}$ that is lower by a factor of 3000 than its $IC_{50}$ for inhibiting the activity of human ALK4. In some such embodiments, the small molecule inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK4. In certain embodiments, the small molecule has a structure of Formula I, II or III as described herein.

In certain embodiments, the invention provides a method of inhibiting the activity of ALK2 in a human, comprising administering to the human a small molecule that selectively inhibits the activity of human ALK2 relative to the activity of human ALK6. In some such embodiments, the small molecule inhibits the activity of human ALK2 with an $IC_{50}$ that is lower by a factor of 2 than its $IC_{50}$ for inhibiting the activity of human ALK6. In some such embodiments, the small molecule inhibits the activity of human ALK2 with an $IC_{50}$ that is lower by a factor of 5 than its $IC_{50}$ for inhibiting the activity of human ALK6. In some such embodiments, the small molecule inhibits the activity of human ALK2 with an $IC_{50}$ that is lower by a factor of 10 than its $IC_{50}$ for inhibiting the activity of human ALK6. In some such embodiments, the small molecule inhibits the activity of human ALK2 with an $IC_{50}$ that is lower by a factor of 15 or 20 or 30 or 40 or 50 or 100 or 200 or 300 or 400 or 500 or 600 or 800 or 1000 or 1500 or 2000 or 5000 or 10000 or 15,000 or 20,000 or 40,000 or 50,000 or 60,000 or 70,000 or 80,000 or 90,000 or 100,000 than its $IC_{50}$ for inhibiting the activity of human ALK6. In certain embodiments, the small molecule has a structure of Formula I, II, or III as described herein.

In one aspect, the invention provides a method of inhibiting the activity of ALK2 in a human, comprising administering to the human a small molecule that selectively inhibits the activity of human ALK2 relative to the activity of human ALK5. In some such embodiments, the small molecule inhibits the activity of human ALK2 with an $IC_{50}$ that is lower by a factor of 1000 than its $IC_{50}$ for inhibiting the activity of human ALK5. In some such embodiments, the small molecule inhibits the activity of human ALK2 with an $IC_{50}$ that is lower by a factor of 2000 than its $IC_{50}$ for inhibiting the activity of human ALK5. In some such embodiments, the small molecule inhibits the activity of human ALK2 with an $IC_{50}$ that is lower by a factor of 3000 than its $IC_{50}$ for inhibiting the activity of human ALK5. In some such embodiments, the small molecule inhibits the activity of human ALK2 with an $IC_{50}$ that is lower by a factor of 4000 or 5000 or 6000 or 7000 or 8000 or 9000 or 10,000 or 12,000 or 14,000 or 16,000 or 18,000 or 20,000 or 25,000 or 30,000 or 40,000 or 50,000 or 60,000 or 70,000 or 80,000 or 90,000 or 100,000 than its $IC_{50}$ for inhibiting the activity of human ALK5. In certain embodiments, the small molecule has a structure of Formula I, II or III as described herein.

Compounds as described herein can be used to treat subjects (e.g., humans, domestic pets, livestock, or other animals) by use of dosages and administration regimens that are determined to be appropriate by those of skill in the art, and these parameters may vary depending on, for example, the type and extent of the disorder treated, the overall health status of the subject, the therapeutic index of the compound, and the route of administration. Standard clinical trials can be used to optimize the dose and dosing frequency for any particular pharmaceutical composition of the invention. Exemplary routes of administration that can be used include oral, parenteral, intravenous, intra-arterial, subcutaneous, intramuscular, topical, intracranial, intraorbital, ophthalmic, intraventricular, intracapsular, intraspinal, intracisternal, intraperitoneal, intranasal, aerosol, or administration by suppository. Methods for making formulations that can be used in the invention are well known in the art and can be found, for example, in Remington: The Science and Practice of Pharmacy (20th edition, Ed., A. R. Gennaro), Lippincott Williams & Wilkins, 2000.

Q. Combination Therapies

In certain instances BMP inhibitors as described herein may be used in combination with other current or future drug therapies, because the effects of inhibiting BMP alone may be less optimal by itself, and/or may be synergistic or more highly effective in combination with therapies acting on distinct pathways which interact functionally with BMP signaling, or on the BMP pathway itself. In certain instances, conjoint administration of a BMP inhibitor as described herein with an additional drug therapy reduces the dose of the additional drug therapy such that it is less than the amount that achieves a therapeutic effect when used in a monotherapy (e.g., in the absence of a BMP inhibitor as described herein). Some examples of combination therapies could include the following.

In certain embodiments, BMP inhibitors as described herein may be administered conjointly with other antihyperlipidemic agents or antilipidemic agents including, but not limited to, HMG-CoA reductase inhibitors (e.g., atorvastatin, cerivastatin, fluvastatin, lovastatin, mevastatin, pitavastain, pravastatin, rosuvastatin, or simvastatin), fibrates (e.g., bezafibrate, ciprofibrate, clofibrate, gemfibrozil, or fenofibrate), ezetimibe, niacin, cholesteryl ester transfer protein (CETP) inhibitors (e.g., torcetrapib, anacetrapib, or dalcetrapib), cholestyramine, colestipol, probucol, dextrothyroxine, bile acid sequestrants, or combinations of the above.

In certain embodiments, BMP inhibitors as described herein may be administered conjointly with a treatment for diabetes including, but not limited to, sulfonyl ureas (e.g., chlorpropamide, tolbutamide, glyburide, glipizide, or glimepiride), medications that decrease the amount of glucose produced by the liver (e.g., metformin), meglitinides (e.g., repaglinide or nateglinide), medications that decrease the absorption of carbohydrates from the intestine (e.g., alpha glucosidase inhibitors such as acarbose), medications that effect glycemic control (e.g., pramlintide or exenatide), DPP-IV inhibitors (e.g., sitagliptin), insulin treatment, thiazolidinones (e.g., troglitazone, ciglitazone, pioglitazone, or rosiglitazone), oxadiazolidinediones, alpha-glucosidase inhibitors (e.g., miglitol or acarbose), agents acting on the ATP-dependent potassium channel of the beta cells (e.g., tolbutamide, glibenclamide, glipizide, glicazide, or repaglinide), nateglinide, glucagon inhibitors, inhibitors of hepatic enzymes involved in stimulation of gluconeogenesis and/or glycogenolysis, or combinations of the above.

In certain embodiments, BMP inhibitors as described herein may be administered conjointly with a treatment for obesity including, but not limited to, orlistat, sibutramine, phendimetrazine, phentermine, diethylpropion, benzphetamine, mazindol, dextroamphetamine, rimonabant, cetilistat, GT 389-255, APD356, pramlintide/AC137, PYY3-36, AC 162352/PYY3-36, oxyntomodulin, TM 30338, AOD 9604, oleoyl-estrone, bromocriptine, ephedrine, leptin, pseudoephedrine, or pharmaceutically acceptable salts thereof, or combinations of the above.

In certain embodiments, BMP inhibitors as described herein may be administered conjointly with an antihypertensive agent including, but not limited to, beta-blockers (e.g., alprenolol, atenolol, timolol, pindolol propranolol and metoprolol), ACE (angiotensin converting enzyme) inhibitors (e.g., benazepril, captopril, enalapril, fosinopril, lisinopril, quinapril and ramipril), calcium channel blockers (e.g., nifedipine, felodipine, nicardipine, isradipine, nimodipine, diltiazem and verapamil), and alpha-blockers (e.g., doxazosin, urapidil, prazosin and terazosin), or combinations of the above.

In certain embodiments, BMP inhibitors as described herein may be administered conjointly with a treatment for anemia (e.g., anemia of inflammation ssociated with renal failure and hemodialysis), including but not limited to erythopoiesis-stimulating agents (e.g. erythropoietin).

Tyrosine kinase receptor inhibitors, such as SU-5416, and BMP inhibitors as described herein may have synergistic effects at inhibiting angiogenesis, particularly for anti-angiogenic therapy against tumors. BMP signals (BMP-4) are thought to be critical for the commitment of stem or precursor cells to a hematopoietic/endothelial common progenitor, and may promote the proliferation, survival, and migration of mature endothelial cells necessary for angiogenesis (Park et al. *Development* 131:2749-2762, 2004). Thus antagonism of BMP signals using compounds as described herein may provide additional inhibition of angiogenesis at the level of endothelial precursors and cells. Similarly, co-treatment with BMP inhibitors as described herein and other tyrosine kinase receptor inhibitors such as imatinib (Gleevec) could be used to inhibit vascular remodeling and angiogenesis of certain tumors.

The combination of a sonic hedgehog agonist and a BMP inhibitor as described herein may be particularly useful for promoting hair growth, as SHH activity is known to stimulate the transition of follicles out of telogen (resting) phase (Paladini et al. *J. Invest. Dermatol.* 125:638-646, 2005), while inhibiting the BMP pathway shortens the telogen phase (Plikus et al. *Nature* 451:340-344, 2008). The use of both would be expected to cause relatively increased time in the anagen or growth phase.

Combined use of Notch modulators (e.g., gamma-secretase inhibitors) and BMP inhibitors as described herein may be more effective than either agent alone in applications designed to inhibit vascular remodeling or bone differentiation, because increasing evidence suggests both pathways function cooperatively to effect cell differentiation, and vascular cell migration (Kluppel et al. *Bioessays* 27:115-118, 2005). These therapies may be synergistic in the treatment of tumors in which one or both pathways is deranged (Katoh, *Stem Cell Rev.* 3:30-38, 2007).

Combined use of an Indian Hedgehog (IHH) antagonist and a BMP inhibitor as described herein may inhibit pathologic bone formation. IHH is responsible for the commitment of bone precursors to chondrocyte or cartilage forming cells. Endochondral bone formation involves coordinated activity of both chondrogenesis (promoted by BMP signals and IHH signals) and their subsequent calcification by mineralization programs initiated by BMP signals (Seki et al. *J. Biol. Chem.* 279:18544-18549, 2004; Minina et al. *Development* 128:4523-4534, 2001). Coadministration of an TRH antagonist with a BMP inhibitor as described herein, therefore, may be more effective in inhibiting pathological bone growth due to hyperactive BMP signaling (such as in FOP), or in any of the inflammatory or traumatic disorders of pathologic bone formation described above.

Strong experimental evidence exists for an effect of both Smo antagonism and BMP antagonism for treating glioblastoma. Compounds as described herein may be used in combination with Smo antagonists to treat glioblastoma.

R. Inhibition of BMP Signaling in Insects

Some of the compounds as described herein may have activity against, and perhaps even selectivity for the BMP receptors of arthropods versus those of chordates. Inhibiting BMP signaling in arthropod larvae or eggs is likely to cause severe developmental abnormalities and perhaps compromise their ability to reproduce, e.g., via the same dorsalization that is observed in zebrafish and drosophila when this pathway is inhibited. If BMP inhibitors as described herein have very strong selectivity for arthropod BMP receptors versus those of humans, they may be used as insecticides or pest control agents that are demonstrably less toxic or more environmentally sound than current strategies.

In addition to being administered to patients in therapeutic methods, compounds as described herein can also be used to treat cells and tissues, as well as structural materials to be implanted into patients (see above), ex vivo. For example, the compounds can be used to treat explanted tissues that may be used, for example, in transplantation.

The invention now being generally described, it will be more readily understood by reference to the following examples which are included merely for purposes of illustration of certain aspects and embodiments of the present invention, and are not intended to limit the invention.

EXEMPLIFICATION

Example 1: Synthetic Protocols

Compound 1

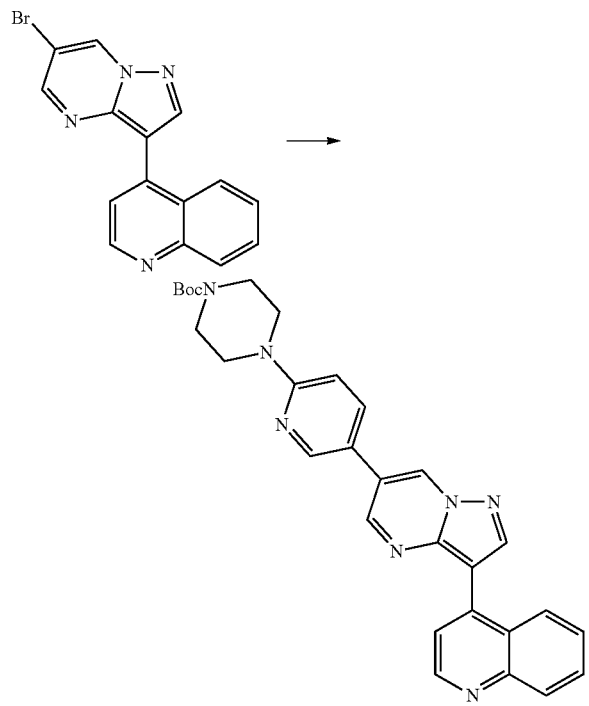

Scheme 1

To a suspension of 4-(6-bromopyrazolo[1,5-a]pyrimidin-3-yl)quinoline (0.325 g, 0.999 mmol) (WO2009/114180 A1, 2009) and tert-butyl 4-(5-(4,4,5,5-tetramethyl-1,3,2-dioxaborolan-2-yl)pyridin-2-yl)piperazine-1-carboxylate (0.584 g, 1.499 mmol) in dioxane degassed with $N_2$ was added $Pd(PPh_3)_4$ (0.058 g, 0.050 mmol) then aqueous sodium carbonate (2 M, 1.5 mL). The mixture was heated to reflux for 1.7 h. The mixture was partitioned between EtOAc (30 mL) and water (30 mL). The organic layer was washed with brine, dried ($Na_2SO_4$), filtered and concentrated. Triturated crude material with EtOH, filtered and washed solid with EtOH. Obtained tert-butyl 4-(5-(3-(quinolin-4-yl)pyrazolo[1,5-a]pyrimidin-6-yl)pyridin-2-yl)piperazine-1-carboxylate (0.22 g, 0.433 mmol, 43.4% yield) as a yellow solid.

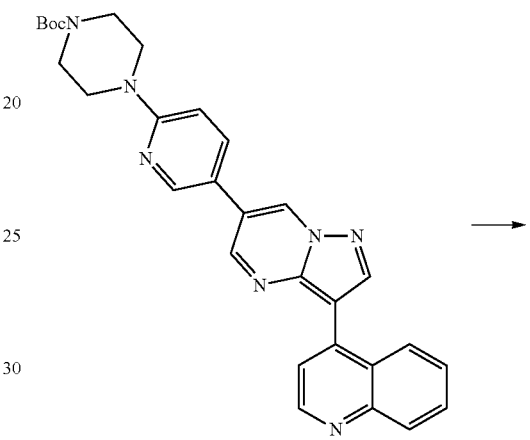

Scheme 2

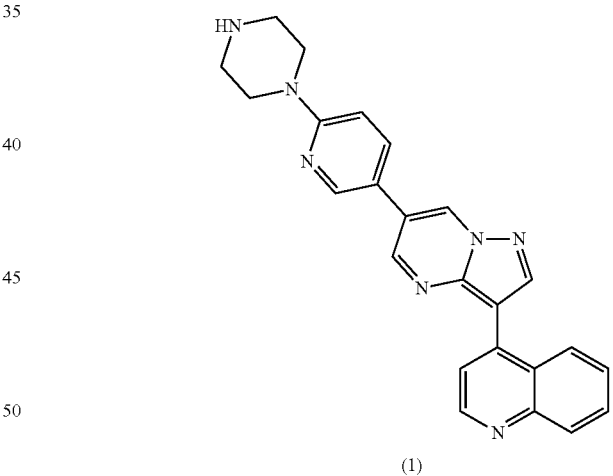

(1)

Dissolved tert-butyl 4-(5-(3-(quinolin-4-yl)pyrazolo[1,5-a]pyrimidin-6-yl)pyridin-2-yl)piperazine-1-carboxylate (0.20 g, 0.394 mmol) in TFA (3 mL) and stirred at RT. LC/MS after 1 h showed complete reaction. Removed TFA in vacuo to obtain 4-(6-(6-(piperazin-1-yl)pyridin-3-yl)pyrazolo[1,5-a]pyrimidin-3-yl)quinoline, TFA (0.14 g, 0.268 mmol, 68.1% yield) as an orange film. $^1$H NMR (400 MHz, DMSO-$d_6$) δ 9.71 (d, J=2.3 Hz, 1H), 9.16 (d, J=2.3 Hz, 1H), 9.09 (d, J=5.1 Hz, 1H), 8.85 (s, 3H), 8.73 (dd, J=2.6, 0.7 Hz, 1H), 8.37 (d, J=8.5 Hz, 1H), 8.23-8.15 (m, 2H), 8.05 (d, J=4.9 Hz, 1H), 7.96 (dd, J=8.5, 6.9 Hz, 1H), 7.75 (t, J=7.8 Hz, 1H), 7.12 (d, J=8.9 Hz, 1H), 3.86-3.79 (m, 4H), 3.23 (s, 4H).

Compound 2

Scheme 3

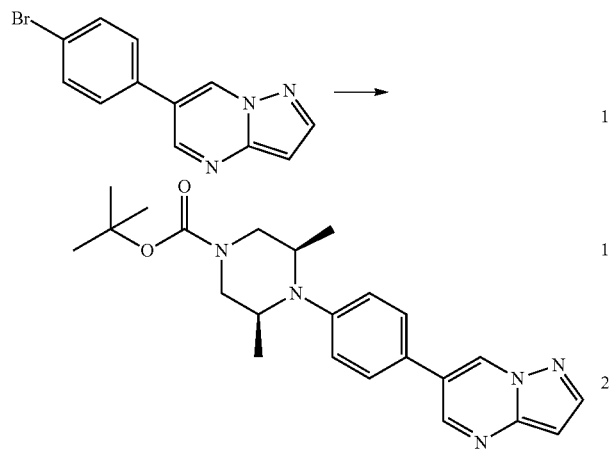

Bubbled N₂ through a suspension of 6-(4-bromophenyl) pyrazolo[1,5-a]pyrimidine (1.14 g, 4.16 mmol) (WO 2009/114180 A1, 2009) and (3R,5S)-tert-butyl 3,5-dimethylpiperazine-1-carboxylate (2.25 g, 10.50 mmol) in toluene (16 mL). Added bis(tri-t-butylphosphino)palladium (0) (0.106 g, 0.208 mmol) then sodium 2-methylpropan-2-olate (0.600 g, 6.24 mmol). Heated in 100 degree bath under N₂. After 5 h, removed solvent. Partitioned between EA and water. Filtered through Celite, washing with ethyl acetate. Washed org layer with brine, dried (Na₂SO₄), filtered and concentrated. Purified on Biotage (50 g) eluting with 25-75% EA/hex. Solid obtained from later peak was triturated in EtOH and filtered to obtain (3R,5S)-tert-butyl 3,5-dimethyl-4-(4-(pyrazolo[1,5-a]pyrimidin-6-yl)phenyl)piperazine-1-carboxylate (0.234 g, 0.574 mmol, 13.81% yield) as a faint yellow solid.

Scheme 4

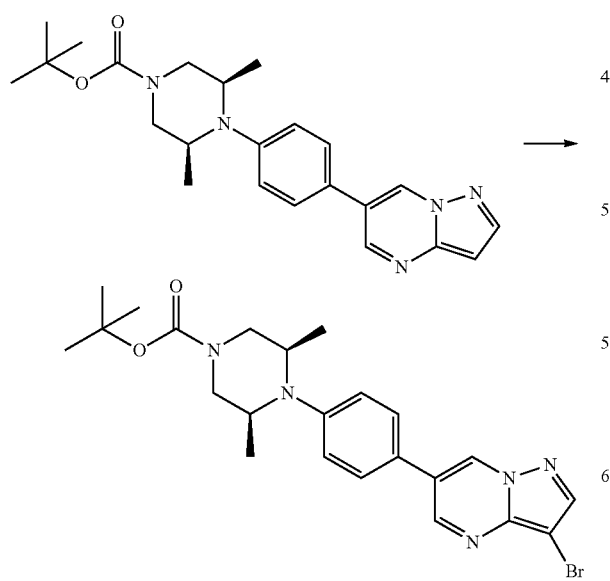

Dissolved (3R,5S)-tert-butyl 3,5-dimethyl-4-(4-(pyrazolo[1,5-a]pyrimidin-6-yl)phenyl)piperazine-1-carboxylate (0.24 g, 0.589 mmol) in DCM (8 mL). Cooled in ice bath then added N-Bromosuccinimide (0.105 g, 0.589 mmol) in DCM (3 mL). Warmed to RT. Added 10 mg×2 until SM gone. 2 h at RT. Removed solvent in vacuo. Suspended between EA and 2 M Na₂CO₃. Washed org. with water, brine, dried (Na₂SO₄), filtered and concentrated. Triturated in EtOH and filtered. Obtained (3R,5S)-tert-butyl 4-(4-(3-bromopyrazolo[1,5-a]pyrimidin-6-yl)phenyl)-3,5-dimethylpiperazine-1-carboxylate (0.159 g, 0.327 mmol, 55.5% yield) as a yellow solid.

Scheme 5

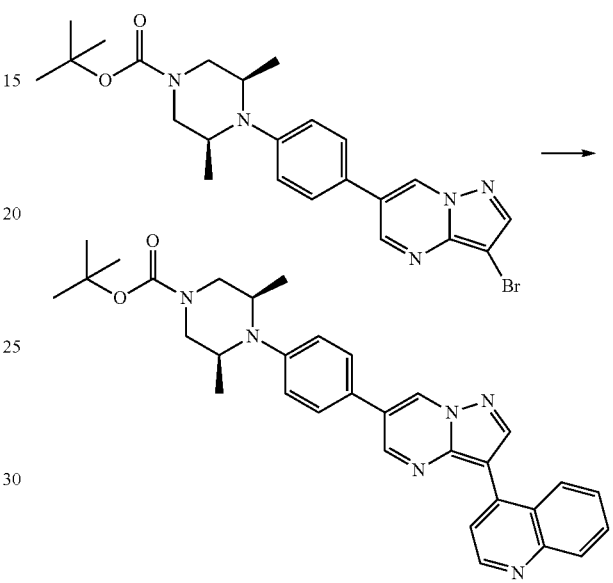

To (3R,5S)-tert-butyl 4-(4-(3-bromopyrazolo[1,5-a]pyrimidin-6-yl)phenyl)-3,5-dimethylpiperazine-1-carboxylate (0.159 g, 0.327 mmol) and quinolin-4-ylboronic acid (0.113 g, 0.654 mmol) in dioxane (3.5 mL) was added 2 M Na₂CO₃ (0.8 mL). Bubbled N₂ through solution for 5 min then added Pd(PPh₃)₄ (0.038 g, 0.033 mmol). Capped and heated in 110 degree bath. After 40 min reaction was complete. Partitioned between EA and water. Washed org layer 2× with brine, dried (Na₂SO₄), filtered and concentrated in vacuo. Obtained (3R,5S)-tert-butyl 3,5-dimethyl-4-(4-(3-(quinolin-4-yl)pyrazolo[1,5-a]pyrimidin-6-yl)phenyl)piperazine-1-carboxylate (0.135 g, 0.253 mmol, 77% yield) as a beige solid after trituration with methanol.

Scheme 6

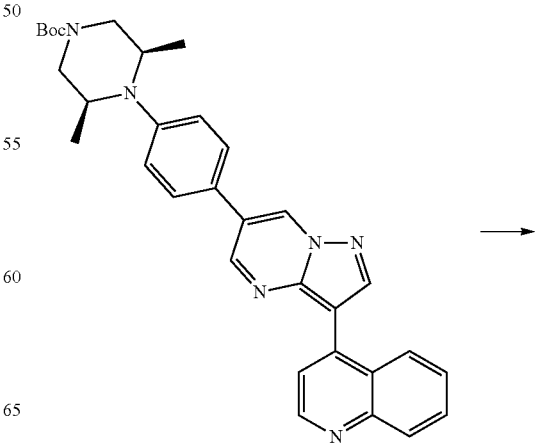

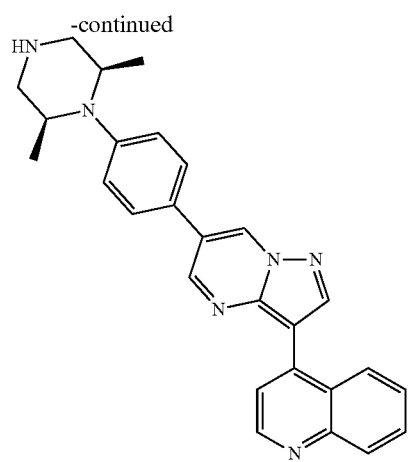

(2)

In an analogous manner to Scheme 2 4-(6-(4-((2R,6S)-2,6-dimethylpiperazin-1-yl)phenyl)pyrazolo[1,5-a]pyrimidin-3-yl)quinoline, TFA was obtained from (3R,5S)-tert-butyl 3,5-dimethyl-4-(4-(3-(quinolin-4-yl)pyrazolo[1,5-a]pyrimidin-6-yl)phenyl)piperazine-1-carboxylate as a yellowish solid in 86% yield. $^1$H NMR (400 MHz, DMSO-d$_6$) δ 9.74 (d, J=2.2 Hz, 1H), 9.25-9.05 (m, 4H), 8.92 (s, 1H), 8.50-8.42 (m, 1H), 8.26-8.15 (m, 2H), 8.06-7.91 (m, 3H), 7.81 (ddd, J=8.3, 6.8, 1.3 Hz, 1H), 7.34-7.26 (m, 2H), 3.52-3.34 (m, 4H), 2.88 (q, J=10.1 Hz, 2H), 0.84 (d, J=6.2 Hz, 6H).

Compound 3

Scheme 7

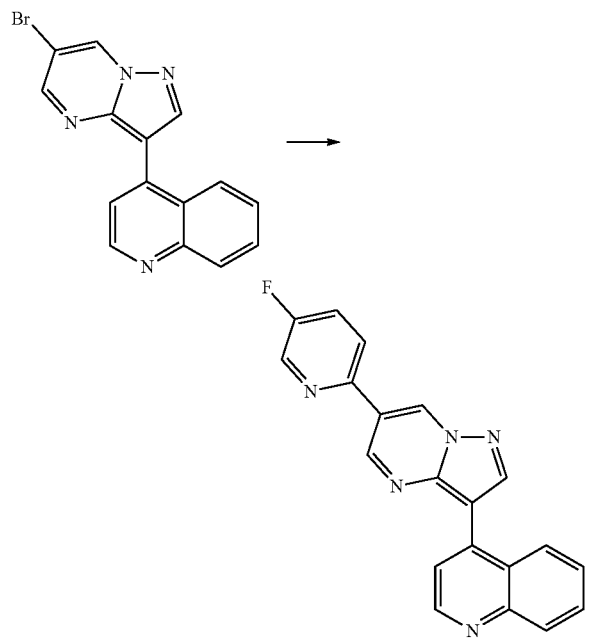

To a suspension of 4-(6-bromopyrazolo[1,5-a]pyrimidin-3-yl)quinoline (0.326 g, 1.003 mmol) in THF (3.5 ml) added a 0.5 M solution of (5-fluoropyridin-2-yl)zinc(II) bromide (2.5 mL, 1.250 mmol). Bubbled N$_2$ through suspension then added Pd(PPh$_3$)$_4$ (0.116 g, 0.100 mmol). Bubbled N$_2$ through solution then capped and heated to 50 deg. Start: 8:15 AM. Added 0.8 mL more organozinc reagent after 1.5 h then let stir for another 30 min. Reaction went to completion. Partitioned between EA and 10% citric acid. Obtained suspension. Neutralized with solid NaHCO3. Product went into organic layer. Washed org. layer with brine, dried (MgSO4), filtered and concentrated. Triturated product with EtOH, filtered and washed with EtOH. Obtained 4-(6-(5-fluoropyridin-2-yl)pyrazolo[1,5-a]pyrimidin-3-yl)quinoline (0.28 g, 0.820 mmol, 82% yield) as a beige/yellow solid.

Scheme 8

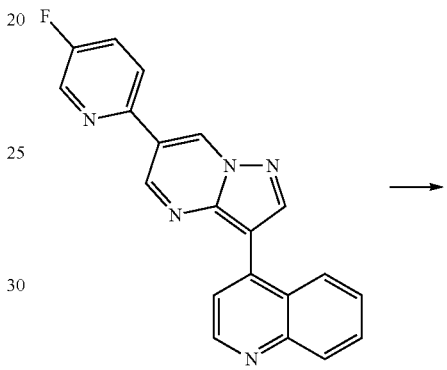

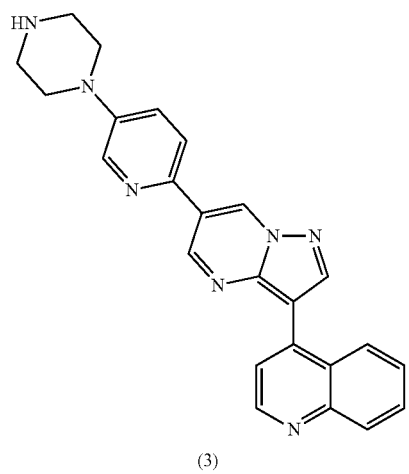

(3)

Combined 4-(6-(5-fluoropyridin-2-yl)pyrazolo[1,5-a]pyrimidin-3-yl)quinoline (0.28 g, 0.820 mmol) and piperazine (0.141 g, 1.641 mmol) in DMSO (3 ml). Heated in mw for 10 min at 160 deg. LC/MS showed about 50% conversion. Heated in mw for an additional 15 minutes without significant improvement. Poured product into water (25 mL), product crashed out, filtered. Obtained dark gray solid. Dissolved in 20% MeOH/DCM then removed solvent (to azeotrope remaining water). Dissolved in DCM (some dark solid insoluble) then loaded onto silica plug (15 g), eluted with 60% EA/hex, then 10% MeOH/DCM (SM came off)

then with 25% MeOH/DCM (product came off). Obtained 79 mg. Triturated this material, filtered and obtained 52 mg yellow solid that will be submitted for purification. ¹H NMR (400 MHz, DMSO-$d_6$) δ 9.83 (d, J=2.2 Hz, 1H), 9.43 (d, J=2.2 Hz, 1H), 9.09 (d, J=4.9 Hz, 1H), 8.84 (d, J=17.5 Hz, 3H), 8.53 (d, J=2.9 Hz, 1H), 8.39-8.32 (m, 1H), 8.22-8.11 (m, 2H), 8.03 (d, J=4.9 Hz, 1H), 7.94 (ddd, J=8.4, 6.8, 1.3 Hz, 1H), 7.74 (ddd, J=8.4, 6.8, 1.3 Hz, 1H), 7.60 (dd, J=8.9, 3.0 Hz, 1H), 3.59-3.51 (m, 4H), 3.29 (s, 4H).

Compound 4

Scheme 9

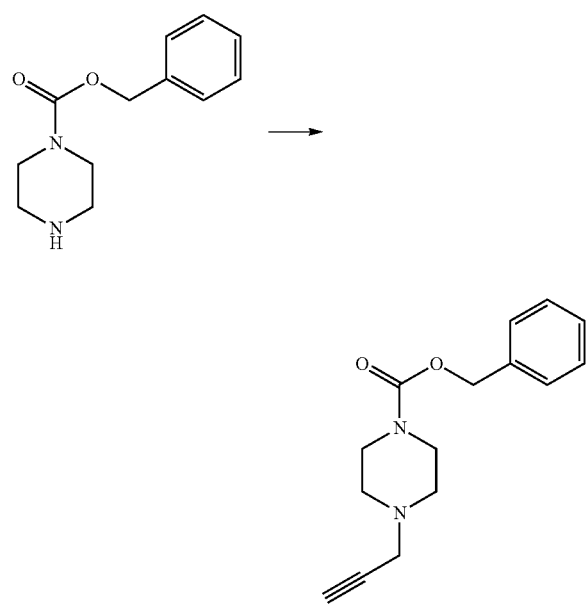

To a solution of 3-bromoprop-1-yne (6.2 g, 41.7 mmol) and benzyl piperazine-1-carboxylate (4.04 g, 18.34 mmol) added Potassium carbonate (6.08 g, 44 mmol). Heated to 80 degree for 2.5 h. Partitioned between ethyl acetate and water (200 mL each). Washed organic layer with brine (150 mL), separated, dried org. layer with Na$_2$CO$_3$, filtered and concentrated. Obtained benzyl 4-(prop-2-ynyl)piperazine-1-carboxylate (4.21 g, 16.30 mmol, 89% yield) as yellow syrup.

Scheme 10

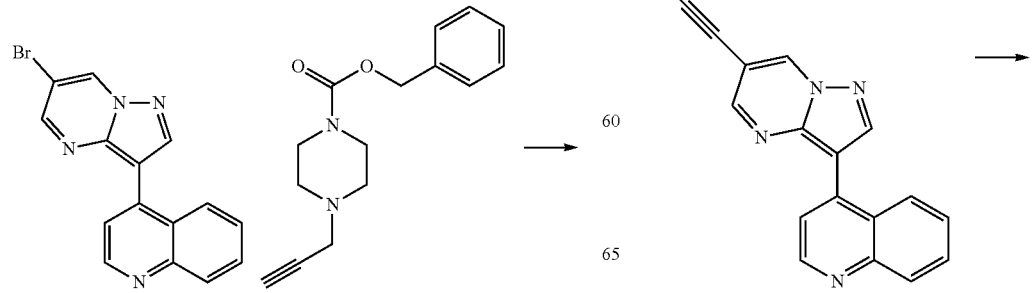

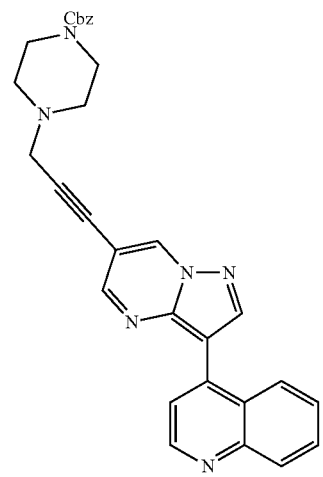

To a suspension of 4-(6-bromopyrazolo[1,5-a]pyrimidin-3-yl)quinoline (0.325 g, 0.999 mmol) and benzyl 4-(prop-2-ynyl)piperazine-1-carboxylate (0.336 g, 1.299 mmol) in DMF (5 mL) with N$_2$ bubbling through added Bis(triphenylphosphine) palladium (II) chloride (0.035 g, 0.050 mmol) then Cuprous Iodide (0.019 g, 0.100 mmol) and Triethylamine (0.417 ml, 3.00 mmol). Let N$_2$ bubble through for 2 minutes then capped and heated in 80 degree bath for 2 h. Partitioned between water and EtOAc. Washed org layer with brine, dried (MgSO$_4$), filtered and concentrated. Purified on silica plug (7 g) eluting with 50% EA/hex to remove less polar impurities then with EA to remove product. Obtained benzyl 4-(3-(3-(quinolin-4-yl)pyrazolo[1,5-a]pyrimidin-6-yl)prop-2-ynyl)piperazine-1-carboxylate (0.404 g, 0.804 mmol, 80% yield) as a yellow solid.

Scheme 11

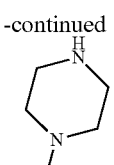

(4)

Dissolved benzyl 4-(3-(3-(quinolin-4-yl)pyrazolo[1,5-a]pyrimidin-6-yl)prop-2-ynyl)piperazine-1-carboxylate (0.1 g, 0.199 mmol) in 33% HBr in AcOH, sonicating. After stirring for 45 min a precipitate formed. LC/MS showed de-Cbz but also HBr addition. Filtered off solid then suspended in THF. Added 200 mg K—O-tBu. LC/MS now showed correct mass. Partitioned between water and DCM. Washed org. layer with brine, dried (MgSO$_4$), filtered and concentrated. Obtained 4-(6-(3-(piperazin-1-yl)prop-1-ynyl)pyrazolo[1,5-a]pyrimidin-3-yl)quinoline, TFA (0.034 g, 0.070 mmol, 35.4% yield) after reverse phase purification. $^1$H NMR (400 MHz, DMSO-d$_6$) δ 9.62 (d, J=2.1 Hz, 1H), 9.07 (d, J=4.8 Hz, 1H), 8.87 (s, 1H), 8.75 (d, J=2.1 Hz, 1H), 8.57 (s, 2H), 8.29-8.22 (m, 1H), 8.16 (dd, J=8.3, 1.2 Hz, 1H), 7.97-7.87 (m, 2H), 7.71 (ddd, J=8.3, 6.8, 1.3 Hz, 1H), 3.73 (s, 2H), 3.17 (d, J=4.7 Hz, 4H), 2.85-2.77 (m, 4H).

Compound 5

Scheme 12

In an analogous manner to Scheme 1, 4-(6-(2-chloropyrimidin-5-yl)pyrazolo[1,5-a]pyrimidin-3-yl)quinoline was obtained in 41.0% yield from 4-(6-bromopyrazolo[1,5-a]pyrimidin-3-yl)quinoline (0.325 g, 0.999 mmol) and (2-chloropyrimidin-5-yl)boronic acid.

Scheme 13

(5)

In an analogous manner to Scheme 8, 4-(6-(2-(piperazin-1-yl)pyrimidin-5-yl)pyrazolo[1,5-a]pyrimidin-3-yl)quinoline, TFA was obtained in 13% yield from 4-(6-(2-chloropyrimidin-5-yl)pyrazolo[1,5-a]pyrimidin-3-yl)quinoline (0.147 g, 0.410 mmol) and piperazine. $^1$H NMR (400 MHz, DMSO-d$_6$) δ 9.76 (d, J=2.2 Hz, 1H), 9.13 (d, J=2.2 Hz, 1H), 9.06 (d, J=4.8 Hz, 1H), 9.00 (s, 2H), 8.85 (d, J=7.9 Hz, 3H), 8.31 (d, J=8.5 Hz, 1H), 8.17 (dd, J=8.3, 1.2 Hz, 1H), 8.00-7.87 (m, 2H), 7.72 (ddd, J=8.3, 6.7, 1.3 Hz, 1H), 4.04 (t, J=5.3 Hz, 4H), 3.23 (s, 4H).

Compound 6

Scheme 14

-continued

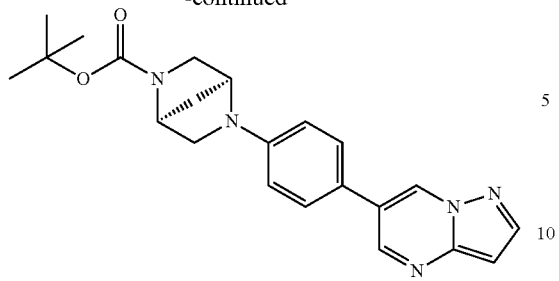

In an analogous manner to Scheme 3, quinolin-4-ylboronic acid and (1S,4S)-tert-butyl 5-(4-(3-bromopyrazolo[1,5-a]pyrimidin-6-yl)phenyl)-2,5-diazabicyclo[2.2.1]heptane-2-carboxylate were reacted to obtain (1S,4S)-tert-butyl 5-(4-(3-(quinolin-4-yl)pyrazolo[1,5-a]pyrimidin-6-yl)phenyl)-2,5-diazabicyclo[2.2.1]heptane-2-carboxylate in 81% yield.

Scheme 15

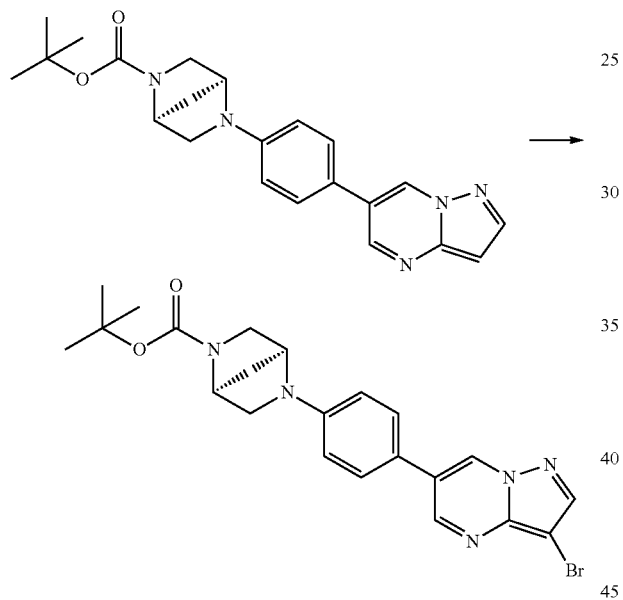

In an analogous manner to Scheme 4, (1S,4S)-tert-butyl 5-(4-(3-bromopyrazolo[1,5-a]pyrimidin-6-yl)phenyl)-2,5-diazabicyclo[2.2.1]heptane-2-carboxylate was obtained from (1S,4S)-tert-butyl 5-(4-(pyrazolo[1,5-a]pyrimidin-6-yl)phenyl)-2,5-diazabicyclo[2.2.1]heptane-2-carboxylate in an 89% yield.

Scheme 16

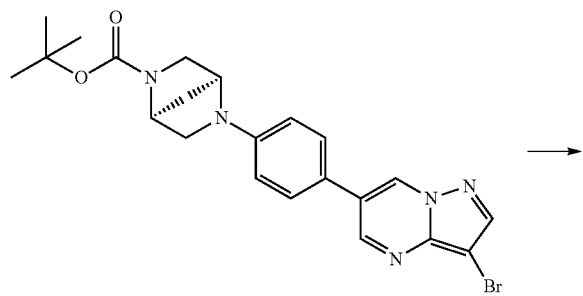

-continued

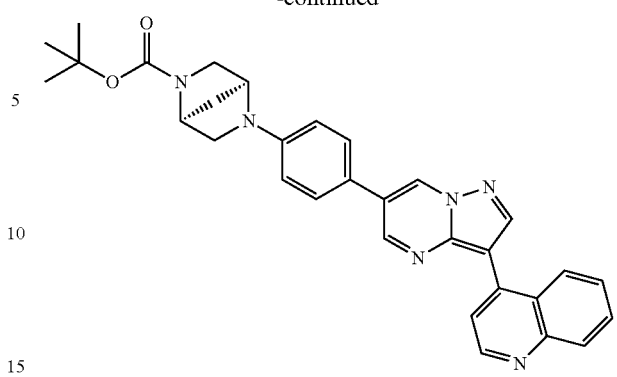

In an analogous manner to Scheme 5, (1S,4S)-tert-butyl 5-(4-(3-(quinolin-4-yl)pyrazolo[1,5-a]pyrimidin-6-yl)phenyl)-2,5-diazabicyclo[2.2.1]heptane-2-carboxylate was obtained from (1S,4S)-tert-butyl 5-(4-(3-bromopyrazolo[1,5-a]pyrimidin-6-yl)phenyl)-2,5-diazabicyclo[2.2.1]heptane-2-carboxylate and quinoline-4-boronic acid in an 81% yield.

Scheme 17

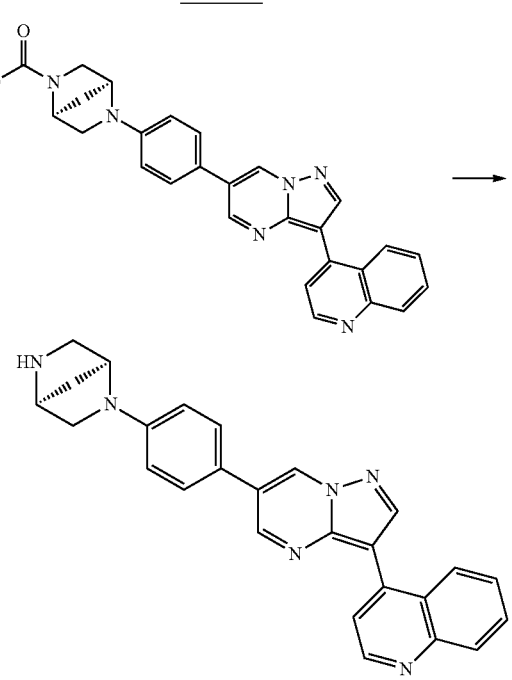

(6)

In an analogous manner to Scheme 2, 4-(6-(4-((1S,4S)-2,5-diazabicyclo[2.2.1]heptan-2-yl)phenyl)pyrazolo[1,5-a]pyrimidin-3-yl)quinoline, TFA was obtained from (1S,4S)-tert-butyl 5-(4-(3-(quinolin-4-yl)pyrazolo[1,5-a]pyrimidin-6-yl)phenyl)-2,5-diazabicyclo[2.2.1]heptane-2-carboxylate in a 75% yield. $^1$H NMR (400 MHz, DMSO-$d_6$) δ 9.60 (d, J=2.2 Hz, 1H), 9.16-9.00 (m, 3H), 8.82 (s, 1H), 8.60 (d, J=9.4 Hz, 1H), 8.38 (d, J=8.6 Hz, 1H), 8.22-8.14 (m, 1H), 8.08-7.90 (m, 2H), 7.86-7.70 (m, 3H), 6.88-6.80 (m, 2H), 4.74 (s, 1H), 4.50 (d, J=2.6 Hz, 1H), 3.68 (d, J=10.4 Hz, 1H), 3.36-3.14 (m, 3H), 2.19 (d, J=10.8 Hz, 1H), 2.00-1.92 (m, 1H).

Compound 7

Scheme 18

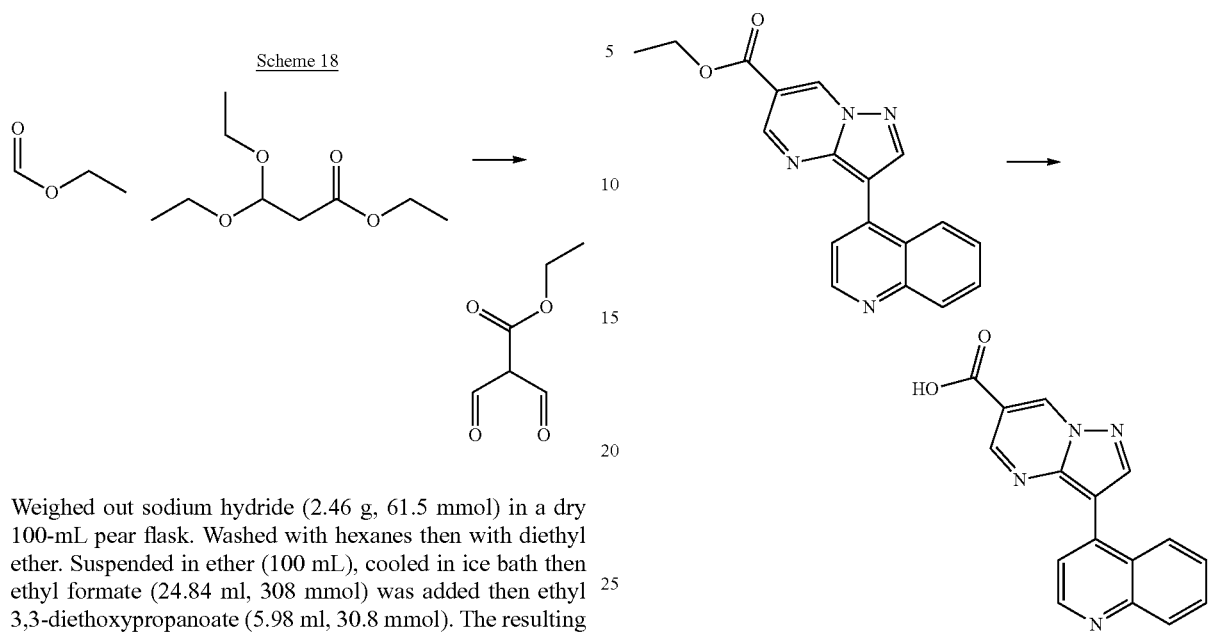

Weighed out sodium hydride (2.46 g, 61.5 mmol) in a dry 100-mL pear flask. Washed with hexanes then with diethyl ether. Suspended in ether (100 mL), cooled in ice bath then ethyl formate (24.84 ml, 308 mmol) was added then ethyl 3,3-diethoxypropanoate (5.98 ml, 30.8 mmol). The resulting mixture was stirred at room temperature for 15 hours to give rise to a reaction. After confirmation of the completion of the reaction, the reaction mixture was poured into water, followed by washing with diethyl ether. The resulting aqueous layer was allowed to have a pH of 1 with hydrochloric acid, followed by extraction with dichloromethane. The resulting organic layer was washed with an aqueous sodium chloride solution and then dried over anhydrous magnesium sulfate, filtered and concentrated to give ethyl 2-formyl-3-oxopropanoate (3.29 g, 22.83 mmol, 74.2% yield) as a golden syrup.

Scheme 19

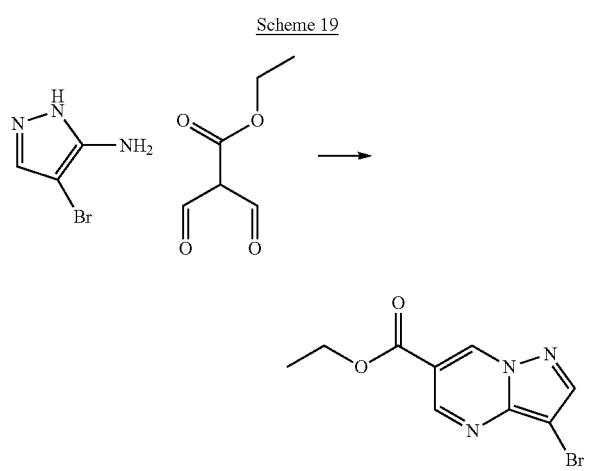

Ethyl 2-formyl-3-oxopropanoate (3.29 g, 22.84 mmol) and 4-bromo-1H-pyrazol-5-amine (3.7 g, 22.84 mmol) were combined in ethanol (30 mL) and heated for 80 min at reflux. The mixture was cooled and the solid product was collected by filtration to give ethyl 3-bromopyrazolo[1,5-a]pyrimidine-6-carboxylate (6.17 g, 22.84 mmol, 100% yield) as a brown solid.

Scheme 20

Dissolved ethyl 3-(quinolin-4-yl)pyrazolo[1,5-a]pyrimidine-6-carboxylate in 1:1 THF/H$_2$O (200 mL). Added LiOH and stirred for 90 min. Added 2 mL AcOH to neutralize, a thick precipitate formed. Filtered and suction dried overnight to obtain 3-(quinolin-4-yl)pyrazolo[1,5-a]pyrimidine-6-carboxylic acid (2.8 g, 9.65 mmol, 107%) as an orange solid.

Scheme 21

Combined 2-(tert-butoxycarbonylamino)acetic acid (1.314 g, 7.5 mmol) and benzyl piperazine-1-carboxylate (1.652 g, 7.50 mmol) in DCM (20 mL) then added 1-(3-Dimethylaminopropyl)-3-ethylcarbodiimide hydrochloride (1.582 g, 8.25 mmol). Stirred at RT for 16 h then removed DCM. Partitioned between water and ethyl acetate, washed org. with water, brine, dried (MgSO$_4$), filtered and concentrated. Obtained benzyl 4-(2-(tert-butoxycarbonylamino)acetyl)piperazine-1-carboxylate (2.24 g, 5.93 mmol, 79% yield) as a colorless oil.

Scheme 22

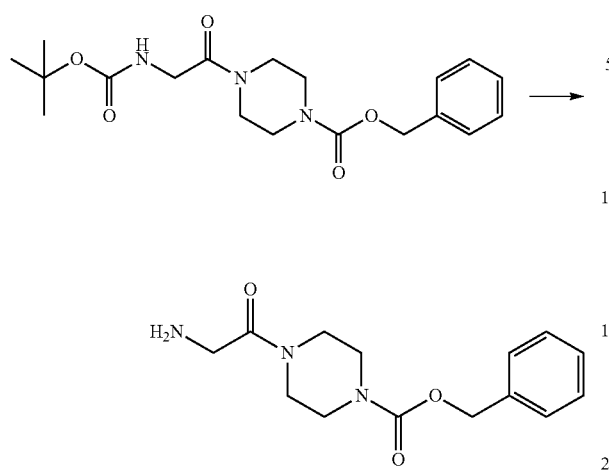

To a solution of benzyl 4-(2-((tert-butoxycarbonyl)amino)acetyl)piperazine-1-carboxylate (2.24 g, 5.93 mmol) in MeOH (Volume: 25 ml) in an ice bath was added dropwise 12 N HCl (1.5 mL, 18 mmol, 3 eq.). Refluxed for 45 min then removed solvent in vacuo. Azeotroped product 3× with methanol then suspended in diethyl ether (25 mL), filtered and vacuum dried to obtain benzyl 4-(2-aminoacetyl)piperazine-1-carboxylate, HCl (1.64 g, 5.23 mmol, 88% yield).

Scheme 23

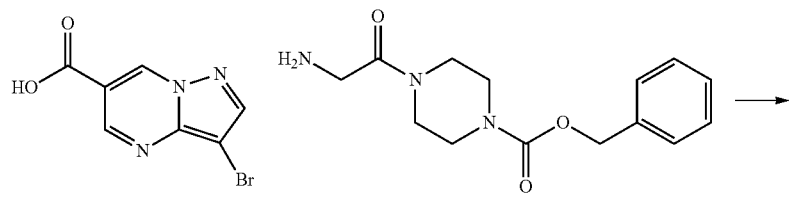

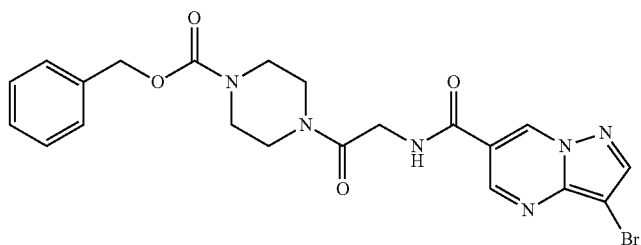

To a mixture of 3-bromopyrazolo[1,5-a]pyrimidine-6-carboxylic acid (0.3 g, 1.240 mmol) and benzyl 4-(2-aminoacetyl)piperazine-1-carboxylate, HCl (0.506 g, 1.611 mmol) and 1-(3-Dimethylaminopropyl)-3-ethylcarbodiimide hydrochloride (0.356 g, 1.859 mmol) was added Triethylamine (0.188 g, 1.859 mmol). The solution was stirred for 16 hours at room temperature. The mixture was diluted with DCM (30 mL), washed with water 2× (25 mL), then with brine (25 mL), dried (MgSO₄), filtered and concentrated to give benzyl 4-(2-(3-bromopyrazolo[1,5-a]pyrimidine-6-carboxamido)acetyl)piperazine-1-carboxylate (0.451 g, 0.900 mmol, 72.6% yield) as a yellow solid.

Scheme 24

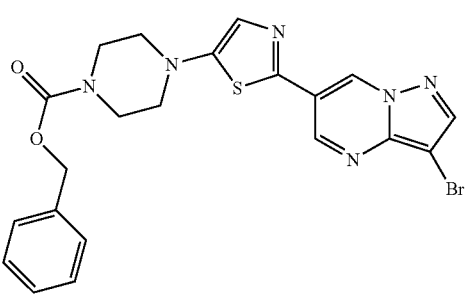

Dissolved benzyl 4-(2-(3-bromopyrazolo[1,5-a]pyrimidine-6-carboxamido)acetyl)piperazine-1-carboxylate (0.22 g, 0.439 mmol) in 2 mL pyridine then added Lawesson's reagent (0.19 g, 0.470 mmol). Microwaved at 150 degree for 15 min. Cooled then diluted with EtOH. Material crashed out. Filtered and washed solid with EtOH to obtain benzyl 4-(2-(3-bromopyrazolo[1,5-a]pyrimidin-6-yl)thiazol-5-yl)piperazine-1-carboxylate (0.188 g, 0.376 mmol, 86% yield).

Scheme 25

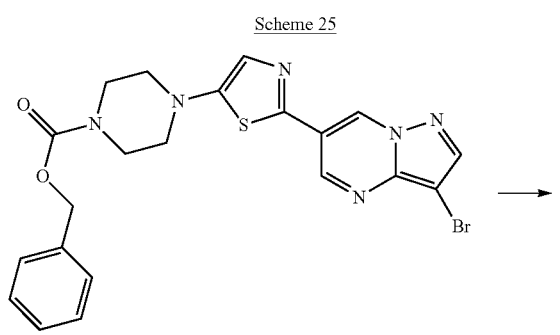

In an analogous manner to Scheme 5, benzyl 4-(2-(3-(quinolin-4-yl)pyrazolo[1,5-a]pyrimidin-6-yl)thiazol-5-yl)piperazine-1-carboxylate was obtained from benzyl 4-(2-(3-bromopyrazolo[1,5-a]pyrimidin-6-yl)thiazol-5-yl)piperazine-1-carboxylate and quinolin-4-ylboronic acid in 66% yield.

Scheme 26

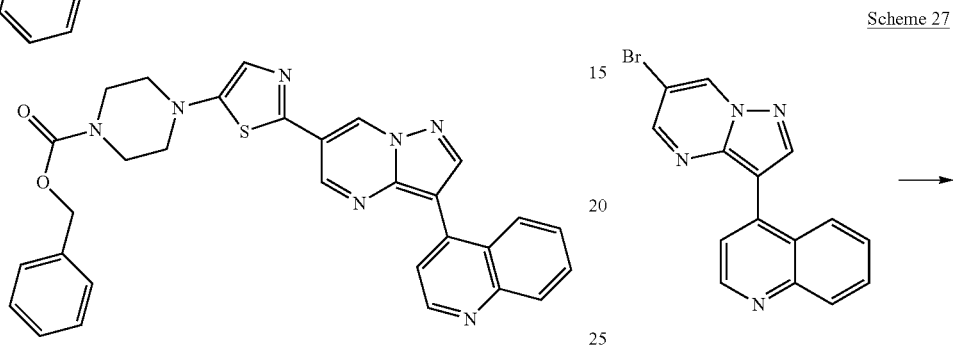

(7)

To benzyl 4-(2-(3-(quinolin-4-yl)pyrazolo[1,5-a]pyrimidin-6-yl)thiazol-5-yl)piperazine-1-carboxylate (0.064 g, 0.117 mmol) added 33% HBr in acetic acid (3 mL), swirled and sonicated. LC/MS showed desired mass (+HBr). Blew off acetic acid then neutralized with saturated NaHCO3. Orange solid became yellow ppt. Filtered and washed with water. Obtained 5-(piperazin-1-yl)-2-(3-(quinolin-4-yl)pyrazolo[1,5-a]pyrimidin-6-yl)thiazole (0.04 g, 0.097 mmol, 83% yield). $^1$H NMR (400 MHz, DMSO-$d_6$) δ 9.68 (d, J=2.2 Hz, 1H), 9.14 (d, J=2.2 Hz, 1H), 9.05 (d, J=4.8 Hz, 1H), 8.83 (d, J=12.4 Hz, 3H), 8.29-8.22 (m, 1H), 8.19-8.12 (m, 1H), 7.94-7.85 (m, 2H), 7.70 (t, J=7.7 Hz, 1H), 7.36 (s, 1H), 3.61 (s, 1H), 3.42 (t, J=5.2 Hz, 4H), 3.32 (s, 4H).

Compound 8

Scheme 27

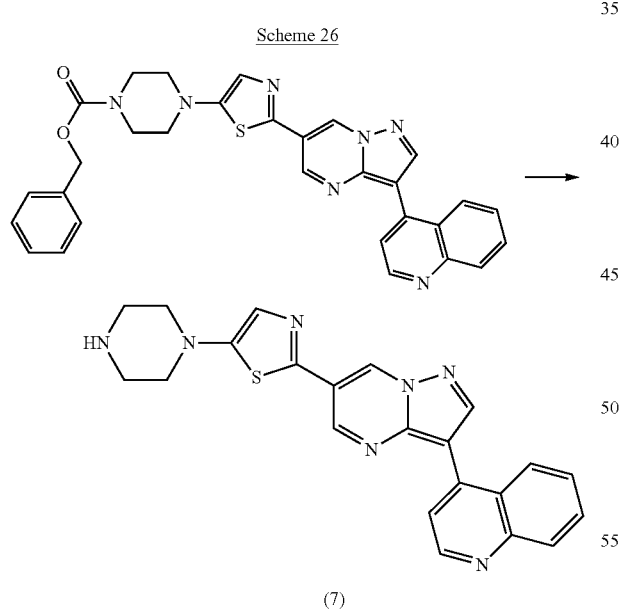

A solution of 4-(6-bromopyrazolo[1,5-a]pyrimidin-3-yl)quinoline (1 g, 3.1 mmol) in DCM (10 mL) at 0 degree C. was treated with m-CPBA (77%, 0.76 g, 1.1 eq.). The reaction mixture was stirred at RT for 4 h. The reaction mixture was diluted with DCM and washed with 1 N NaOH and dried (Na$_2$SO$_4$). Evaporation of the solvent under reduced pressure afforded (0.99 g, 2.8 mmol, 94 percent) 4-(6-bromopyrazolo[1,5-a]pyrimidin-3-yl)quinoline 1-oxide as a beige solid.

Scheme 28

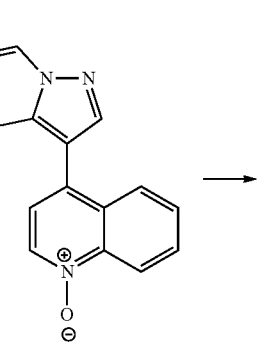

-continued

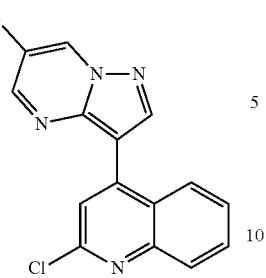

To 4-(6-bromopyrazolo[1,5-a]pyrimidin-3-yl)quinoline 1-oxide (0.99 g, 2.8 mmol) in toluene was added phosphorus (V)oxychloride (2 mL), and the reaction was heated to 80° C. for 2 hours. The reaction was cooled to ambient temperature and poured over ice water (40 mL). Mixture was neutralized with solid sodium bicarbonate and extracted onto dichloromethane (25 mL). The organic layer was washed with water, dried over anhydrous magnesium sulfate, filtered, and concentrated to yield 4-(6-bromopyrazolo[1,5-a]pyrimidin-3-yl)-2-chloroquinoline (0.96 g, 2.66 mmol, 95 percent yield). Used as is.

Scheme 29

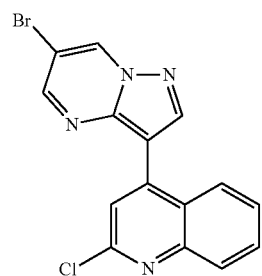

In an analogous manner to Scheme 1, tert-butyl 4-(4-(3-(2-chloroquinolin-4-yl)pyrazolo[1,5-a]pyrimidin-6-yl)phenyl)piperazine-1-carboxylate was obtained from the reaction of 4-(6-bromopyrazolo[1,5-a]pyrimidin-3-yl)-2-chloroquinoline (0.95 g, 2.64 mmol) and (4-(4-(tert-butoxycarbonyl)piperazin-1-yl)phenyl)boronic acid in a 80% yield.

Scheme 30

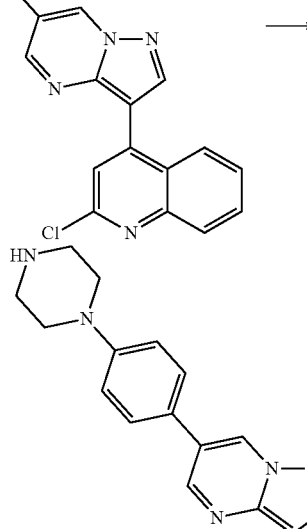

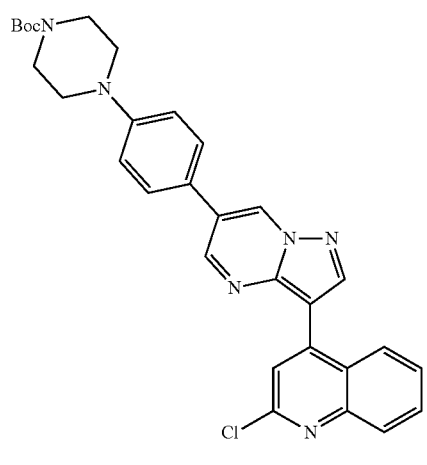
(8)

In an analogous manner to Scheme 2, 2-chloro-4-(6-(4-(piperazin-1-yl)phenyl)pyrazolo[1,5-a]pyrimidin-3-yl)quinoline, TFA was obtained from tert-butyl 4-(4-(3-(2-chloroquinolin-4-yl)pyrazolo[1,5-a]pyrimidin-6-yl)phenyl)piperazine-1-carboxylate in a 95% yield. $^1$H NMR (400 MHz, DMSO-d$_6$) δ 9.62 (d, J=2.2 Hz, 1H), 9.15 (d, J=2.2 Hz, 1H), 8.81 (s, 1H), 8.73 (s, 2H), 8.32-8.24 (m, 1H), 8.04 (dd, J=8.4, 1.2 Hz, 1H), 7.93-7.80 (m, 4H), 7.69 (ddd, J=8.3, 6.9, 1.3 Hz, 1H), 7.21-7.12 (m, 2H), 3.46 (dd, J=6.7, 3.8 Hz, 4H), 3.26 (d, J=6.9 Hz, 4H).

Compound 9

Scheme 31

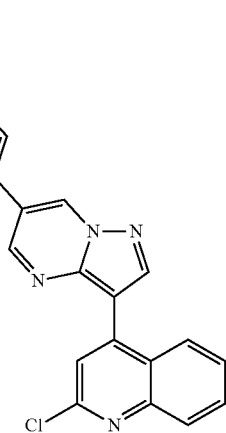

-continued

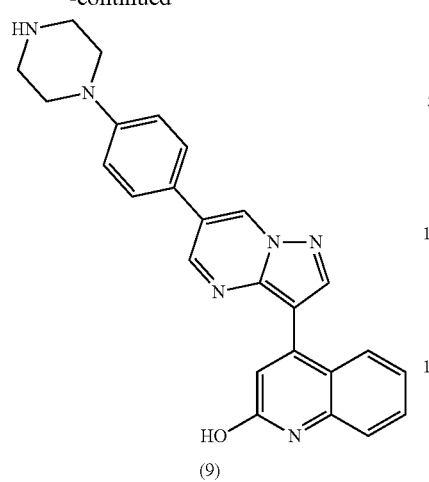

(9)

In a capped microwave tube, tert-butyl 4-(4-(3-(2-chloroquinolin-4-yl)pyrazolo[1,5-a]pyrimidin-6-yl)phenyl)piperazine-1-carboxylate was heated with 6 N aq. HCl for 72 hours. After removal of solvent and reverse phase purification 4-(6-(4-(piperazin-1-yl)phenyl)pyrazolo[1,5-a]pyrimidin-3-yl)quinolin-2-ol, TFA was obtained in 40% yield. $^1$H NMR (400 MHz, DMSO-$d_6$) δ 11.85-11.80 (m, 1H), 9.56 (d, J=2.2 Hz, 1H), 9.06 (d, J=2.2 Hz, 1H), 8.72 (s, 2H), 8.63 (s, 1H), 7.86-7.75 (m, 3H), 7.55 (ddd, J=8.4, 7.1, 1.3 Hz, 1H), 7.41 (dd, J=8.4, 1.1 Hz, 1H), 7.22-7.12 (m, 3H), 6.76 (d, J=2.0 Hz, 1H), 3.46 (t, J=5.2 Hz, 4H), 3.27 (s, 4H).

Compound 10

Scheme 32

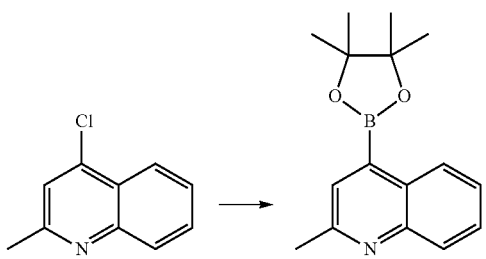

Bubbled N2 though a solution of 4-chloro-2-methylquinoline (0.888 g, 5 mmol) and 4,4,4',4',5,5,5',5'-octamethyl-2,2'-bi(1,3,2-dioxaborolane) (1.524 g, 6.00 mmol) in THF (Volume: 16 ml) for 3 min. Added tris(dibenzylidineacetone)dipalladium (0.114 g, 0.125 mmol) then [1,1'-biphenyl]-2-yldicyclohexylphosphine (0.175 g, 0.500 mmol) then bubbled N$_2$ through mixture for 5 min. Added potassium acetate (1.080 g, 11.00 mmol) then bubbled N$_2$ through for 2 min. Capped vial and heated in 80 degree bath for 3.5 h. Cooled and partitioned between water and ethyl acetate (60 mL each). Washed organic layer with brine, filtered through Celite, dried (MgSO$_4$), filtered and concentrated. Used as is.

Scheme 33

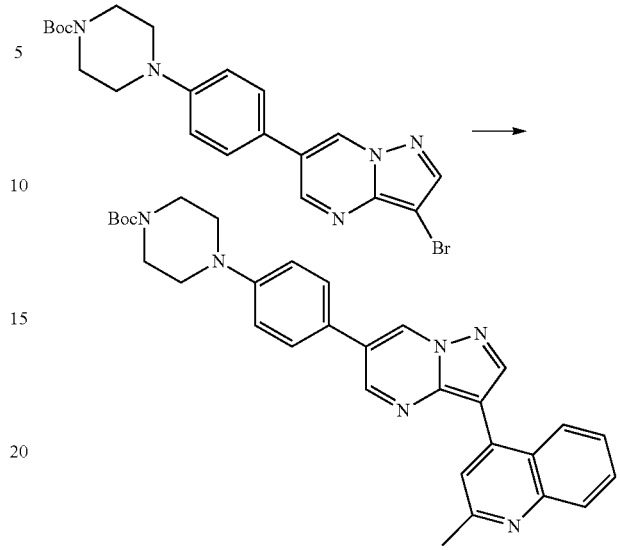

In an analogous manner to Scheme 5, tert-butyl 4-(4-(3-(2-methylquinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)phenyl)piperazine-1-carboxylate and 2-methyl-4-(4,4,5,5-tetramethyl-1,3,2-dioxaborolan-2-yl) in a 77% yield.

Scheme 34

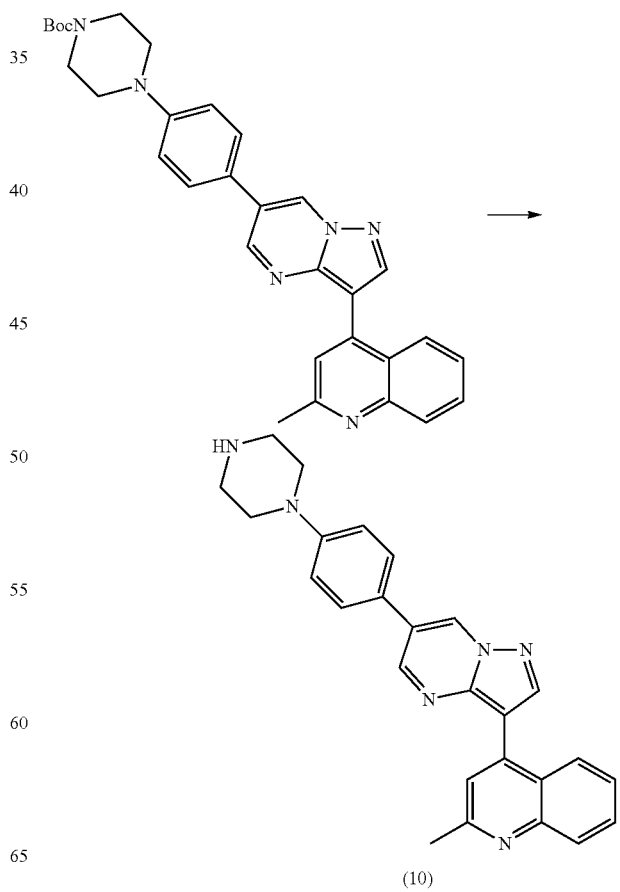

(10)

In an analogous manner to Scheme 2, 2-methyl-4-(6-(4-(piperazin-1-yl)phenyl)pyrazolo[1,5-a]pyrimidin-3-yl)quinoline, TFA was obtained from tert-butyl 4-(4-(3-(2-methylquinolin-4-yl)pyrazolo[1,5-a]pyrimidin-6-yl)phenyl)piperazine-1-carboxylate in a 92% yield. $^1$H NMR (400 MHz, DMSO-d$_6$) δ 9.67 (d, J=2.3 Hz, 1H), 9.18 (d, J=2.3 Hz, 1H), 8.86 (s, 1H), 8.80 (s, 2H), 8.39 (d, J=4.3 Hz, 1H), 8.13 (d, J=8.4 Hz, 1H), 8.06 (s, 1H), 7.98 (t, J=7.6 Hz, 1H), 7.89-7.81 (m, 2H), 7.75 (t, J=7.7 Hz, 1H), 7.21-7.14 (m, 2H), 3.47 (t, J=5.2 Hz, 4H), 3.28 (d, J=5.4 Hz, 4H), 2.86 (s, 3H).

Compound 11

Scheme 35

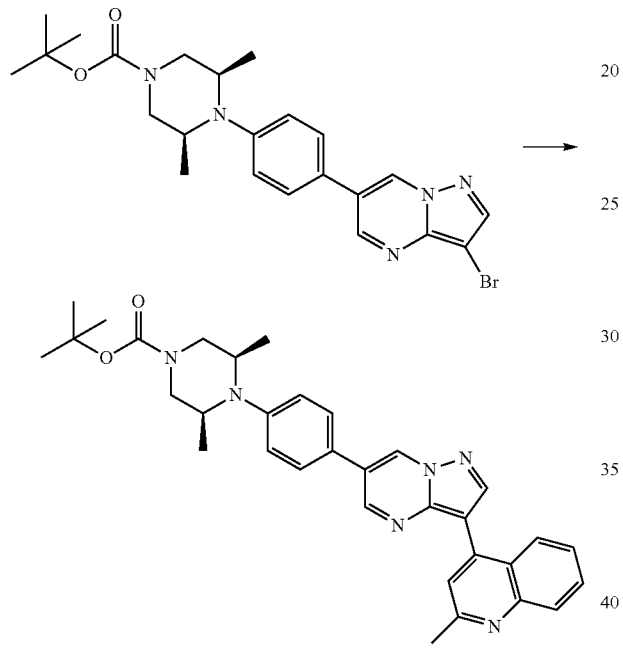

In an analogous manner to Scheme 5, (3R,5S)-tert-butyl 3,5-dimethyl-4-(4-(3-(2-methylquinolin-4-yl)pyrazolo[1,5-a]pyrimidin-6-yl)phenyl)piperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate and 2-methyl-4-(4,4,5,5-tetramethyl-1,3,2-dioxaborolan-2-yl) in a 75% yield.

Scheme 36

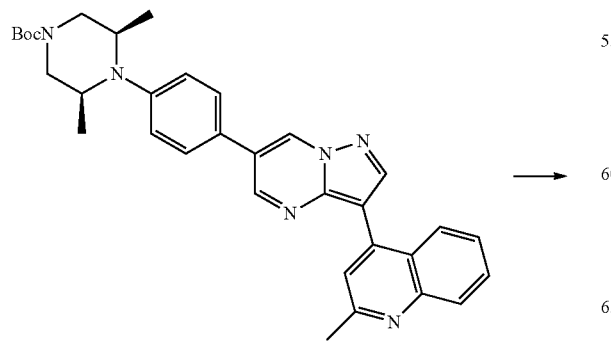

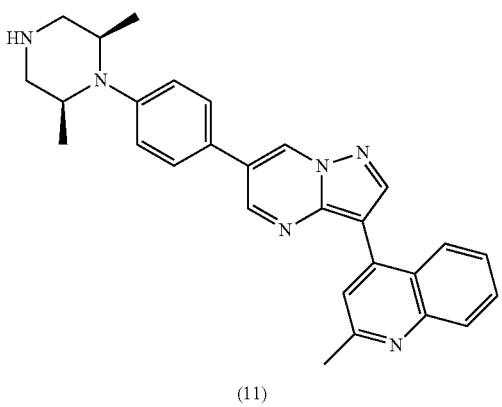

(11)

In an analogous manner to Scheme 2, 4-(6-(4-((2R,6S)-2,6-dimethylpiperazin-1-yl)phenyl)pyrazolo[1,5-a]pyrimidin-3-yl)-2-methylquinoline, TFA was obtained from (3R,5S)-tert-butyl 3,5-dimethyl-4-(4-(3-(2-methylquinolin-4-yl)pyrazolo[1,5-a]pyrimidin-6-yl)phenyl)piperazine-1-carboxylate in a 93% yield. $^1$H NMR (400 MHz, DMSO-d$_6$) δ 9.74 (d, J=2.2 Hz, 1H), 9.21 (d, J=2.2 Hz, 1H), 9.12 (d, J=10.7 Hz, 1H), 9.04 (s, 1H), 8.90 (s, 1H), 8.44-8.37 (m, 1H), 8.15 (d, J=8.5 Hz, 1H), 8.08 (s, 1H), 8.04-7.90 (m, 3H), 7.77 (t, J=7.7 Hz, 1H), 7.33-7.25 (m, 2H), 3.51-3.34 (m, 4H), 2.95-2.82 (m, 5H), 0.84 (d, J=6.2 Hz, 6H).

Compound 12

Scheme 37

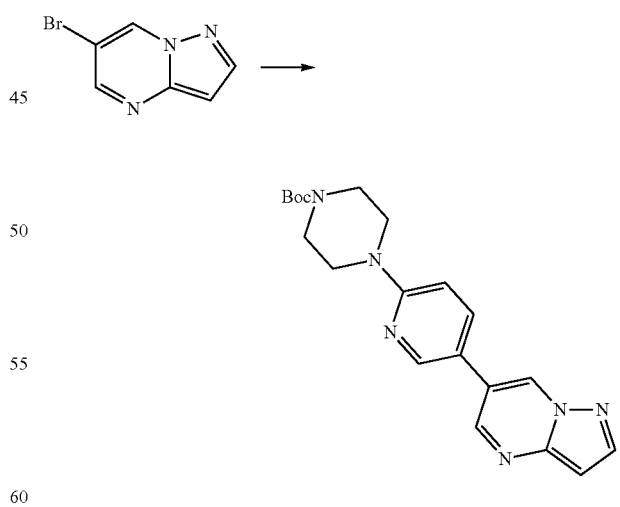

In an analogous manner to Scheme 1, tert-butyl 4-(5-(pyrazolo[1,5-a]pyrimidin-6-yl)pyridin-2-yl)piperazine-1-carboxylate was produced from 6-bromopyrazolo[1,5-a]pyrimidine and tert-butyl 4-(5-(4,4,5,5-tetramethyl-1,3,2-dioxaborolan-2-yl)pyridin-2-yl)piperazine-1-carboxylate in a 61% yield.

Scheme 38

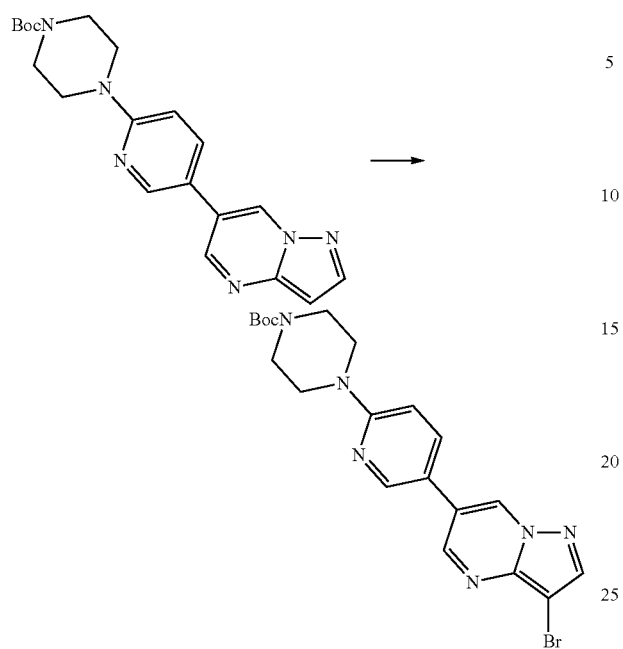

In an analogous manner to Scheme 4, tert-butyl 4-(5-(3-bromopyrazolo[1,5-a]pyrimidin-6-yl)pyridin-2-yl)piperazine-1-carboxylate was produced from tert-butyl 4-(5-(pyrazolo[1,5-a]pyrimidin-6-yl)pyridin-2-yl)piperazine-1-carboxylate in a 71% yield.

Scheme 39

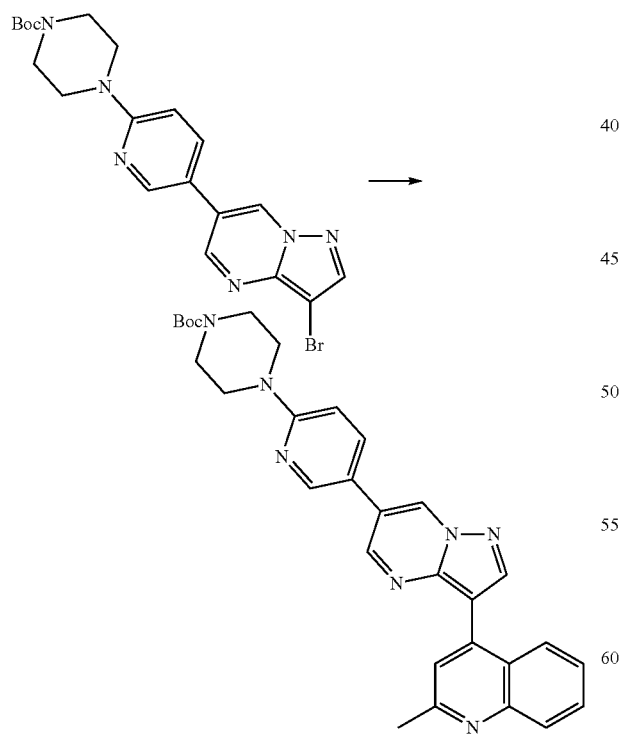

In an analogous manner to Scheme 5, tert-butyl 4-(5-(3-(2-methylquinolin-4-yl)pyrazolo[1,5-a]pyrimidin-6-yl)pyridin-2-yl)piperazine-1-carboxylate was produced from tert-butyl 4-(5-(3-bromopyrazolo[1,5-a]pyrimidin-6-yl)pyridin-2-yl)piperazine-1-carboxylate and 2-methyl-4-(4,4,5,5-tetramethyl-1,3,2-dioxaborolan-2-yl)quinoline in a 41% yield.

Scheme 40

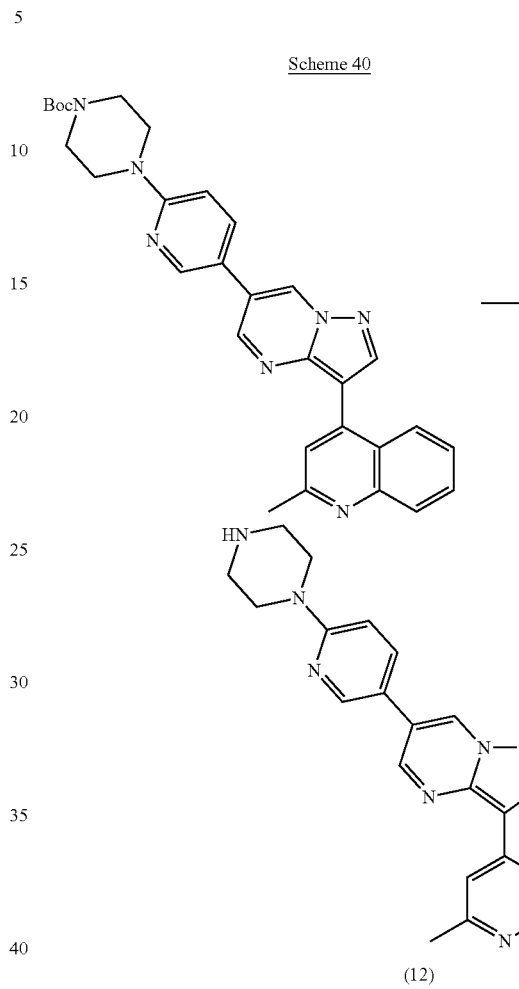

(12)

In an analogous manner to Scheme 2, 2-methyl-4-(6-(6-(piperazin-1-yl)pyridin-3-yl)pyrazolo[1,5-a]pyrimidin-3-yl)quinoline, TFA was produced from tert-butyl 4-(5-(3-(2-methylquinolin-4-yl)pyrazolo[1,5-a]pyrimidin-6-yl)pyridin-2-yl)piperazine-1-carboxylate in a 94% yield. $^1$H NMR (400 MHz, DMSO-d$_6$) δ 9.74 (d, J=2.2 Hz, 1H), 9.21 (d, J=2.2 Hz, 1H), 8.94-8.87 (m, 3H), 8.74 (d, J=2.5 Hz, 1H), 8.43 (d, J=8.4 Hz, 1H), 8.24-7.97 (m, 4H), 7.83-7.68 (m, 1H), 7.13 (d, J=9.0 Hz, 1H), 3.83 (s, 3H), 3.24 (d, J=5.7 Hz, 4H), 2.88 (s, 4H).

Compound 13

Scheme 41

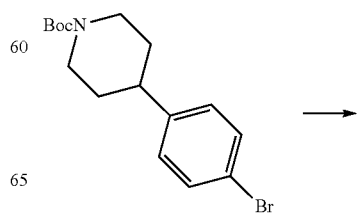

-continued

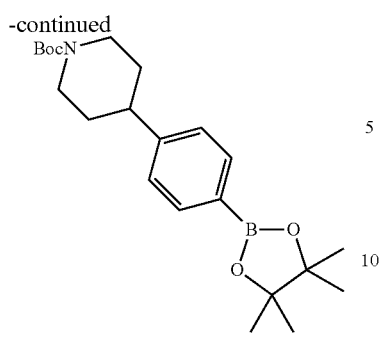

In an analogous manner to Scheme 32, ter t-butyl 4-(4-(4,4,5,5-tetramethyl-1,3,2-dioxaborolan-2-yl)phenyl)piperidine-1-carboxylate was produced from tert-butyl 4-(4-bromophenyl)piperidine-1-carboxylate and 4,4,4',4',5,5,5',5'-octamethyl-2,2'-bi(1,3,2-dioxaborolane).

Scheme 42

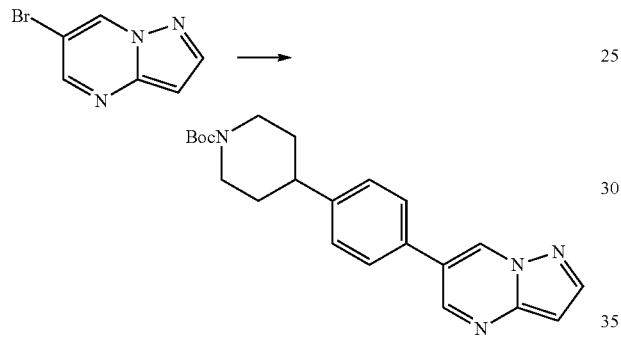

In an analogous manner to Scheme 1, tert-butyl 4-(4-(pyrazolo[1,5-a]pyrimidin-6-yl)phenyl)piperidine-1-carboxylate was produced from 6-bromopyrazolo[1,5-a]pyrimidine and tert-butyl 4-(4-(4,4,5,5-tetramethyl-1,3,2-dioxaborolan-2-yl)phenyl)piperidine-1-carboxylate in a 65% yield.

Scheme 43

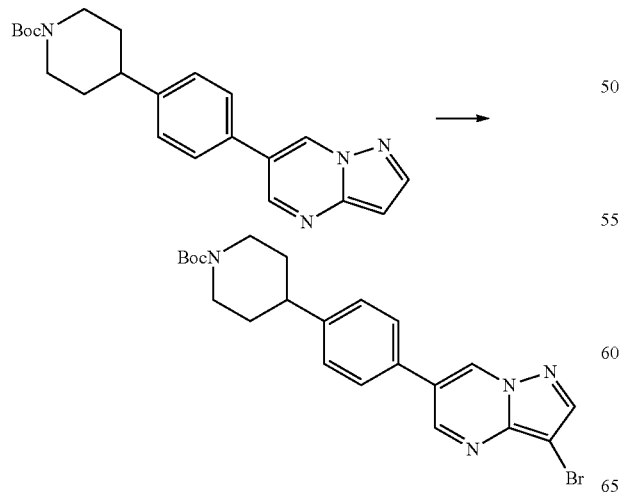

In an analogous manner to Scheme 4, tert-butyl 4-(4-(3-bromopyrazolo[1,5-a]pyrimidin-6-yl)phenyl)piperidine-1-carboxylate was produced from tert-butyl 4-(4-(pyrazolo[1,5-a]pyrimidin-6-yl)phenyl)piperidine-1-carboxylate in a 91% yield.

Scheme 44

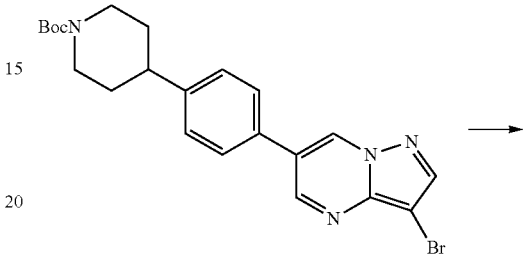

In an analogous manner to Scheme 5, tert-butyl 4-(4-(3-(2-methylquinolin-4-yl)pyrazolo[1,5-a]pyrimidin-6-yl)phenyl)piperidine-1-carboxylate was produced from tert-butyl 4-(4-(3-bromopyrazolo[1,5-a]pyrimidin-6-yl)phenyl)piperidine-1-carboxylate and 2-methyl-4-(4,4,5,5-tetramethyl-1,3,2-dioxaborolan-2-yl)quinoline in a 62% yield.

Scheme 45

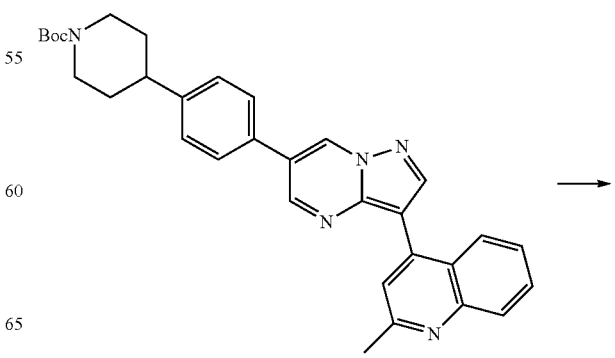

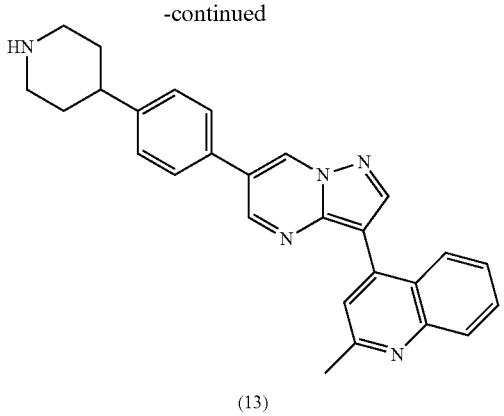

(13)

In an analogous manner to Scheme 2, 2-methyl-4-(6-(6-(piperazin-1-yl)pyridin-3-yl)pyrazolo[1,5-a]pyrimidin-3-yl)quinoline, TFA was produced from tert-butyl 4-(5-(3-(2-methylquinolin-4-yl)pyrazolo[1,5-a]pyrimidin-6-yl)pyridin-2-yl)piperazine-1-carboxylate in a 92% yield. $^1$H NMR (400 MHz, DMSO-$d_6$) δ 9.72 (d, J=2.3 Hz, 1H), 9.19 (d, J=2.2 Hz, 1H), 8.90 (s, 1H), 8.74 (d, J=11.2 Hz, 1H), 8.52 (d, J=11.8 Hz, 1H), 8.41 (d, J=8.5 Hz, 1H), 8.16 (d, J=8.5 Hz, 1H), 8.12-7.84 (m, 4H), 7.82-7.68 (m, 1H), 7.47-7.39 (m, 2H), 3.42 (d, J=12.4 Hz, 2H), 3.12-2.81 (m, 6H), 2.04-1.95 (m, 2H), 1.86 (qd, J=13.5, 4.2 Hz, 2H).

Compound 14

Scheme 63

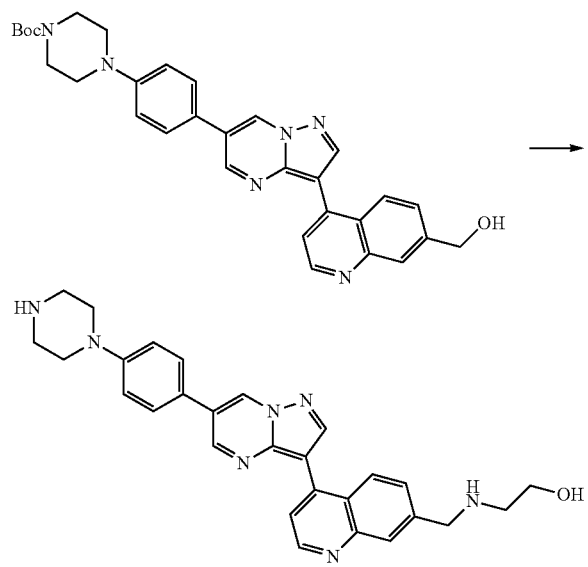

Suspended tert-butyl 4-(4-(3-(7-(hydroxymethyl)quinolin-4-yl)pyrazolo[1,5-a]pyrimidin-6-yl)phenyl)piperazine-1-carboxylate (0.054 g, 0.101 mmol) in DCM (4 mL) then added dropwise a 1 M solution of triethylamine in DCM (0.4 mL, 0.400 mmol). Added dropwise a 1 M solution of methanesulfonyl chloride in DCM (0.30 mL, 0.300 mmol). Stirred for 5 minutes (became clear yellow solution) then added 5 drops of ethanolamine. Heated in 50 deg bath for 45 min. LC/MS showed complete conversion to amine. Evaporated solvent then added 2 mL TFA, stirred for 5 min, evaporated solvent. Obtained 2-(((4-(6-(4-(piperazin-1-yl)phenyl)pyrazolo[1,5-a]pyrimidin-3-yl)quinolin-7-yl)methyl)amino)ethanol, 2 TFA (0.033 g, 0.047 mmol, 46.6% yield) after reverse phase chromatography. $^1$H NMR (400 MHz, DMSO-$d_6$) δ 9.61 (d, J=2.3 Hz, 1H), 9.10-9.00 (m, 4H), 8.73 (s, 3H), 8.32-8.25 (m, 2H), 7.91-7.80 (m, 3H), 7.73 (dd, J=8.8, 1.8 Hz, 1H), 7.20-7.13 (m, 2H), 4.45 (t, J=5.6 Hz, 2H), 3.70 (t, J=5.4 Hz, 2H), 3.46 (t, J=5.2 Hz, 4H), 3.28 (s, 4H), 3.07 (s, 2H).

Compound 15

Scheme 52

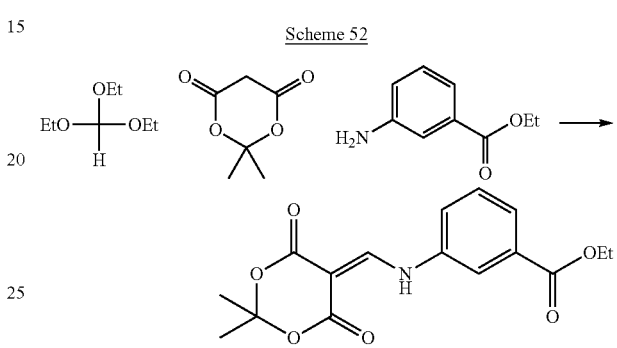

In an analogous manner to Scheme 46, ethyl 3-((2,2-dimethyl-4,6-dioxo-1,3-dioxan-5-ylidene)methylamino)benzoate was produced from ethyl 3-aminobenzoate, triethylorthoformate and 2,2-dimethyl-1,3-dioxane-4,6-dione in a 88% yield.

Scheme 53

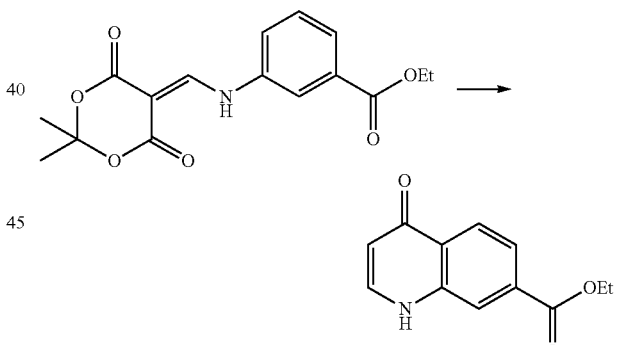

In an analogous manner to Scheme 47, ethyl 4-oxo-1,4-dihydroquinoline-7-carboxylate was produced from ethyl 3-((2,2-dimethyl-4,6-dioxo-1,3-dioxan-5-ylidene)methylamino)benzoate in an 89% yield.

Scheme 54

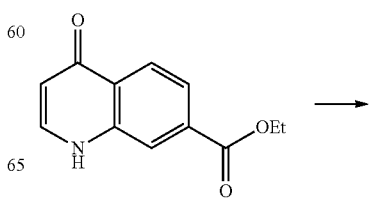

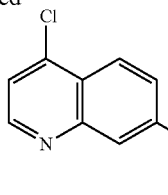

In an analogous manner to Scheme 48, ethyl 4-chloroquinoline-7-carboxylate was produced from ethyl 4-oxo-1,4-dihydroquinoline-7-carboxylate in a 55% yield.

Scheme 55

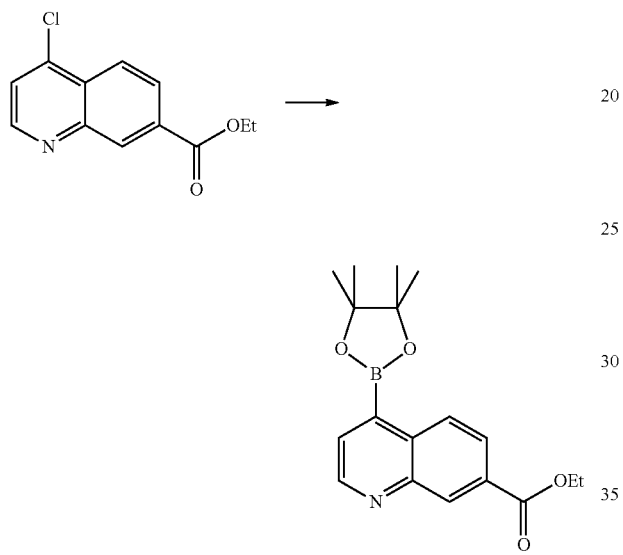

In an analogous manner to Scheme 32, ethyl 4-(4,4,5,5-tetramethyl-1,3,2-dioxaborolan-2-yl)quinoline-7-carboxylate was produced from ethyl 4-chloroquinoline-7-carboxylate.

Scheme 56

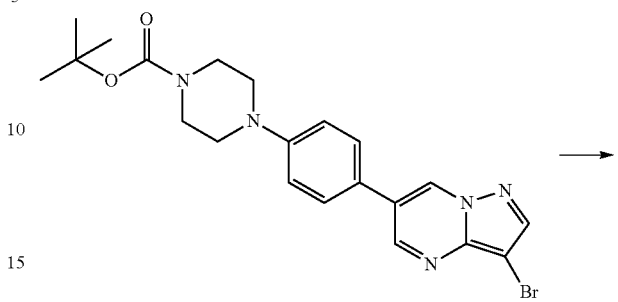

In an analogous manner to Scheme 5, ethyl 4-(6-(4-(4-(tert-butoxycarbonyl)piperazin-1-yl)phenyl)pyrazolo[1,5-a]pyrimidin-3-yl)quinoline-7-carboxylate was produced from ethyl 4-(4,4,5,5-tetramethyl-1,3,2-dioxaborolan-2-yl)quinoline-7-carboxylate in a 75% yield.

Scheme 57

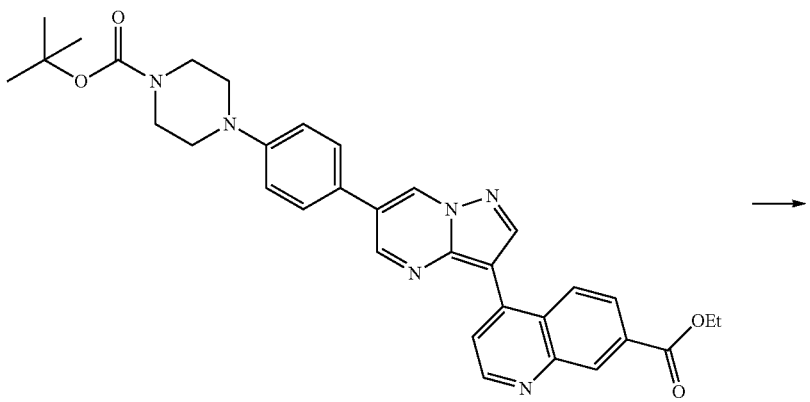

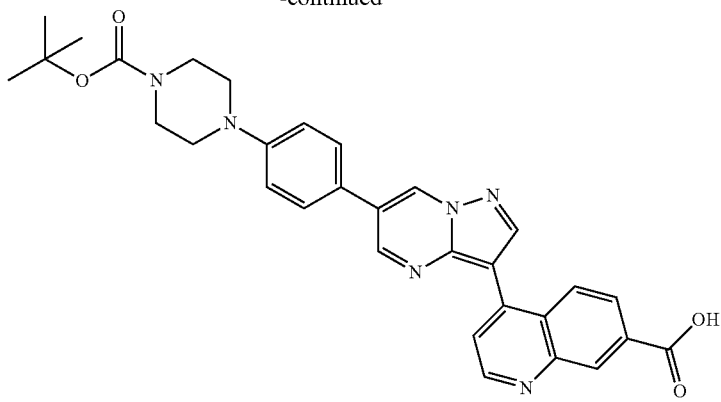

To a solution of ethyl 4-(6-(4-(4-(tert-butoxycarbonyl)piperazin-1-yl)phenyl)pyrazolo[1,5-a]pyrimidin-3-yl)quinoline-7-carboxylate (0.20 g, 0.35 mmol) in THF/water (1:1, 78 mL) was added dropwise a solution of LiOH (83 mg, 3.5 mmol) in water (2 mL). After 30 min, the reaction was partitioned between ethyl acetate and 10% citric acid (25 mL each). The organic layer was washed with water, brine, dried (MgSO$_4$) and filtered to obtain 4-(6-(4-(4-(tert-butoxycarbonyl)piperazin-1-yl)phenyl)pyrazolo[1,5-a]pyrimidin-3-yl)quinoline-7-carboxylic acid (0.18 g, 95%).

Scheme 58

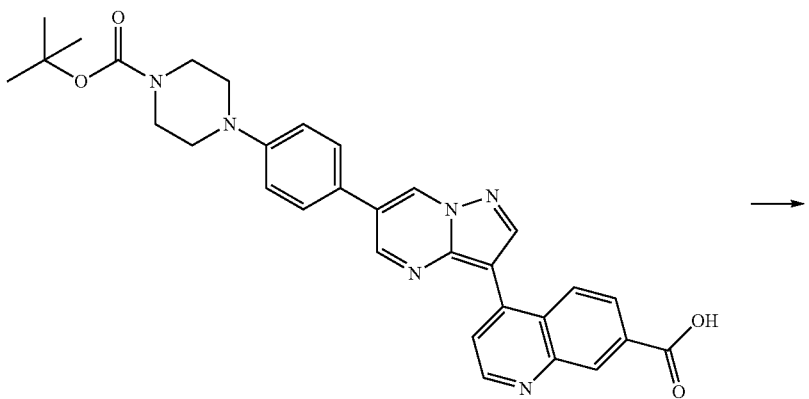

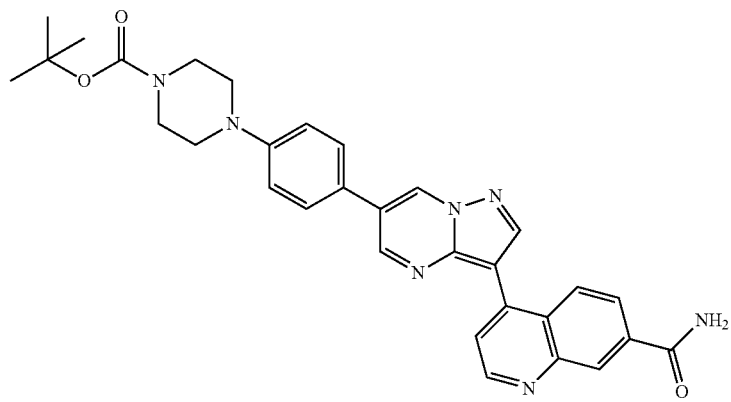

Suspended 4-(6-(4-(4-(tert-butoxycarbonyl)piperazin-1-yl)phenyl)pyrazolo[1,5-a]pyrimidin-3-yl)quinoline-7-carboxylic acid, (0.055 g, 0.100 mmol) in DCM (3 mL). Added triethylamine (0.056 mL, 0.402 mmol). Added HATU (0.057 g, 0.151 mmol). Added DMF (1 mL). Suspension became solution. Stirred for 30 min then bubbled NH₃ gas through solution for 5 min. Precipitate formed. Removed DCM the diluted with water (20 mL), filtered and washed solid with water and dried. Obtained tert-butyl 4-(4-(3-(7-carbamoylquinolin-4-yl)pyrazolo[1,5-a]pyrimidin-6-yl)phenyl)piperazine-1-carboxylate in 53% yield.

Scheme 59

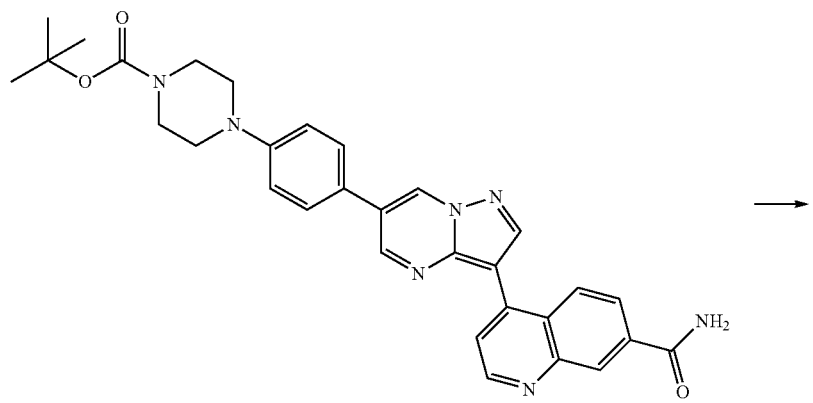

In an analogous manner to Scheme 2, 4-(6-(4-(piperazin-1-yl)phenyl)pyrazolo[1,5-a]pyrimidin-3-yl)quinoline-7-carboxamide, TFA was obtained from tert-butyl 4-(4-(3-(7-carbamoylquinolin-4-yl)pyrazolo[1,5-a]pyrimidin-6-yl)phenyl)piperazine-1-carboxylate in 92% yield. ¹H NMR (400 MHz, DMSO-d₆) δ 9.61 (d, J=2.3 Hz, 1H), 9.12-9.03 (m, 2H), 8.77 (s, 3H), 8.65 (d, J=1.8 Hz, 1H), 8.37-8.25 (m, 2H), 8.06 (dd, J=8.8, 1.9 Hz, 1H), 7.92 (d, J=4.6 Hz, 1H), 7.88-7.79 (m, 2H), 7.62 (s, 1H), 7.24-7.12 (m, 2H), 3.46 (dd, J=6.6, 3.8 Hz, 4H), 3.27 (s, 4H).

Compound 16

Scheme 60

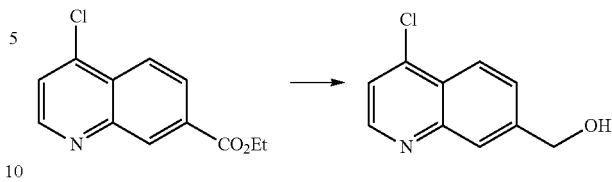

A solution of Boron trifluoride ether complex (0.277 mL, 2.184 mmol) in THF (60 mL) was added to a solution of ethyl 4-chloroquinoline-7-carboxylate (1.17 g, 4.96 mmol) in THF (100 mL) to which Sodium borohydride (0.263 mL, 7.45 mmol) had been added. The mixture was heated to reflux for 2 hours, then cooled in an ice bath. The reaction was quenched with addition of water (30 mL) and stirred vigorously for 10 min. The THF was removed in vacuo and the product was extracted into CH₂Cl₂. The organic layer was washed with brine, dried (MgSO₄), filtered and concentrated to yield (4-chloroquinolin-7-yl)methanol (0.857 g, 4.43 mmol, 89% yield) as an off-white solid.

Scheme 61

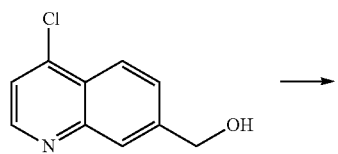

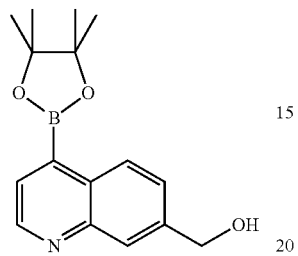

In an analogous manner to Scheme 32, crude (4-(4,4,5,5-tetramethyl-1,3,2-dioxaborolan-2-yl)quinolin-7-yl)methanol was obtained from (4-chloroquinolin-7-yl)methanol.

In an analogous manner to Scheme 5, tert-butyl 4-(4-(3-(7-(hydroxymethyl)quinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)phenyl)piperazine-1-carboxylate and (4-(4,4,5,5-tetramethyl-1,3,2-dioxaborolan-2-yl)quinolin-7-yl)methanol in an 81% yield.

Scheme 62b

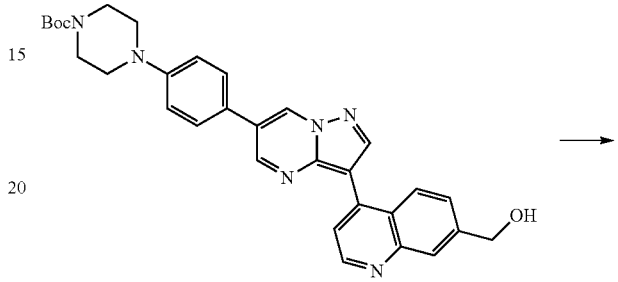

Scheme 62a

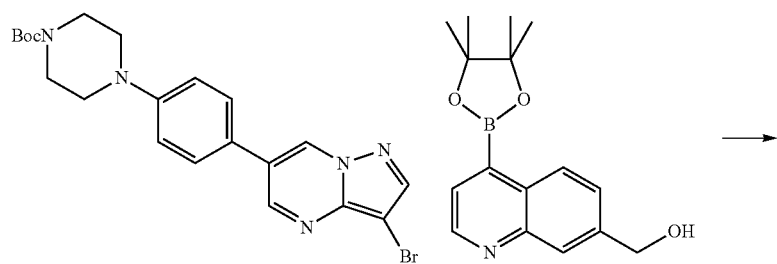

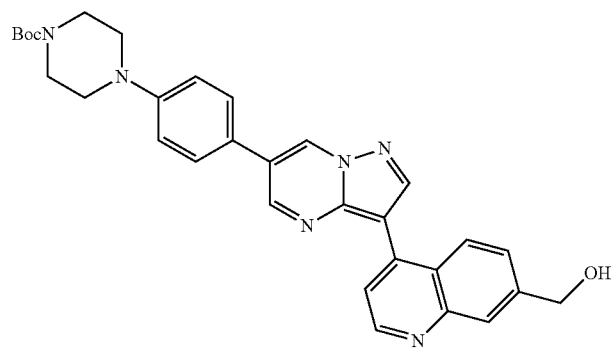

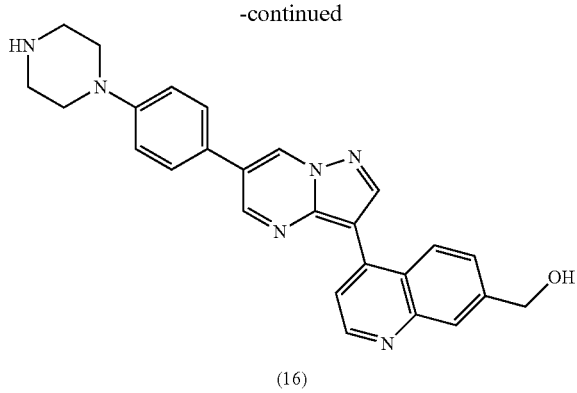

(16)

In an analogous manner to Scheme 2, (4-(6-(4-(piperazin-1-yl)phenyl)pyrazolo[1,5-a]pyrimidin-3-yl)quinolin-7-yl)methanol, TFA was obtained from tert-butyl 4-(4-(3-(7-(hydroxymethyl)quinolin-4-yl)pyrazolo[1,5-a]pyrimidin-6-yl)phenyl)piperazine-1-carboxylate in in a 78% yield. ¹H NMR (400 MHz, DMSO-d₆) δ 9.65 (d, J=2.3 Hz, 1H), 9.15 (d, J=2.3 Hz, 1H), 9.07 (d, J=5.2 Hz, 1H), 8.85 (s, 1H), 8.75 (s, 2H), 8.35 (d, J=8.7 Hz, 1H), 8.11 (d, J=1.6 Hz, 1H), 8.05 (s, 1H), 7.89-7.80 (m, 2H), 7.72-7.65 (m, 1H), 7.21-7.14 (m, 2H), 4.80 (s, 2H), 3.47 (t, J=5.2 Hz, 4H), 3.27 (s, 4H).

Compound 17

Scheme 46

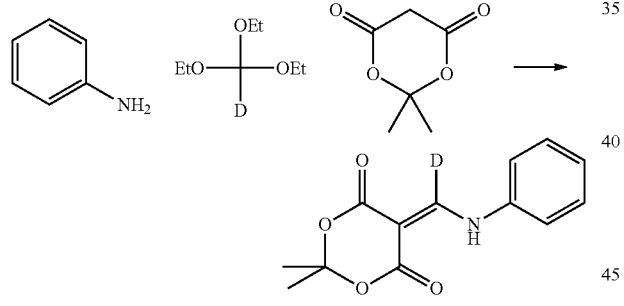

To a solution of aniline (0.316 g, 3.39 mmol) and 2,2-dimethyl-1,3-dioxane-4,6-dione (0.538 g, 3.73 mmol) in ethanol (7 mL) was added 2,2-dimethyl-1,3-dioxane-4,6-dione (0.538 g, 3.73 mmol). The mixture was heated to reflux for 1.5 hours. The mixture was cooled in an ice/water bath upon which solid crystallized. The solid was collected and washed with cold ethanol then dried to yield 2,2-dimethyl-5-((phenylamino)(2H)methylene)-1,3-dioxane-4,6-dione (0.733 g, 2.95 mmol, 87% yield).

Scheme 47

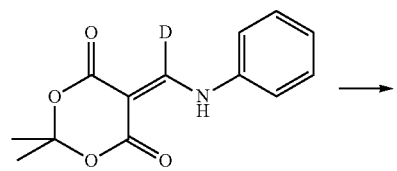

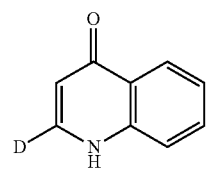

To diphenylether (8 mL) heated to 250 degrees was added solid 2,2-dimethyl-5-((phenylamino)(2H)methylene)-1,3-dioxane-4,6-dione (0.73 g, 2.94 mmol). After 4 minutes, the mixture was removed from heat and was allowed to come to room temperature. The precipitate that formed was filtered and washed with hexanes and dried to afford 2-(2H)quinoline-4(1H)-one (0.183 g, 1.252 mmol, 42.6% yield) as a tan solid.

Scheme 48

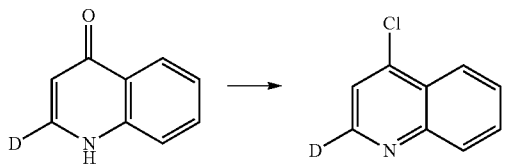

Heated 2-(2H)quinoline-4(1H)-one (0.182 g, 1.245 mmol) in phosphorus(V)oxychloride (3 mL) at reflux for 1 hour. Poured over ice water (60 mL) then added sodium bicarbonate (8 g) to neutralize excess reagent. Extracted with dichloromethane (50 mL), washed organic layer with water, brine, dried (MgSO₄), filtered and concentrated. Obtained 4-chloro-2-(2H)quinoline (0.192 g, 1.166 mmol, 94% yield) as a beige solid.

Scheme 49

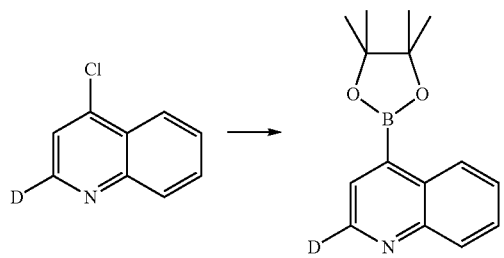

In an analogous manner to Scheme 32, 4-(4,4,5,5-tetramethyl-1,3,2-dioxaboran-2-yl)-2-(2H)quinoline was obtained from 4-chloro-2-(2H)quinoline.

Scheme 50

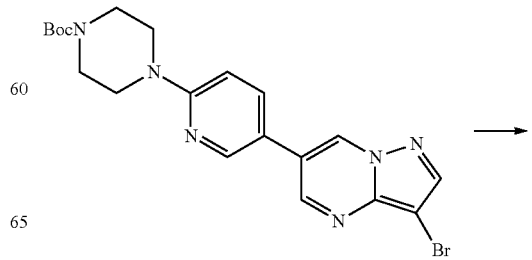

-continued

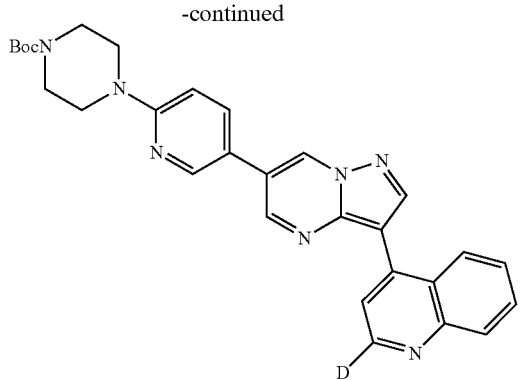

In an analogous manner to Scheme 5, tert-butyl 4-(5-(3-(2-(2H)quinolin-4-yl)pyrazolo[1,5-a]pyrimidin-6-yl)pyridin-2-yl)piperazine-1-carboxylate was produced from tert-butyl 4-(5-(3-bromopyrazolo[1,5-a]pyrimidin-6-yl)pyridin-2-yl)piperazine-1-carboxylate and 4-(4,4,5,5-tetramethyl-1,3,2-dioxaboran-2-yl)-2-(2H)-quinoline in a 61% yield.

Scheme 51

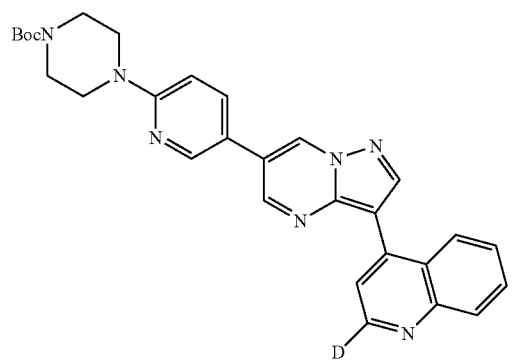

(17)

In an analogous manner to Scheme 2, 4-(6-(6-(piperazin-1-yl)pyridin-3-yl)pyrazolo[1,5-a]pyrimidin-3-yl)quinoline, TFA, was obtained from tert-butyl 4-(5-(3-(2-(2H)quinolin-4-yl)pyrazolo[1,5-a]pyrimidin-6-yl)pyridin-2-yl)piperazine-1-carboxylate in a 94% yield. ¹H NMR (400 MHz, DMSO-$d_6$) δ 9.71 (d, J=2.3 Hz, 1H), 9.15 (d, J=2.2 Hz, 1H), 8.85 (d, J=6.6 Hz, 3H), 8.73 (dd, J=2.6, 0.7 Hz, 1H), 8.40-8.33 (m, 1H), 8.23-8.14 (m, 2H), 8.04 (s, 1H), 7.95 (ddd, J=8.3, 6.9, 1.4 Hz, 1H), 7.75 (ddd, J=8.3, 6.9, 1.3 Hz, 1H), 7.12 (d, J=9.0 Hz, 1H), 3.83 (dd, J=6.3, 4.2 Hz, 4H), 3.24 (d, J=8.6 Hz, 4H).

Compound 18

Scheme 64

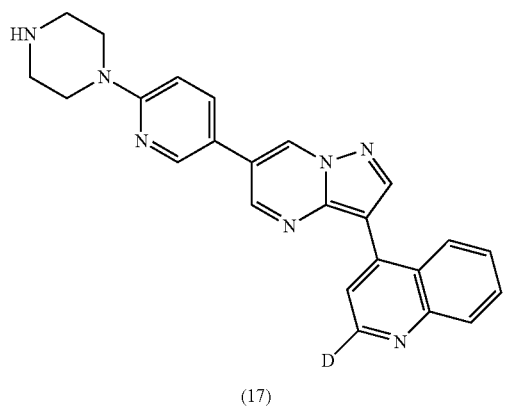

(18)

In an analogous manner to Scheme 63, N-methyl-1-(4-(6-(4-(piperazin-1-yl)phenyl)pyrazolo[1,5-a]pyrimidin-3-yl)quinolin-7-yl)methanamine, 2TFA was obtained from tert-butyl 4-(4-(3-(7-(hydroxy methyl)quinolin-4-yl)pyrazolo[1,5-a]pyrimidin-6-yl)phenyl)piperazine-1-carboxylate and a solution of methylamine in THF in 47%. ¹H NMR (400 MHz, DMSO-$d_6$) δ 9.61 (d, J=2.3 Hz, 1H), 9.10-8.96 (m, 4H), 8.79 (s, 2H), 8.74 (s, 1H), 8.34-8.23 (m, 2H), 7.92-7.79 (m, 3H), 7.69 (dd, J=8.7, 1.9 Hz, 1H), 7.20-7.13 (m, 2H), 4.42 (t, J=5.8 Hz, 2H), 3.46 (t, J=5.2 Hz, 4H), 3.28 (s, 4H), 2.66 (t, J=5.3 Hz, 3H).

Compound 19

Scheme 65

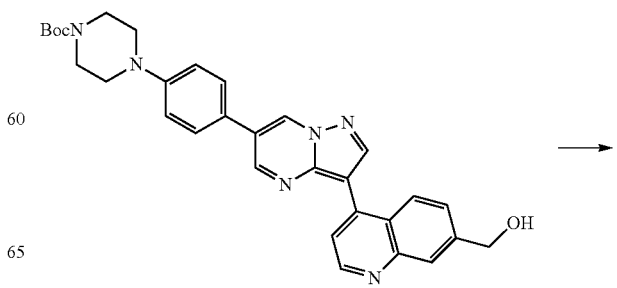

-continued

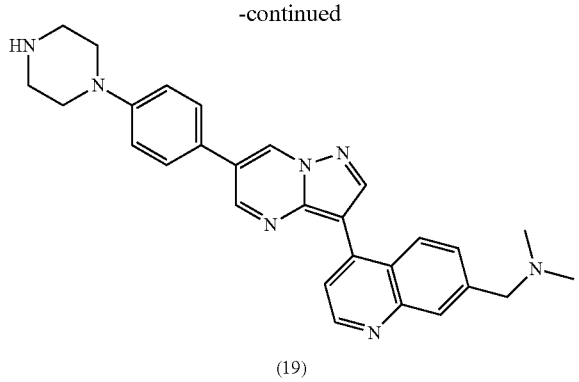

(19)

In an analogous manner to Scheme 63, N,N-dimethyl-1-(4-(6-(4-(piperazin-1-yl)phenyl)pyrazolo[1,5-a]pyrimidin-3-yl)quinolin-7-yl)methanamine, 2TFA was obtained from tert-butyl 4-(4-(3-(7-(hydroxymethyl)quinolin-4-yl)pyrazolo[1,5-a]pyrimidin-6-yl)phenyl)piperazine-1-carboxylate and and a solution of dimethyl amine in THF in 62% yield. ¹H NMR (400 MHz, DMSO-d₆) δ 9.90 (s, 1H), 9.61 (d, J=2.3 Hz, 1H), 9.11-9.01 (m, 2H), 8.74 (s, 3H), 8.36-8.26 (m, 2H), 7.93-7.80 (m, 3H), 7.71 (dd, J=8.7, 1.9 Hz, 1H), 7.20-7.13 (m, 2H), 4.56 (d, J=5.0 Hz, 2H), 3.46 (t, J=5.2 Hz, 4H), 3.27 (s, 4H), 2.83 (d, J=4.4 Hz, 6H).

Compound 20

Scheme 66

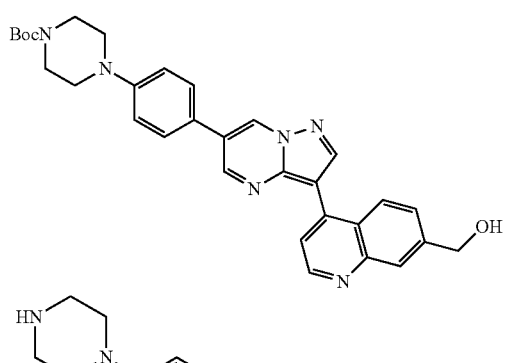

(20)

In an analogous manner to Scheme 63, (4-(6-(4-(piperazin-1-yl)phenyl)pyrazolo[1,5-a]pyrimidin-3-yl)quinolin-7-yl)methanamine, 2TFA was obtained from tert-butyl 4-(4-(3-(7-(hydroxymethyl)quinolin-4-yl)pyrazolo[1,5-a]pyrimidin-6-yl)phenyl)piperazine-1-carboxylate and ammonium hydroxide in 55% yield. ¹H NMR (400 MHz, DMSO-d₆) δ 9.61 (d, J=2.2 Hz, 1H), 9.10-8.99 (m, 2H), 8.81 (s, 2H), 8.74 (s, 1H), 8.38 (s, 3H), 8.29 (d, J=8.7 Hz, 1H), 8.25-8.19 (m, 1H), 7.92-7.79 (m, 3H), 7.69 (dd, J=8.8, 1.9 Hz, 1H), 7.20-7.13 (m, 2H), 4.33 (q, J=5.8 Hz, 2H), 3.46 (t, J=5.2 Hz, 4H), 3.28 (d, J=5.5 Hz, 4H).

Compound 21

Scheme 67

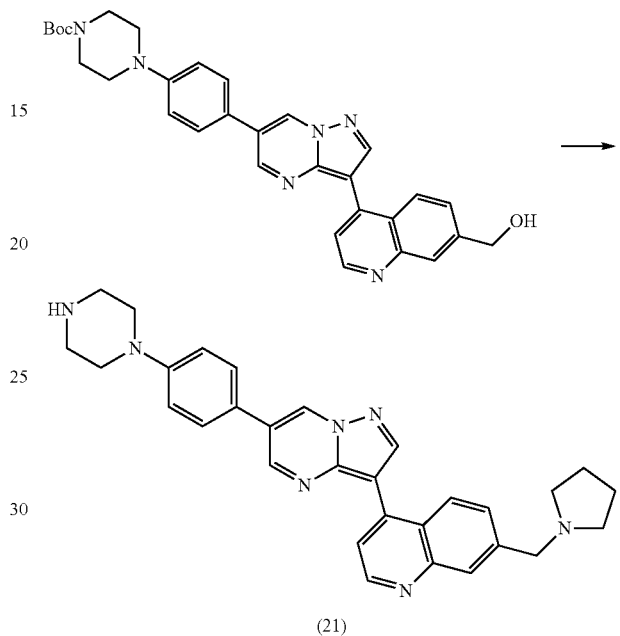

(21)

In an analogous manner to Scheme 63, 4-(6-(4-(piperazin-1-yl)phenyl)pyrazolo[1,5-a]pyrimidin-3-yl)-7-(pyrrolidin-1-ylmethyl)quinoline, 2TFA was obtained from tert-butyl 4-(4-(3-(7-(hydroxymethyl)quinolin-4-yl)pyrazolo[1,5-a]pyrimidin-6-yl)phenyl)piperazine-1-carboxylate and pyrrolidine in a 45% yield. ¹H NMR (400 MHz, DMSO-d₆) δ 10.11 (s, 1H), 9.61 (d, J=2.3 Hz, 1H), 9.11-9.02 (m, 2H), 8.83 (s, 2H), 8.74 (s, 1H), 8.36-8.29 (m, 2H), 7.91 (d, J=4.6 Hz, 1H), 7.88-7.79 (m, 2H), 7.74 (dd, J=8.7, 1.9 Hz, 1H), 7.21-7.12 (m, 2H), 4.64 (d, J=5.5 Hz, 2H), 3.50-3.41 (m, 6H), 3.28 (s, 4H), 2.09 (h, J=7.5 Hz, 2H), 1.89 (q, J=6.2 Hz, 2H).

Compound 22

Scheme 68

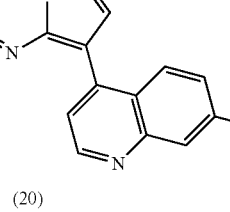

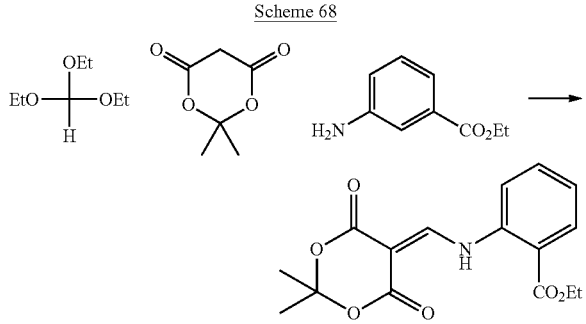

In an analogous manner to Scheme 46, ethyl 2-((2,2-dimethyl-4,6-dioxo-1,3-dioxan-5-ylidene)methylamino)benzoate was produced from ethyl 2-aminobenzoate, triethylorthoformate and 2,2-dimethyl-1,3-dioxane-4,6-dione in a 80% yield.

Scheme 69

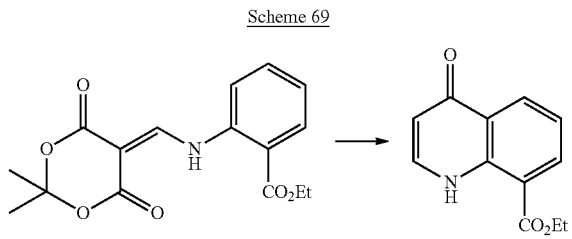 [SMILES: CCOC(=O)c1ccccc1NC=C1C(=O)OC(C)(C)OC1=O ; CCOC(=O)c1cccc2c(=O)cc[nH]c12]

In an analogous manner to Scheme 47, ethyl 4-oxo-1,4-dihydroquinoline-8-carboxylate was produced from ethyl 2-((2,2-dimethyl-4,6-dioxo-1,3-dioxan-5-ylidene)methylamino)benzoate in an 78% yield.

Scheme 70

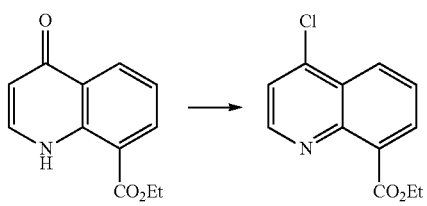

In an analogous manner to Scheme 48, ethyl 4-chloroquinoline-8-carboxylate was produced from ethyl 4-oxo-1,4-dihydroquinoline-8-carboxylate in a 68% yield.

Scheme 71

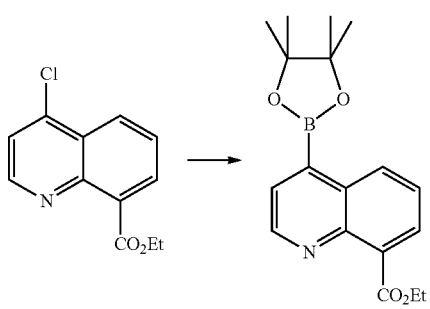

In an analogous manner to Scheme 32, ethyl 4-(4,4,5,5-tetramethyl-1,3,2-dioxaborolan-2-yl)quinoline-8-carboxylate was obtained from ethyl 4-chloroquinoline-8-carboxylate.

Scheme 72

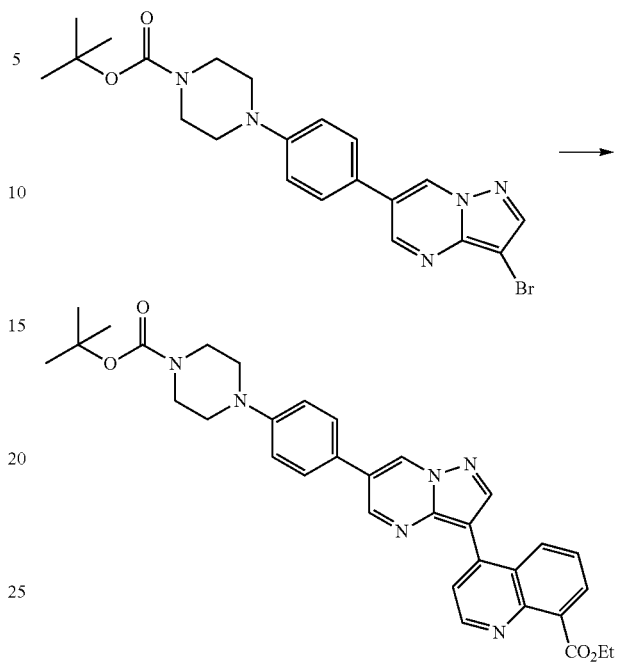

In an analogous manner to Scheme 5, ethyl 4-(6-(4-(4-(tert-butoxycarbonyl)piperazin-1-yl)phenyl)pyrazolo[1,5-a]pyrimidin-3-yl)quinoline-8-carboxylate was produced from ethyl 4-(4,4,5,5-tetramethyl-1,3,2-dioxaborolan-2-yl)quinoline-8-carboxylate in a 67% yield.

Scheme 73

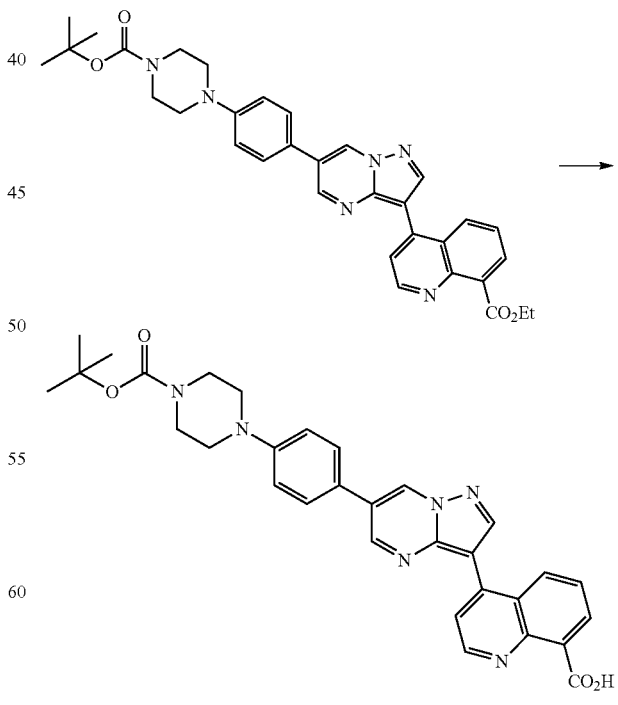

In an analogous manner to Scheme 57, obtain 4-(6-(4-(4-(tert-butoxycarbonyl)piperazin-1-yl)phenyl)pyrazolo[1,5-a]

pyrimidin-3-yl)quinoline-8-carboxylic acid was obtained from ethyl 4-(6-(4-(4-(tert-butoxycarbonyl)piperazin-1-yl)phenyl)pyrazolo[1,5-a]pyrimidin-3-yl)quinoline-7-carboxylate in 93% yield.

Scheme 74

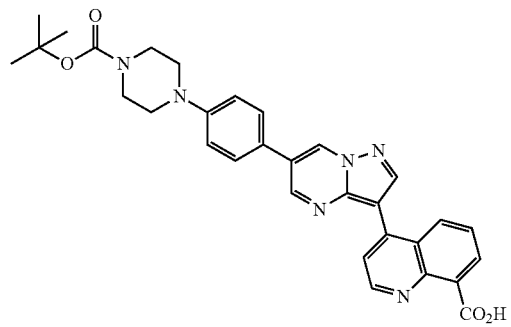

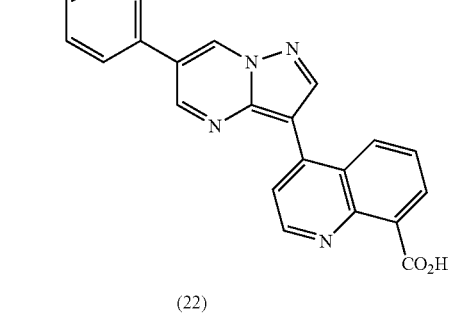

(22)

In an analogous manner to Scheme 2, 4-(6-(4-(piperazin-1-yl)phenyl)pyrazolo[1,5-a]pyrimidin-3-yl)quinoline-8-carboxylic acid, TFA was obtained from 4-(6-(4-(4-(tert-butoxycarbonyl)piperazin-1-yl)phenyl)pyrazolo[1,5-a]pyrimidin-3-yl)quinoline-8-carboxylic acid in a 38% after reverse phase purification. $^1$H NMR (400 MHz, DMSO-$d_6$) δ 9.64 (d, J=2.3 Hz, 1H), 9.20-9.11 (m, 2H), 8.83 (s, 1H), 8.76 (s, 2H), 8.70-8.57 (m, 2H), 8.11 (d, J=4.9 Hz, 1H), 7.91-7.80 (m, 3H), 7.21-7.12 (m, 2H), 3.47 (dd, J=6.7, 3.9 Hz, 4H), 3.27 (d, J=7.0 Hz, 4H).

Compound 23

Scheme 75

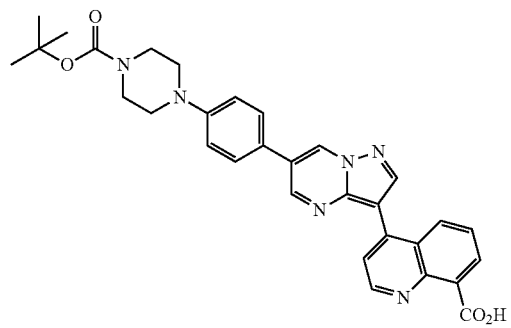

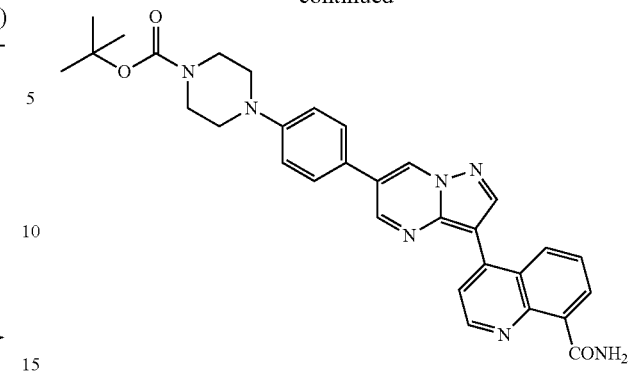

In an analogous manner to Scheme 58, tert-butyl 4-(4-(3-(8-carbamoylquinolin-4-yl)pyrazolo[1,5-a]pyrimidin-6-yl)phenyl)piperazine-1-carboxylate was obtained from 4-(6-(4-(4-(tert-butoxycarbonyl)piperazin-1-yl)phenyl)pyrazolo[1,5-a]pyrimidin-3-yl)quinoline-8-carboxylic acid in 62% yield.

Scheme 76

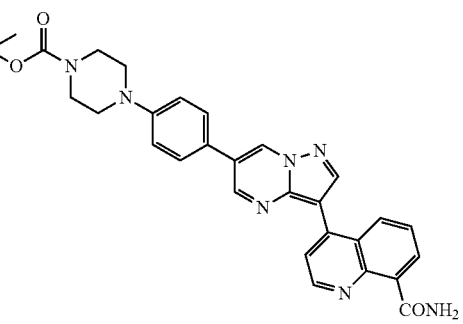

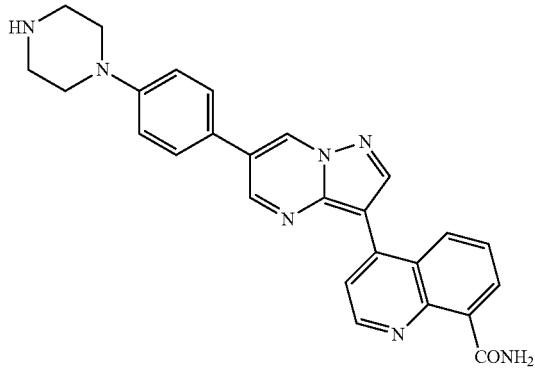

(23)

In an analogous manner to Scheme 2, 4-(6-(4-(piperazin-1-yl)phenyl)pyrazolo[1,5-a]pyrimidin-3-yl)quinoline-8-carboxamide, TFA was obtained from tert-butyl 4-(4-(3-(8-carbamoylquinolin-4-yl)pyrazolo[1,5-a]pyrimidin-6-yl)phenyl)piperazine-1-carboxylate in 82% yield. $^1$H NMR (400 MHz, DMSO-$d_6$) δ 10.20 (s, 1H), 9.62 (d, J=2.3 Hz, 1H), 9.13-9.06 (m, 2H), 8.75 (s, 3H), 8.62 (dd, J=7.3, 1.5 Hz, 1H), 8.42 (dd, J=8.4, 1.6 Hz, 1H), 7.94 (d, J=4.7 Hz, 2H), 7.88-7.80 (m, 2H), 7.75 (dd, J=8.4, 7.3 Hz, 1H), 7.20-7.13 (m, 2H), 3.46 (dd, J=6.6, 3.8 Hz, 4H), 3.28 (d, J=7.5 Hz, 4H).

Compound 24

Scheme 77

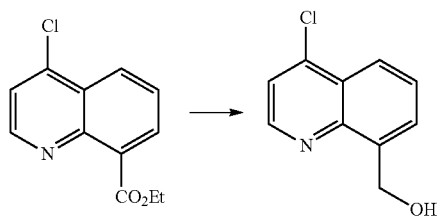

In an analogous manner to Scheme 60, (4-chloroquinolin-7-yl)methanol was obtained from ethyl 4-chloroquinoline-7-carboxylate in a, 77% yield.

Scheme 78

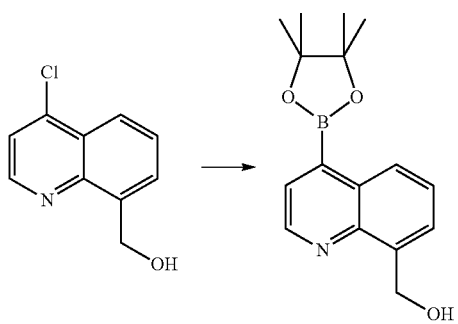

In an analogous manner to Scheme 32, (4-(4,4,5,5-tetramethyl-1,3,2-dioxaborolan-2-yl)quinolin-8-yl)methanol was obtained from (4-chloroquinolin-8-yl)methanol.

Scheme 79

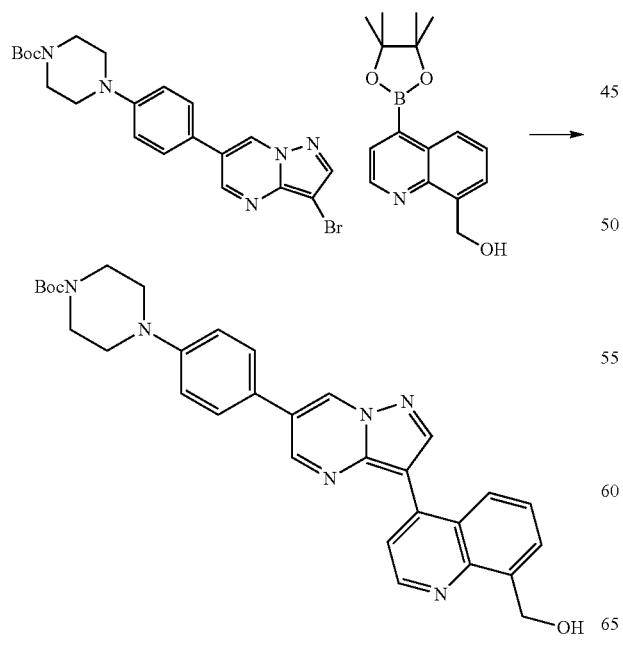

In an analogous manner to Scheme 5, tert-butyl 4-(4-(3-(8-(hydroxymethyl)quinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)phenyl)piperazine-1-carboxylate and (4-(4,4,5,5-tetramethyl-1,3,2-dioxaborolan-2-yl)quinolin-8-yl)methanol in 5.2% yield.

Scheme 80

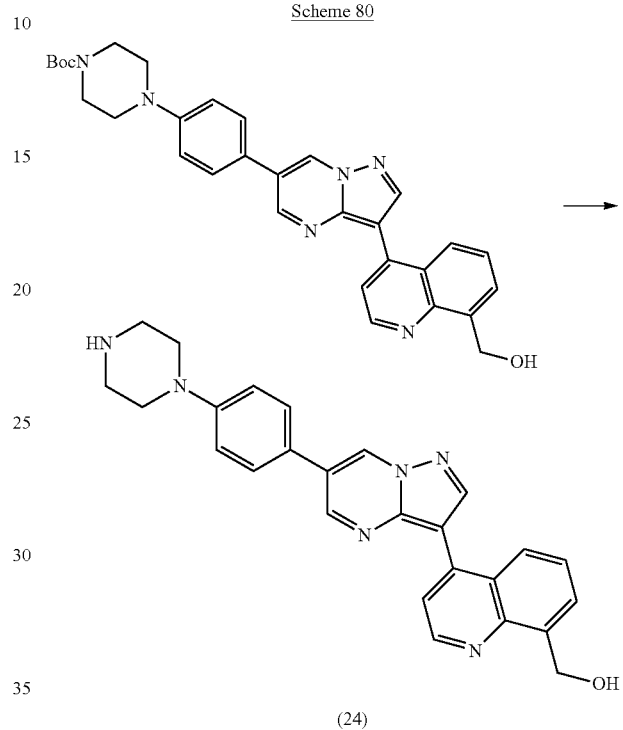

(24)

In an analogous manner to Scheme 2, (4-(6-(4-(piperazin-1-yl)phenyl)pyrazolo[1,5-a]pyrimidin-3-yl)quinolin-8-yl)methanol, TFA was obtained from tert-butyl 4-(4-(3-(8-(hydroxymethyl)quinolin-4-yl)pyrazolo[1,5-a]pyrimidin-6-yl)phenyl)piperazine-1-carboxylate in a 80% yield. $^1$H NMR (400 MHz, DMSO-d$_6$) δ 9.59 (d, J=2.2 Hz, 1H), 9.08 (d, J=2.2 Hz, 1H), 8.96 (d, J=4.6 Hz, 1H), 8.71 (s, 1H), 8.10 (d, J=8.3 Hz, 1H), 7.93-7.80 (m, 4H), 7.63 (dd, J=8.5, 7.0 Hz, 1H), 7.20-7.13 (m, 2H), 5.23 (s, 2H), 3.50-3.42 (m, 4H), 3.27 (s, 4H).

Compound 25

Scheme 81

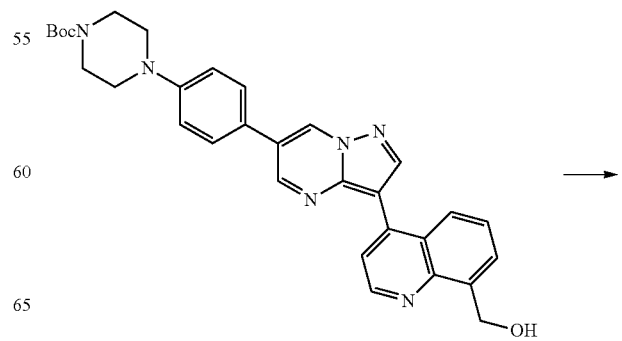

-continued

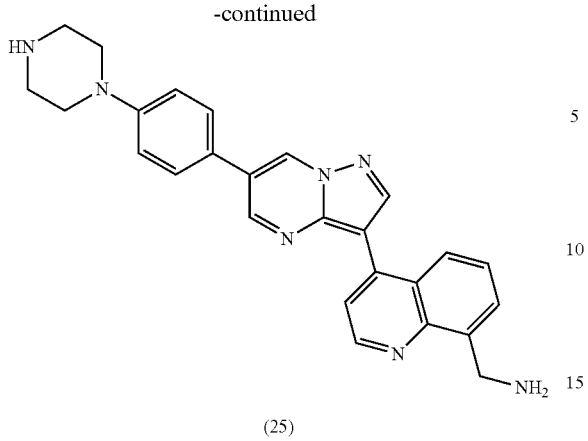

(25)

In an analogous manner to Scheme 63, (4-(6-(4-(piperazin-1-yl)phenyl)pyrazolo[1,5-a]pyrimidin-3-yl)quinolin-8-yl)methanamine, 2TFA was obtained from tert-butyl 4-(4-(3-(8-(hydroxymethyl)quinolin-4-yl)pyrazolo[1,5-a]pyrimidin-6-yl)phenyl)piperazine-1-carboxylate and ammonium hydroxide in 66% yield. $^1$H NMR (400 MHz, DMSO-d$_6$) δ 9.61 (d, J=2.3 Hz, 1H), 9.11-9.01 (m, 2H), 8.75 (d, J=16.5 Hz, 3H), 8.32-8.24 (m, 4H), 7.95-7.78 (m, 4H), 7.67 (dd, J=8.6, 7.0 Hz, 1H), 7.17 (d, J=8.8 Hz, 2H), 4.67 (q, J=5.7 Hz, 2H), 3.47 (m, 4H), 3.27 (bs, 4H).

Compound 26

Scheme 82

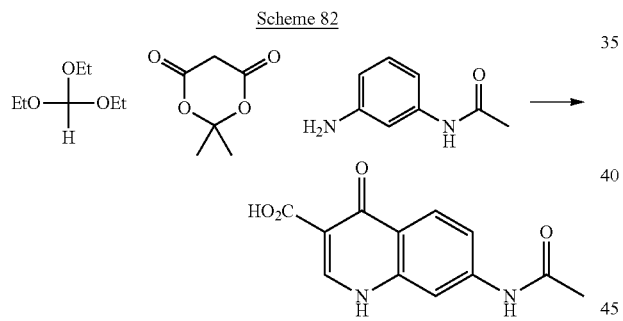

In an analogous manner to Scheme 46, 7-acetamido-4-oxo-1,4-dihydroquinoline-3-carboxylic acid was produced from 3'-aminoacetanilide in a 93% yield.

Scheme 83

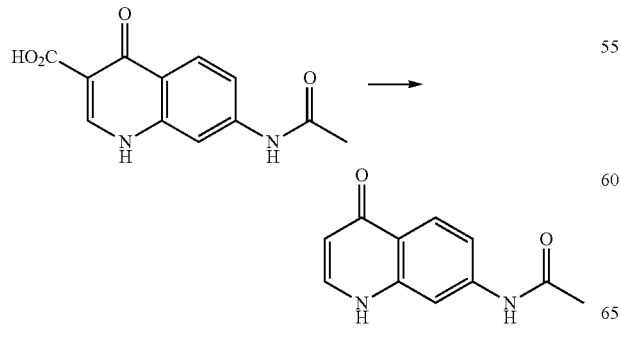

In an analogous manner to Scheme 47, N-(4-oxo-1,4-dihydroquinolin-7-yl)acetamide was obtained from 7-acetamido-4-oxo-1,4-dihydroquinoline-3-carboxylic acid in 56% yield.

Scheme 84

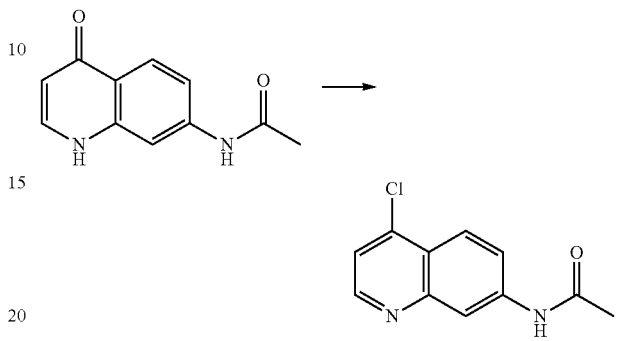

In an analogous manner to Scheme 48, N-(4-chloroquinolin-7-yl)acetamide was obtained from N-(4-oxo-1,4-dihydroquinolin-7-yl)acetamide in a 73% yield.

Scheme 85

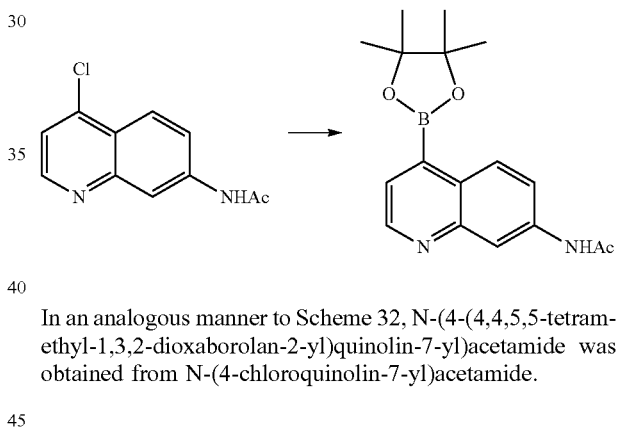

In an analogous manner to Scheme 32, N-(4-(4,4,5,5-tetramethyl-1,3,2-dioxaborolan-2-yl)quinolin-7-yl)acetamide was obtained from N-(4-chloroquinolin-7-yl)acetamide.

Scheme 86

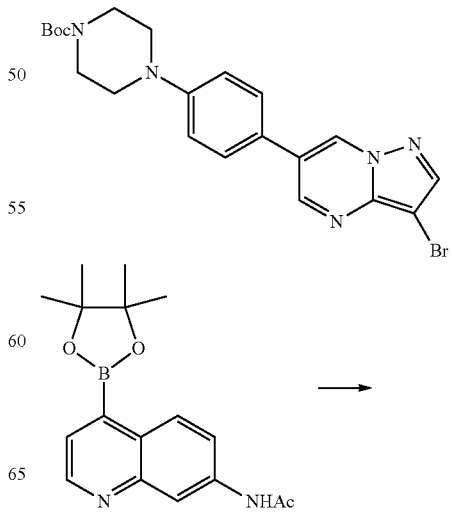

-continued

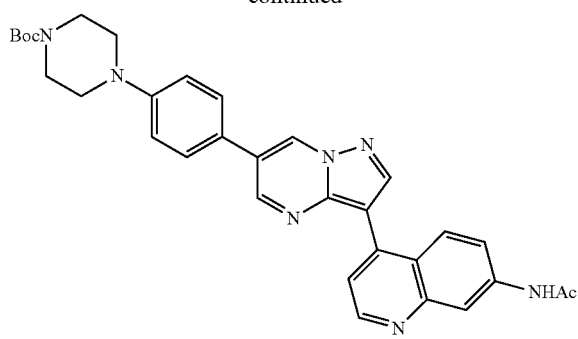

In an analogous manner to Scheme 5, tert-butyl 4-(4-(3-(7-acetamidoquinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)phenyl)piperazine-1-carboxylate and N-(4-(4,4,5,5-tetramethyl-1,3,2-dioxaborolan-2-yl)quinolin-7-yl)acetamide in a 45% yield.

Scheme 87

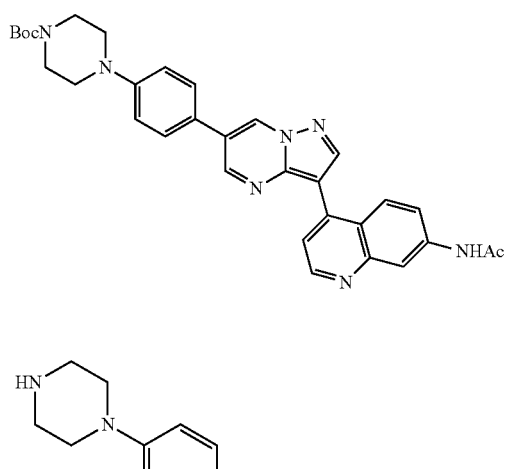

(26)

In an analogous manner to Scheme 2, N-(4-(6-(4-(piperazin-1-yl)phenyl)pyrazolo[1,5-a]pyrimidin-3-yl)quinolin-7-yl)acetamide, TFA was obtained from tert-butyl 4-(4-(3-(7-acetamidoquinolin-4-yl)pyrazolo[1,5-a]pyrimidin-6-yl)phenyl)piperazine-1-carboxylate in 52% yield. $^1$H NMR (400 MHz, DMSO-$d_6$) δ 10.61 (s, 1H), 9.66 (d, J=2.2 Hz, 1H), 9.17 (d, J=2.3 Hz, 1H), 9.01 (d, J=5.3 Hz, 1H), 8.87 (s, 1H), 8.74 (s, 2H), 8.68 (s, 1H), 8.38 (d, J=10.1 Hz, 1H), 8.01 (s, 1H), 7.89-7.74 (m, 3H), 7.17 (d, J=8.8 Hz, 2H), 3.51-3.43 (m, 4H), 3.27 (s, 4H), 2.18 (s, 3H).

Compound 27

Scheme 88

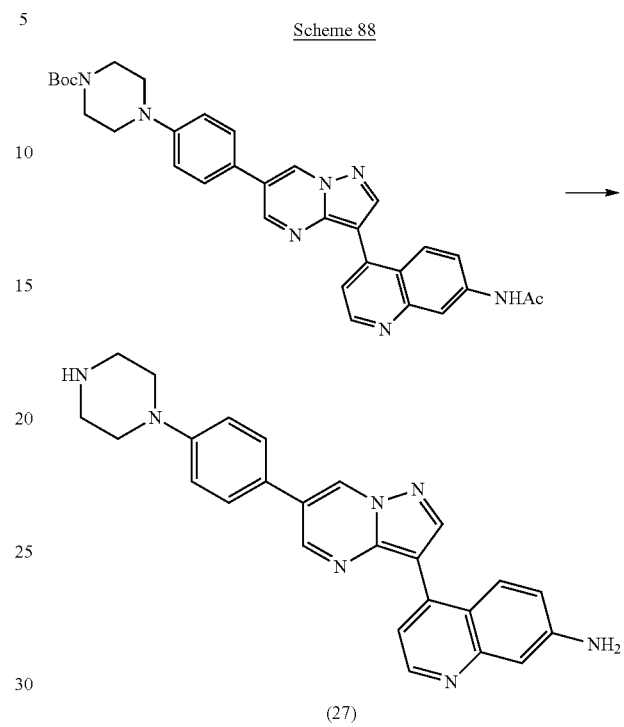

(27)

In a 5-mL mw vial suspended tert-butyl 4-(4-(3-(7-acetamidoquinolin-4-yl)pyrazolo[1,5-a]pyrimidin-6-yl)phenyl)piperazine-1-carboxylate (0.050 g, 0.089 mmol) in 6 N HCl (4 mL). Heated in microwave at 150 degrees for 15 min. Removed solvent and obtained 4-(6-(4-(piperazin-1-yl)phenyl)pyrazolo[1,5-a]pyrimidin-3-yl)quinolin-7-amine, TFA after reverse phase chromatography. $^1$H NMR (400 MHz, DMSO-$d_6$) δ 9.68 (d, J=2.3 Hz, 1H), 9.20 (d, J=2.3 Hz, 1H), 8.91-8.72 (m, 4H), 8.23 (d, J=9.3 Hz, 1H), 7.89-7.80 (m, 3H), 7.27-7.07 (m, 5H), 6.98 (d, J=2.2 Hz, 1H), 3.47 (dd, J=6.7, 3.8 Hz, 4H), 3.27 (s, 4H).

Compound 28

Scheme 89

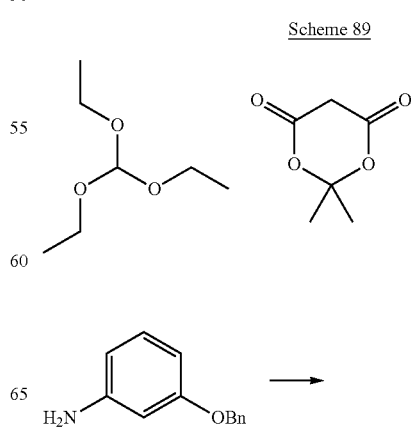

-continued

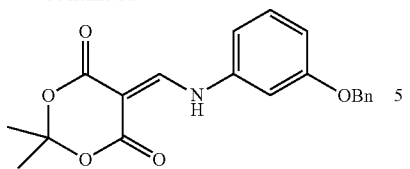

In an analogous manner to Scheme 46, 5-((3-(benzyloxy)phenylamino)methylene)-2,2-dimethyl-1,3-dioxane-4,6-dione was obtained from 3-(benzyloxy)aniline in a 98% yield.

Scheme 90

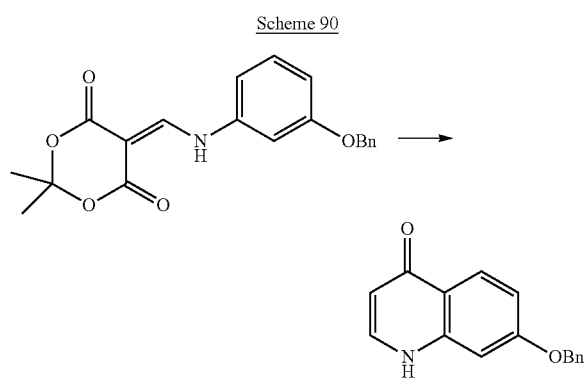

In an analogous manner to Scheme 47, 7-(benzyloxy)quinolin-4(1H)-one was obtained from 5-((3-(benzyloxy)phenylamino)methylene)-2,2-dimethyl-1,3-dioxane-4,6-dione in an 87% yield.

Scheme 91

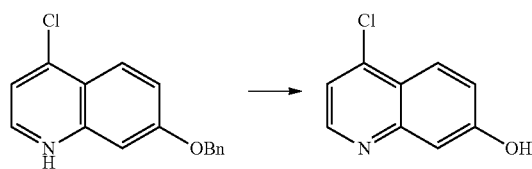

In an analogous manner to Scheme 48, 7-(benzyloxy)-4-chloroquinoline was obtained from 7-(benzyloxy)quinolin-4(1H)-one in a 95% yield.

Scheme 92

In a 5-mL microwave tube dissolved 7-(benzyloxy)-4-chloroquinoline (0.54 g, 2.002 mmol) in 33% HBr in AcOH (2 mL). Heated at 100 degrees in microwave for 10 min. Neutralized mixture with saturated NaHCO$_3$, extracted into EtOAc, washed organic layer with water then with brine. Dried organic layer with MgSO$_4$, filtered and concentrated to obtain 4-chloroquinolin-7-ol (0.284 g, 1.581 mmol, 79% yield) as a white solid.

Scheme 93

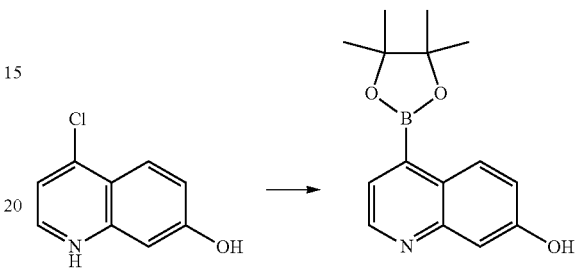

In an analogous manner to Scheme 32, 4-(4,4,5,5-tetramethyl-1,3,2-dioxaborolan-2-yl)quinolin-7-ol was obtained from 4-chloroquinolin-7-ol.

Scheme 94

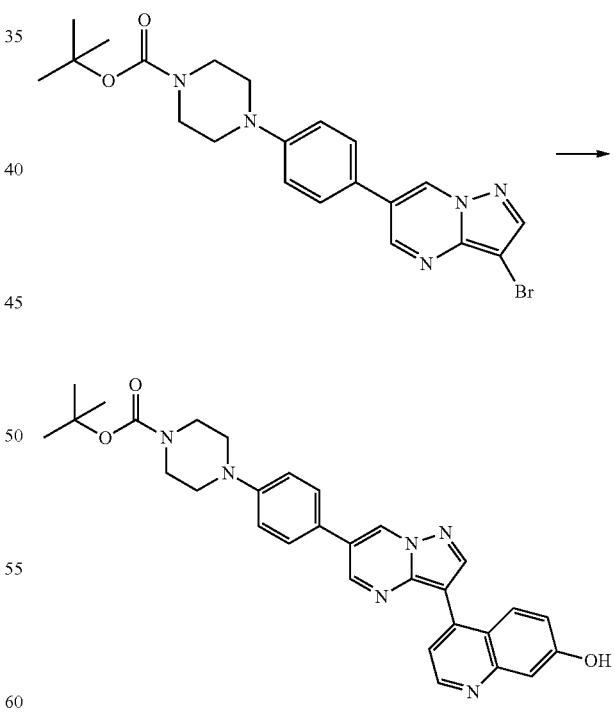

In an analogous manner to Scheme 5, tert-butyl 4-(4-(3-(7-hydroxyquinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)phenyl)piperazine-1-carboxylate in a 48% yield.

Scheme 95

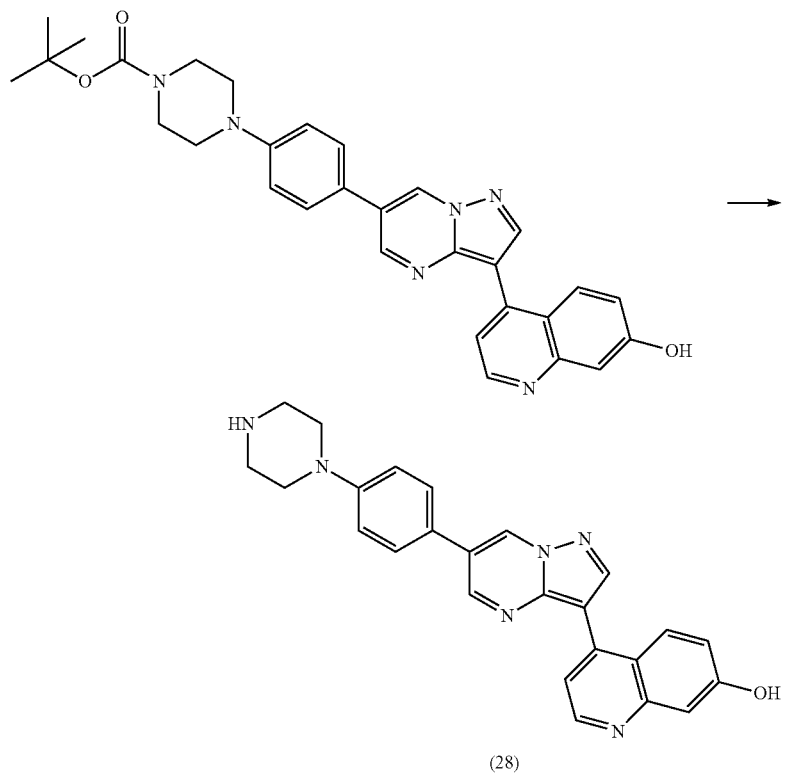

(28)

In an analogous manner to Scheme 2, 4-(6-(4-(piperazin-1-yl)phenyl)pyrazolo[1,5-a]pyrimidin-3-yl)quinolin-7-ol, TFA was obtained from tert-butyl 4-(4-(3-(7-hydroxyquinolin-4-yl)pyrazolo[1,5-a]pyrimidin-6-yl)phenyl)piperazine-1-carboxylate in a 60% yield. $^1$H NMR (400 MHz, DMSO-$d_6$) δ 11.37 (s, 1H), 9.68 (d, J=2.2 Hz, 1H), 9.20 (d, J=2.3 Hz, 1H), 9.00 (d, J=5.7 Hz, 1H), 8.90 (s, 1H), 8.85 (s, 2H), 8.40 (d, J=9.2 Hz, 1H), 8.04 (d, J=5.7 Hz, 1H), 7.90-7.81 (m, 2H), 7.48-7.35 (m, 2H), 7.22-7.13 (m, 2H), 3.47 (dd, J=6.7, 3.8 Hz, 4H), 3.28 (s, 4H).

Compound 29

Scheme 96

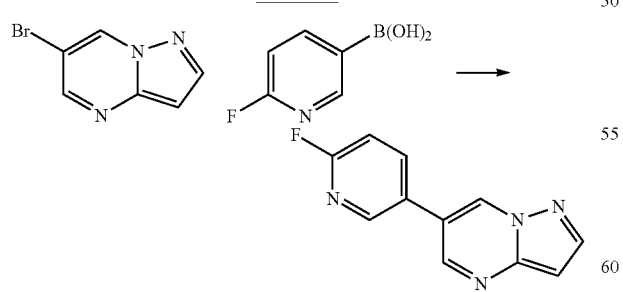

In an analogous manner to Scheme 5, 6-(6-fluoropyridin-3-yl)pyrazolo[1,5-a]pyrimidine was obtained from the reaction of commercially available 6-bromopyrazolo[1,5-a]pyrimidine and (6-fluoropyridin-3-yl)boronic acid in a 75% yield.

Scheme 97

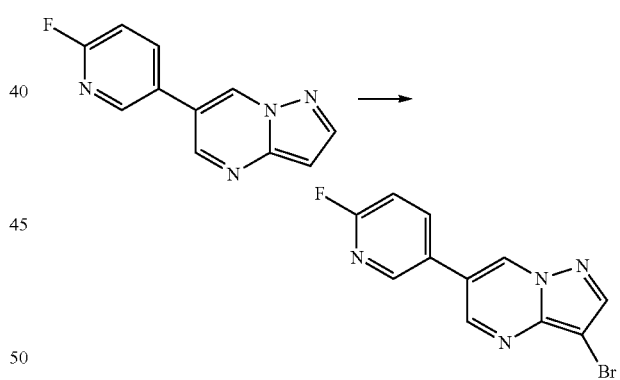

In an analogous manner to Scheme 4, 3-bromo-6-(6-fluoropyridin-3-yl)pyrazolo[1,5-a]pyrimidine was obtained from 6-(6-fluoropyridin-3-yl)pyrazolo[1,5-a]pyrimidine in a 92% yield.

Scheme 98

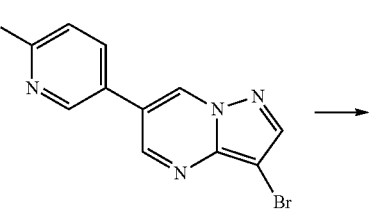

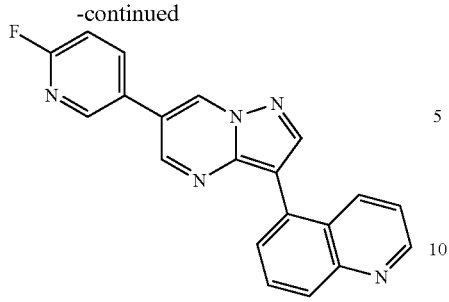

In an analogous manner to Scheme 5, 5-(6-(6-fluoropyridin-3-yl)pyrazolo[1,5-a]pyrimidin-3-yl)quinoline was obtained from 3-bromo-6-(6-fluoropyridin-3-yl)pyrazolo[1,5-a]pyrimidine and commercially available quinoline-5-ylboronic acid.

Scheme 99

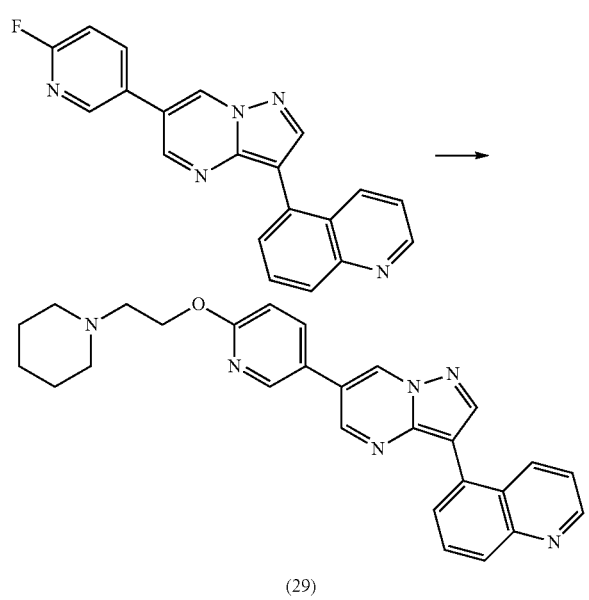

(29)

In a 5-mL mw vial, added 5-(6-(6-fluoropyridin-3-yl)pyrazolo[1,5-a]pyrimidin-3-yl)quinoline (0.068 g, 0.199 mmol) to DMSO (3 mL). Stirred at RT then added 2-(piperidin-1-yl)ethanol (0.257 g, 1.992 mmol). Stirred for 1 min then added potassium 2-methylpropan-2-olate (0.201 g, 1.793 mmol). Became burgandy colored. Heated in microwave at 80 deg for 15 min. LC/MS showed complete reaction. Partitioned mixture between water (20 mL) and dichloromethane (80 mL). Washed organic layer with brine, dried (MgSO$_4$), filtered and concentrated to obtain 5-(6-(6-(2-(piperidin-1-yl)ethoxy)pyridin-3-yl)pyrazolo[1,5-a]pyrimidin-3-yl)quinoline, TFA in 60% yield after reverse phase purification. $^1$H NMR (400 MHz, DMSO-d$_6$) δ 9.69 (d, J=2.2 Hz, 1H), 9.38 (s, 1H), 9.01 (q, J=1.8 Hz, 2H), 8.74 (dd, J=2.6, 0.8 Hz, 1H), 8.64 (s, 1H), 8.51 (dt, J=8.5, 1.3 Hz, 1H), 8.31 (dd, J=8.7, 2.6 Hz, 1H), 8.11 (dt, J=8.4, 1.1 Hz, 1H), 7.98-7.82 (m, 2H), 7.60 (dd, J=8.6, 4.3 Hz, 1H), 7.07 (dd, J=8.6, 0.7 Hz, 1H), 4.73-4.65 (m, 2H), 3.55 (dd, J=10.0, 4.5 Hz, 4H), 3.03 (dt, J=13.5, 9.5 Hz, 2H), 1.85 (d, J=13.9 Hz, 2H), 1.70 (q, J=15.6, 14.0 Hz, 3H), 1.41 (dd, J=17.6, 9.3 Hz, 1H).

Compound 30

Scheme 100

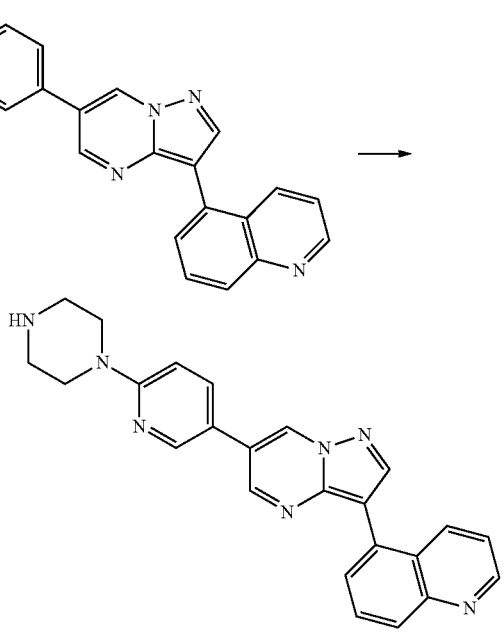

(30)

In a 5-mL mw vial, added 5-(6-(6-fluoropyridin-3-yl)pyrazolo[1,5-a]pyrimidin-3-yl)quinoline (0.068 g, 0.199 mmol) to DMSO (3 mL). Added piperazine (0.172 g, 1.992 mmol). Heated in microwave at 160 deg for 10 min. LC/MS showed complete reaction. Water (20 mL) was added and the aqueous mixture was extracted 2 times with dichloromethane (80 mL). Washed organic layer with brine, dried (MgSO$_4$), filtered and concentrated to obtain 5-(6-(6-(piperazin-1-yl)pyridin-3-yl)pyrazolo[1,5-a]pyrimidin-3-yl)quinoline, TFA (44%) after reverse phase purification. $^1$H NMR (400 MHz, DMSO-d$_6$) δ 9.62 (d, J=2.2 Hz, 1H), 9.07-8.98 (m, 2H), 8.85 (s, 2H), 8.73-8.65 (m, 1H), 8.64-8.54 (m, 2H), 8.21-8.08 (m, 2H), 8.00-7.82 (m, 2H), 7.64 (dd, J=8.6, 4.4 Hz, 1H), 7.11 (dd, J=8.9, 0.9 Hz, 1H), 5.13 (s, 2H), 3.85-3.78 (m, 4H), 3.24 (d, J=8.8 Hz, 4H).

Compound 31

Scheme 101

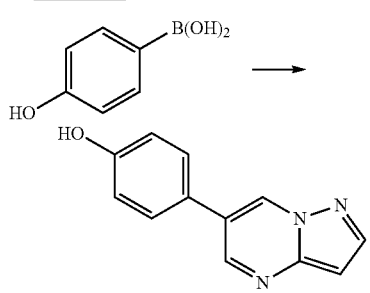

In an analogous manner to Scheme 5, 4-(pyrazolo[1,5-a]pyrimidin-6-yl)phenol was obtained from 6-bromopyrazolo[1,5-a]pyrimidine and 4-hydroxyphenylboronic acid in an 88% yield.

Scheme 102

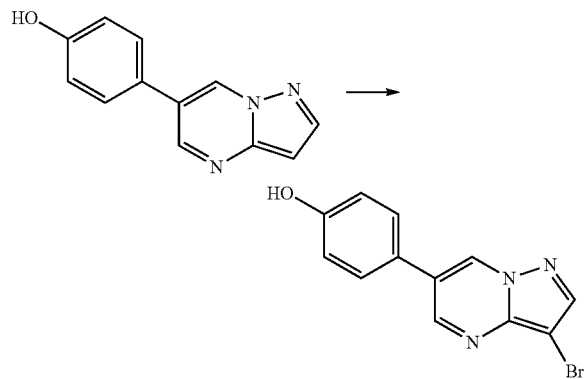

In an analogous manner to Scheme 4, 4-(3-bromopyrazolo[1,5-a]pyrimidin-6-yl)phenol was obtained from 4-(pyrazolo[1,5-a]pyrimidin-6-yl)phenol in a 77% yield.

Scheme 103

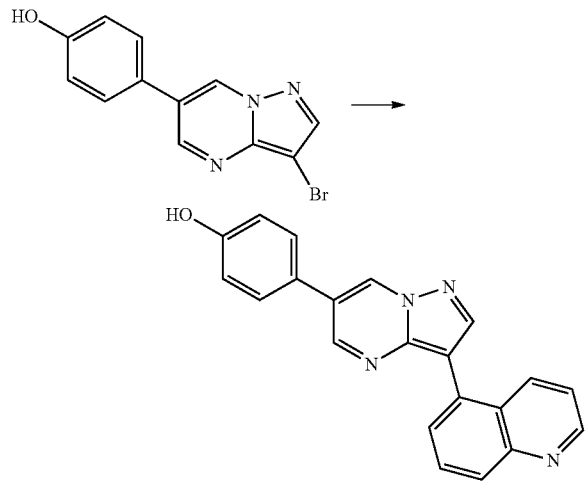

In an analogous manner to Scheme 5, 4-(3-(quinolin-5-yl)pyrazolo[1,5-a]pyrimidin-6-yl)phenol was obtained from 4-(3-bromopyrazolo[1,5-a]pyrimidin-6-yl)phenol and quinoline-5-boronic acid in an 89% yield.

Scheme 104

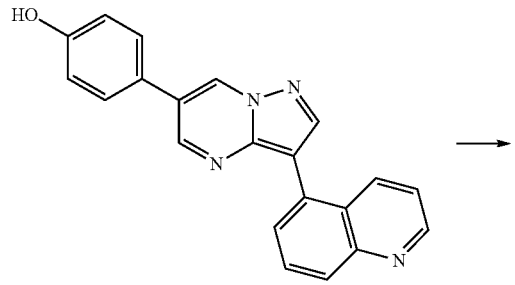

-continued

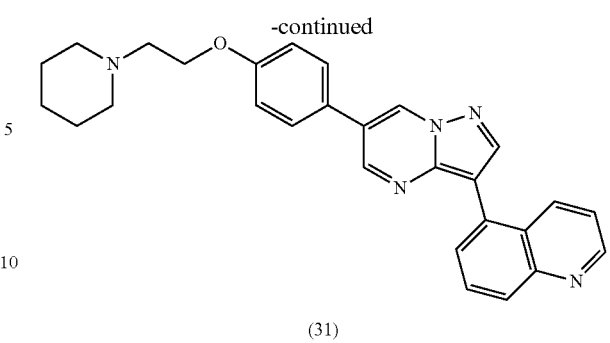

(31)

Suspended 4-(3-(quinolin-5-yl)pyrazolo[1,5-a]pyrimidin-6-yl)phenol (0.073 g, 0.216 mmol) in DCM (10 mL). Added 2-(piperidin-1-yl)ethanol (0.279 g, 2.157 mmol) then triphenylphosphine (0.0425 g, 1.62 mmol) and diisopropyl azodicarboxylate (0.325 g, 1.62 mmol). Stirred for 45 minutes at room temperature. Partitioned reaction between water and DCM (60 mL each). Washed org. layer with brine, dried (MgSO$_4$), filtered and concentrated. Purified on Biotage (SNAP 10 g) eluting with 4-14% MeOH/DCM over 15 CV. Obtained 5-(6-(4-(2-(piperidin-1-yl)ethoxy)phenyl)pyrazolo[1,5-a]pyrimidin-3-yl)quinoline, TFA (48%) after reverse phase purification. $^1$H NMR (400 MHz, DMSO-d$_6$) δ 9.58 (d, J=2.2 Hz, 1H), 9.45 (s, 1H), 9.05-8.97 (m, 2H), 8.61 (s, 1H), 8.54 (dd, J=8.6, 1.4 Hz, 1H), 8.11 (dt, J=8.3, 1.1 Hz, 1H), 7.98-7.83 (m, 4H), 7.61 (dd, J=8.6, 4.3 Hz, 1H), 7.23-7.14 (m, 2H), 4.43 (t, J=5.0 Hz, 2H), 3.03 (dt, J=13.2, 9.4 Hz, 2H), 1.89-1.81 (m, 2H), 1.78-1.63 (m, 3H), 1.42 (t, J=13.3 Hz, 1H).

Compound 32

Scheme 105

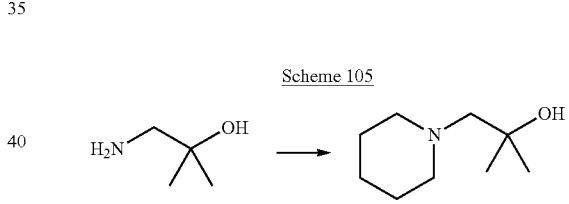

In a 50-mL round bottom flask containing 1-amino-2-methylpropan-2-ol (0.9 g, 10.10 mmol) and finely ground potassium carbonate (4.19 g, 30.3 mmol) was added 1,5-Dibromopentane (2.55 g, 11.11 mmol). The mixture was allowed to stir at 80 degrees for 40 minutes. The reaction was poured into ice water (75 mL) and was then extracted twice with dichloromethane (100 mL). The combined organic extracts were washed with brine, dried (MgSO$_4$), filtered and concentrated to obtain 2-methyl-1-(piperidin-1-yl)propan-2-ol (0.90 g, 5.72 mmol, 56.7% yield).

Scheme 106

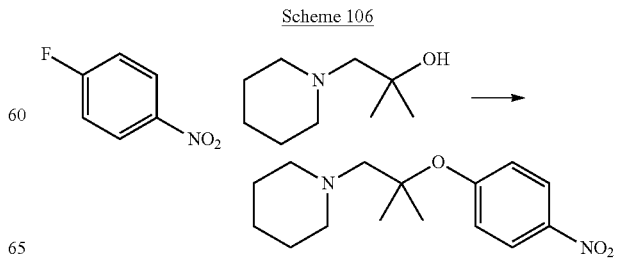

To a solution of 2-methyl-1-(piperidin-1-yl)propan-2-ol (0.9 g, 5.72 mmol) in DMF was added sodium hydride (60% in mineral oil, 0.32 g, 8 mmol). After 5 minutes of stirring, 1-fluoro-4-nitrobenzene (0.808 g, 5.72 mmol) was added. The mixture was heated to 80 degrees Celcius for 25 minutes then poured over ice water (60 mL), extracted twice with dichloromethane (75 mL). The combined extracts were dried (MgSO$_4$), filtered and concentrated to obtain 1-(2-methyl-2-(4-nitrophenoxy)propyl)piperidine (1.22 g, 4.38 mmol, 77% yield) after column purification.

Scheme 107

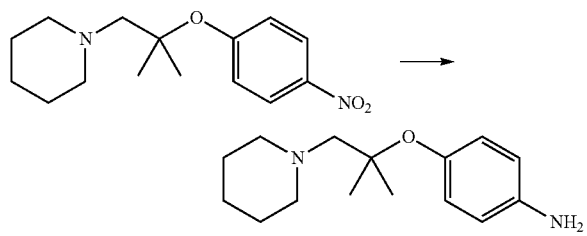

To a solution of 1-(2-methyl-2-(4-nitrophenoxy)propyl)piperidine (1.2 g, 4.31 mmol) in ethyl acetate/ethanol (1:1, 60 mL) was added tin(II) chloride, dihydrate (1.436 mL, 17.24 mmol). The mixture was heated for 45 min at 80 degrees. The mixture was neutralized by adding to a rapidly stirring suspension of ethyl acetate (200 mL), water (40 mL) and sodium bicarbonate (8 g). After neutralization, Celite (10 g) was added to the slurry and the mixture was filtered through a plug of Celite. The plug was eluted with additional Ethyl acetate (150 mL). The combined organics was washed with brine, dried (MgSO$_4$), filtered and concentrated to obtain 4-((2-methyl-1-(piperidin-1-yl)propan-2-yl)oxy)aniline (0.68 g, 2.74 mmol, 63.5% yield) as a yellow syrup.

Scheme 108

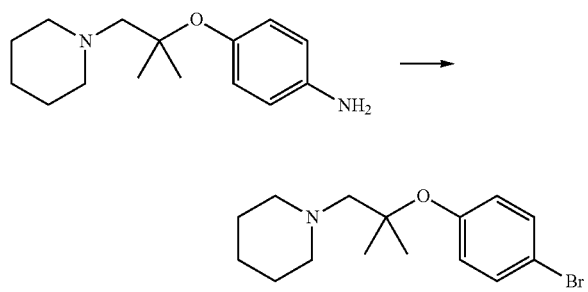

Cupric bromide (6.12 mg, 0.027 mmol) was added to a solution of 4-((2-methyl-1-(piperidin-1-yl)propan-2-yl)oxy)aniline (0.68 g, 2.74 mmol) in acetonitrile (20 mL), p-Toluenesulfonic acid monohydrate (1.250 g, 6.57 mmol), t-Butyl nitrite (0.391 mL, 3.29 mmol), and Sodium bromide (0.563 g, 5.48 mmol). The reaction mixture was stirred for 2 h at room temperature. The solvent was in vacuo. The solid was washed with water and extracted with CH$_2$Cl$_2$. The resulting solution was dried over anhydrous MgSO4 and the solvent was removed under reduced pressure to obtain 1-(2-(4-bromophenoxy)-2-methylpropyl)piperidine (0.33 g, 1.057 mmol, 38.6% yield) after column chromatography.

Scheme 109

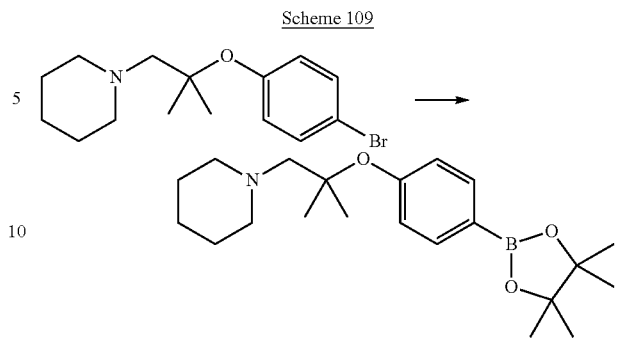

In an analogous manner to Scheme 32, 1-(2-methyl-2-(4-(4,4,5,5-tetramethyl-1,3,2-dioxaborolan-2-yl)phenoxy)propyl)piperidine was obtained from 1-(2-methyl-2-(4-(4,4,5,5-tetramethyl-1,3,2-dioxaborolan-2-yl)phenoxy)propyl)piperidine.

Scheme 110

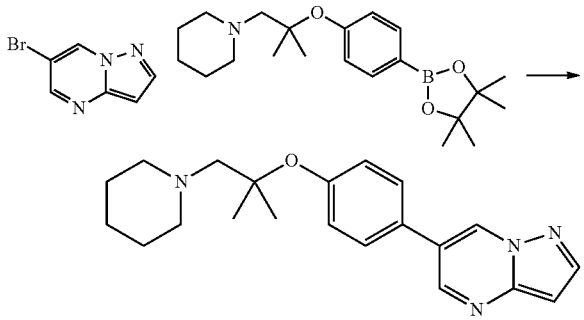

In an analogous manner to Scheme 5, 6-(4-((2-methyl-1-(piperidin-1-yl)propan-2-yl)oxy)phenyl)pyrazolo[1,5-a]pyrimidine was obtained from 1-(2-methyl-2-(4-(4,4,5,5-tetramethyl-1,3,2-dioxaborolan-2-yl)phenoxy)propyl)piperidine in a 65% yield.

Scheme 111

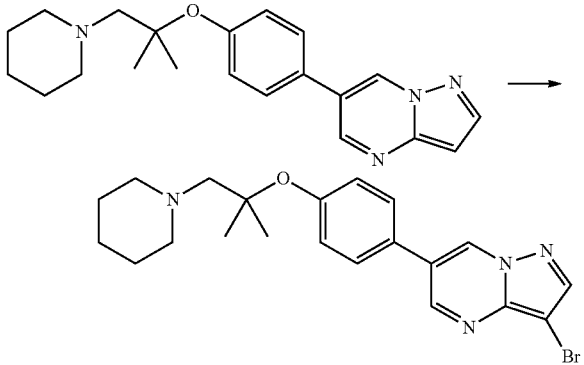

To a solution of 6-(4-((2-methyl-1-(piperidin-1-yl)propan-2-yl)oxy)phenyl)pyrazolo[1,5-a]pyrimidine (0.20 g, 0.571 mmol) in acetic acid (4 mL) added Potassium acetate (0.102 g, 0.856 mmol) and then a solution of bromine (0.091 g, 0.571 mmol) in acetic acid (1 mL). After 10 minutes, added the reaction mixture to a vigorously stirring solution of sodium bicarbonate (10 g) in water (100 mL). After 20 minutes of vigorous stirring, the product was extracted into dichloromethane (75 mL). The organic phase was washed with water, brine, dried (MgSO$_4$), filtered and concentrated to yield 3-bromo-6-(4-((2-methyl-1-(piperidin-1-yl)propan-2-yl)oxy)phenyl)pyrazolo[1,5-a]pyrimidine (0.18 g, 0.419 mmol, 73.5% yield) as a beige solid.

Scheme 112

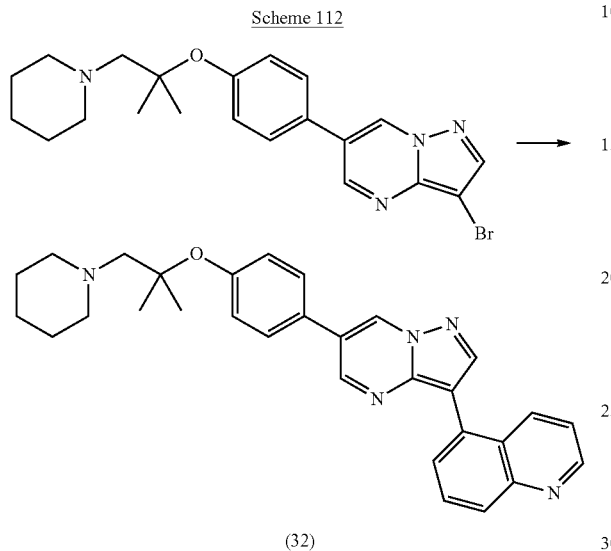

(32)

In an analogous manner to Scheme 5, 5-(6-(4-((2-methyl-1-(piperidin-1-yl)propan-2-yl)oxy)phenyl)pyrazolo[1,5-a]pyrimidin-3-yl)quinoline, TFA was obtained from 3-bromo-6-(4-((2-methyl-1-(piperidin-1-yl)propan-2-yl)oxy)phenyl)pyrazolo[1,5-a]pyrimidine and quinoline-5-boronic acid in a 34% yield after reverse phase purification. $^1$H NMR (400 MHz, DMSO-d$_6$) δ 9.61 (d, J=2.2 Hz, 1H), 9.00 (dd, J=3.9, 1.9 Hz, 3H), 8.62 (s, 1H), 8.54-8.46 (m, 1H), 8.10 (dt, J=8.4, 1.1 Hz, 1H), 7.96-7.82 (m, 4H), 7.59 (dd, J=8.6, 4.2 Hz, 1H), 7.33-7.24 (m, 2H), 3.59 (d, J=12.1 Hz, 2H), 3.49 (d, J=4.7 Hz, 2H), 3.16 (q, J=6.8 Hz, 2H), 1.84 (dq, J=7.7, 4.4 Hz, 4H), 1.68 (dt, J=13.5, 4.7 Hz, 1H), 1.43 (s, 7H).

Compound 33

Scheme 113

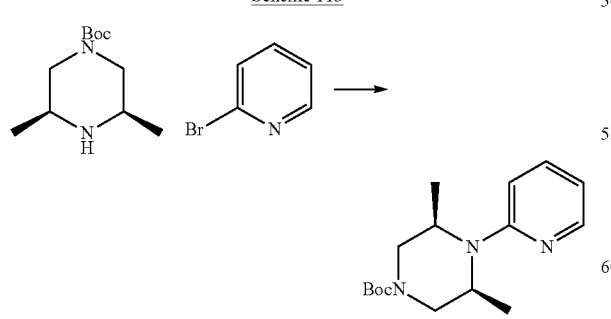

In an analogous manner to Scheme 3, (3R,5S)-tert-butyl 3,5-dimethyl-4-(pyridin-2-yl)piperazine-1-carboxylate was obtained from (3S,5R)-tert-butyl 3,5-dimethylpiperazine-1-carboxylate and 2-bromopyridine in a 91% yield.

Scheme 114

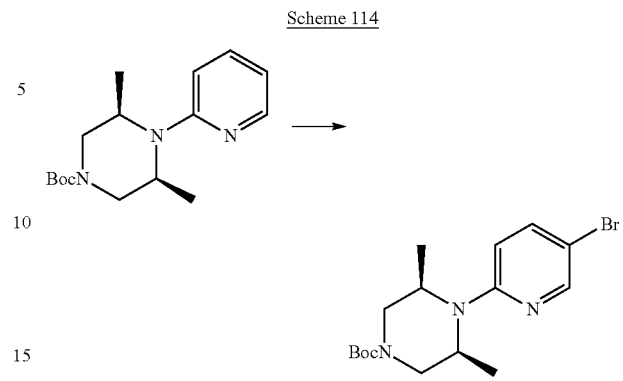

In an analogous manner to Scheme 111, (3R,5S)-tert-butyl 4-(5-bromopyridin-2-yl)-3,5-dimethylpiperazine-1-carboxylate was obtained from (3R,5S)-tert-butyl 3,5-dimethyl-4-(pyridin-2-yl)piperazine-1-carboxylate in an 89% yield.

Scheme 115

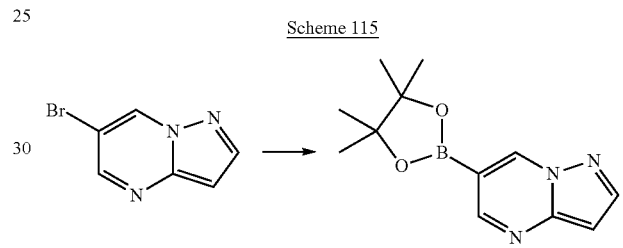

In an analogous manner to Scheme 32, 6-(4,4,5,5-tetramethyl-1,3,2-dioxaborolan-2-yl)pyrazolo[1,5-a]pyrimidine was obtained from 6-bromopyrazolo[1,5-a]pyrimidine. Used as is.

Scheme 116

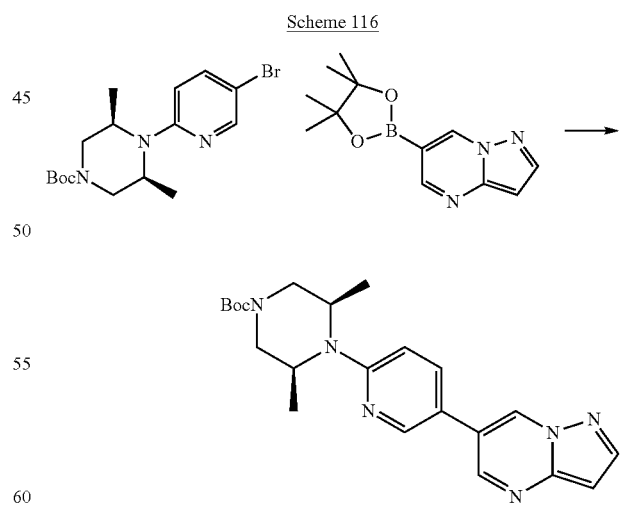

In an analogous manner to Scheme 5, (3R,5S)-tert-butyl 3,5-dimethyl-4-(5-(pyrazolo[1,5-a]pyrimidin-6-yl)pyridin-2-yl)piperazine-1-carboxylate was obtained from 6-(4,4,5,5-tetramethyl-1,3,2-dioxaborolan-2-yl)pyrazolo[1,5-a]pyrimidine in a 37% yield.

Scheme 117

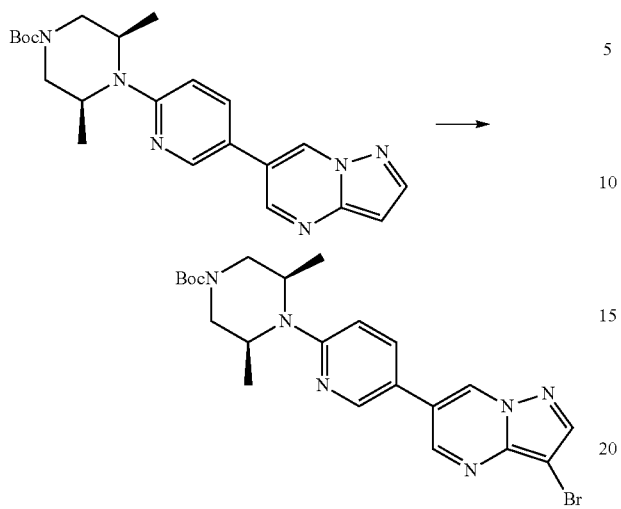

In an analogous manner to Scheme 4, (3R,5S)-tert-butyl 4-(5-(3-bromopyrazolo[1,5-a]pyrimidin-6-yl)pyridin-2-yl)-3,5-dimethylpiperazine-1-carboxylate was obtained from (3R,5S)-tert-butyl 3,5-dimethyl-4-(5-(pyrazolo[1,5-a]pyrimidin-6-yl)pyridin-2-yl)piperazine-1-carboxylate in 72% yield.

Scheme 118

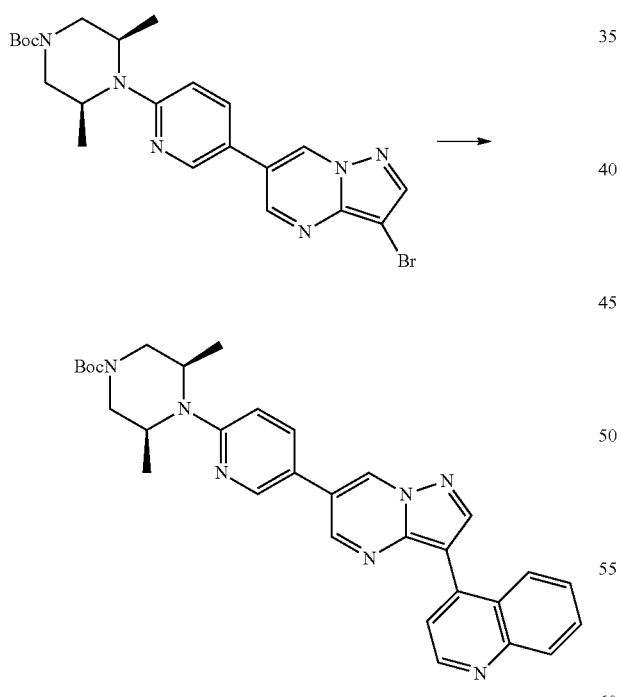

In an analogous manner to Scheme 5, (3R,5S)-tert-butyl 3,5-dimethyl-4-(5-(3-(quinolin-4-yl)pyrazolo[1,5-a]pyrimidin-6-yl)pyridin-2-yl)piperazine-1-carboxylate was obtained from (3R,5S)-tert-butyl 4-(5-(3-bromopyrazolo[1,5-a]pyrimidin-6-yl)pyridin-2-yl)-3,5-dimethylpiperazine-1-carboxylate and quinoline-4-boronic acid in a 75% yield.

Scheme 119

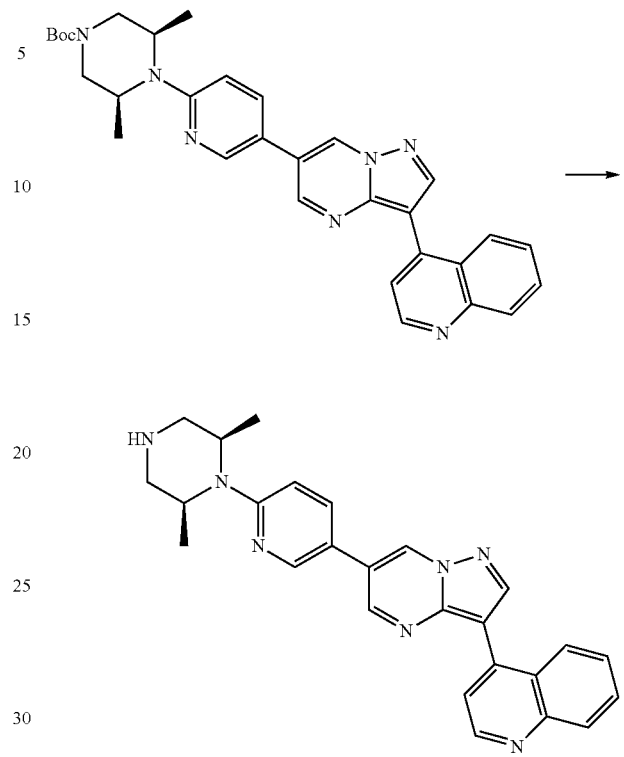

(33)

In an analogous manner to Scheme 2, 4-(6-(6-((2R,6S)-2,6-dimethylpiperazin-1-yl)pyridin-3-yl)pyrazolo[1,5-a]pyrimidin-3-yl)quinoline, TFA was obtained from (3R,5S)-tert-butyl 3,5-dimethyl-4-(5-(3-(quinolin-4-yl)pyrazolo[1,5-a]pyrimidin-6-yl)pyridin-2-yl)piperazine-1-carboxylate in quantitative yield. $^1$H NMR (400 MHz, DMSO-$d_6$) δ 9.70 (d, J=2.2 Hz, 1H), 9.40 (d, J=6.5 Hz, 1H), 9.16 (d, J=2.2 Hz, 1H), 9.10 (d, J=5.1 Hz, 1H), 8.98 (s, 1H), 8.86 (s, 1H), 8.76 (dd, J=2.6, 0.7 Hz, 1H), 8.39 (dd, J=8.3, 1.3 Hz, 1H), 8.23-8.14 (m, 2H), 8.08 (d, J=5.0 Hz, 1H), 7.97 (ddd, J=8.4, 6.9, 1.4 Hz, 1H), 7.77 (ddd, J=8.3, 6.9, 1.3 Hz, 1H), 6.98 (d, J=9.0 Hz, 1H), 4.82-4.71 (m, 2H), 3.41-3.32 (m, 2H), 3.26 (d, J=9.9 Hz, 2H), 1.30 (d, J=7.0 Hz, 6H).

Compound 34

Scheme 120

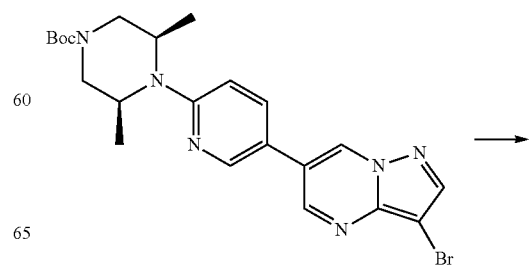

-continued

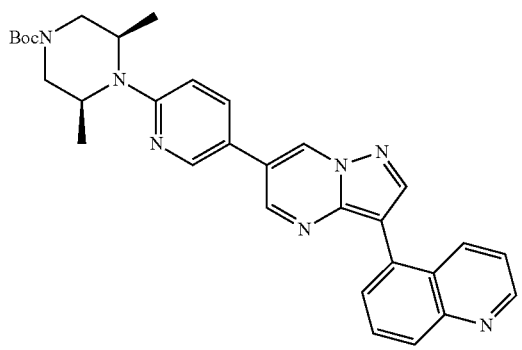

In an analogous manner to Scheme 5, (3R,5S)-tert-butyl 3,5-dimethyl-4-(5-(3-(quinolin-5-yl)pyrazolo[1,5-a]pyrimidin-6-yl)pyridin-2-yl)piperazine-1-carboxylate was obtained from (3R,5S)-tert-butyl 4-(5-(3-bromopyrazolo[1,5-a]pyrimidin-6-yl)pyridin-2-yl)-3,5-dimethylpiperazine-1-carboxylate and quinoline-5-boronic acid in a 72% yield.

Scheme 121

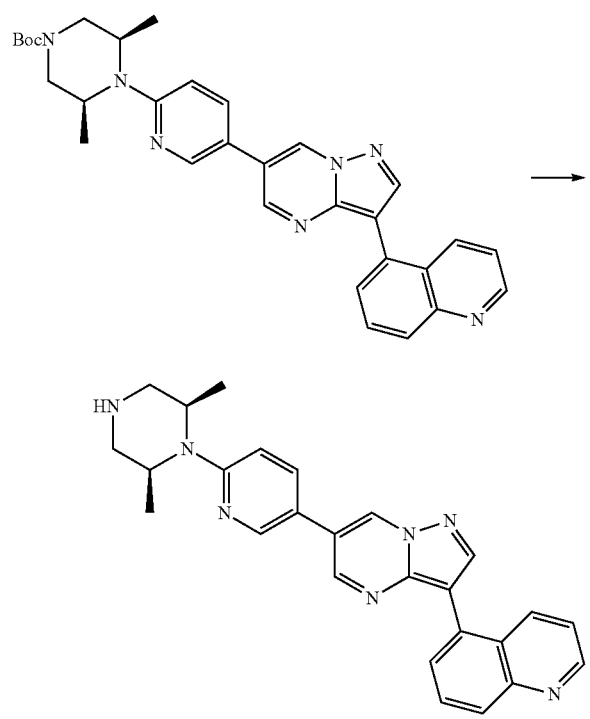

In an analogous manner to Scheme 2, (3R,5S)-tert-butyl 3,5-dimethyl-4-(4-(3-(quinolin-5-yl)pyrazolo[1,5-a]pyrimidin-6-yl)phenyl)piperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate in a 72% yield. $^1$H NMR (400 MHz, DMSO-d$_6$) δ 9.60 (d, J=2.3 Hz, 1H), 9.38 (s, 1H), 9.06-8.98 (m, 2H), 8.95 (s, 1H), 8.73 (dd, J=2.5, 0.7 Hz, 1H), 8.63-8.52 (m, 2H), 8.19-8.07 (m, 2H), 7.99-7.84 (m, 2H), 7.62 (dd, J=8.6, 4.3 Hz, 1H), 6.96 (d, J=9.0 Hz, 1H), 4.75 (p, J=6.6 Hz, 2H), 3.36 (d, J=12.6 Hz, 2H), 3.25 (d, J=9.5 Hz, 2H), 1.30 (d, J=7.0 Hz, 6H).

Compound 35

Scheme 122

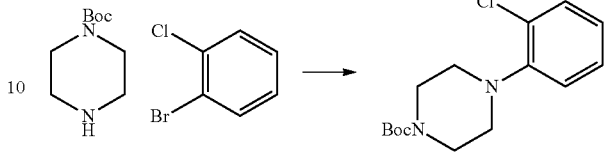

In an analogous manner to Scheme 3, tert-butyl 4-(2-chlorophenyl)piperazine-1-carboxylate was obtained from 1-bromo-2-chlorobenzene and tert-butyl 1-piperazinecarboxylate in a 69% yield.

Scheme 123

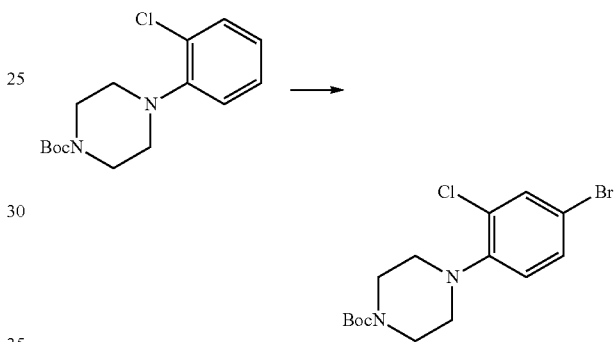

In an analogous manner to Scheme 4, tert-butyl 4-(4-bromo-2-chlorophenyl)piperazine-1-carboxylate was obtained from tert-butyl 4-(2-chlorophenyl)piperazine-1-carboxylate in a 92% yield.

Scheme 124

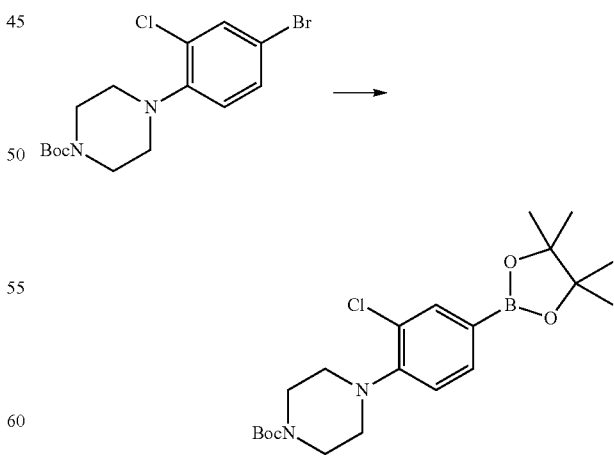

In an analogous manner to Scheme 32, tert-butyl 4-(2-chloro-4-(4,4,5,5-tetramethyl-1,3,2-dioxaborolan-2-yl)phenyl)piperazine-1-carboxylate was obtained from tert-butyl 4-(4-bromo-2-chlorophenyl)piperazine-1-carboxylate.

Scheme 125

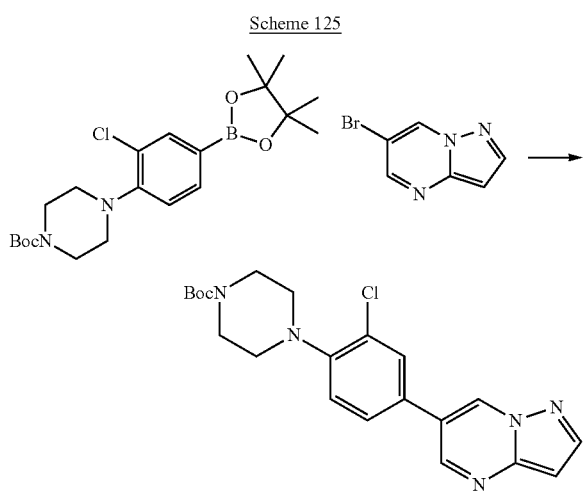

In an analogous manner to Scheme 5, tert-butyl 4-(2-chloro-4-(pyrazolo[1,5-a]pyrimidin-6-yl)phenyl)piperazine-1-carboxylate was obtained from tert-butyl 4-(2-chloro-4-(4,4,5,5-tetramethyl-1,3,2-dioxaborolan-2-yl)phenyl)piperazine-1-carboxylate in a 66% yield.

Scheme 126

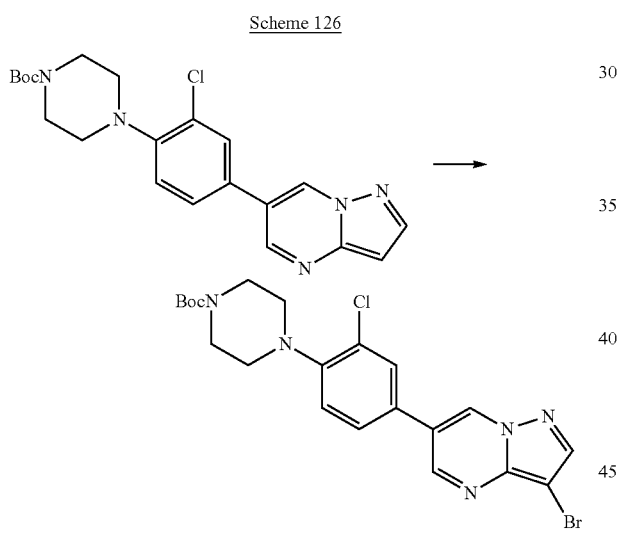

In an analogous manner to Scheme 4, tert-butyl 4-(4-(3-bromopyrazolo[1,5-a]pyrimidin-6-yl)-2-chlorophenyl)piperazine-1-carboxylate was obtained from tert-butyl 4-(2-chloro-4-(pyrazolo[1,5-a]pyrimidin-6-yl)phenyl)piperazine-1-carboxylate in a 90% yield.

Scheme 127

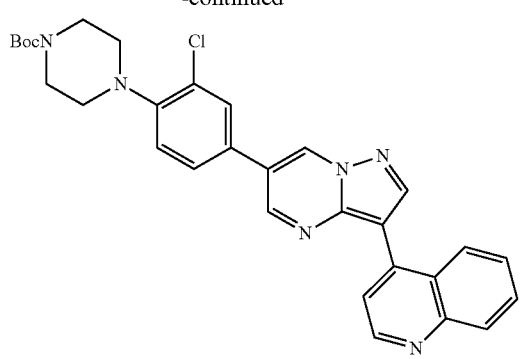

In an analogous manner to Scheme 5, tert-butyl 4-(2-chloro-4-(3-(quinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)-2-chlorophenyl)piperazine-1-carboxylate and quinoline-4-boronic acid in a 61% yield.

Scheme 128

In an analogous manner to Scheme 2, 4-(6-(3-chloro-4-(piperazin-1-yl)phenyl)pyrazolo[1,5-a]pyrimidin-3-yl)quinoline, TFA was obtained from tert-butyl 4-(2-chloro-4-(3-(quinolin-4-yl)pyrazolo[1,5-a]pyrimidin-6-yl)phenyl)piperazine-1-carboxylate in a 66% yield after reverse phase purification. $^1$H NMR (400 MHz, DMSO-$d_6$) δ 9.74 (d, J=2.3 Hz, 1H), 9.14 (d, J=2.3 Hz, 1H), 9.07 (d, J=4.9 Hz, 1H), 8.82 (d, J=15.2 Hz, 3H), 8.35-8.28 (m, 1H), 8.17 (dd, J=8.6, 1.2 Hz, 1H), 8.09 (d, J=2.2 Hz, 1H), 8.01-7.86 (m, 3H), 7.72 (ddd, J=8.3, 6.8, 1.3 Hz, 1H), 7.38 (d, J=8.4 Hz, 1H), 3.33-3.22 (m, 8H).

Compound 36

Scheme 129

In an analogous manner to Scheme 5, tert-butyl 4-(2-chloro-4-(3-(quinolin-5-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)-2-chlorophenyl)piperazine-1-carboxylate and quinoline-5-boronic acid in a 7% yield.

Scheme 130

In an analogous manner to Scheme 2, 5-(6-(3-chloro-4-(piperazin-1-yl)phenyl)pyrazolo[1,5-a]pyrimidin-3-yl)quinoline, TFA was obtained from tert-butyl 4-(2-chloro-4-(3-(quinolin-5-yl)pyrazolo[1,5-a]pyrimidin-6-yl)phenyl)piperazine-1-carboxylate in quantitative yield. $^1$H NMR (400 MHz, DMSO-d$_6$) δ 9.66 (d, J=2.3 Hz, 1H), 9.03-8.95 (m, 2H), 8.75 (s, 2H), 8.62 (s, 1H), 8.49-8.42 (m, 1H), 8.13-8.03 (m, 2H), 7.95-7.80 (m, 3H), 7.57 (dd, J=8.6, 4.2 Hz, 1H), 7.37 (d, J=8.4 Hz, 1H), 3.33-3.21 (m, 8H).

Compound 37

Scheme 131

In an analogous manner to Scheme 3, tert-butyl 4-(2-chlorophenyl)piperazine-1-carboxylate was obtained from 2-chlorobenzonitrile and tert-butyl 1-piperazinecarboxylate in a 71% yield.

Scheme 132

In an analogous manner to Scheme 4, tert-butyl 4-(4-bromo-2-cyanophenyl)piperazine-1-carboxylate was obtained tert-butyl 4-(2-cyanophenyl)piperazine-1-carboxylate in an 86% yield.

Scheme 133

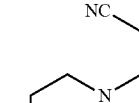

In an analogous manner to Scheme 32, tert-butyl 4-(2-chloro-4-(4,4,5,5-tetramethyl-1,3,2-dioxaborolan-2-yl)phenyl)piperazine-1-carboxylate was obtained from tert-butyl 4-(4-bromo-2-chlorophenyl)piperazine-1-carboxylate.

Scheme 134

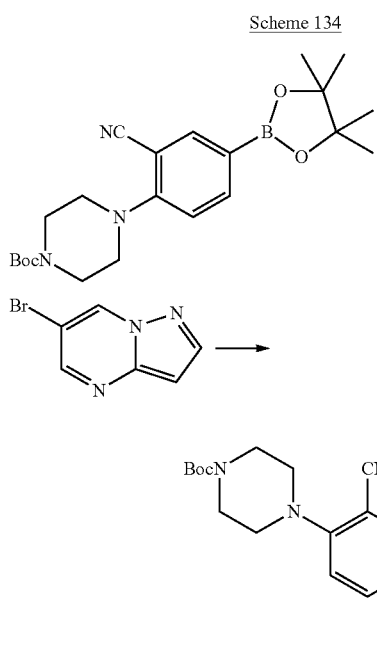

In an analogous manner to Scheme 5, tert-butyl 4-(2-cyano-4-(4,4,5,5-tetramethyl-1,3,2-dioxaborolan-2-yl)phenyl)piperazine-1-carboxylate was obtained from tert-butyl 4-(4-bromo-2-cyanophenyl)piperazine-1-carboxylate in a 53% yield.

Scheme 135

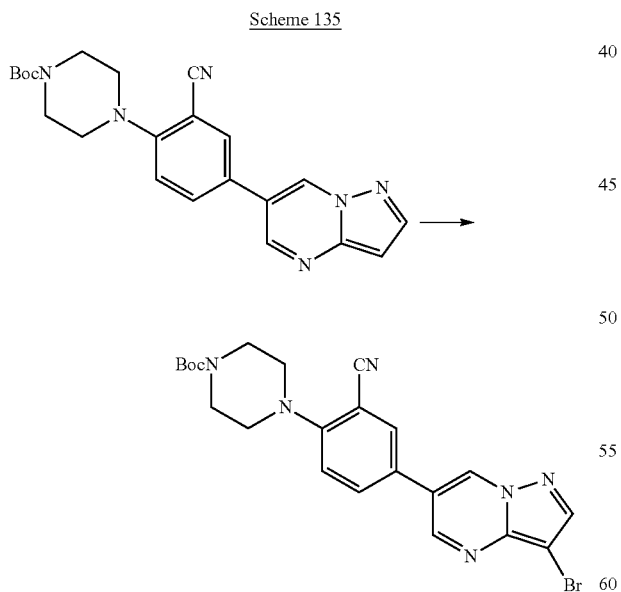

In an analogous manner to Scheme 4, tert-butyl 4-(4-(3-bromopyrazolo[1,5-a]pyrimidin-6-yl)-2-cyanophenyl)piperazine-1-carboxylate was obtained from tert-butyl 4-(2-cyano-4-(pyrazolo[1,5-a]pyrimidin-6-yl)phenyl)piperazine-1-carboxylate in a 88% yield.

Scheme 136

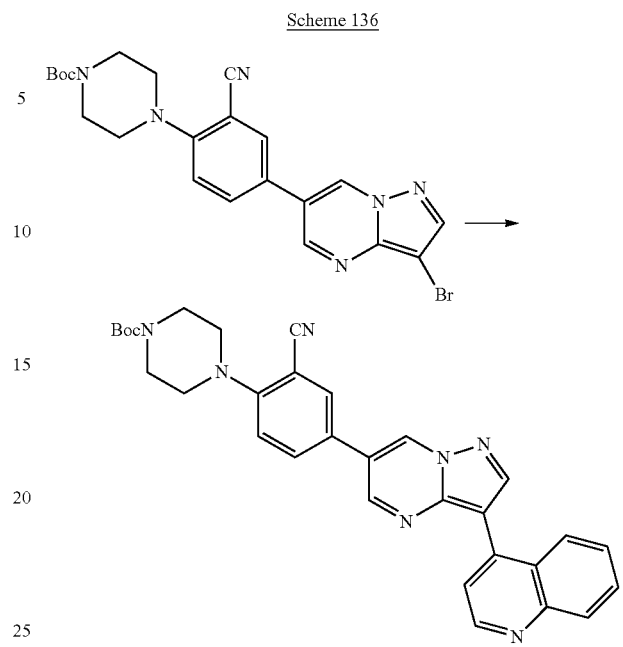

In an analogous manner to Scheme 5, tert-butyl 4-(2-cyano-4-(3-(quinolin-4-yl)pyrazolo[1,5-a]pyrimidin-6-yl)phenyl)piperazine-1-carboxylate was obtained tert-butyl 4-(4-(3-bromopyrazolo[1,5-a]pyrimidin-6-yl)-2-cyanophenyl)piperazine-1-carboxylate and quinoline-4-boronic acid in a 59% yield.

Scheme 137

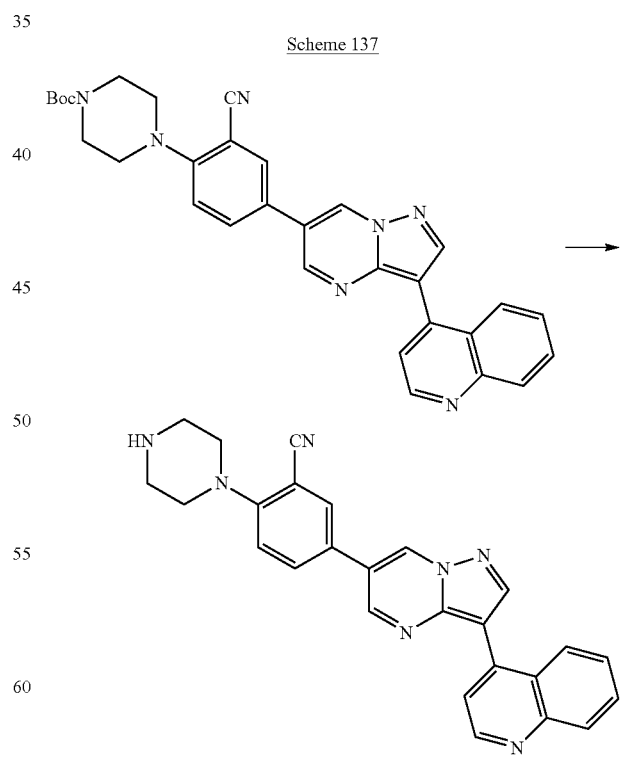

(37)

In an analogous manner to Scheme 2, 2-(piperazin-1-yl)-5-(3-(quinolin-4-yl)pyrazolo[1,5-a]pyrimidin-6-yl)benzonitrile, TFA was obtained from tert-butyl 4-(2-cyano-4-(3-(quinolin-4-yl)pyrazolo[1,5-a]pyrimidin-6-yl)phenyl)piperazine-1-carboxylate in a 44% yield after reverse phase purification. 1H), 8.85 (s, 1H), 8.40 (d, J=2.3 Hz, 1H), 8.31 (d, J=8.7 Hz, 1H), 8.25-8.13 (m, 2H), 8.00-7.87 (m, 2H), 7.71 (ddd, J=8.2, 6.8, 1.3 Hz, 1H), 7.42 (d, J=8.7 Hz, 1H), 3.46 (dd, J=6.0, 4.0 Hz, 4H), 3.34 (s, 4H).

Compound 38

Scheme 138

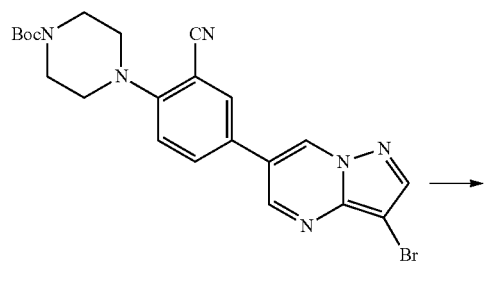

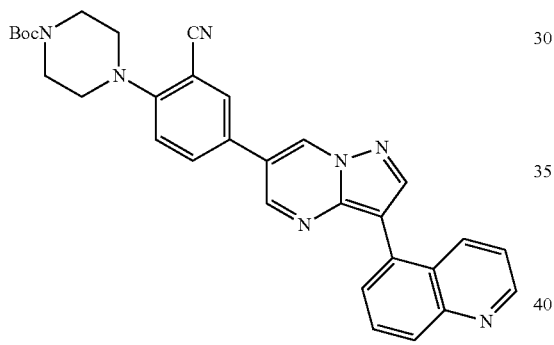

In an analogous manner to Scheme 5 tert-butyl 4-(2-cyano-4-(3-(quinolin-5-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)-2-cyanophenyl)piperazine-1-carboxylate and quinoline-5-boronic acid in a 45% yield.

Scheme 139

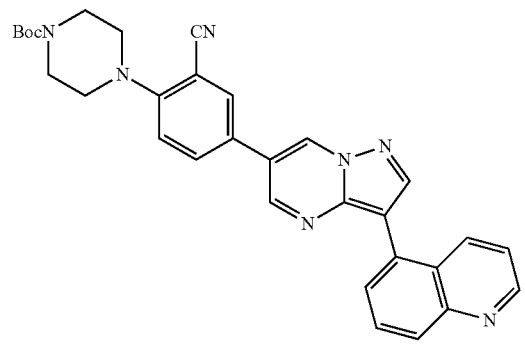

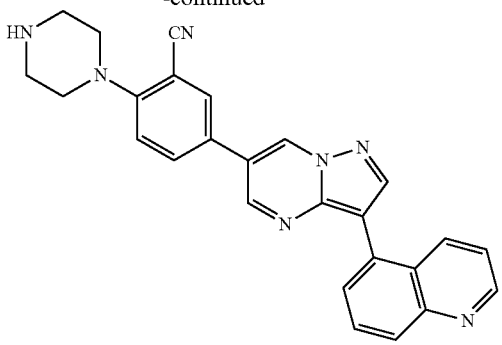

(38)

In an analogous manner to Scheme 2, 2-(piperazin-1-yl)-5-(3-(quinolin-4-yl)pyrazolo[1,5-a]pyrimidin-6-yl)benzonitrile, TFA was obtained from tert-butyl 4-(2-cyano-4-(3-(quinolin-4-yl)pyrazolo[1,5-a]pyrimidin-6-yl)phenyl)piperazine-1-carboxylate in 78% yield. $^{1}$H NMR (400 MHz, DMSO-$d_6$) δ 9.71 (d, J=2.3 Hz, 1H), 9.06-8.96 (m, 2H), 8.86 (s, 2H), 8.63 (s, 1H), 8.47 (dt, J=8.6, 1.3 Hz, 1H), 8.37 (d, J=2.3 Hz, 1H), 8.18 (dd, J=8.7, 2.4 Hz, 1H), 8.10 (dt, J=8.4, 1.1 Hz, 1H), 7.96-7.81 (m, 2H), 7.58 (dd, J=8.6, 4.3 Hz, 1H), 7.41 (d, J=8.7 Hz, 1H), 3.44 (dd, J=6.7, 3.4 Hz, 4H), 3.34 (s, 4H).

Compound 39

Scheme 140

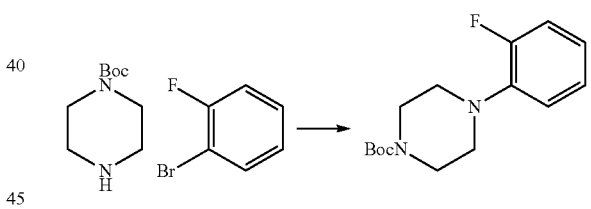

In an analogous manner to Scheme 3, tert-butyl 4-(2-fluorophenyl)piperazine-1-carboxylate was obtained from 1-bromo-2-fluorobenzene in 73% yield.

Scheme 141

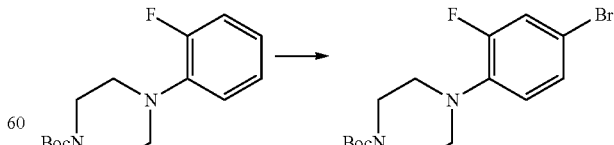

In an analogous manner to Scheme 4, tert-butyl 4-(4-bromo-2-fluorophenyl)piperazine-1-carboxylate was obtained from tert-butyl 4-(2-fluorophenyl)piperazine-1-carboxylate in an 86% yield.

Scheme 142

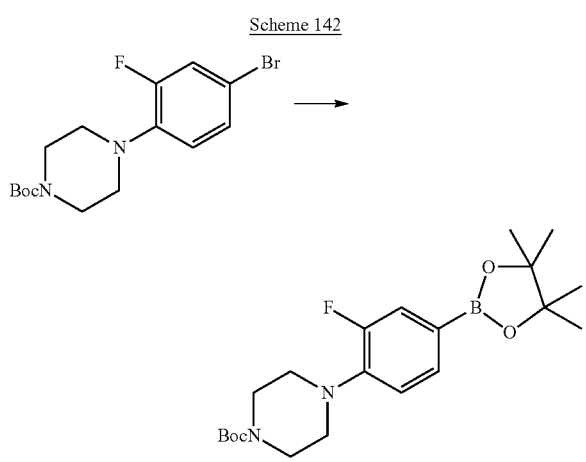

In an analogous manner to Scheme 32, ter t-butyl 4-(2-fluoro-4-(4,4,5,5-tetramethyl-1,3,2-dioxaborolan-2-yl)phenyl)piperazine-1-carboxylate was obtained from tert-butyl 4-(4-bromo-2-fluorophenyl)piperazine-1-carboxylate.

Scheme 143

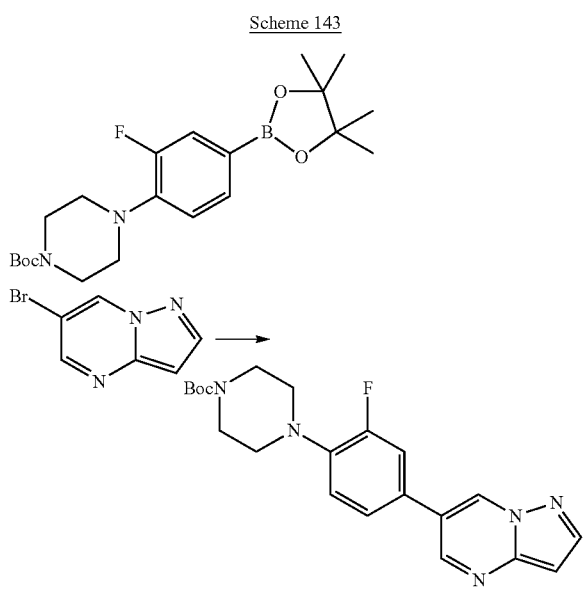

In an analogous manner to Scheme 5, tert-butyl 4-(2-fluoro-4-(pyrazolo[1,5-a]pyrimidin-6-yl)phenyl)piperazine-1-carboxylate was obtained from ter t-butyl 4-(2-fluoro-4-(4,4,5,5-tetramethyl-1,3,2-dioxaborolan-2-yl)phenyl)piperazine-1-carboxylate and 6-bromopyrazolo[1,5-a]pyrimidine in a 53% yield.

Scheme 144

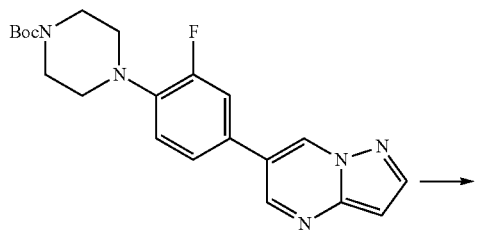

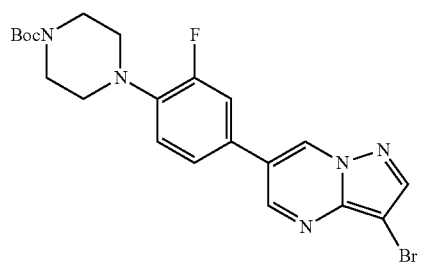

In an analogous manner to Scheme 4, tert-butyl 4-(4-(3-bromopyrazolo[1,5-a]pyrimidin-6-yl)-2-fluorophenyl)piperazine-1-carboxylate was obtained from tert-butyl 4-(2-fluoro-4-(pyrazolo[1,5-a]pyrimidin-6-yl)phenyl)piperazine-1-carboxylate in a 100% yield.

Scheme 145

In an analogous manner to Scheme 5, tert-butyl 4-(2-fluoro-4-(3-(quinolin-4-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)-2-fluorophenyl)piperazine-1-carboxylate and quinoline-4-boronic acid in a 26% yield.

Scheme 146

-continued

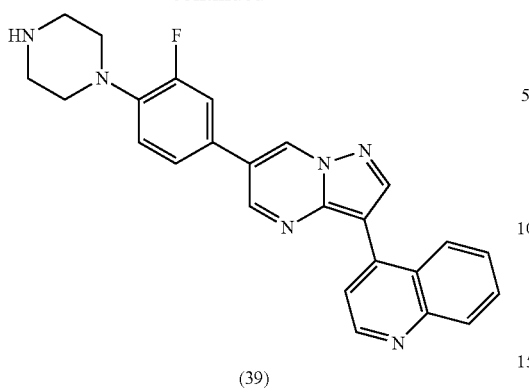

(39)

In an analogous manner to Scheme 2, tert-butyl 4-(4-(3-bromopyrazolo[1,5-a]pyrimidin-6-yl)-2-fluorophenyl)piperazine-1-carboxylate was obtained from tert-butyl 4-(2-fluoro-4-(3-(quinolin-4-yl)pyrazolo[1,5-a]pyrimidin-6-yl)phenyl)piperazine-1-carboxylate in 56% yield after reverse phase purification. $^1$H NMR (400 MHz, DMSO-d$_6$) δ 9.72 (d, J=2.3 Hz, 1H), 9.15 (d, J=2.3 Hz, 1H), 9.07 (d, J=4.9 Hz, 1H), 8.84 (s, 3H), 8.37-8.29 (m, 1H), 8.21-8.13 (m, 1H), 8.03-7.83 (m, 3H), 7.80-7.66 (m, 2H), 7.32-7.20 (m, 1H), 3.31 (s, 8H).

Compound 40

Scheme 147

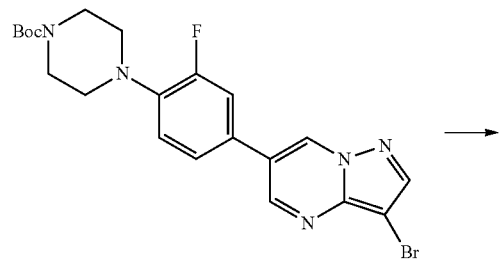

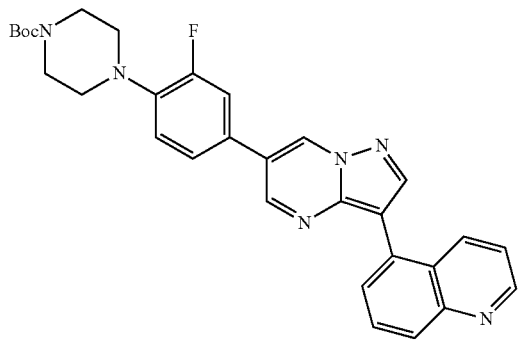

In an analogous manner to Scheme 5, tert-butyl 4-(2-fluoro-4-(3-(quinolin-5-yl)pyrazolo[1,5-a]pyrimidin-6-yl)phenyl)piperazine-1-carboxylate was obtained from tert-butyl 4-(4-(3-bromopyrazolo[1,5-a]pyrimidin-6-yl)-2-fluorophenyl)piperazine-1-carboxylate and quinoline-5-boronic acid in 30% yield.

Scheme 148

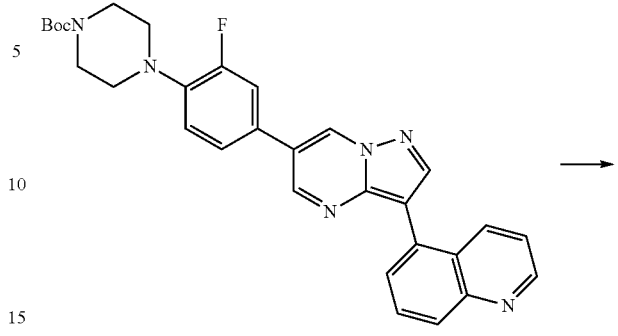

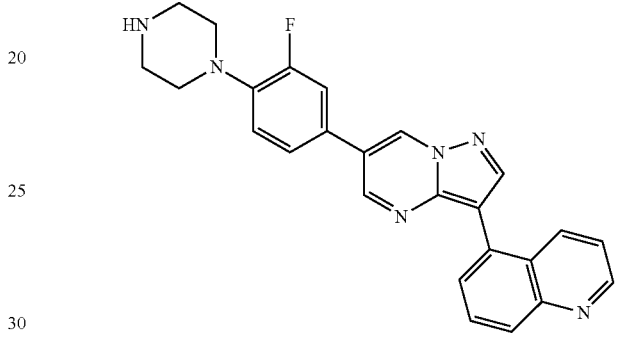

(40)

In an analogous manner to Scheme 2, 4-(6-(3-fluoro-4-(piperazin-1-yl)phenyl)pyrazolo[1,5-a]pyrimidin-3-yl)quinoline, TFA was obtained from tert-butyl 4-(2-fluoro-4-(3-(quinolin-4-yl)pyrazolo[1,5-a]pyrimidin-6-yl)phenyl)piperazine-1-carboxylate in 56% yield after reverse phase purification. $^1$H NMR (400 MHz, DMSO-d$_6$) δ 9.64 (d, J=2.3 Hz, 1H), 9.01 (dd, J=5.1, 2.0 Hz, 2H), 8.83 (s, 2H), 8.62 (s, 1H), 8.51 (dt, J=8.4, 1.3 Hz, 1H), 8.10 (dt, J=8.4, 1.1 Hz, 1H), 7.97-7.80 (m, 3H), 7.72 (dd, J=8.3, 2.2 Hz, 1H), 7.60 (dd, J=8.6, 4.3 Hz, 1H), 7.25 (dd, J=9.4, 8.4 Hz, 1H), 3.31 (s, 8H).

Compound 41

Scheme 149

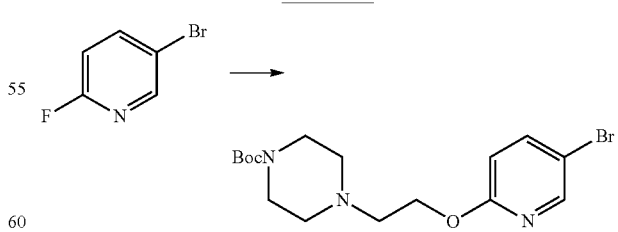

In an analogous manner to Scheme 106, tert-butyl 4-(2-((5-bromopyridin-2-yl)oxy)ethyl)piperazine-1-carboxylate was obtained from the reaction of 5-bromo-2-fluoropyridine and tert-butyl 4-(2-hydroxyethyl)piperazine-1-carboxylate in an 89% yield.

Scheme 150

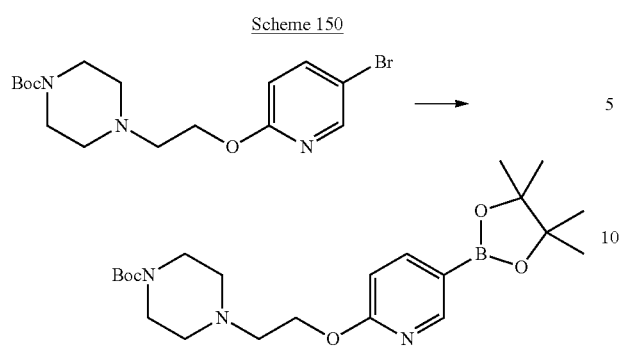

In an analogous manner to Scheme 32, tert-butyl 4-(2-((5-(4,4,5,5-tetramethyl-1,3,2-dioxaborolan-2-yl)pyridin-2-yl)oxy)ethyl)piperazine-1-carboxylate was obtained from tert-butyl 4-(2-((5-bromopyridin-2-yl)oxy)ethyl)piperazine-1-carboxylate.

Scheme 151

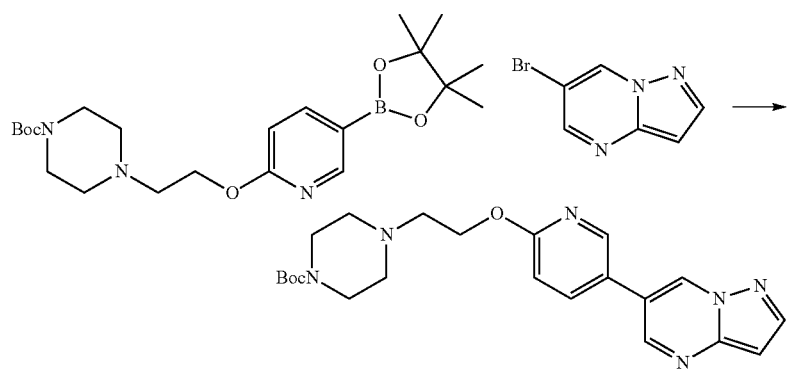

In an analogous manner to Scheme 5, tert-butyl 4-(2-((5-(pyrazolo[1,5-a]pyrimidin-6-yl)pyridin-2-yl)oxy)ethyl)piperazine-1-carboxylate was obtained from tert-butyl 4-(2-((5-(4,4,5,5-tetramethyl-1,3,2-dioxaborolan-2-yl)pyridin-2-yl)oxy)ethyl)piperazine-1-carboxylate and 6-bromopyrazolo[1,5-a]pyrimidine in an 80% yield.

Scheme 152

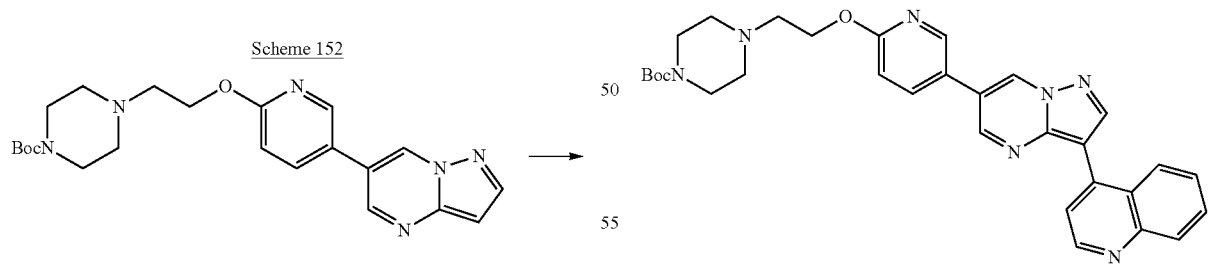

In an analogous manner to Scheme 111, tert-butyl 4-(2-((5-(3-bromopyrazolo[1,5-a]pyrimidin-6-yl)pyridin-2-yl)oxy)ethyl)piperazine-1-carboxylate was obtained from tert-butyl 4-(2-((5-(pyrazolo[1,5-a]pyrimidin-6-yl)pyridin-2-yl)oxy)ethyl)piperazine-1-carboxylate in an 88% yield.

Scheme 153

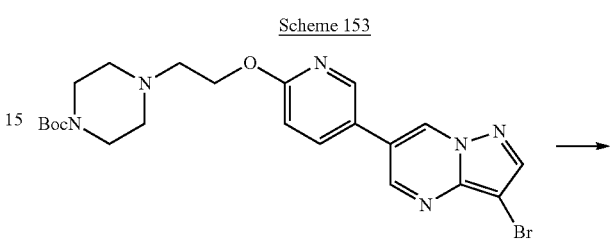

-continued

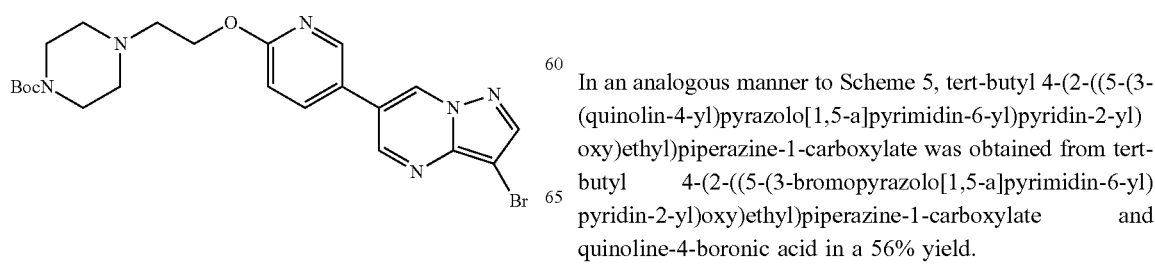

In an analogous manner to Scheme 5, tert-butyl 4-(2-((5-(3-(quinolin-4-yl)pyrazolo[1,5-a]pyrimidin-6-yl)pyridin-2-yl)oxy)ethyl)piperazine-1-carboxylate was obtained from tert-butyl 4-(2-((5-(3-bromopyrazolo[1,5-a]pyrimidin-6-yl)pyridin-2-yl)oxy)ethyl)piperazine-1-carboxylate and quinoline-4-boronic acid in a 56% yield.

Scheme 154

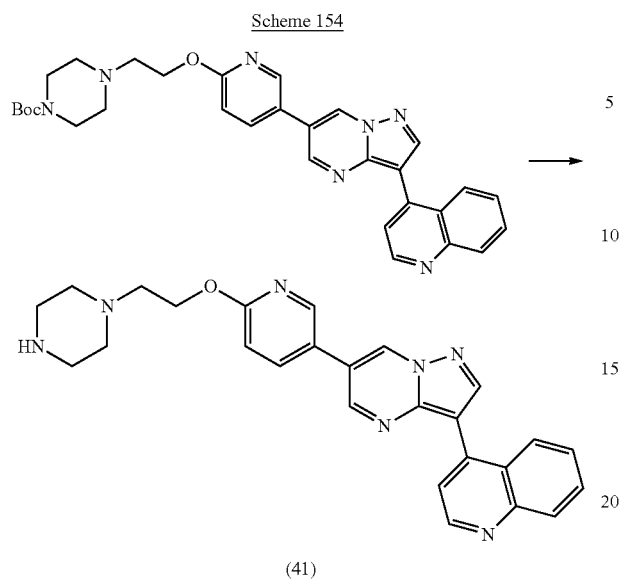

(41)

In an analogous manner to Scheme 2, 4-(6-(6-(2-(piperazin-1-yl)ethoxy)pyridin-3-yl)pyrazolo[1,5-a]pyrimidin-3-yl)quinoline, TFA was obtained from tert-butyl 4-(2-((5-(3-(quinolin-4-yl)pyrazolo[1,5-a]pyrimidin-6-yl)pyridin-2-yl)oxy)ethyl)piperazine-1-carboxylate in a 98% yield. $^1$H NMR (400 MHz, DMSO-$d_6$) δ 9.74 (d, J=2.3 Hz, 1H), 9.13 (d, J=2.2 Hz, 1H), 9.06 (d, J=4.8 Hz, 1H), 8.84 (s, 1H), 8.73 (dd, J=2.7, 0.8 Hz, 1H), 8.61 (s, 2H), 8.34-8.25 (m, 2H), 8.20-8.13 (m, 1H), 7.99-7.87 (m, 2H), 7.71 (t, J=7.6 Hz, 1H), 7.03 (d, J=8.6 Hz, 1H), 4.52 (s, 2H), 3.18 (s, 4H), 2.96-2.88 (m, 6H).

Compound 42

Scheme 156

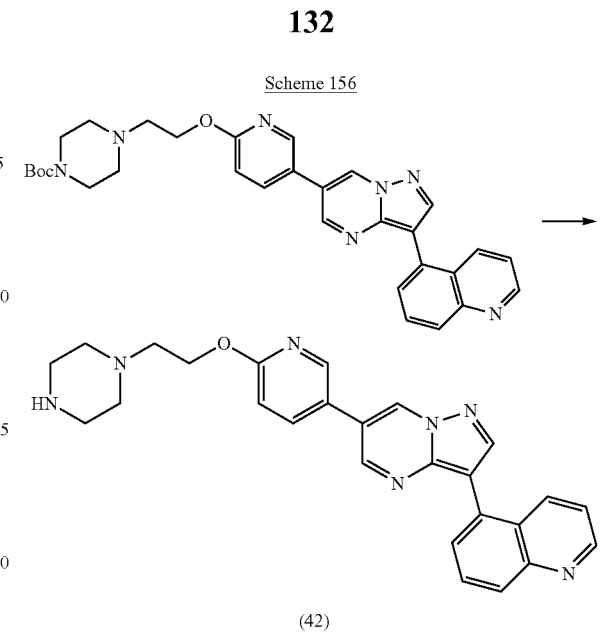

(42)

In an analogous manner to Scheme 2, 5-(6-(6-(2-(piperazin-1-yl)ethoxy)pyridin-3-yl)pyrazolo[1,5-a]pyrimidin-3-yl)quinoline, TFA was obtained from tert-butyl 4-(2-((5-(3-(quinolin-5-yl)pyrazolo[1,5-a]pyrimidin-6-yl)pyridin-2-yl)oxy)ethyl)piperazine-1-carboxylate in a 95% yield. $^1$H NMR (400 MHz, DMSO-$d_6$) δ 9.67 (d, J=2.3 Hz, 1H), 9.00 (dq, J=2.9, 1.6, 1.2 Hz, 2H), 8.71 (dd, J=2.6, 0.8 Hz, 1H), 8.63 (s, 1H), 8.49 (d, J=8.5 Hz, 1H), 8.27 (dd, J=8.7, 2.6 Hz, 1H), 8.10 (dt, J=8.3, 1.1 Hz, 1H), 7.96-7.81 (m, 2H), 7.58 (dd, J=8.6, 4.3 Hz, 1H), 7.02 (dd, J=8.6, 0.8 Hz, 1H), 4.54 (t, J=5.2 Hz, 2H), 3.21 (s, 4H), 2.98 (s, 6H).

Compound 43

Scheme 155

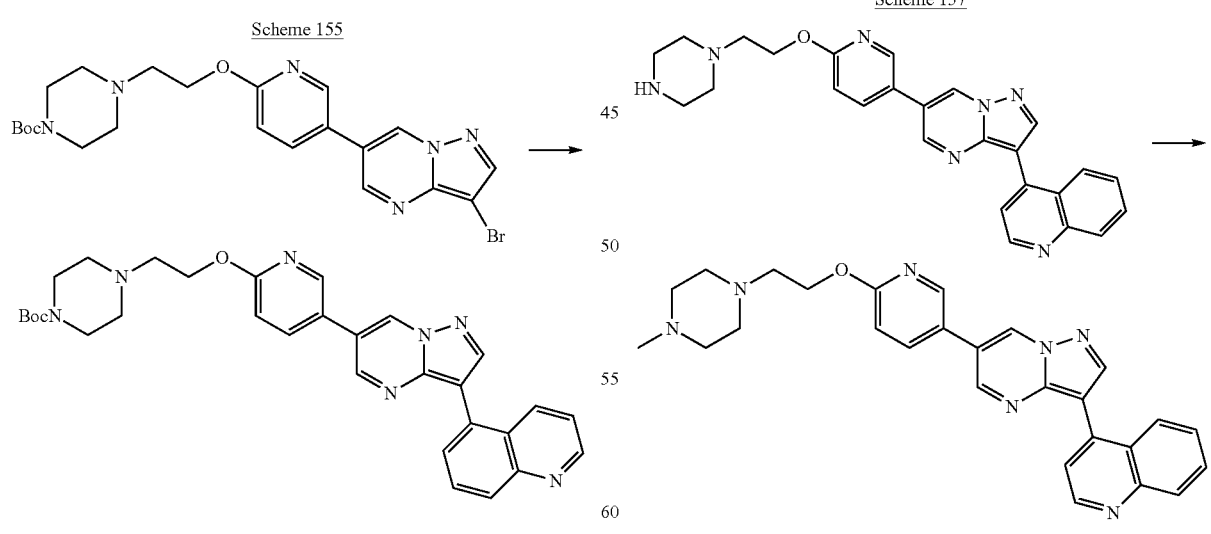

(43)

In an analogous manner to Scheme 5, tert-butyl 4-(2-((5-(3-(quinolin-5-yl)pyrazolo[1,5-a]pyrimidin-6-yl)pyridin-2-yl)oxy)ethyl)piperazine-1-carboxylate was obtained from tert-butyl 4-(2-((5-(3-bromopyrazolo[1,5-a]pyrimidin-6-yl)pyridin-2-yl)oxy)ethyl)piperazine-1-carboxylate and quinoline-5-boronic acid in a 76% yield.

4-(6-(6-(2-(piperazin-1-yl)ethoxy)pyridin-3-yl)pyrazolo[1,5-a]pyrimidin-3-yl)quinoline, TFA (0.03 g, 0.053 mmol) was dissolved in 1:1 THF/DCE (4 mL). 500 uL of a 37% aq. formaldehyde solution was added. Sodium triacetoxyborohydride (0.112 g, 0.530 mmol) was added and the mixture was heated to 80 deg in a capped vial for 4 hours. The solvent was removed and 2 mL of 2 M $Na_2CO_3$ was added upon which the product crashed out. Solid was extracted into DCM (20 mL), dried (MgSO4), filtered and concentrated to obtain 4-(6-(6-(2-(4-methylpiperazin-1-yl)ethoxy)pyridin-3-yl)pyrazolo[1,5-a]pyrimidin-3-yl)quinoline, TFA (42%) after reverse phase purification. $^1$H NMR (400 MHz, DMSO-$d_6$) δ 9.73 (d, J=2.3 Hz, 1H), 9.12 (d, J=2.2 Hz, 1H), 9.05 (d, J=4.8 Hz, 1H), 8.84 (s, 1H), 8.71 (dd, J=2.7, 0.8 Hz, 1H), 8.61 (s, 2H), 8.33-8.24 (m, 2H), 8.20-8.13 (m, 1H), 7.99-7.87 (m, 2H), 7.71 (t, J=7.6 Hz, 1H), 7.02 (d, J=8.6 Hz, 1H), 4.51 (s, 2H), 3.17 (s, 4H), 2.96-2.88 (m, 6H), 2.77 (s, 3H).

Compound 44

Scheme 158

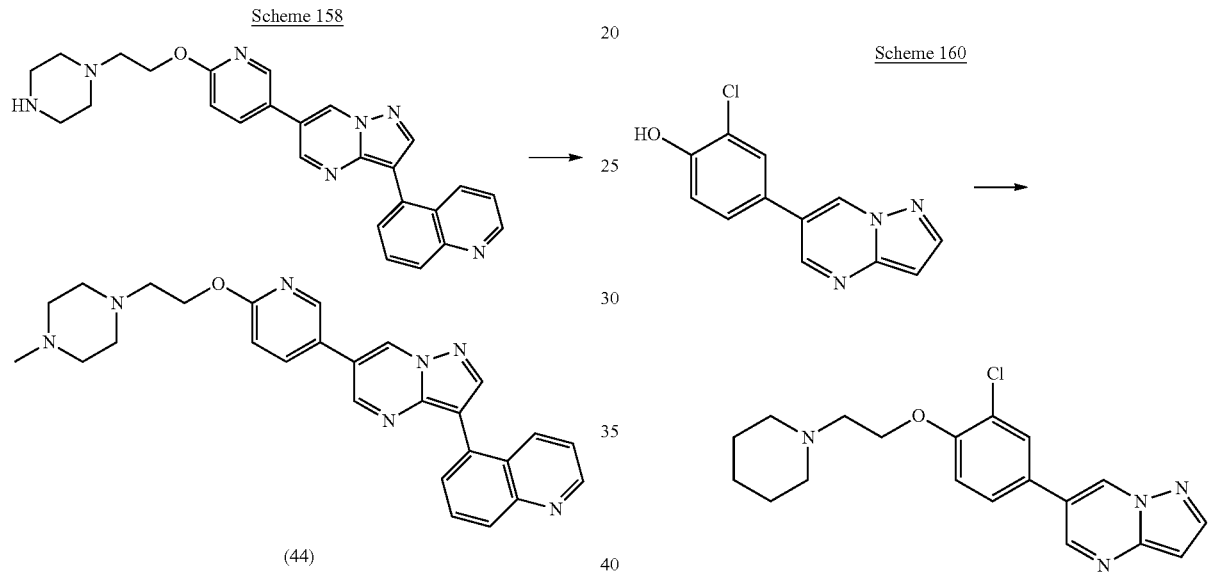

(44)

In an analogous manner to Scheme 157, 5-(6-(6-(2-(4-methylpiperazin-1-yl)ethoxy)pyridin-3-yl)pyrazolo[1,5-a]pyrimidin-3-yl)quinoline, TFA was obtained from 5-(6-(6-(2-(piperazin-1-yl)ethoxy)pyridin-3-yl)pyrazolo[1,5-a]pyrimidin-3-yl)quinoline, TFA in a 27% yield after reverse phase purification. $^1$H NMR (400 MHz, DMSO-$d_6$) δ 9.66 (d, J=2.2 Hz, 1H), 8.99 (dd, J=5.8, 1.9 Hz, 2H), 8.70 (d, J=2.8 Hz, 1H), 8.63 (s, 1H), 8.47 (d, J=8.4 Hz, 1H), 8.26 (dd, J=8.7, 2.6 Hz, 1H), 8.13-8.05 (m, 1H), 7.95-7.80 (m, 2H), 7.57 (dd, J=8.6, 4.3 Hz, 1H), 7.00 (d, J=8.6 Hz, 1H), 4.49 (s, 2H), 3.19 (s, 4H), 3.02 (s, 6H), 2.78 (s, 3H).

Compound 45

Scheme 159

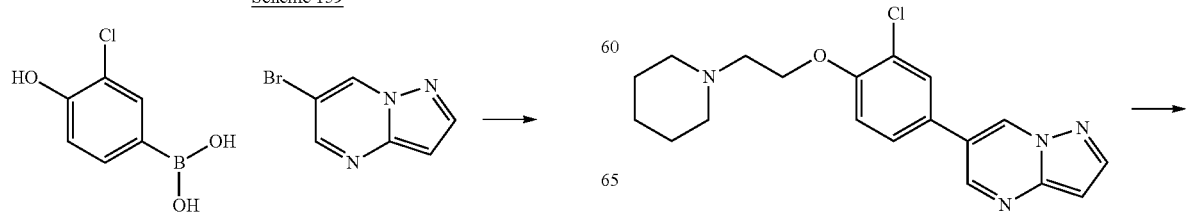

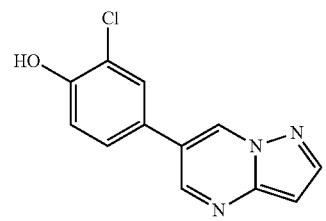

In an analogous manner to Scheme 5, 2-chloro-4-(pyrazolo[1,5-a]pyrimidin-6-yl)phenol was obtained from (3-chloro-4-hydroxyphenyl)boronic acid and 6-bromopyrazolo[1,5-a]pyrimidine in a 73% yield.

Scheme 160

To a solution of triphenylphosphine (1.153 g, 4.40 mmol) in DCM (Volume: 15 mL) added dropwise diisopropyl azodicarboxylate (0.889 g, 4.40 mmol). The mixture was stirred for 5 minutes then 2-chloro-4-(pyrazolo[1,5-a]pyrimidin-6-yl)phenol (0.72 g, 2.93 mmol) was added. After 5 minutes of stirring, 2-(piperidin-1-yl)ethanol (1.136 g, 8.79 mmol) was added. After aging for 20 minutes the reaction the mixture was purified on a silica plug (30 g) eluting with ethyl acetate and then 10% methanol/DCM until product eluted. Obtained 6-(3-chloro-4-(2-(piperidin-1-yl)ethoxy)phenyl)pyrazolo[1,5-a]pyrimidine (0.73 g, 2.046 mmol, 69.8% yield).

Scheme 161

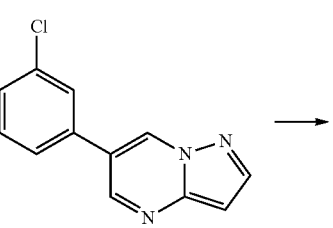

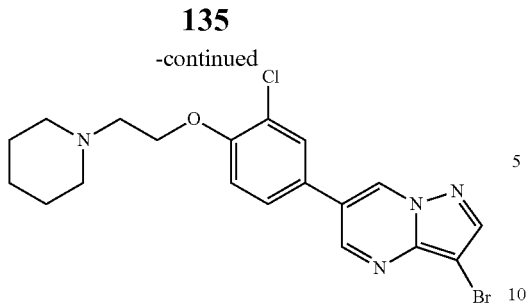

In an analogous manner to Scheme 111, 3-bromo-6-(3-chloro-4-(2-(piperidin-1-yl)ethoxy)phenyl)pyrazolo[1,5-a]pyrimidine was obtained from 6-(3-chloro-4-(2-(piperidin-1-yl)ethoxy)phenyl)pyrazolo[1,5-a]pyrimidine in a 94% yield Scheme 162

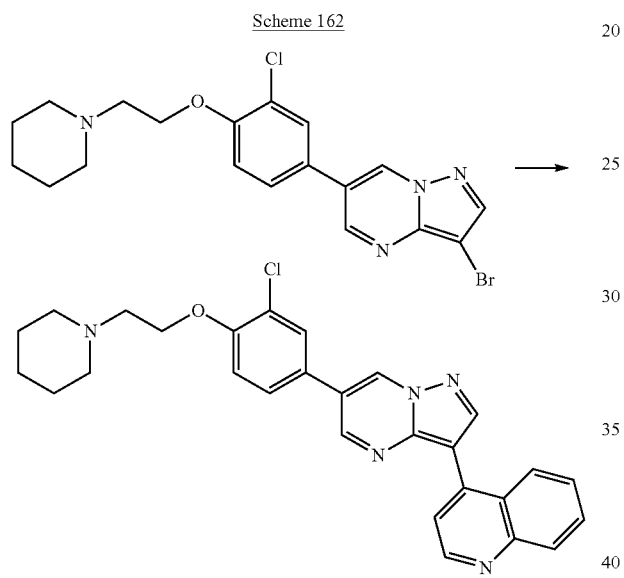

In an analogous manner to Scheme 5, 4-(6-(3-chloro-4-(2-(piperidin-1-yl)ethoxy)phenyl)pyrazolo[1,5-a]pyrimidin-3-yl)quinoline, TFA was obtained from 3-bromo-6-(3-chloro-4-(2-(piperidin-1-yl)ethoxy)phenyl)pyrazolo[1,5-a]pyrimidine and quinoline-4-boronic acid in 54% yield after reverse phase purification. $^1$H NMR (400 MHz, DMSO-$d_6$) δ 9.73 (d, J=2.3 Hz, 1H), 9.39 (s, 1H), 9.13 (d, J=2.3 Hz, 1H), 9.04 (d, J=4.7 Hz, 1H), 8.81 (s, 1H), 8.27 (d, J=8.2 Hz, 1H), 8.18-8.09 (m, 2H), 7.97-7.84 (m, 3H), 7.69 (t, J=7.7 Hz, 1H), 7.41 (d, J=8.7 Hz, 1H), 4.53 (t, J=4.9 Hz, 2H), 3.60 (d, J=5.1 Hz, 4H), 3.12 (d, J=11.4 Hz, 2H), 1.87 (d, J=13.3 Hz, 2H), 1.71 (s, 3H), 1.42 (s, 1H).

Compound 46

Scheme 163

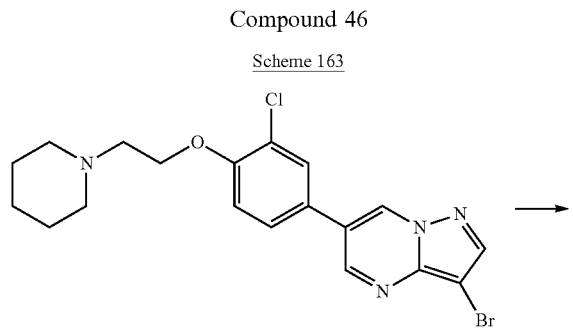

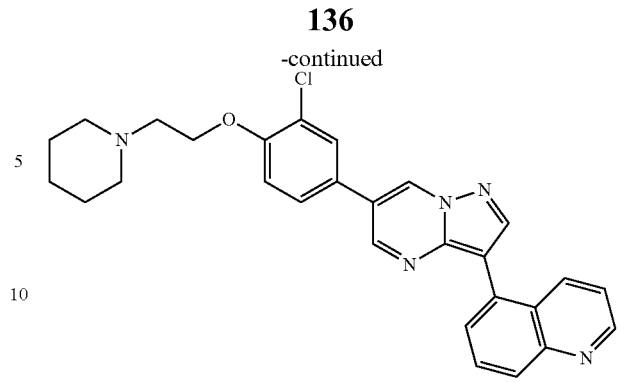

In an analogous manner to Scheme 5, 4-(6-(3-chloro-4-(2-(piperidin-1-yl)ethoxy)phenyl)pyrazolo[1,5-a]pyrimidin-3-yl)quinoline, TFA was obtained from 3-bromo-6-(3-chloro-4-(2-(piperidin-1-yl)ethoxy)phenyl)pyrazolo[1,5-a]pyrimidine and quinoline-5-boronic acid in 61% yield after reverse phase purification. $^1$H NMR (400 MHz, DMSO-$d_6$) δ 9.66 (d, J=2.3 Hz, 1H), 9.40 (s, 1H), 9.00 (dd, J=12.0, 3.2 Hz, 2H), 8.62 (s, 1H), 8.46 (d, J=8.6 Hz, 1H), 8.09 (dd, J=8.3, 1.7 Hz, 2H), 7.95-7.80 (m, 3H), 7.56 (dd, J=8.6, 4.3 Hz, 1H), 7.40 (d, J=8.7 Hz, 1H), 4.52 (t, J=4.8 Hz, 2H), 3.61 (dd, J=10.3, 5.3 Hz, 4H), 3.10 (dd, J=12.6, 9.3 Hz, 2H), 1.87 (d, J=13.7 Hz, 2H), 1.71 (s, 3H), 1.42 (s, 1H).

Compound 47

Scheme 164

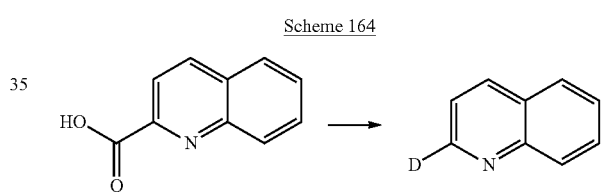

2-quinoline carboxylic acid (1.73 g, 10 mmol) was dissolved in DMSO (50 mL) containing $D_2O$ (10 mL). Silver carbonate (0.28 g, 1 mmol) was added and the mixture was heated at 120 deg for 16 hours. The solid was filtered off through a bed of Celite and washed with ethyl acetate (200 mL). The filtrate was washed with water, separated and the organic layer was washed with brine, dried ($MgSO_4$), filtered and concentrated to yield 2-$^2$H-quinoline in a 95% yield.

Scheme 165

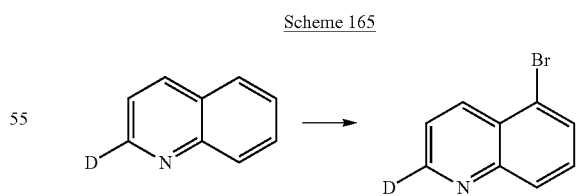

To a solution of 2-$^2$H-quinoline (1.25 g, 9.5 mmol) in concd $H_2SO_4$ (15 mL) at r.t. was added NBS (3.5 g, 19.7 mmol). The reaction mixture was stirred for 8. The reaction mixture was poured onto crushed ice (5× the volume of $H_2SO_4$), pH was adjusted to 9.0 using concd aq $NH_3$ and the alkaline slurry was then extracted with diethyl ether (3× double the volume of $H_2SO_4$). The combined organic fractions were washed with 1.0 M NaOH then water, dried ($MgSO_4$), filtered, evaporated to dryness and purified by column chromatography (eluent: CH₂Cl₂-Et₂O, 9:1) to give 5-bromo-2-²H-quinoline (0.87 g, 4.2 mmol) in a 44% yield.

Scheme 166

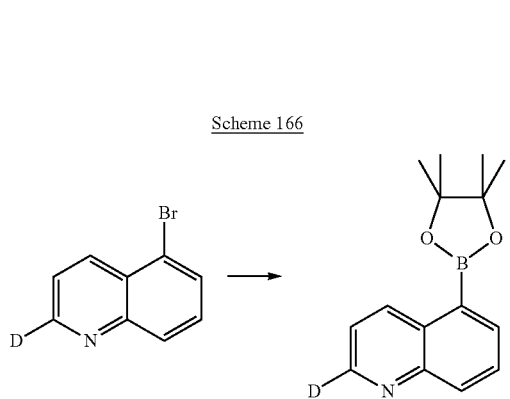 [SMILES: [2H]c1ccc2c(Br)cccc2n1 ; [2H]c1ccc2c(B3OC(C)(C)C(C)(C)O3)cccc2n1]

In an analogous manner to Scheme 32, 5-(4,4,5,5-tetramethyl-1,3,2-dioxaborolan-2-yl)-2-²H-quinoline was obtained from 5-bromo-2-²H-quinoline.

Scheme 167

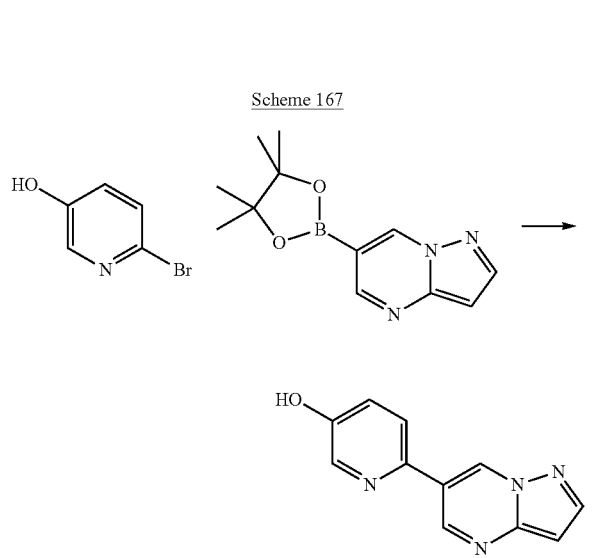

In an analogous manner to Scheme 5, 6-(pyrazolo[1,5-a]pyrimidin-6-yl)pyridin-3-ol was obtained from 2-bromo-5-hydroxypyridine in a 56% yield.

Scheme 168

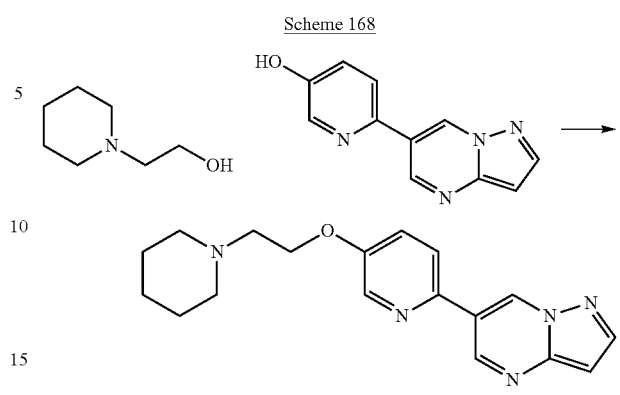

In an analogous manner to Scheme 160, 6-(5-(2-(piperidin-1-yl)ethoxy)pyridin-2-yl)pyrazolo[1,5-a]pyrimidine was obtained from 6-(pyrazolo[1,5-a]pyrimidin-6-yl)pyridin-3-ol and 2-(piperidin-1-yl)ethanol in a 68% yield.

Scheme 169

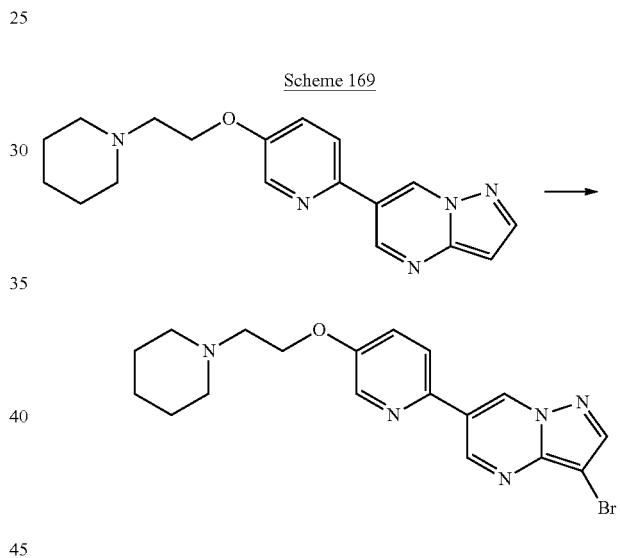

In an analogous manner to Scheme 111, 3-bromo-6-(5-(2-(piperidin-1-yl)ethoxy)pyridin-2-yl)pyrazolo[1,5-a]pyrimidine was obtained from 6-(5-(2-(piperidin-1-yl)ethoxy)pyridin-2-yl)pyrazolo[1,5-a]pyrimidine in a 87% yield.

Scheme 170

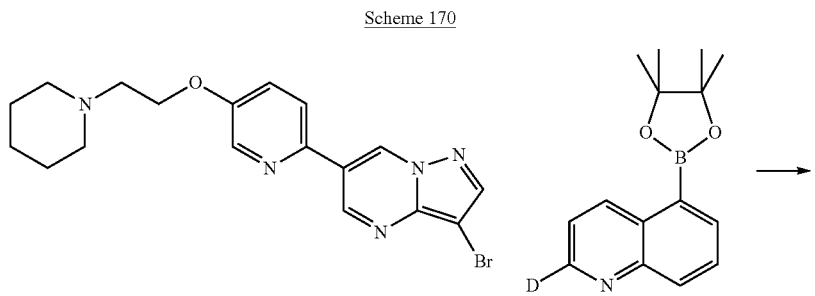

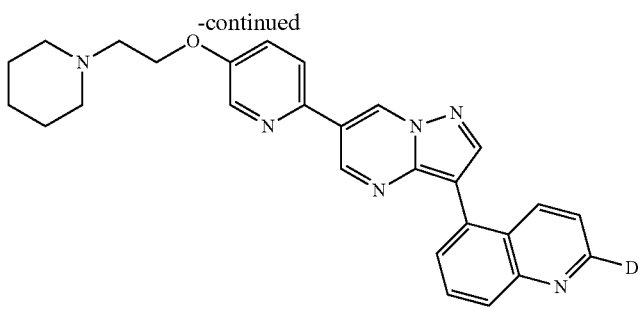

In an analogous manner to Scheme 5, 5-(6-(5-(2-(piperidin-1-yl)ethoxy)pyridin-2-yl)pyrazolo[1,5-a]pyrimidin-3-yl)-2-$^2$H-quinoline, TFA was obtained from 3-bromo-6-(5-(2-(piperidin-1-yl)ethoxy)pyridin-2-yl)pyrazolo[1,5-a]pyrimidine and 5-(4,4,5,5-tetramethyl-1,3,2-dioxaborolan-2-yl)-2-$^2$H-quinoline in a 40% yield after reverse phase purification. $^1$H NMR (400 MHz, DMSO-d$_6$) δ 9.81 (d, J=2.0 Hz, 1H), 9.66 (s, 1H), 9.30 (d, J=1.9 Hz, 1H), 8.66 (d, J=1.4 Hz, 1H), 8.59-8.48 (m, 2H), 8.24 (d, J=8.8 Hz, 1H), 8.12 (d, J=8.4 Hz, 1H), 7.95 (t, J=7.8 Hz, 1H), 7.88 (d, J=7.3 Hz, 1H), 7.65 (ddd, J=14.7, 8.7, 2.1 Hz, 2H), 4.53 (t, J=4.8 Hz, 2H), 3.66-3.43 (m, 4H), 3.04 (q, J=11.4, 10.7 Hz, 2H), 1.85 (d, J=13.6 Hz, 2H), 1.73 (t, J=12.8 Hz, 3H), 1.42 (t, J=13.6 Hz, 1H).

Compound 48'

Scheme 171

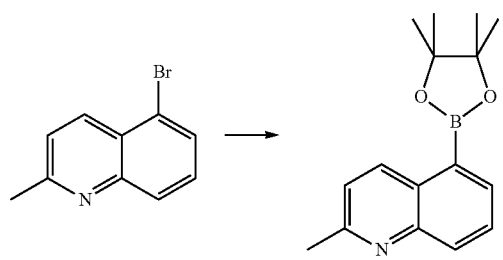

In an analogous manner to Scheme 32, 2-methyl-5-(4,4,5,5-tetramethyl-1,3,2-dioxaborolan-2-yl)quinoline was obtained from 5-bromo-2-methylquinoline.

Scheme 172

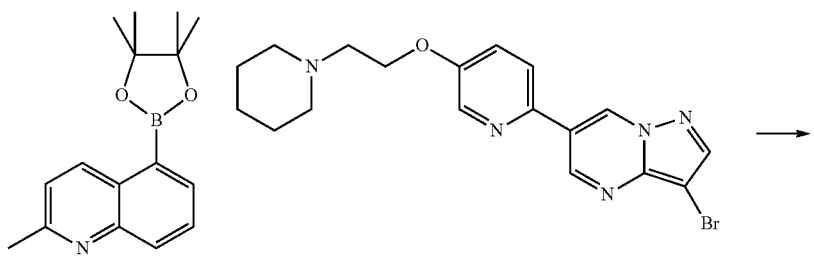

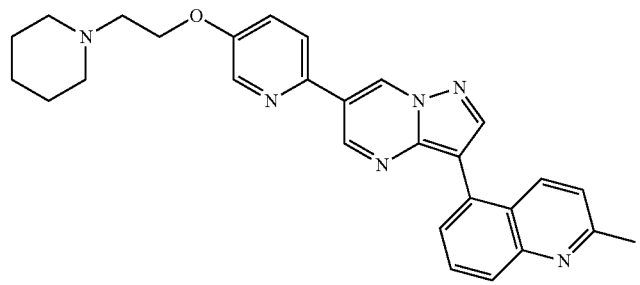

In an analogous manner to Scheme 5, 2-methyl-5-(6-(5-(2-(piperidin-1-yl)ethoxy)pyridin-2-yl)pyrazolo[1,5-a]pyrimidin-3-yl)quinoline, TFA was obtained from 3-bromo-6-(5-(2-(piperidin-1-yl)ethoxy)pyridin-2-yl)pyrazolo[1,5-a]pyrimidine and 2-methyl-5-(4,4,5,5-tetramethyl-1,3,2-dioxaborolan-2-yl)quinoline in a 33% yield after reverse phase purification. $^1$H NMR (400 MHz, DMSO-d$_6$) δ 9.86-9.76 (m, 2H), 9.30 (d, J=2.0 Hz, 1H), 8.73-8.65 (m, 2H), 8.50 (d, J=2.9 Hz, 1H), 8.24 (d, J=8.8 Hz, 1H), 8.12 (d, J=8.4 Hz, 1H), 8.03 (t, J=7.9 Hz, 1H), 7.93 (d, J=7.2 Hz, 1H), 7.72-7.62 (m, 2H), 4.53 (t, J=4.8 Hz, 2H), 3.64-3.50 (m, 4H), 3.05 (t, J=10.9 Hz, 2H), 2.85 (s, 3H), 1.85 (d, J=13.5 Hz, 2H), 1.73 (t, J=13.2 Hz, 3H), 1.40 (d, J=13.1 Hz, 1H).

Compound 49

In an analogous manner to Scheme 160, tert-butyl 4-(2-((6-(pyrazolo[1,5-a]pyrimidin-6-yl)pyridin-3-yl)oxy)ethyl)piperazine-1-carboxylate was obtained from 6-(pyrazolo[1,5-a]pyrimidin-6-yl)pyridin-3-ol and tert-butyl 4-(2-hydroxyethyl)piperazine-1-carboxylate in a 67% yield.

Scheme 173

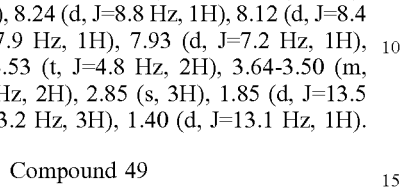

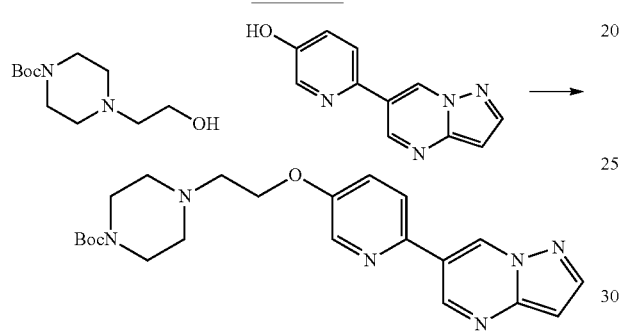

Scheme 174

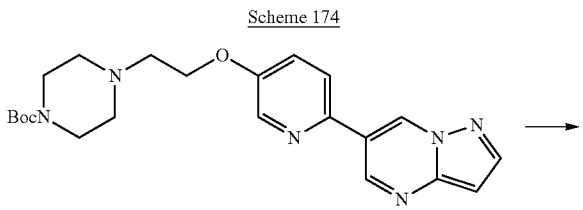

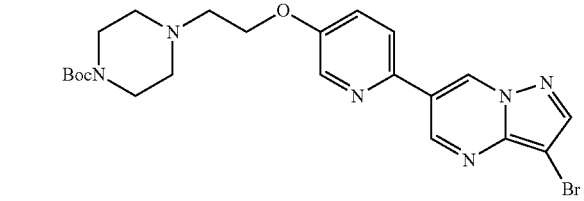

In an analogous manner to Scheme 111, tert-butyl 4-(2-((6-(3-bromopyrazolo[1,5-a]pyrimidin-6-yl)pyridin-3-yl)oxy)ethyl)piperazine-1-carboxylate was obtained from tert-butyl 4-(2-((6-(pyrazolo[1,5-a]pyrimidin-6-yl)pyridin-3-yl)oxy)ethyl)piperazine-1-carboxylate in 89% yield.

Scheme 175

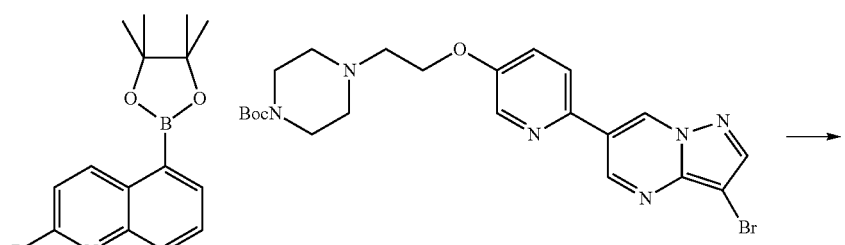

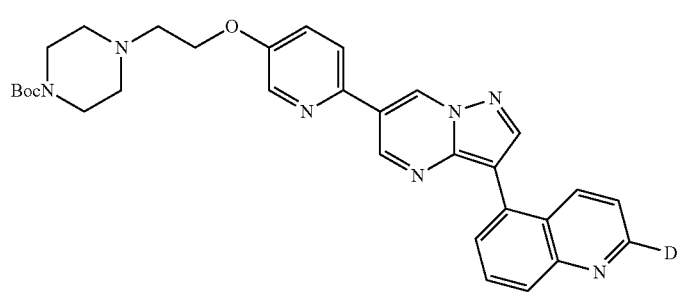

In an analogous manner to Scheme 5, tert-butyl 4-(2-((6-(3-2-$^2$H-(quinolin-5-yl)pyrazolo[1,5-a]pyrimidin-6-yl)pyridin-3-yl)oxy)ethyl)piperazine-1-carboxylate was obtained from ter t-butyl 4-(2-((6-(3-bromopyrazolo[1,5-a]pyrimidin-6-yl)pyridin-3-yl)oxy)ethyl)piperazine-1-carboxylate in a 28% yield.

Scheme 176

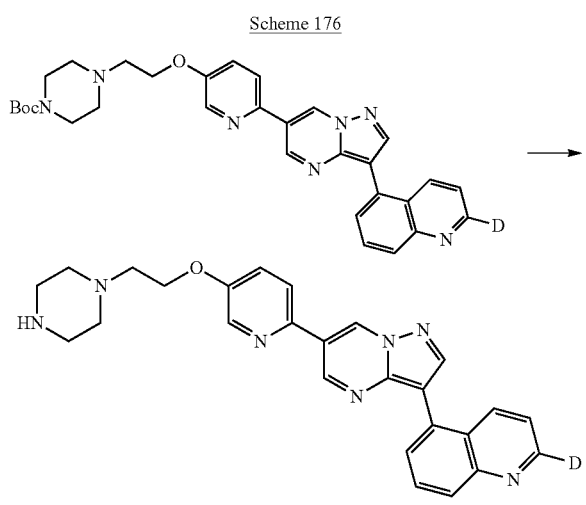

In an analogous manner to Scheme 2, 5-(6-(5-(2-(piperazin-1-yl)ethoxy)pyridin-2-yl)pyrazolo[1,5-a]pyrimidin-3-yl)-2-²H-quinoline, TFA was obtained from, tert-butyl 4-(2-((6-(3-2-²H-(quinolin-5-yl)pyrazolo[1,5-a]pyrimidin-6-yl)pyridin-3-yl)oxy)ethyl)piperazine-1-carboxylate in a 74% yield. ¹H NMR (400 MHz, DMSO-d₆) δ 9.80 (d, J=2.2 Hz, 1H), 9.30 (d, J=2.2 Hz, 1H), 8.77 (s, 2H), 8.65 (s, 1H), 8.57-8.45 (m, 2H), 8.21 (d, J=8.8 Hz, 1H), 8.11 (dt, J=8.4, 1.1 Hz, 1H), 7.94 (dd, J=8.4, 7.2 Hz, 1H), 7.87 (dd, J=7.1, 1.3 Hz, 1H), 7.67-7.58 (m, 2H), 4.37 (s, 2H), 3.24 (s, 4H), 3.17 (s, 2H), 3.04 (s, 4H).

Compound 50 from ter t-butyl 4-(2-((6-(3-bromopyrazolo[1,5-a]pyrimidin-6-yl)pyridin-3-yl)oxy)ethyl)piperazine-1-carboxylate and 2-methyl-5-(4,4,5,5-tetramethyl-1,3,2-dioxaborolan-2-yl)quinoline in a 21% yield.

Scheme 178

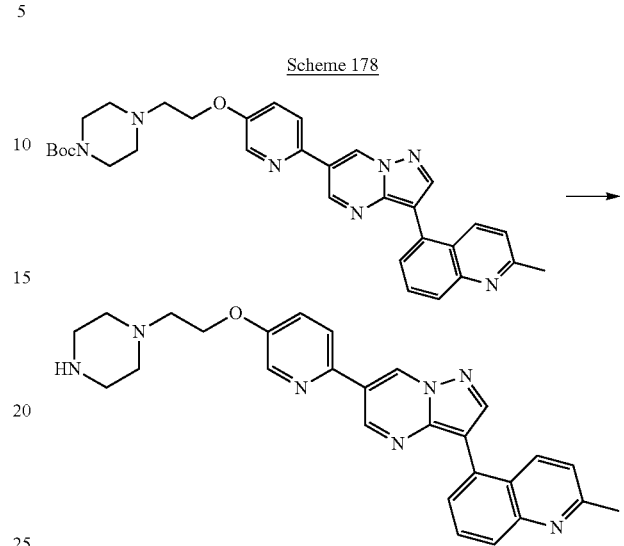

In an analogous manner to Scheme 2, 2-methyl-5-(6-(5-(2-(piperazin-1-yl)ethoxy)pyridin-2-yl)pyrazolo[1,5-a]pyrimidin-3-yl)quinoline, TFA was obtained from tert-butyl 4-(2-((6-(3-(2-methylquinolin-5-yl)pyrazolo[1,5-a]pyrimidin-6-yl)pyridin-3-yl)oxy)ethyl)piperazine-1-carboxylate in a 81% yield. ¹H NMR (400 MHz, DMSO-d₆) δ 9.81 (d, J=2.2 Hz, 1H), 9.30 (d, J=2.2 Hz, 1H), 8.66 (s, 1H), 8.47 (d, J=3.0 Hz, 1H), 8.21 (d, J=8.8 Hz, 1H), 8.07 (d, J=8.4 Hz, 1H), 7.99

Scheme 177

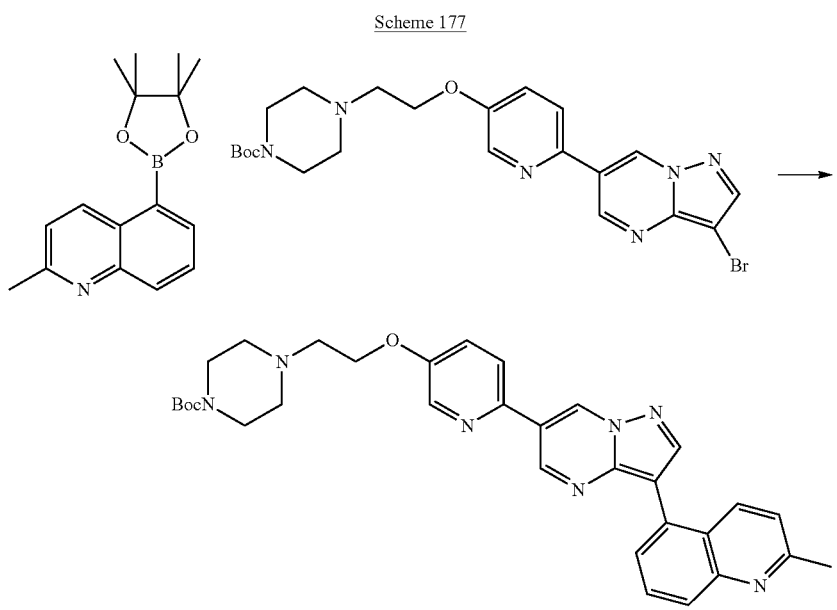

In an analogous manner to Scheme 5, tert-butyl 4-(2-((6-(3-(2-methylquinolin-5-yl)pyrazolo[1,5-a]pyrimidin-6-yl)pyridin-3-yl)oxy)ethyl)piperazine-1-carboxylate was obtained (t, J=8.1 Hz, 1H), 7.90 (d, J=7.2 Hz, 1H), 7.67-7.59 (m, 2H), 4.33 (s, 2H), 3.20 (s, 4H), 3.06 (s, 2H), 2.93 (s, 4H), 2.82 (s, 3H).

Compound 51

Scheme 179

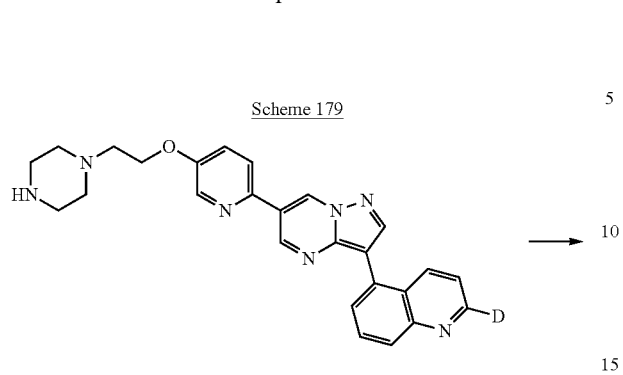

Suspended 5-(6-(5-(2-(piperazin-1-yl)ethoxy)pyridin-2-yl)pyrazolo[1,5-a]pyrimidin-3-yl)-2-$^2$H-quinoline, TFA (0.13 g, 0.287 mmol) in DCE/THF (2:1, 9 mL) then added 40% formalin solution (3 mL). Added Sodium triacetoxyborohydride (0.609 g, 2.87 mmol), capped vial and heated to 80 deg for 14 h. Vigorously stirred mixture with sat'd NaHCO$_3$ for 10 min. Partitioned between DCM and water (60 mL each). Dried organic layer with MgSO$_4$, filtered and concentrated. Obtained 5-(6-(5-(2-(4-methylpiperazin-1-yl)ethoxy)pyridin-2-yl)pyrazolo[1,5-a]pyrimidin-3-yl)-2-$^2$H-quinoline in a 33% yield after reverse phase purification. $^1$H NMR (400 MHz, DMSO-d$_6$) δ 9.78 (d, J=2.2 Hz, 1H), 9.28 (d, J=2.2 Hz, 1H), 8.64 (s, 1H), 8.55 (d, J=8.6 Hz, 1H), 8.51-8.41 (m, 1H), 8.19 (d, J=8.8 Hz, 1H), 8.10 (dt, J=8.4, 1.1 Hz, 1H), 7.94 (dd, J=8.4, 7.1 Hz, 1H), 7.87 (dd, J=7.2, 1.3 Hz, 1H), 7.61 (dq, J=8.8, 2.7 Hz, 2H), 4.31 (t, J=5.2 Hz, 2H), 3.42 (s, 2H), 3.24 (s, 4H), 3.03 (s, 4H), 2.78 (s, 3H).

Compound 52

Scheme 180

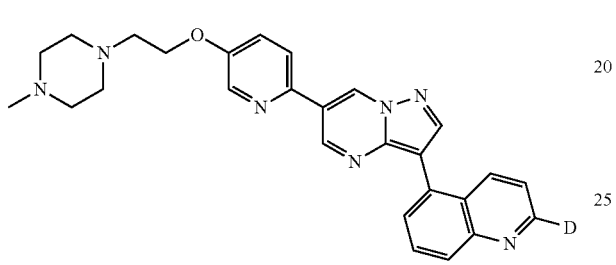

In an analogous manner to Scheme 5, (3R,5S)-tert-butyl 3,5-dimethyl-4-(4-(3-(2-$^2$H-quinolin-4-yl)pyrazolo[1,5-a]pyrimidin-6-yl)phenyl)piperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate and 4-(4,4,5,5-tetramethyl-1,3,2-dioxaborolan-2-yl)-2-$^2$H-quinoline in a 44% yield.

Scheme 181

In an analogous manner to Scheme 2, 4-(6-(4-((2R,6S)-2,6-dimethylpiperazin-1-yl)phenyl)pyrazolo[1,5-a]pyrimidin-3-yl)-2-$^2$H-quinoline, TFA was obtained from (3R,5S)-tert-butyl 3,5-dimethyl-4-(4-(3-(2-$^2$H-quinolin-4-yl)pyrazolo[1,5-a]pyrimidin-6-yl)phenyl)piperazine-1-carboxylate in a 75% yield. $^1$H NMR (400 MHz, DMSO-d$_6$) δ 9.82 (s, 1H), 9.40 (s, 1H), 9.28 (d, J=2.3 Hz, 1H), 9.05 (s, 1H), 8.64 (d, J=8.5 Hz, 1H), 8.46-8.37 (m, 2H), 8.16 (t, J=7.7 Hz, 1H), 8.02 (s, 2H), 7.94 (t, J=7.7 Hz, 1H), 7.37 (s, 2H), 4.10 (s, 4H), 3.42 (s, 2H), 0.90 (s, 6H).

147

Compound 53

Scheme 182

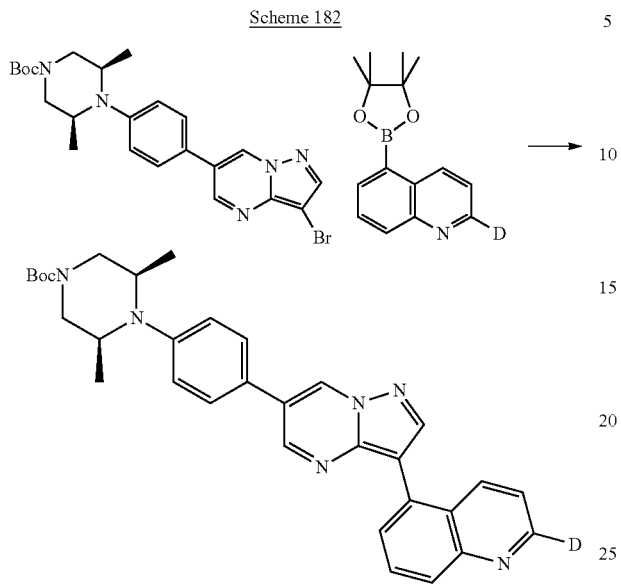

In an analogous manner to Scheme 5, 5-(6-(4-((2R,6S)-2,6-dimethylpiperazin-1-yl)phenyl)pyrazolo[1,5-a]pyrimidin-3-yl)-2-²H-quinoline was obtained from (3R,5S)-tert-butyl 4-(4-(3-bromopyrazolo[1,5-a]pyrimidin-6-yl)phenyl)-3,5-dimethylpiperazine-1-carboxylate and 5-(4,4,5,5-tetramethyl-1,3,2-dioxaborolan-2-yl)-2-²H-quinoline in a 39% yield.

Scheme 183

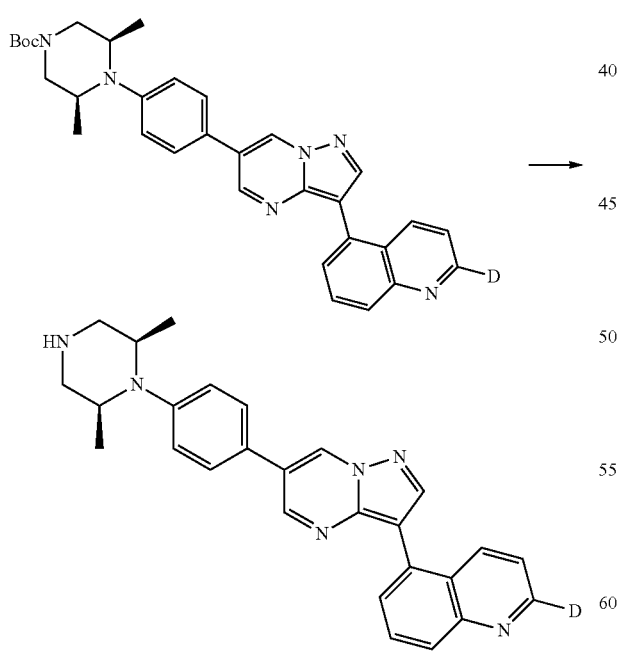

In an analogous manner to Scheme 2, 5-(6-(4-((2R,6S)-2,6-dimethylpiperazin-1-yl)phenyl)pyrazolo[1,5-a]pyrimidin-3-yl)-2-²H-quinoline, TFA was obtained from 5-(6-(4-((2R,6S)-2,6-dimethylpiperazin-1-yl)phenyl)pyrazolo[1,5-a]

148 pyrimidin-3-yl)-2-²H-quinoline in an 88% yield. ¹H NMR (400 MHz, DMSO-d₆) δ 9.63 (d, J=2.3 Hz, 1H), 9.03 (d, J=2.3 Hz, 1H), 9.00 (s, 2H), 8.66-8.55 (m, 2H), 8.12 (dt, J=8.3, 1.1 Hz, 1H), 8.00-7.86 (m, 4H), 7.64 (d, J=8.6 Hz, 1H), 7.33-7.22 (m, 2H), 3.45-3.32 (m, 4H), 2.86 (q, J=10.9 Hz, 2H), 0.82 (d, J=6.3 Hz, 6H).

Compound 54

Scheme 184

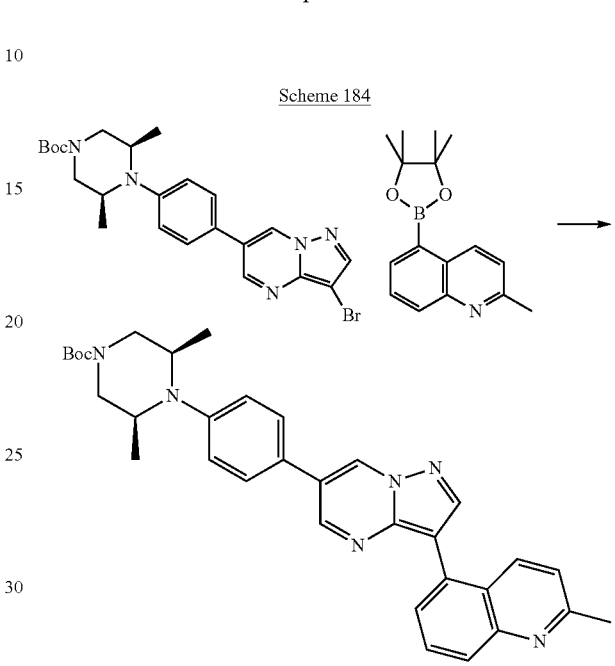

In an analogous manner to Scheme 5, (3R,5S)-tert-butyl 3,5-dimethyl-4-(4-(3-(2-methylquinolin-5-yl)pyrazolo[1,5-a]pyrimidin-6-yl)phenyl)piperazine-1-carboxylate was obtained from (3R,5S)-tert-butyl 4-(4-(3-bromopyrazolo[1,5-a]pyrimidin-6-yl)phenyl)-3,5-dimethylpiperazine-1-carboxylate and 2-methyl-5-(4,4,5,5-tetramethyl-1,3,2-dioxaborolan-2-yl)quinoline in a 45% yield.

Scheme 185

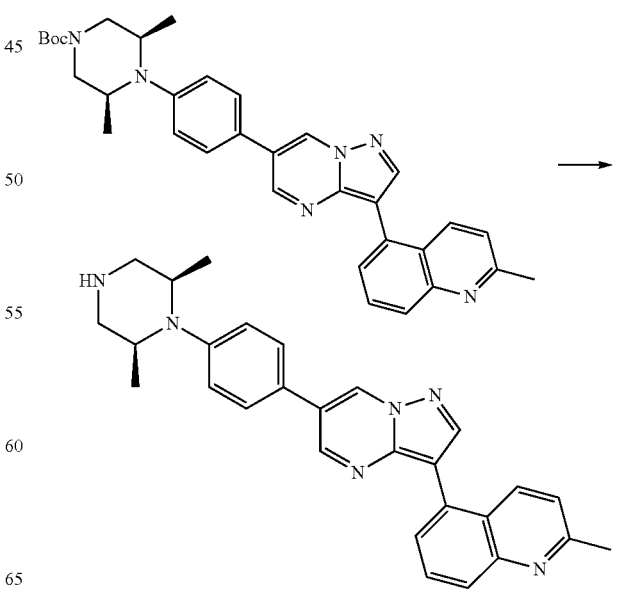

In an analogous manner to Scheme 2, 5-(6-(4-((2R,6S)-2,6-dimethylpiperazin-1-yl)phenyl)pyrazolo[1,5-a]pyrimidin-3-yl)-2-methylquinoline, TFA was obtained from (3R,5S)-tert-butyl 3,5-dimethyl-4-(4-(3-(2-methylquinolin-5-yl)pyrazolo[1,5-a]pyrimidin-6-yl)phenyl)piperazine-1-carboxylate in a 76% yield. ¹H NMR (400 MHz, DMSO-$d_6$) δ 9.64 (d, J=2.2 Hz, 1H), 9.03 (d, J=2.3 Hz, 1H), 8.97 (s, 2H), 8.65 (s, 2H), 8.11-7.95 (m, 2H), 7.95-7.88 (m, 3H), 7.64 (d, J=8.9 Hz, 1H), 7.32-7.25 (m, 2H), 3.57-3.24 (m, 4H), 2.93-2.80 (m, 5H), 0.82 (d, J=6.3 Hz, 6H).

Compound 55

Scheme 186

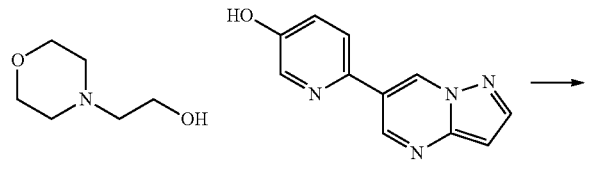

-continued

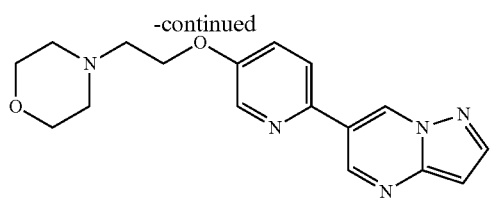

In an analogous manner to Scheme 160, 4-(2-((6-(pyrazolo[1,5-a]pyrimidin-6-yl)pyridin-3-yl)oxy)ethyl)morpholine was obtained from 6-(pyrazolo[1,5-a]pyrimidin-6-yl)pyridin-3-ol and 2-morpholinoethanol in a 66% yield.

Scheme 187

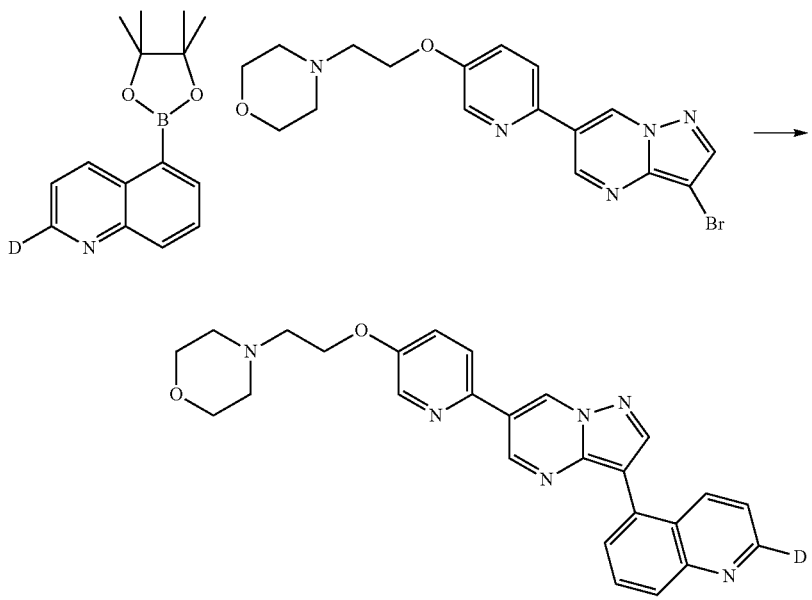

In an analogous manner to Scheme 111, 4-(2-((6-(3-bromopyrazolo[1,5-a]pyrimidin-6-yl)pyridin-3-yl)oxy)ethyl)morpholine was obtained from 4-(2-((6-(pyrazolo[1,5-a]pyrimidin-6-yl)pyridin-3-yl)oxy)ethyl)morpholine in a 56% yield.

Scheme 188

In an analogous manner to Scheme 5, 4-(2-((6-(3-(2-²H-quinolin-5-yl)pyrazolo[1,5-a]pyrimidin-6-yl)pyridin-3-yl)oxy)ethyl)morpholine, TFA was obtained from 4-(2-((6-(3-bromopyrazolo[1,5-a]pyrimidin-6-yl)pyridin-3-yl)oxy)ethyl)morpholine and 5-(4,4,5,5-tetramethyl-1,3,2-dioxaborolan-2-yl)-2-²H-quinoline in a 33% yield after reverse phase purification. ¹H NMR (400 MHz, DMSO-$d_6$) δ 10.16 (s, 1H), 9.82 (d, J=2.1 Hz, 1H), 9.30 (d, J=2.1 Hz, 1H), 8.66 (s, 1H), 8.57-8.49 (m, 2H), 8.24 (d, J=8.8 Hz, 1H), 8.11 (d, J=8.4 Hz, 1H), 7.99-7.84 (m, 2H), 7.72-7.58 (m, 2H), 4.54 (t, J=4.7 Hz, 2H), 4.00 (s, 2H), 3.65 (t, J=4.7 Hz, 2H), 3.55 (s, 2H), 3.24 (s, 2H).

Compound 56

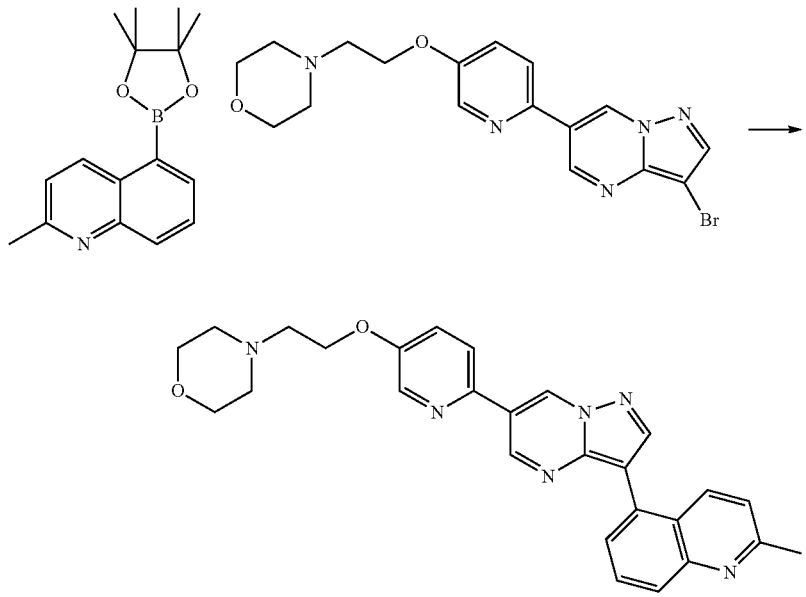

Scheme 189

In an analogous manner to Scheme 5, 4-(2-((6-(3-(2-methylquinolin-5-yl)pyrazolo[1,5-a]pyrimidin-6-yl)pyridin-3-yl)oxy)ethyl)morpholine, TFA was obtained from 4-(2-((6-(3-bromopyrazolo[1,5-a]pyrimidin-6-yl)pyridin-3-yl)oxy)ethyl)morpholine and 5-(4,4,5,5-tetramethyl-1,3,2-dioxaborolan-2-yl)-2-$^2$H-quinoline and 2-methyl-5-(4,4,5,5-tetramethyl-1,3,2-dioxaborolan-2-yl)quinoline in a 28% yield after reverse phase purification. $^1$H NMR (400 MHz, DMSO-d$_6$) δ 10.27 (s, 1H), 9.83 (d, J=2.2 Hz, 1H), 9.31 (d, J=2.2 Hz, 1H), 8.67 (s, 2H), 8.54-8.48 (m, 1H), 8.24 (d, J=8.8 Hz, 1H), 8.09 (d, J=8.4 Hz, 1H), 8.01 (t, J=7.8 Hz, 1H), 7.91 (d, J=7.0 Hz, 1H), 7.71-7.62 (m, 2H), 4.54 (t, J=4.8 Hz, 2H), 3.99 (s, 2H), 3.74 (s, 2H), 3.64 (d, J=5.4 Hz, 2H), 3.55 (s, 2H), 3.24 (s, 2H), 2.83 (s, 3H).

Compound 57

Scheme 190

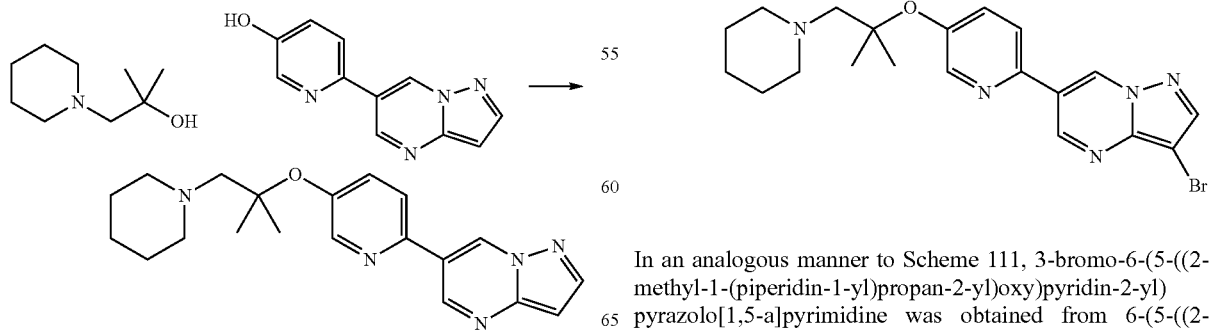

In an analogous manner to Scheme 160, 6-(5-((2-methyl-1-(piperidin-1-yl)propan-2-yl)oxy)pyridin-2-yl)pyrazolo[1,5-a]pyrimidine was obtained from 6-(pyrazolo[1,5-a]pyrimidin-6-yl)pyridin-3-ol and 2-methyl-1-(piperidin-1-yl)propan-2-ol in a 72% yield.

Scheme 191

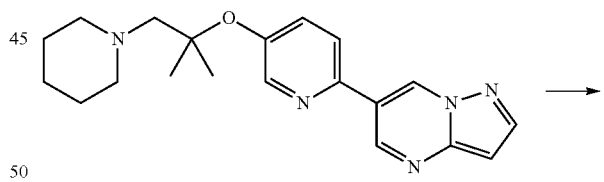

In an analogous manner to Scheme 111, 3-bromo-6-(5-((2-methyl-1-(piperidin-1-yl)propan-2-yl)oxy)pyridin-2-yl)pyrazolo[1,5-a]pyrimidine was obtained from 6-(5-((2-methyl-1-(piperidin-1-yl)propan-2-yl)oxy)pyridin-2-yl)pyrazolo[1,5-a]pyrimidine in a 84% yield.

Scheme 192

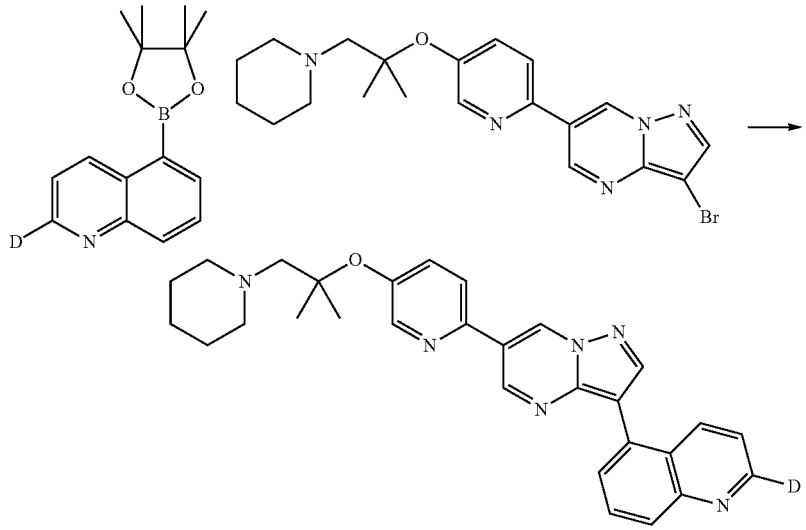

In an analogous manner to Scheme 5, 5-(6-(5-((2-methyl-1-(piperidin-1-yl)propan-2-yl)oxy)pyridin-2-yl)pyrazolo[1,5-a]pyrimidin-3-yl)-2-$^2$H-quinoline, TFA was obtained from 3-bromo-6-(5-((2-methyl-1-(piperidin-1-yl)propan-2-yl)oxy)pyridin-2-yl)pyrazolo[1,5-a]pyrimidine and 5-(4,4,5,5-tetramethyl-1,3,2-dioxaborolan-2-yl)-2-$^2$H-quinoline in a 47% yield after reverse phase purification. $^1$H NMR (400 MHz, DMSO-d$_6$) δ 9.86 (d, J=2.2 Hz, 1H), 9.32 (d, J=2.2 Hz, 1H), 9.01 (s, 1H), 8.67 (s, 1H), 8.59-8.46 (m, 2H), 8.27-8.20 (m, 1H), 8.10 (dt, J=8.4, 1.1 Hz, 1H), 7.97-7.83 (m, 2H), 7.79 (dd, J=8.7, 2.8 Hz, 1H), 7.59 (d, J=8.6 Hz, 1H), 3.60 (d, J=12.6 Hz, 2H), 3.52 (d, J=4.7 Hz, 2H), 3.16 (dq, J=13.9, 7.3 Hz, 2H), 1.88-1.81 (m, 4H), 1.74-1.64 (m, 1H), 1.54-1.41 (m, 1H), 1.45 (s, 6H).

Compound 58

In an analogous manner to Scheme 5, 2-methyl-5-(6-(5-((2-methyl-1-(piperidin-1-yl)propan-2-yl)oxy)pyridin-2-yl)pyrazolo[1,5-a]pyrimidin-3-yl)quinoline, TFA was obtained from 3-bromo-6-(5-((2-methyl-1-(piperidin-1-yl)propan-2-yl)oxy)pyridin-2-yl)pyrazolo[1,5-a]pyrimidine and 2-methyl-5-(4,4,5,5-tetramethyl-1,3,2-dioxaborolan-2-yl)quinoline in a 29% yield after reverse phase purification. $^1$H NMR (400 MHz, DMSO-d$_6$) δ 9.87 (d, J=2.2 Hz, 1H), 9.32 (d, J=2.2 Hz, 1H), 9.00 (s, 1H), 8.68 (s, 1H), 8.56 (d, J=2.8 Hz, 1H), 8.24 (d, J=8.7 Hz, 1H), 8.05 (d, J=8.4 Hz, 1H), 7.94 (d, J=8.8 Hz, 1H), 7.89-7.76 (m, 2H), 7.57 (d, J=8.9 Hz, 1H), 3.60 (d, J=12.7 Hz, 2H), 3.52 (d, J=4.7 Hz, 2H), 3.16 (dq, J=13.8, 7.2 Hz, 2H), 2.78 (s, 3H), 1.84 (t, J=4.7 Hz, 4H), 1.68 (dd, J=8.9, 4.6 Hz, 1H), 1.49 (d, J=7.1 Hz, 1H), 1.45 (s, 6H).

Scheme 193

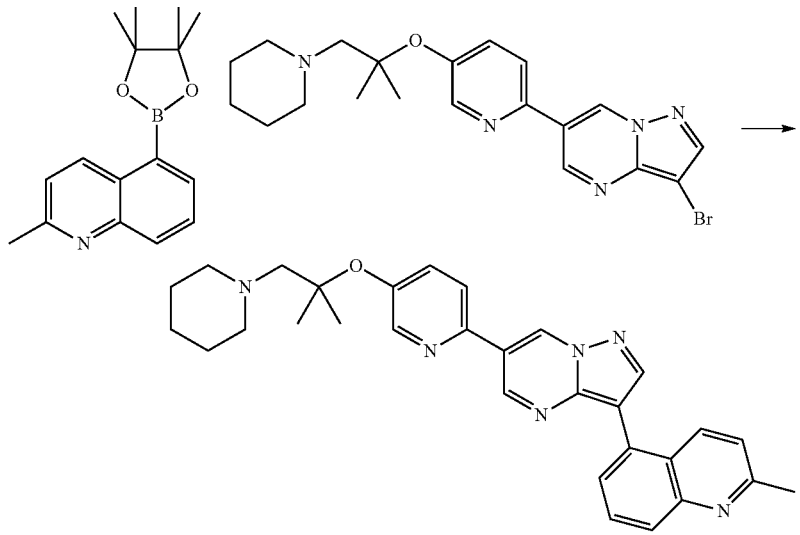

Compound 59

Scheme 194

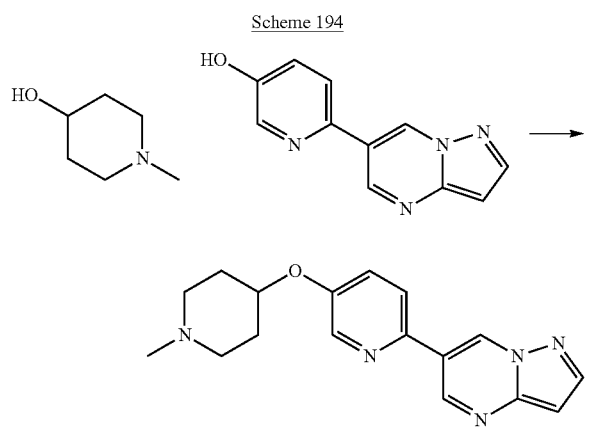

In an analogous manner to Scheme 160, 6-(5-((1-methylpiperidin-4-yl)oxy)pyridin-2-yl)pyrazolo[1,5-a]pyrimidine was obtained from 6-(pyrazolo[1,5-a]pyrimidin-6-yl)pyridin-3-ol and 1-methylpiperidin-4-ol in a 75% yield.

Scheme 195

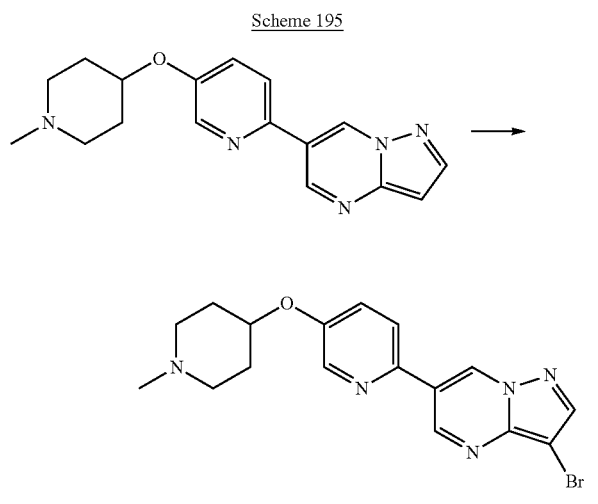

In an analogous manner to Scheme 111, 3-bromo-6-(5-((1-methylpiperidin-4-yl)oxy)pyridin-2-yl)pyrazolo[1,5-a]pyrimidine was obtained from 6-(5-((1-methylpiperidin-4-yl)oxy)pyridin-2-yl)pyrazolo[1,5-a]pyrimidine in a 84% yield.

Scheme 196

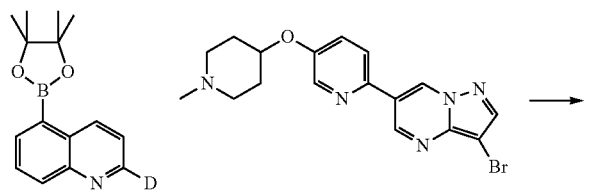

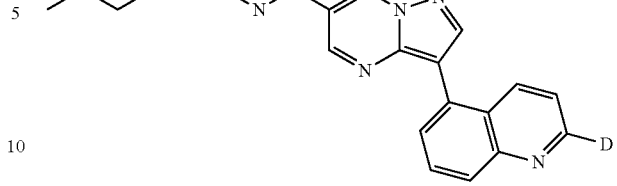

In an analogous manner to Scheme 5, 5-(6-(5-(((1-methylpiperidin-4-yl)oxy)pyridin-2-yl)pyrazolo[1,5-a]pyrimidin-3-yl)-2-²H-quinoline, TFA was obtained from 3-bromo-6-(5-((1-methylpiperidin-4-yl)oxy)pyridin-2-yl)pyrazolo[1,5-a]pyrimidine and and 5-(4,4,5,5-tetramethyl-1,3,2-dioxaborolan-2-yl)-2-²H-quinoline in a 37% yield after reverse phase purification. ¹H NMR (400 MHz, DMSO-d₆) δ 9.81 (t, J=2.5 Hz, 1H), 9.58 (d, J=11.4 Hz, 1H), 9.30 (dd, J=2.2, 1.4 Hz, 1H), 8.65 (s, 1H), 8.58-8.44 (m, 2H), 8.21 (dd, J=8.8, 5.7 Hz, 1H), 8.19-8.08 (m, 1H), 7.99-7.84 (m, 2H), 7.69 (ddd, J=8.9, 3.0, 1.0 Hz, 1H), 7.69-7.58 (m, 1H), 4.93 (s, 1H), 4.71 (dt, J=10.8, 6.0 Hz, 1H), 3.36 (d, J=12.4 Hz, 1H), 3.23 (t, J=11.0 Hz, 1H), 3.11 (d, J=11.6 Hz, 1H), 2.89-2.80 (m, 3H), 2.34 (d, J=14.3 Hz, 1H), 2.14 (d, J=15.3 Hz, 1H), 2.02 (t, J=14.1 Hz, 1H), 1.90-1.72 (m, 1H).

Compound 60

Scheme 197

[structure image]

In an analogous manner to Scheme 5, 2-methyl-5-(6-(5-(((1-methylpiperidin-4-yl)oxy)pyridin-2-yl)pyrazolo[1,5-a]pyrimidin-3-yl)quinoline, TFA was obtained from 3-bromo-6-(5-((1-methylpiperidin-4-yl)oxy)pyridin-2-yl)pyrazolo[1,5-a]pyrimidine and 2-methyl-5-(4,4,5,5-tetramethyl-1,3,2-dioxaborolan-2-yl)quinoline in a 23% yield after reverse phase purification. ¹H NMR (400 MHz, DMSO-d₆) δ 9.82 (dd, J=3.2, 2.2 Hz, 1H), 9.70 (s, 1H), 9.30 (dd, J=2.2, 1.2 Hz, 1H), 8.67 (s, 2H), 8.51 (dd, J=11.4, 2.9 Hz, 1H), 8.21 (dd, J=8.8, 5.5 Hz, 1H), 8.09 (d, J=8.4 Hz, 1H), 8.00 (t, J=7.8 Hz, 1H), 7.91 (d, J=7.1 Hz, 1H), 7.74-7.61 (m, 2H), 4.96-4.68 (m, 1H), 3.55 (d, J=12.7 Hz, 1H), 3.36 (d, J=12.0 Hz, 1H), 3.18 (dt, J=39.1, 11.1 Hz, 2H), 2.88-2.81 (m, 3H), 2.83 (s, 3H), 2.34 (d, J=13.7 Hz, 1H), 2.14 (d, J=15.4 Hz, 1H), 2.03 (t, J=13.8 Hz, 1H), 1.80 (q, J=10.4 Hz, 1H).

Compound 61

Scheme 198

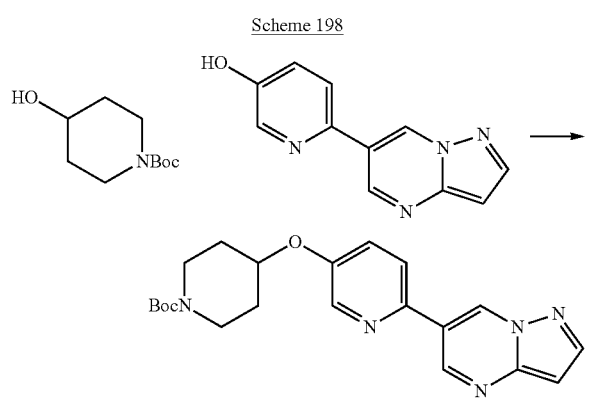

In an analogous manner to Scheme 160, tert-butyl 4-((6-(pyrazolo[1,5-a]pyrimidin-6-yl)pyridin-3-yl)oxy)piperidine-1-carboxylate was obtained from 6-(pyrazolo[1,5-a]pyrimidin-6-yl)pyridin-3-ol and tert-butyl 4-hydroxypiperidine-1-carboxylate in a 68% yield.

Scheme 199

In an analogous manner to Scheme 111, tert-butyl 4-((6-(3-bromopyrazolo[1,5-a]pyrimidin-6-yl)pyridin-3-yl)oxy)piperidine-1-carboxylate was obtained from tert-butyl 4-((6-(pyrazolo[1,5-a]pyrimidin-6-yl)pyridin-3-yl)oxy)piperidine-1-carboxylate in a 77% yield.

Scheme 200

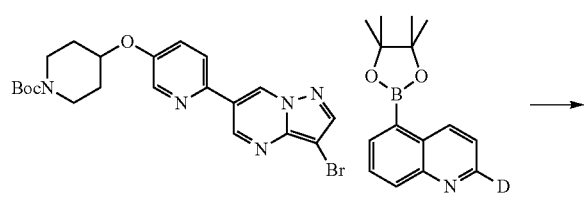

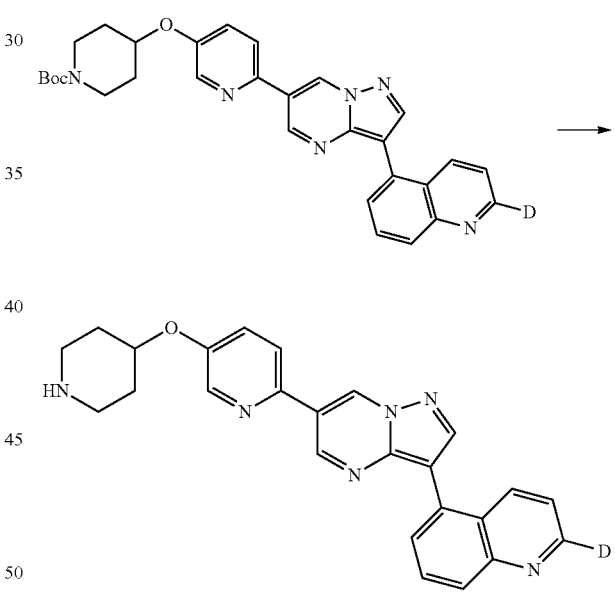

In an analogous manner to Scheme 5, tert-butyl 4-((6-(3-(2-$^2$H-quinolin-5-yl)pyrazolo[1,5-a]pyrimidin-6-yl)pyridin-3-yl)oxy)piperidine-1-carboxylate was obtained from tert-butyl 4-((6-(3-bromopyrazolo[1,5-a]pyrimidin-6-yl)pyridin-3-yl)oxy)piperidine-1-carboxylate and 5-(4,4,5,5-tetramethyl-1,3,2-dioxaborolan-2-yl)-2-$^2$H-quinoline in a 50% yield.

Scheme 201

In an analogous manner to Scheme 2, 5-(6-(5-(piperidin-4-yloxy)pyridin-2-yl)pyrazolo[1,5-a]pyrimidin-3-yl)-2-$^2$H-quinoline was obtained from tert-butyl 4-((6-(3-(2-$^2$H-quinolin-5-yl)pyrazolo[1,5-a]pyrimidin-6-yl)pyridin-3-yl)oxy)piperidine-1-carboxylate in a 73% yield. $^1$H NMR (400 MHz, DMSO-d$_6$) δ 9.81 (d, J=2.2 Hz, 1H), 9.30 (d, J=2.2 Hz, 1H), 8.65 (s, 1H), 8.53-8.45 (m, 4H), 8.21 (d, J=8.8 Hz, 1H), 8.10 (dt, J=8.3, 1.1 Hz, 1H), 7.92 (dd, J=8.4, 7.2 Hz, 1H), 7.86 (dd, J=7.2, 1.4 Hz, 1H), 7.69 (dd, J=8.9, 2.9 Hz, 1H), 7.58 (d, J=8.6 Hz, 1H), 4.83 (p, J=4.0 Hz, 1H), 3.29 (s, 2H), 3.11 (d, J=8.6 Hz, 2H), 2.14 (s, 2H), 1.87 (dtd, J=11.9, 8.2, 7.8, 3.4 Hz, 2H).

Compound 62

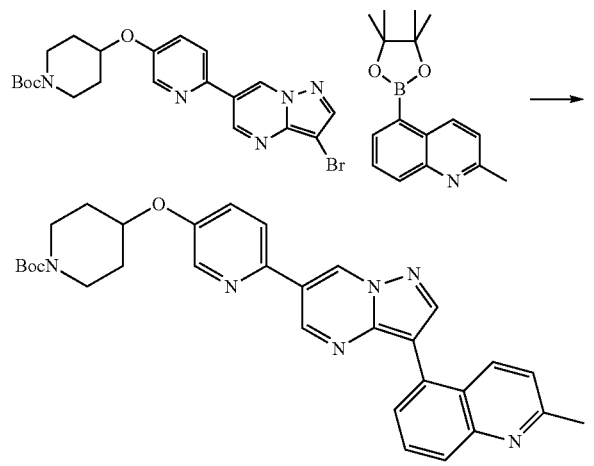

Scheme 202

In an analogous manner to Scheme 5, tert-butyl 4-((6-(3-(2-methylquinolin-5-yl)pyrazolo[1,5-a]pyrimidin-6-yl)pyridin-3-yl)oxy)piperidine-1-carboxylate was obtained from tert-butyl 4-((6-(3-bromopyrazolo[1,5-a]pyrimidin-6-yl)pyridin-3-yl)oxy)piperidine-1-carboxylate and 2-methyl-5-(4,4,5,5-tetramethyl-1,3,2-dioxaborolan-2-yl)quinoline in a 34% yield.

Scheme 203

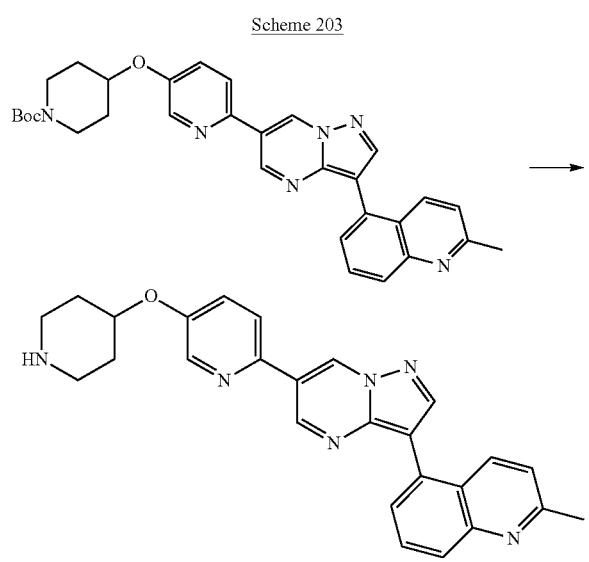

In an analogous manner to Scheme 2, 2-methyl-5-(6-(5-(piperidin-4-yloxy)pyridin-2-yl)pyrazolo[1,5-a]pyrimidin-3-yl)quinoline, TFA was obtained from tert-butyl 4-((6-(3-(2-methylquinolin-5-yl)pyrazolo[1,5-a]pyrimidin-6-yl)pyridin-3-yl)oxy)piperidine-1-carboxylate in a 68% yield.
¹H NMR (400 MHz, DMSO-d₆) δ 9.82 (d, J=2.2 Hz, 1H), 9.30 (d, J=2.2 Hz, 1H), 8.66 (s, 1H), 8.56 (s, 3H), 8.50 (d, J=2.9 Hz, 1H), 8.21 (d, J=8.8 Hz, 1H), 8.07 (d, J=8.4 Hz, 1H), 7.98 (t, J=7.8 Hz, 1H), 7.88 (d, J=7.1 Hz, 1H), 7.69 (dd, J=8.9, 3.0 Hz, 1H), 7.62 (d, J=8.8 Hz, 1H), 4.84 (dt, J=7.8, 4.1 Hz, 1H), 3.30 (s, 2H), 3.12 (d, J=9.7 Hz, 2H), 2.81 (s, 3H), 2.20-2.10 (m, 2H), 1.94-1.80 (m, 2H).

Compound 63

Scheme 204

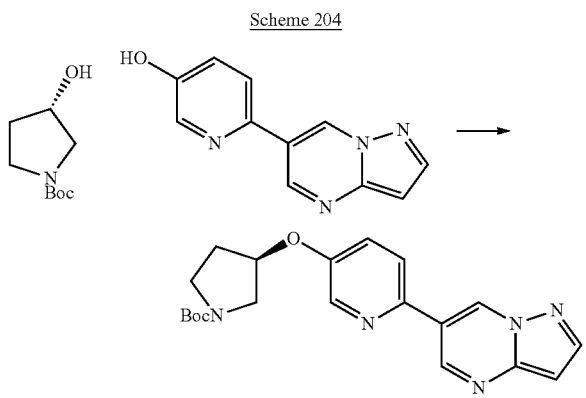

In an analogous manner to Scheme 160, (R)-tert-butyl 3-((6-(pyrazolo[1,5-a]pyrimidin-6-yl)pyridin-3-yl)oxy)pyrrolidine-1-carboxylate was obtained from 6-(pyrazolo[1,5-a]pyrimidin-6-yl)pyridin-3-ol and (S)-tert-butyl 3-hydroxypyrrolidine-1-carboxylate in an 84% yield.

Scheme 205

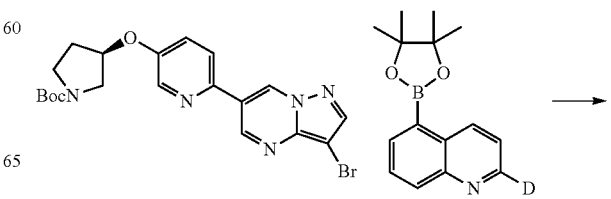

In an analogous manner to Scheme 111, (R)-tert-butyl 3-((6-(3-bromopyrazolo[1,5-a]pyrimidin-6-yl)pyridin-3-yl)oxy)pyrrolidine-1-carboxylate was obtained from (R)-tert-butyl 3-((6-(pyrazolo[1,5-a]pyrimidin-6-yl)pyridin-3-yl)oxy)pyrrolidine-1-carboxylate in a 66% yield.

Scheme 206

-continued

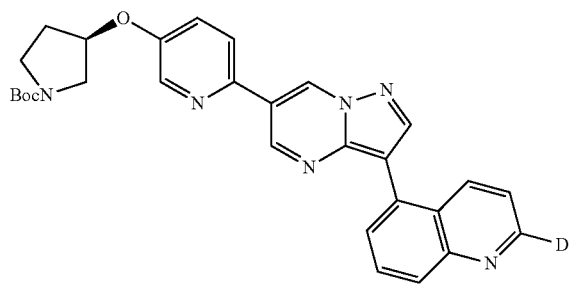

In an analogous manner to Scheme 5, (R)-tert-butyl 3-((6-(3-(2-²H-quinolin-5-yl)pyrazolo[1,5-a]pyrimidin-6-yl)pyridin-3-yl)oxy)pyrrolidine-1-carboxylate was obtained from (R)-tert-butyl 3-((6-(3-bromopyrazolo[1,5-a]pyrimidin-6-yl)pyridin-3-yl)oxy)pyrrolidine-1-carboxylate and 5-(4,4,5,5-tetramethyl-1,3,2-dioxaborolan-2-yl)-2-²H-quinoline in a 32% yield.

Scheme 207

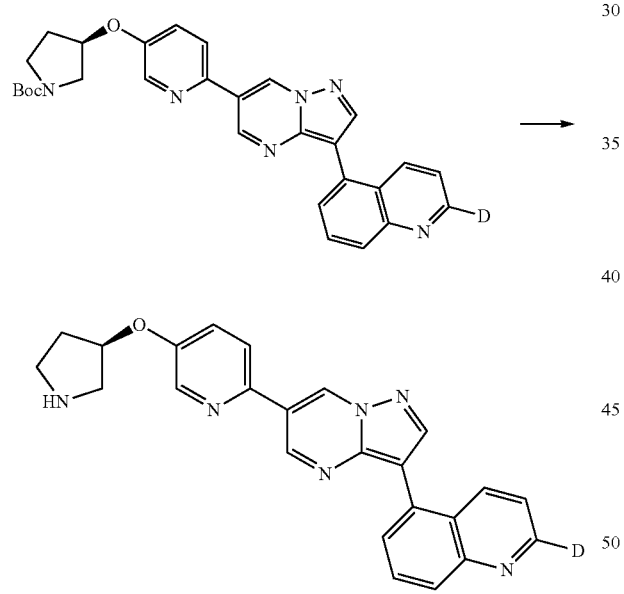

In an analogous manner to Scheme 2, (R)-5-(6-(5-(pyrrolidin-3-yloxy)pyridin-2-yl)pyrazolo[1,5-a]pyrimidin-3-yl)-2-²H-quinoline, TFA was obtained from (R)-tert-butyl 3-((6-(3-(2-²H-quinolin-5-yl)pyrazolo[1,5-a]pyrimidin-6-yl)pyridin-3-yl)oxy)pyrrolidine-1-carboxylate in a 68% yield. ¹H NMR (400 MHz, DMSO-d₆) δ 9.82 (d, J=2.2 Hz, 1H), 9.30 (d, J=2.2 Hz, 1H), 9.14 (s, 1H), 8.98 (s, 1H), 8.65 (s, 1H), 8.53-8.44 (m, 2H), 8.23 (d, J=8.9 Hz, 1H), 8.10 (dt, J=8.3, 1.1 Hz, 1H), 7.92 (dd, J=8.4, 7.2 Hz, 1H), 7.86 (dd, J=7.2, 1.3 Hz, 1H), 7.67 (dd, J=8.9, 3.0 Hz, 1H), 7.59 (d, J=8.6 Hz, 1H), 5.34 (d, J=4.9 Hz, 1H), 3.48 (s, 2H), 3.35 (dq, J=12.3, 6.2 Hz, 2H), 2.38-2.23 (m, 1H), 2.21 (s, 1H).

Compound 64

Scheme 208

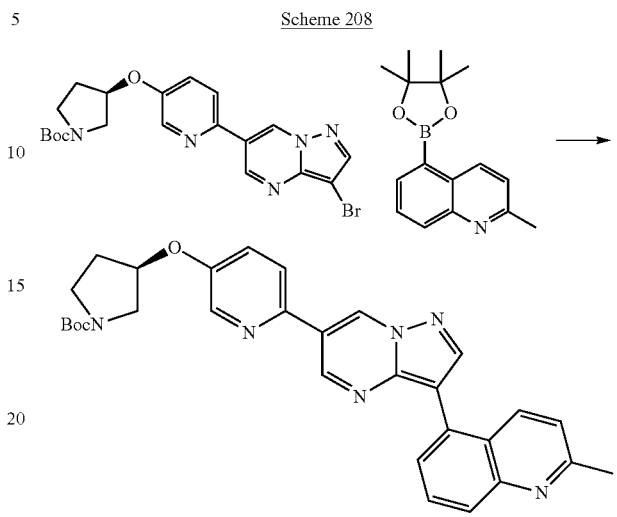

In an analogous manner to Scheme 5, (R)-tert-butyl 3-((6-(3-(2-methylquinolin-5-yl)pyrazolo[1,5-a]pyrimidin-6-yl)pyridin-3-yl)oxy)pyrrolidine-1-carboxylate was obtained from (R)-tert-butyl 3-((6-(3-bromopyrazolo[1,5-a]pyrimidin-6-yl)pyridin-3-yl)oxy)pyrrolidine-1-carboxylate and 2-methyl-5-(4,4,5,5-tetramethyl-1,3,2-dioxaborolan-2-yl)quinoline in a 44% yield.

Scheme 209

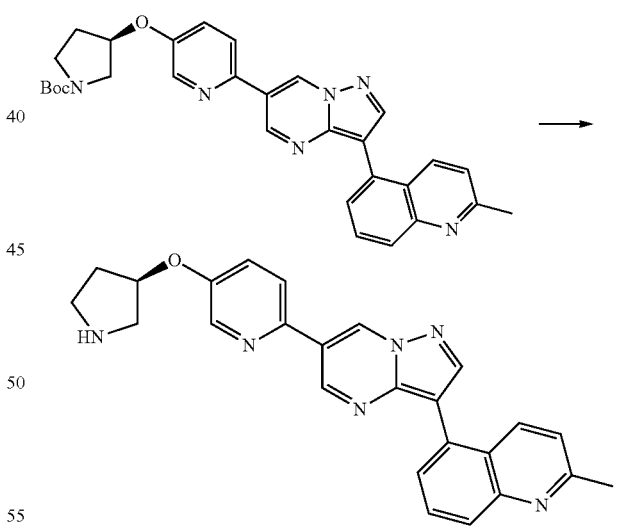

In an analogous manner to Scheme 2, (R)-2-methyl-5-(6-(5-(pyrrolidin-3-yloxy)pyridin-2-yl)pyrazolo[1,5-a]pyrimidin-3-yl)quinoline, TFA was obtained from (R)-tert-butyl 3-((6-(3-(2-methylquinolin-5-yl)pyrazolo[1,5-a]pyrimidin-6-yl)pyridin-3-yl)oxy)pyrrolidine-1-carboxylate in an 82% yield. ¹H NMR (400 MHz, DMSO-d₆) δ 9.83 (d, J=2.2 Hz, 1H), 9.30 (d, J=2.2 Hz, 1H), 9.17 (s, 1H), 9.02 (s, 1H), 8.66 (s, 1H), 8.56 (s, 1H), 8.47 (d, J=2.9 Hz, 1H), 8.23 (d, J=8.8 Hz, 1H), 8.06 (d, J=8.4 Hz, 1H), 7.96 (t, J=7.8 Hz, 1H), 7.87 (d, J=7.1 Hz, 1H), 7.67 (dd, J=8.9, 3.0 Hz, 1H), 7.59 (d, J=8.7 Hz, 1H), 5.34 (d, J=5.1 Hz, 1H), 3.48 (s, 2H), 3.36 (s, 2H), 2.79 (s, 3H), 2.29 (td, J=9.3, 4.8 Hz, 1H), 2.19 (d, J=14.7 Hz, 1H).

Compound 65

Scheme 210

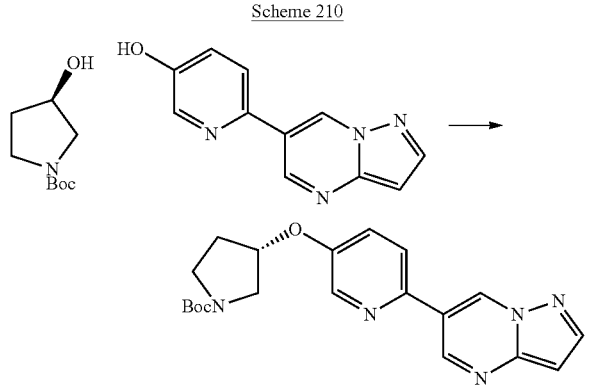

In an analogous manner to Scheme 160, (S)-tert-butyl 3-((6-(pyrazolo[1,5-a]pyrimidin-6-yl)pyridin-3-yl)oxy)pyrrolidine-1-carboxylate was obtained from 6-(pyrazolo[1,5-a]pyrimidin-6-yl)pyridin-3-ol and (R)-tert-butyl 3-hydroxypyrrolidine-1-carboxylate in an 74% yield.

Scheme 211

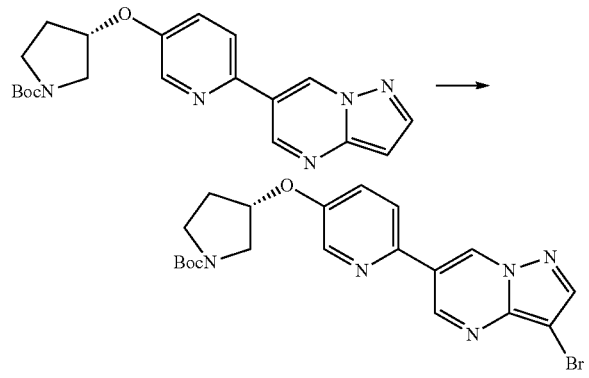

In an analogous manner to Scheme 111, (S)-tert-butyl 3-((6-(3-bromopyrazolo[1,5-a]pyrimidin-6-yl)pyridin-3-yl)oxy)pyrrolidine-1-carboxylate was obtained from (S)-tert-butyl 3-((6-(pyrazolo[1,5-a]pyrimidin-6-yl)pyridin-3-yl)oxy)pyrrolidine-1-carboxylate in a 55% yield.

Scheme 212

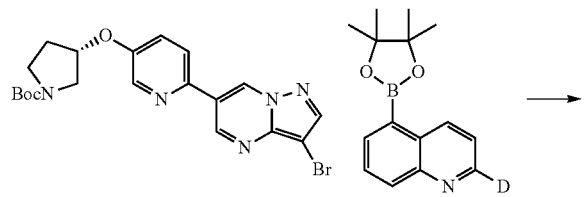

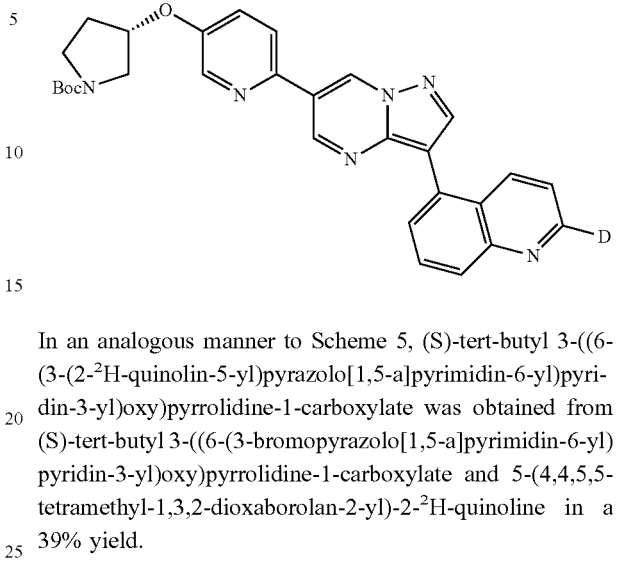

In an analogous manner to Scheme 5, (S)-tert-butyl 3-((6-(3-(2-$^2$H-quinolin-5-yl)pyrazolo[1,5-a]pyrimidin-6-yl)pyridin-3-yl)oxy)pyrrolidine-1-carboxylate was obtained from (S)-tert-butyl 3-((6-(3-bromopyrazolo[1,5-a]pyrimidin-6-yl)pyridin-3-yl)oxy)pyrrolidine-1-carboxylate and 5-(4,4,5,5-tetramethyl-1,3,2-dioxaborolan-2-yl)-2-$^2$H-quinoline in a 39% yield.

Scheme 213

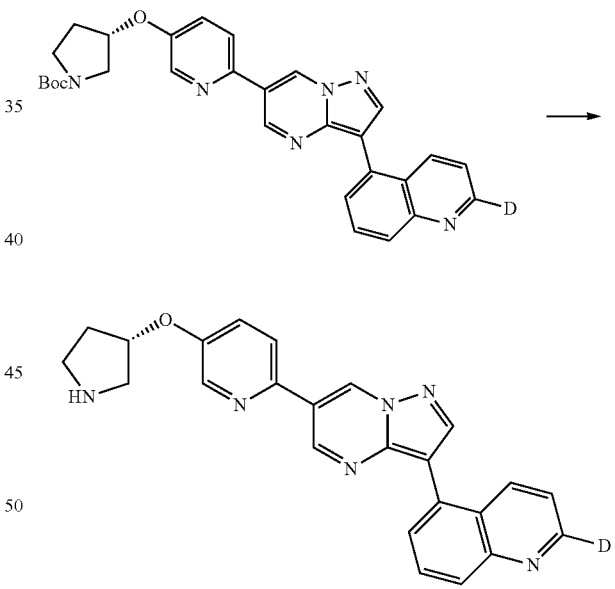

In an analogous manner to Scheme 2, (S)-5-(6-(5-(pyrrolidin-3-yloxy)pyridin-2-yl)pyrazolo[1,5-a]pyrimidin-3-yl)-2-$^2$H-quinoline, TFA was obtained from (S)-tert-butyl 3-((6-(3-(2-$^2$H-quinolin-5-yl)pyrazolo[1,5-a]pyrimidin-6-yl)pyridin-3-yl)oxy)pyrrolidine-1-carboxylate in a 68% yield. $^1$H NMR (400 MHz, DMSO-d$_6$) δ 9.83 (d, J=2.2 Hz, 1H), 9.30 (d, J=2.2 Hz, 1H), 9.22 (s, 1H), 9.10 (s, 1H), 8.67 (s, 2H), 8.47 (dd, J=2.9, 0.6 Hz, 1H), 8.26-8.19 (m, 1H), 8.08 (d, J=8.4 Hz, 1H), 7.99 (t, J=7.8 Hz, 1H), 7.89 (d, J=7.1 Hz, 1H), 7.71-7.60 (m, 2H), 5.38-5.30 (m, 1H), 3.47 (s, 2H), 3.42-3.28 (m, 2H), 2.82 (s, 3H), 2.37-2.14 (m, 2H).

Compound 66

Scheme 214

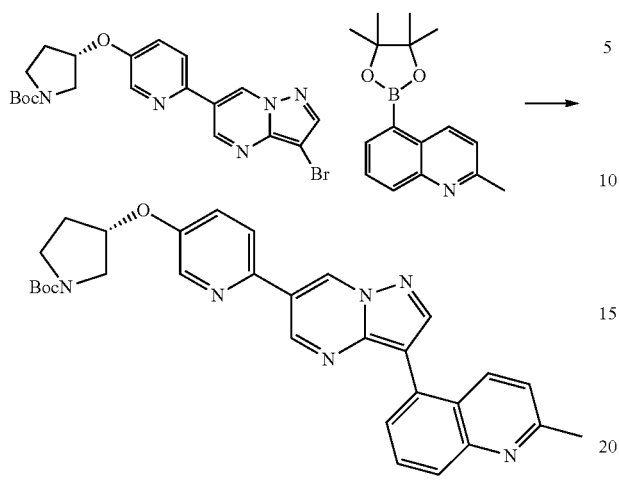

In an analogous manner to Scheme 5, (S)-tert-butyl 3-((6-(3-(2-methylquinolin-5-yl)pyrazolo[1,5-a]pyrimidin-6-yl)pyridin-3-yl)oxy)pyrrolidine-1-carboxylate was obtained from (S)-tert-butyl 3-((6-(3-bromopyrazolo[1,5-a]pyrimidin-6-yl)pyridin-3-yl)oxy)pyrrolidine-1-carboxylate and 2-methyl-5-(4,4,5,5-tetramethyl-1,3,2-dioxaborolan-2-yl)quinoline in a 44% yield.

Scheme 215

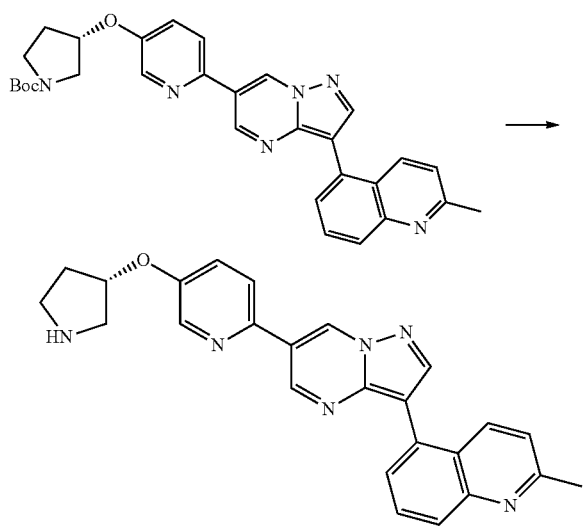

In an analogous manner to Scheme 2, (S)-2-methyl-5-(6-(5-(pyrrolidin-3-yloxy)pyridin-2-yl)pyrazolo[1,5-a]pyrimidin-3-yl)quinoline, TFA was obtained from (S)-tert-butyl 3-((6-(3-(2-methylquinolin-5-yl)pyrazolo[1,5-a]pyrimidin-6-yl)pyridin-3-yl)oxy)pyrrolidine-1-carboxylate in an 82% yield. $^1$H NMR (400 MHz, DMSO-d$_6$) δ 9.83 (d, J=2.2 Hz, 1H), 9.30 (d, J=2.2 Hz, 1H), 9.17 (s, 1H), 9.02 (s, 1H), 8.66 (s, 1H), 8.56 (s, 1H), 8.47 (d, J=2.9 Hz, 1H), 8.23 (d, J=8.8 Hz, 1H), 8.06 (d, J=8.4 Hz, 1H), 7.96 (t, J=7.8 Hz, 1H), 7.87 (d, J=7.1 Hz, 1H), 7.67 (dd, J=8.9, 3.0 Hz, 1H), 7.59 (d, J=8.7 Hz, 1H), 5.34 (d, J=5.1 Hz, 1H), 3.48 (s, 2H), 3.36 (s, 2H), 2.79 (s, 3H), 2.29 (td, J=9.3, 4.8 Hz, 1H), 2.19 (d, J=14.7 Hz, 1H).

Compound 67 and Compound 68

Scheme 216

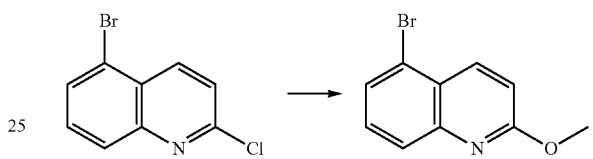

To a solution of 5-bromo-2-chloroquinoline (2.40 g, 10 mmol) in methanol (60 mL) at 0 deg was added sodium hydride (60% oil dispersion, 0.60 g, 1.5 eq). The mixture was brought to room temperature and stirred for 1 hour. A saturated solution of sodium bicarbonate (25 mL) was added and the mixture was partitioned between ethyl acetate and water. The organic later was washed with water, brine, dried (MgSO$_4$), filtered and concentrated to yield 5-bromo-2-methoxyquinoline (1.88 g, 79%) after chromatography.

Scheme 217

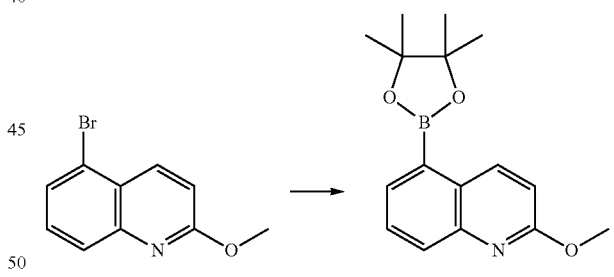

In an analogous manner to Scheme 32, 2-methoxy-5-(4,4,5,5-tetramethyl-1,3,2-dioxaborolan-2-yl)quinoline was obtained from 5-bromo-2-methoxyquinoline.

Scheme 218

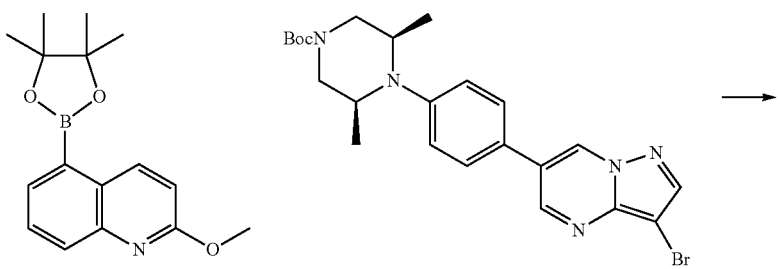

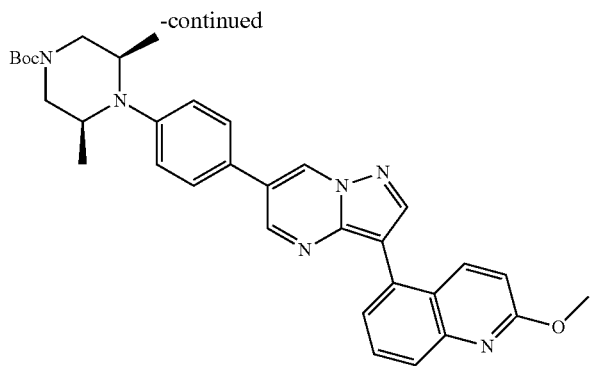

In an analogous manner to Scheme 5, (3S,5R)-tert-butyl 4-(4-(3-(2-methoxyquinolin-5-yl)pyrazolo[1,5-a]pyrimidin-6-yl)phenyl)-3,5-dimethylpiperazine-1-carboxylate was obtained from (3S,5R)-tert-butyl 4-(4-(3-bromopyrazolo[1,5-a]pyrimidin-6-yl)phenyl)-3,5-dimethylpiperazine-1-carboxylate and 2-methoxy-5-(4,4,5,5-tetramethyl-1,3,2-dioxaborolan-2-yl)quinoline in a 54% yield.

Scheme 219

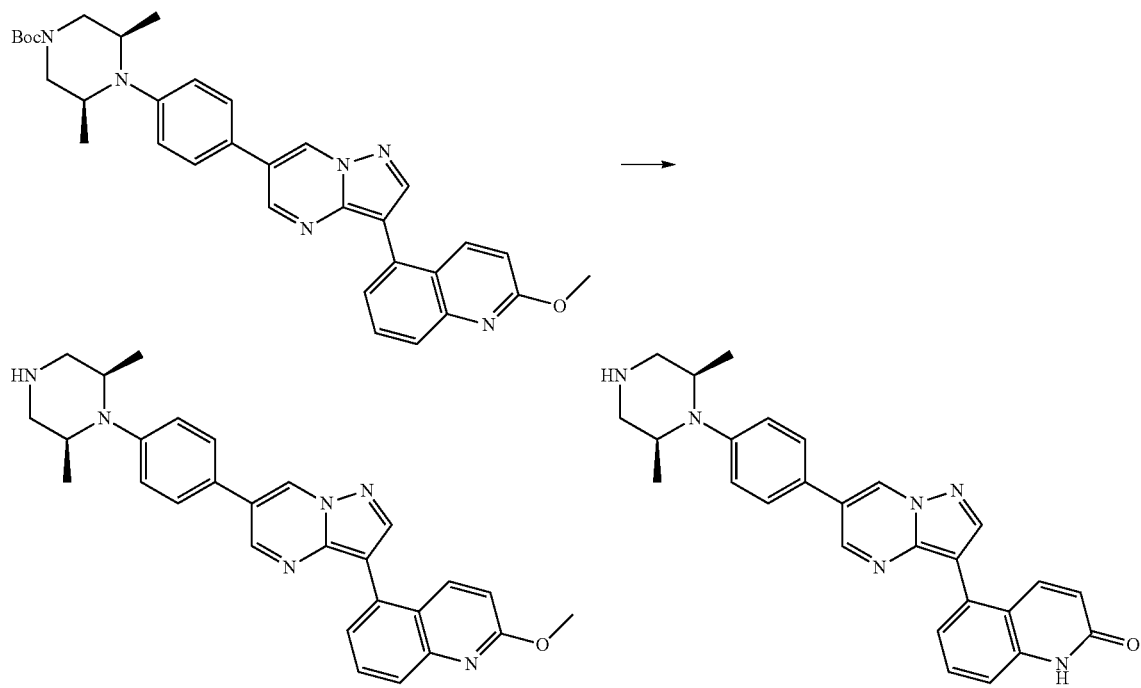

(3S,5R)-tert-butyl 4-(4-(3-(2-methoxyquinolin-5-yl)pyrazolo[1,5-a]pyrimidin-6-yl)phenyl)-3,5-dimethylpiperazine-1-carboxylate (0.13 g, 0.23 mmol) was refluxed in 12 N HCl (0.5 mL) for 40 min, cooled and concentrated to give 5-(6-(4-((2S,6R)-2,6-dimethylpiperazin-1-yl)phenyl)pyrazolo[1,5-a]pyrimidin-3-yl)-2-methoxyquinoline, TFA and 5-(6-(4-((2S,6R)-2,6-dimethylpiperazin-1-yl)phenyl)pyrazolo[1,5-a]pyrimidin-3-yl)quinolin-2(1H)-one, TFA after reverse phase purification. Compound 67: $^1$H NMR (400 MHz, DMSO-$d_6$) δ 9.60 (d, J=2.2 Hz, 1H), 9.01 (d, J=2.3 Hz, 1H), 8.90 (s, 2H), 8.57 (s, 1H), 8.26 (dd, J=9.1, 0.8 Hz, 1H), 7.95-7.87 (m, 2H), 7.86-7.72 (m, 2H), 7.63 (dd, J=7.1, 1.4 Hz, 1H), 7.27 (d, J=8.5 Hz, 2H), 7.00 (d, J=9.1 Hz, 1H), 4.03 (s, 3H), 3.37 (d, J=10.1 Hz, 4H), 2.86 (d, J=9.9 Hz, 2H), 0.82 (d, J=6.2 Hz, 6H). Compound 68: $^1$H NMR (400 MHz, DMSO-$d_6$) δ 11.85 (s, 1H), 9.59 (d, J=2.3 Hz, 1H), 9.02 (d, J=2.3 Hz, 1H), 8.92 (s, 2H), 8.51 (s, 1H), 7.91 (dd, J=9.3, 2.6 Hz, 3H), 7.59 (t, J=7.9 Hz, 1H), 7.39-7.31 (m, 2H), 7.31-7.23 (m, 2H), 6.46 (dd, J=9.8, 2.1 Hz, 1H), 3.37 (d, J=11.5 Hz, 4H), 2.86 (d, J=10.1 Hz, 2H), 0.82 (d, J=6.2 Hz, 6H).

Example 2: Enzyme Assays

Compounds were assessed in ALK1-6 enzymatic assays. Specifically, compounds were assayed using LANCE® Ultra ULight™ technology (Perkin Elmer) against human ALK1-6 enzymes (ALK1: Life Technologies, ALK2-6: Carna Biosciences). Briefly, ALK enzyme (10 nM) was prepared in kinase buffer (50 mM HEPES, pH 7.5, 10 mM $MgCl_2$, 3 mM $MgCl_2$, 0.005% Tween-20 and 2 mM DTT) and dispensed at 2.5 µL/well into a 1536 well, white, solid bottom, microtiter plate (Greiner, 789175-F). Negative controls for the assay were generated by adding one column containing kinase buffer only. Compounds in DMSO solution were transferred to the assay plates at 23 nL/well via a NX-TR pin tool workstation (WAKO, San Diego, Calif.) and incubated with enzyme for 10 minutes at ambient temperature. ULight Topo IIa Substrate (50 nM) was prepared in kinase buffer containing either 10 µM or 1000 µM ATP and dispensed at 2.5 µL/well into the assay plate. Following a 1 hour incubation at ambient temperature, Europium anti-phospho DNA Topoisomerase 2-alpha antibody (4 nM) was prepared in 1× LANCE detection buffer containing 12 mM EDTA and dispensed at 5 µL/well into the assay plate. Plates were measured using the EnVision plate reader (Perkin Elmer), with excitation 320 nm and emissions of 615 nm and 665 nm.

Results from the FOP Enzymatic assays for several compounds of the invention are shown in Table 1. In certain instances where multiple tests were performed for a particular compound in a particular assay, the data shown in Table 1 represents an average of the individual results.

TABLE 1

FOP Enzymatic Assay Results

| | | $IC_{50}$ (nM) at 10 µM ATP | | | | | |
| --- | --- | --- | --- | --- | --- | --- | --- |
| CMPD | STRUCTURE | ALK1 | ALK2 | ALK3 | ALK4 | ALK5 | ALK6 |
| 48 | 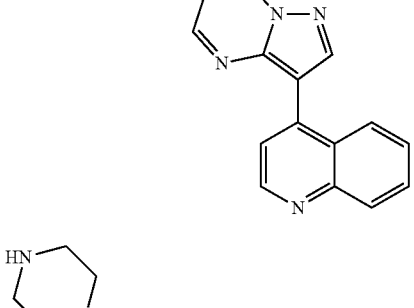 | 11 | 677 | 206 | 3239 | 11580 | 278 |
| 1 | 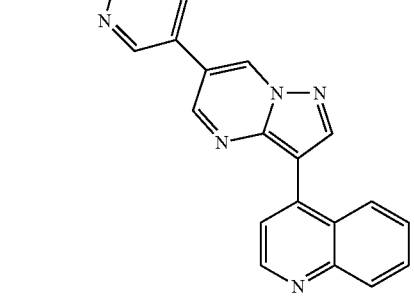 | 83 | 29 | 864 | 26965 | 20586 | 2246 |
| 2 | 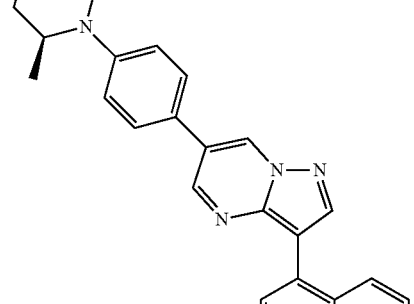 | 5.8 | 10 | 9.1 | 556 | 1682 | 213 |

TABLE 1-continued
FOP Enzymatic Assay Results
| | | IC$_{50}$ (nM) at 10 μM ATP | | | | | |
|---|---|---|---|---|---|---|---|
| CMPD | STRUCTURE | ALK1 | ALK2 | ALK3 | ALK4 | ALK5 | ALK6 |
| 3 | 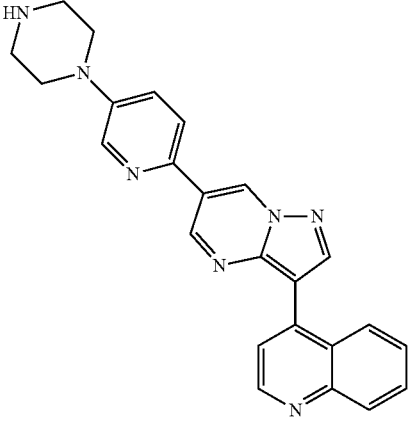 [SMILES: c1ccc2c(-c3cnn4cc(-c5ccc(N6CCNCC6)cn5)cnc34)ccnc2c1] | 27 | 16 | 278 | 3683 | 8190 | 823 |
| 4 | 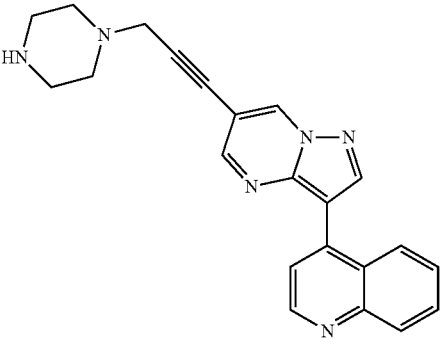 [SMILES: C(#Cc1cnc2c(-c3ccnc4ccccc34)cnn2c1)CN1CCNCC1] | 340 | 68 | 7603 | 59700 | 31150 | 35000 |
| 5 | 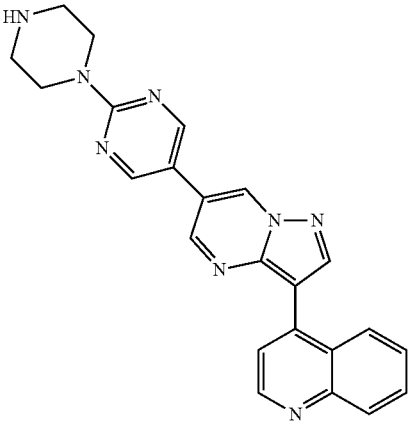 [SMILES: c1ccc2c(-c3cnn4cc(-c5cnc(N6CCNCC6)nc5)cnc34)ccnc2c1] | 519 | 103 | 7816 | 31900 | | |

TABLE 1-continued
FOP Enzymatic Assay Results
| CMPD | STRUCTURE | IC$_{50}$ (nM) at 10 μM ATP ||||||
|---|---|---|---|---|---|---|---|
| | | ALK1 | ALK2 | ALK3 | ALK4 | ALK5 | ALK6 |
| 6 | 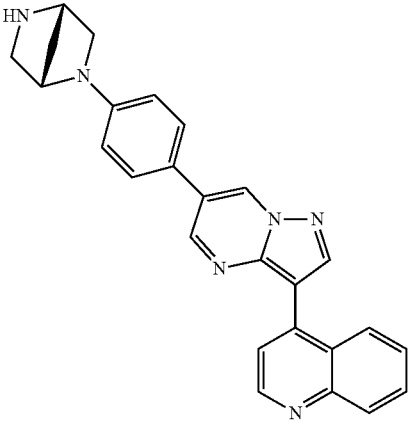 [SMILES: c1ccc2c(-c3cnn4cc(-c5ccc(N6C[C@@H]7C[C@H]6CN7)cc5)cnc34)ccnc2c1] | 23 | 12 | 383 | 3217 | 31620 | 1376 |
| 7 | 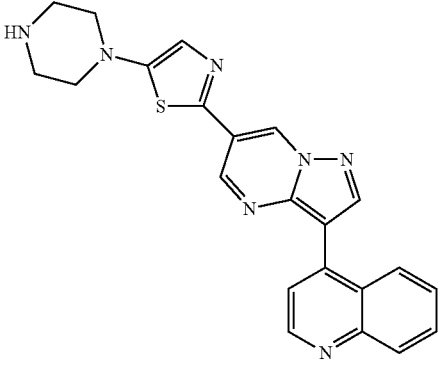 [SMILES: c1ccc2c(-c3cnn4cc(-c5ncc(N6CCNCC6)s5)cnc34)ccnc2c1] | 25 | 19 | 189 | 3480 | 105000 | 6720 |
| 8 | 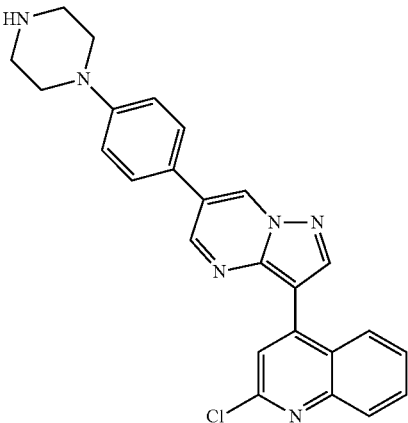 | 22 | 24 | 212 | 353 | 1110 | 204 |

TABLE 1-continued
FOP Enzymatic Assay Results
| CMPD | STRUCTURE | IC$_{50}$ (nM) at 10 μM ATP ||||||
|---|---|---|---|---|---|---|---|
| | | ALK1 | ALK2 | ALK3 | ALK4 | ALK5 | ALK6 |
| 9 | 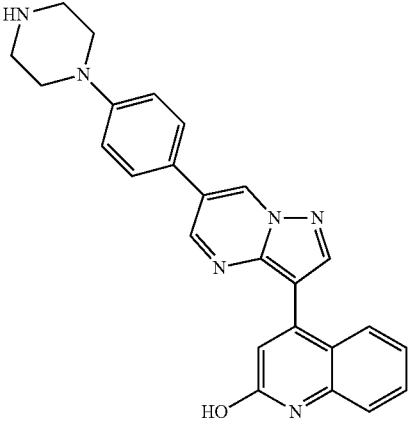 [SMILES: Oc1cc(-c2cnn3cc(-c4ccc(N5CCNCC5)cc4)cnc23)c2ccccc2n1] | 4690 | 792 | | | | 55600 |
| 10 | 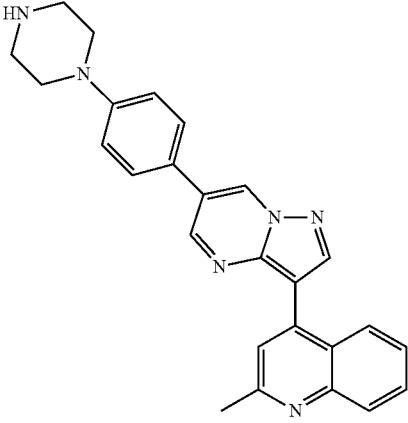 [SMILES: Cc1cc(-c2cnn3cc(-c4ccc(N5CCNCC5)cc4)cnc23)c2ccccc2n1] | 19 | 23 | 54 | 116 | 314 | 38 |
| 11 | 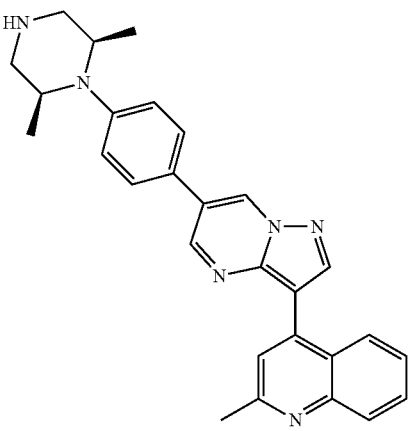 [SMILES: Cc1cc(-c2cnn3cc(-c4ccc(N5[C@H](C)CNC[C@@H]5C)cc4)cnc23)c2ccccc2n1] | 4 | 7.7 | 9.2 | 25 | 62 | 22 |

TABLE 1-continued
FOP Enzymatic Assay Results
| | | IC$_{50}$ (nM) at 10 µM ATP | | | | | |
|---|---|---|---|---|---|---|---|
| CMPD | STRUCTURE | ALK1 | ALK2 | ALK3 | ALK4 | ALK5 | ALK6 |
| 12 | 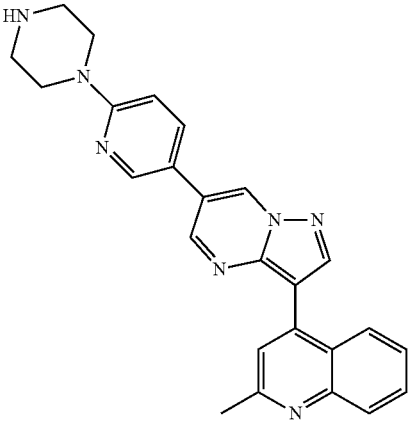 [SMILES: Cc1cc(-c2cnn3cc(-c4ccc(N5CCNCC5)nc4)cnc23)c2ccccc2n1] | | 43 | 62 | 259 | 718 | 150 |
| 13 | 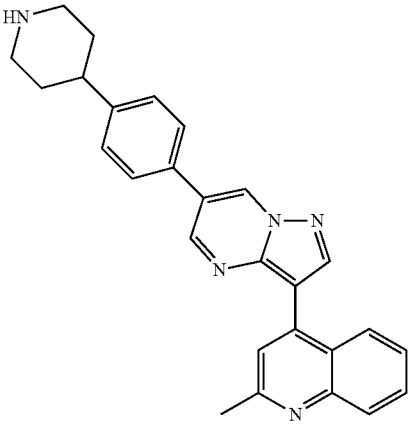 [SMILES: Cc1cc(-c2cnn3cc(-c4ccc(C5CCNCC5)cc4)cnc23)c2ccccc2n1] | | 16 | 23 | 29 | 125 | 277 | 51 |
| 14 | 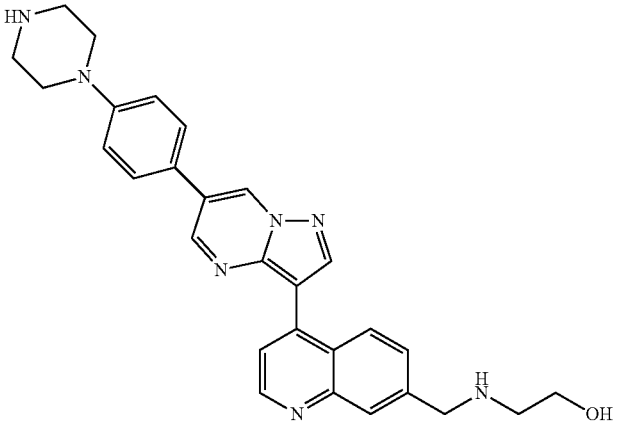 [SMILES: OCCNCc1ccc2c(-c3cnn4cc(-c5ccc(N6CCNCC6)cc5)cnc34)ccnc2c1] | 1950 | 517 | 2930 | | | 1760 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 15 | 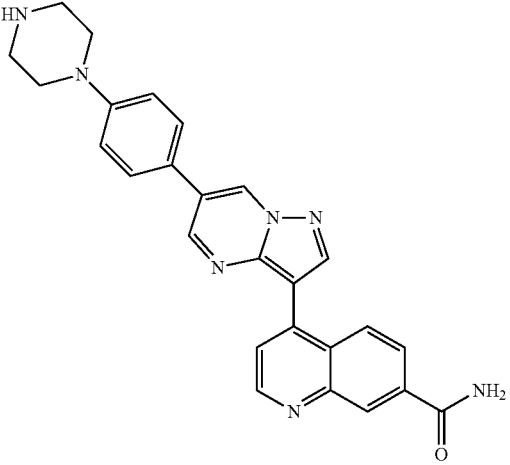 [SMILES: NC(=O)c1ccc2c(-c3cnn4cc(-c5ccc(N6CCNCC6)cc5)cnc34)ccnc2c1] | 1200 | 127 | | 18000 | | 605 |
| 16 | 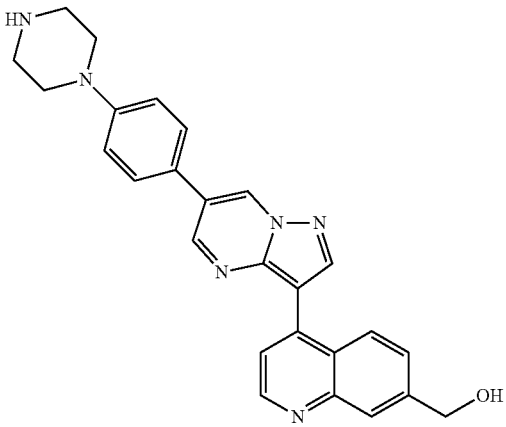 [SMILES: OCc1ccc2c(-c3cnn4cc(-c5ccc(N6CCNCC6)cc5)cnc34)ccnc2c1] | 207 | 102 | 573 | | | 424 |
| 17 | 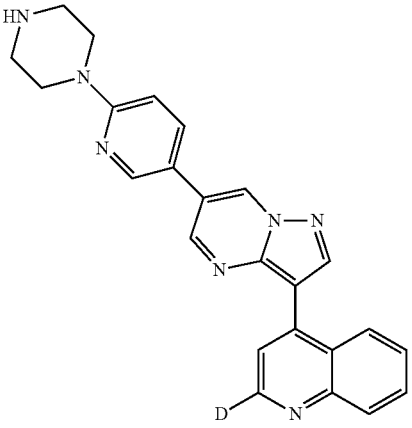 [SMILES: [2H]c1cc(-c2cnn3cc(-c4ccc(N5CCNCC5)nc4)cnc23)c2ccccc2n1] | 112 | 40 | 146 | 6486 | | 229 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 18 | 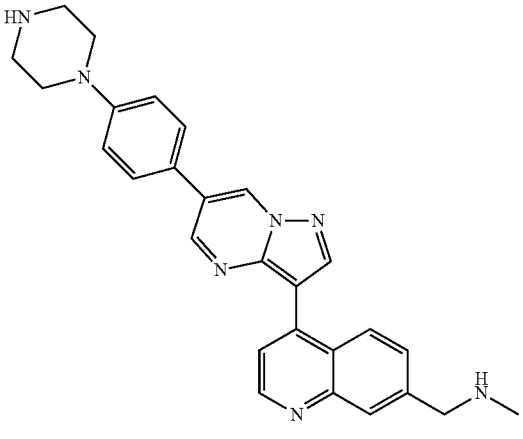 [SMILES: CNCc1ccc2c(-c3cnn4cc(-c5ccc(N6CCNCC6)cc5)cnc34)ccnc2c1] | 2500 | 906 | 4370 | | | 2590 |
| 19 | 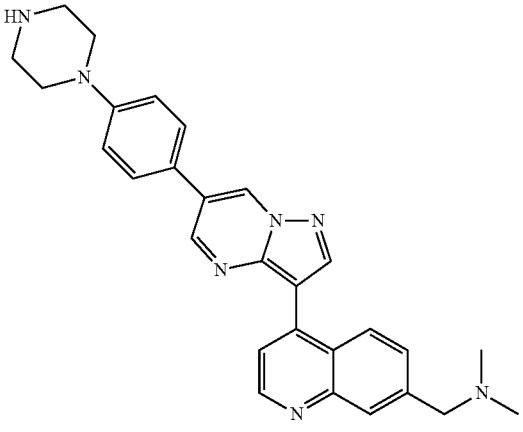 [SMILES: CN(C)Cc1ccc2c(-c3cnn4cc(-c5ccc(N6CCNCC6)cc5)cnc34)ccnc2c1] | 1460 | 407 | 5280 | | | 2970 |
| 20 | 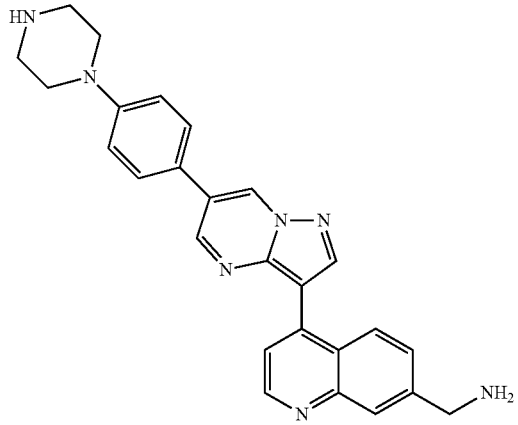 [SMILES: NCc1ccc2c(-c3cnn4cc(-c5ccc(N6CCNCC6)cc5)cnc34)ccnc2c1] | 1332 | 706 | 2525 | | 183 | 1510 |

TABLE 1-continued

FOP Enzymatic Assay Results

| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 21 | | 7860 | 2140 | 5260 | | | 3510 |
| 22 | | 660 | 88 | 78 | | | 15 |
| 23 | | 52 | 26 | 280 | 15235 | | 106 |

TABLE 1-continued

FOP Enzymatic Assay Results

| | | IC$_{50}$ (nM) at 10 μM ATP | | | | | |
|---|---|---|---|---|---|---|---|
| CMPD | STRUCTURE | ALK1 | ALK2 | ALK3 | ALK4 | ALK5 | ALK6 |
| 24 | | 94 | 62 | 138 | 818 | 3910 | 52 |
| 25 | | 981 | 482 | 1405 | | | 590 |
| 26 | | 1340 | 105 | 2959 | 81000 | | 1049 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 27 | 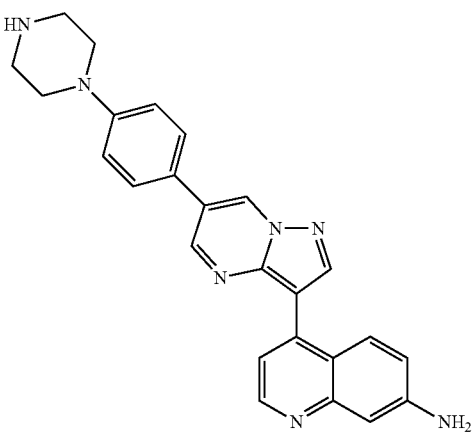 [SMILES: Nc1ccc2c(-c3cnn4cc(-c5ccc(N6CCNCC6)cc5)cnc34)ccnc2c1] | 106 | 44 | 153 | 2600 | 3404 | 140 |
| 28 | 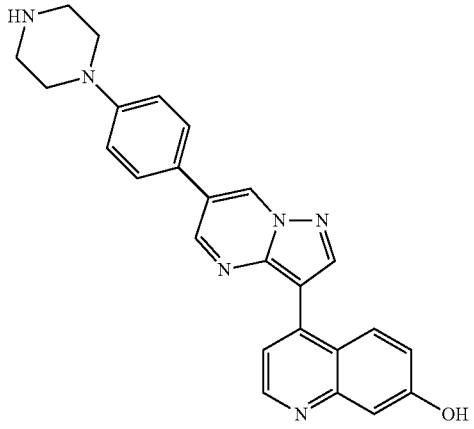 [SMILES: Oc1ccc2c(-c3cnn4cc(-c5ccc(N6CCNCC6)cc5)cnc34)ccnc2c1] | 232 | 31 | 180 | 6704 | 5119 | 361 |
| 29 | 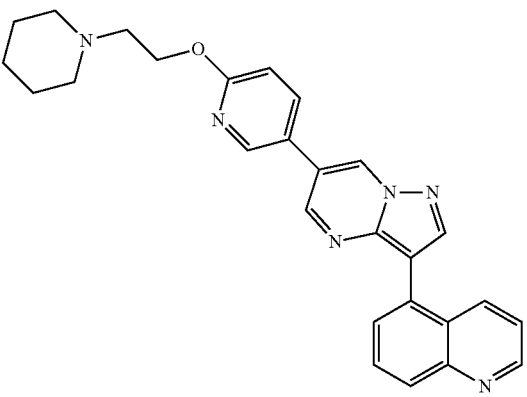 [SMILES: c1cc(-c2cnn3cc(-c4ccc(OCCN5CCCCC5)nc4)cnc23)c2cccnc2c1] | 591 | 127 | 7589 | | | 6891 |

TABLE 1-continued
FOP Enzymatic Assay Results
| CMPD | STRUCTURE | IC$_{50}$ (nM) at 10 μM ATP ||||||
|---|---|---|---|---|---|---|---|
| | | ALK1 | ALK2 | ALK3 | ALK4 | ALK5 | ALK6 |
| 30 | 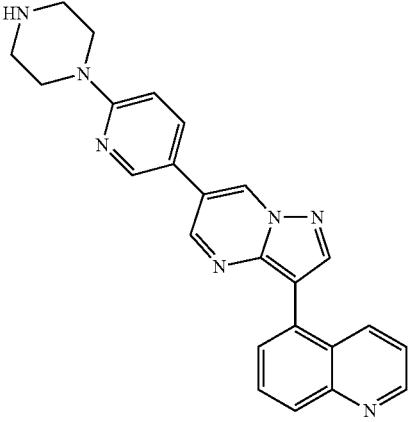 [SMILES: c1cc(-c2cnn3cc(-c4ccc(N5CCNCC5)nc4)cnc23)c2cccnc2c1] | 254 | 84 | 4141 | | | 2481 |
| 31 | 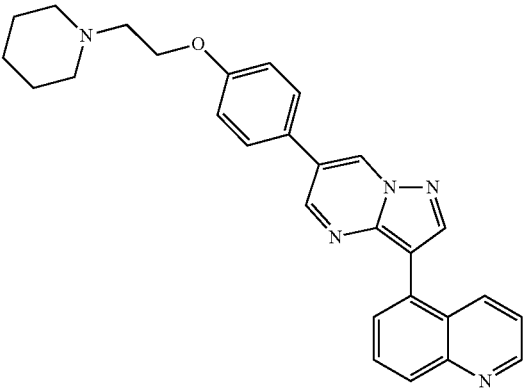 [SMILES: c1cc(-c2cnn3cc(-c4ccc(OCCN5CCCCC5)cc4)cnc23)c2cccnc2c1] | 84 | 38 | 768 | 14140 | 21300 | 2192 |
| 32 | 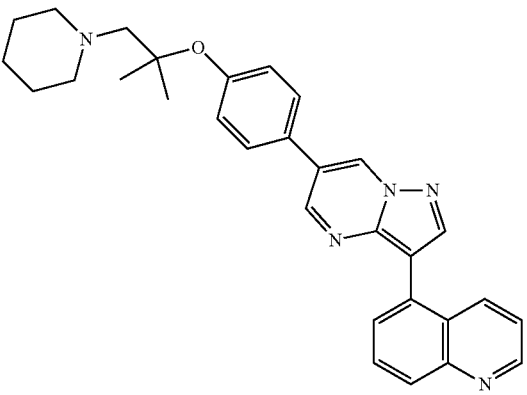 [SMILES: CC(C)(CN1CCCCC1)Oc1ccc(-c2cnc3c(-c4cccc5ncccc45)cnn3c2)cc1] | 17 | 106 | 370 | 5620 | | 2910 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 33 | 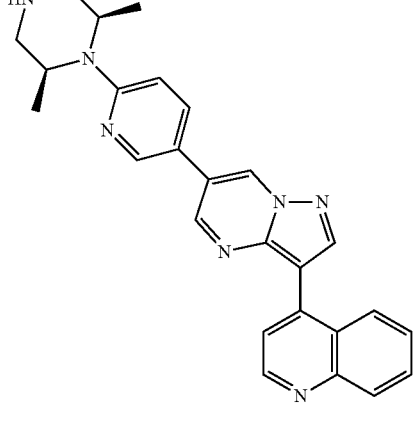 | 82 | 22 | 89 | 1390 | 4010 | 5280 |
| 34 | 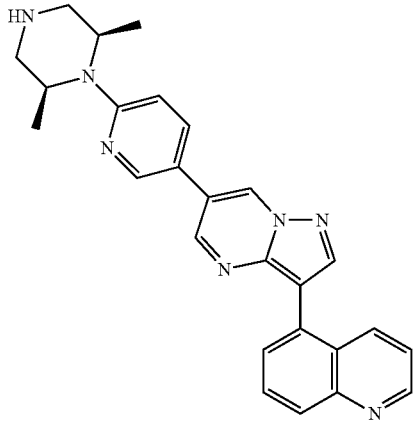 [SMILES: C[C@@H]1CNC[C@H](C)N1c1ccc(-c2cnc3c(-c4cccc5ncccc45)cnn3c2)cn1] | 189 | 56 | 1280 | 6080 | | |
| 35 | 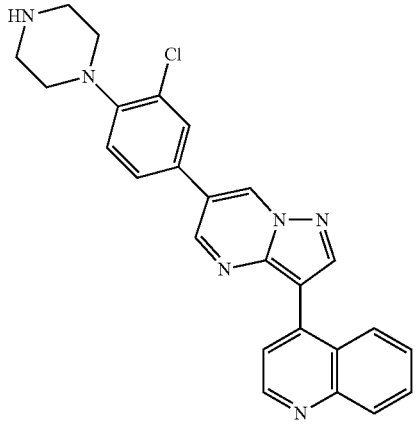 [SMILES: Clc1cc(-c2cnc3c(-c4ccnc5ccccc45)cnn3c2)ccc1N1CCNCC1] | 44 | 30 | 190 | 5420 | 7635 | 4183 |

TABLE 1-continued

FOP Enzymatic Assay Results

| | | IC$_{50}$ (nM) at 10 μM ATP | | | | | |
|---|---|---|---|---|---|---|---|
| CMPD | STRUCTURE | ALK1 | ALK2 | ALK3 | ALK4 | ALK5 | ALK6 |
| 36 | | 79 | 46 | 6570 | 14550 | 13150 | 18400 |
| 37 | | 91 | 24 | 225 | 2715 | 18000 | 10346 |
| 38 | | 110 | 47 | 1590 | 14100 | | 21500 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 39 | 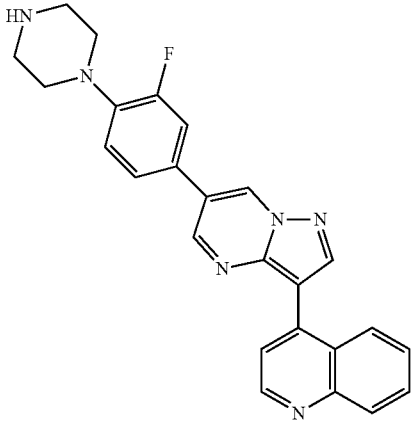 [SMILES: Fc1cc(-c2cnc3c(-c4ccnc5ccccc45)cnn3c2)ccc1N1CCNCC1] | 41 | 15 | 57 | 12000 | 7160 | |
| 40 | 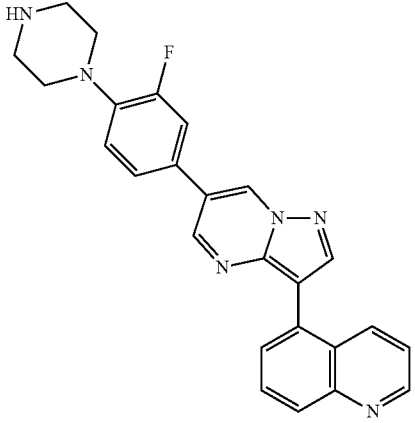 [SMILES: Fc1cc(-c2cnc3c(-c4cccc5ncccc45)cnn3c2)ccc1N1CCNCC1] | 84 | 32 | 787 | 13700 | | 26100 |
| 41 | 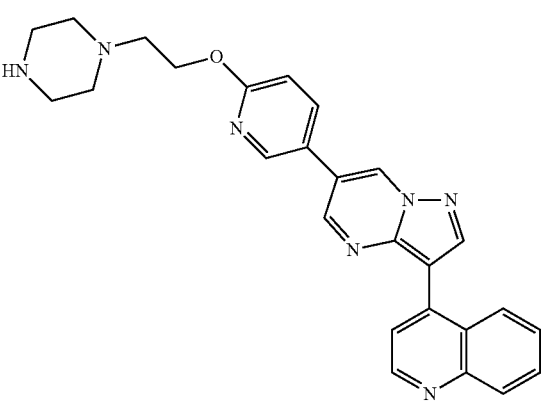 [SMILES: c1ccc2c(-c3cnn4cc(-c5ccc(OCCN6CCNCC6)nc5)cnc34)ccnc2c1] | 211 | 22 | 4320 | 13700 | 1500 | |

TABLE 1-continued
FOP Enzymatic Assay Results
| CMPD | STRUCTURE | IC$_{50}$ (nM) at 10 μM ATP ||||||
|---|---|---|---|---|---|---|---|
| | | ALK1 | ALK2 | ALK3 | ALK4 | ALK5 | ALK6 |
| 42 | 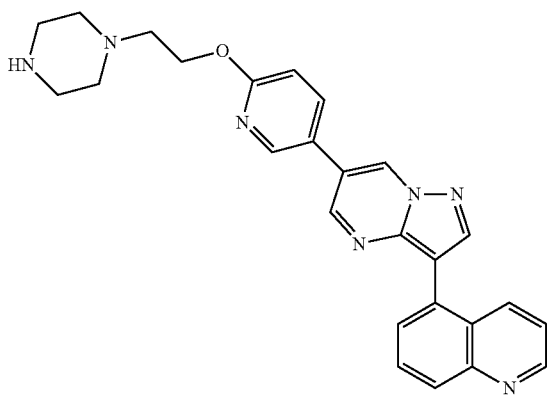 [SMILES: c1cc(-c2cnn3cc(-c4ccc(OCCN5CCNCC5)nc4)cnc23)c2cccnc2c1] | 401 | 14 | | 56100 | | 5000 |
| 43 | 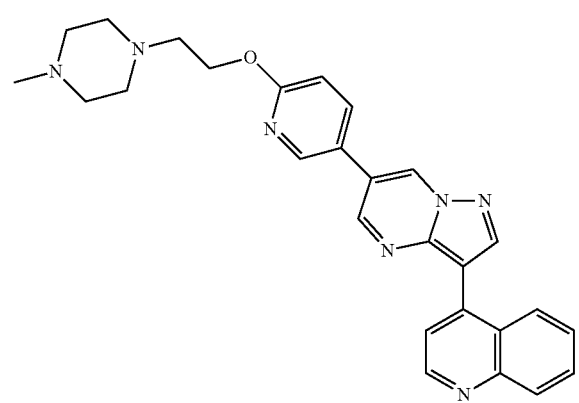 [SMILES: CN1CCN(CCOc2ccc(-c3cnc4c(-c5ccnc6ccccc56)cnn4c3)cn2)CC1] | 193 | 122 | | 7480 | 20300 | 3740 |
| 44 | 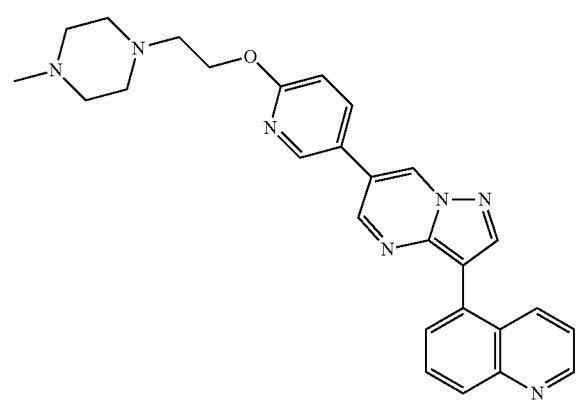 [SMILES: CN1CCN(CCOc2ccc(-c3cnc4c(-c5cccc6ncccc56)cnn4c3)cn2)CC1] | 521 | 17 | | | | 6600 |

TABLE 1-continued

FOP Enzymatic Assay Results

| CMPD | STRUCTURE | IC$_{50}$ (nM) at 10 µM ATP | | | | | |
|---|---|---|---|---|---|---|---|
| | | ALK1 | ALK2 | ALK3 | ALK4 | ALK5 | ALK6 |
| 45 | 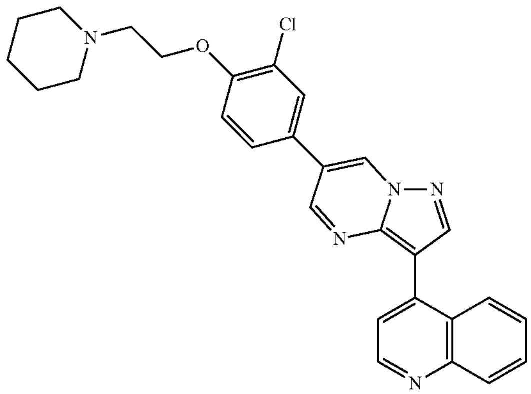 [SMILES: Clc1cc(-c2cnc3c(-c4ccnc5ccccc45)cnn3c2)ccc1OCCN1CCCCC1] | 89 | 56 | | | 10200 | 184 |
| 46 | 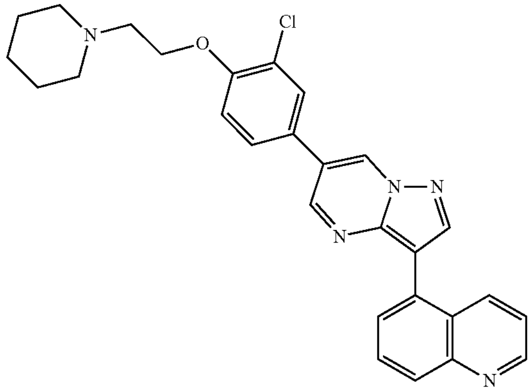 [SMILES: Clc1cc(-c2cnc3c(-c4cccc5ncccc45)cnn3c2)ccc1OCCN1CCCCC1] | 142 | 16 | | | | |
| 47 | 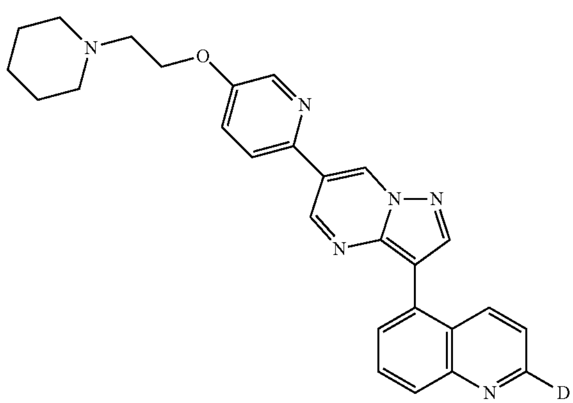 [SMILES: [2H]c1ccc2c(-c3cnn4cc(-c5ccc(OCCN6CCCCC6)cn5)cnc34)cccc2n1] | 257 | 94 | 1970 | | | 4080 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 48' | | 358 | 85 | 1850 | 10800 | | 3920 |
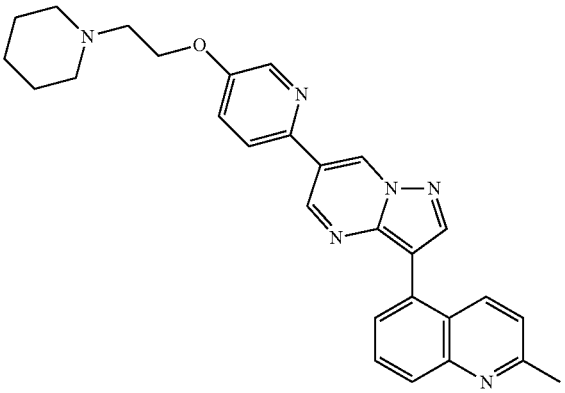 [SMILES: Cc1ccc2c(-c3cnn4cc(-c5ccc(OCCN6CCCCC6)cn5)cnc34)cccc2n1]
| 49 | | 341 | 157 | 3280 | | | 7850 |
|---|---|---|---|---|---|---|---|
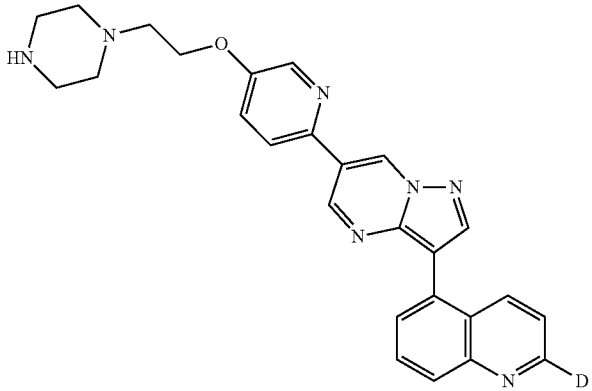 [SMILES: [2H]c1ccc2c(-c3cnn4cc(-c5ccc(OCCN6CCNCC6)cn5)cnc34)cccc2n1]
| 50 | | 3010 | 643 | 14200 | | | |
|---|---|---|---|---|---|---|---|
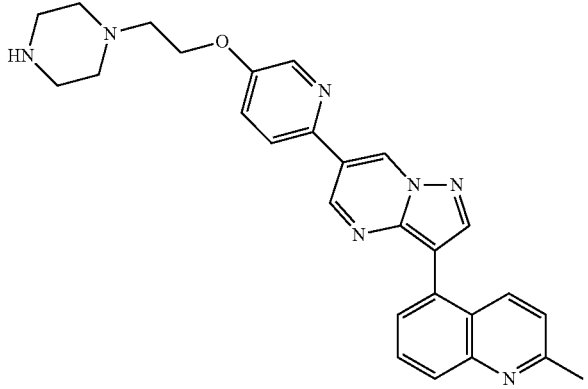 [SMILES: Cc1ccc2c(-c3cnn4cc(-c5ccc(OCCN6CCNCC6)cn5)cnc34)cccc2n1]

TABLE 1-continued

FOP Enzymatic Assay Results

| | | IC$_{50}$ (nM) at 10 µM ATP | | | | | |
|---|---|---|---|---|---|---|---|
| CMPD | STRUCTURE | ALK1 | ALK2 | ALK3 | ALK4 | ALK5 | ALK6 |
| 51 | | 349 | 151 | 2990 | | | 7570 |
| 52 | | 4 | 8.6 | 6.5 | 110 | 330 | 226 |
| 53 | | 30 | 8 | 336 | 8090 | | 5205 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 54 | 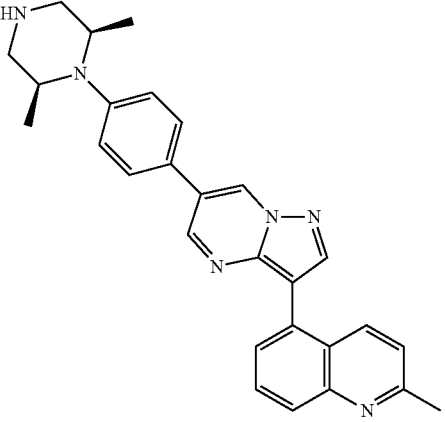 [SMILES: Cc1ccc2c(-c3cnn4cc(-c5ccc(N6[C@H](C)CNC[C@@H]6C)cc5)cnc34)cccc2n1] | 219 | 32 | 3295 | 2630 | 20010 | 19280 |
| 55 | 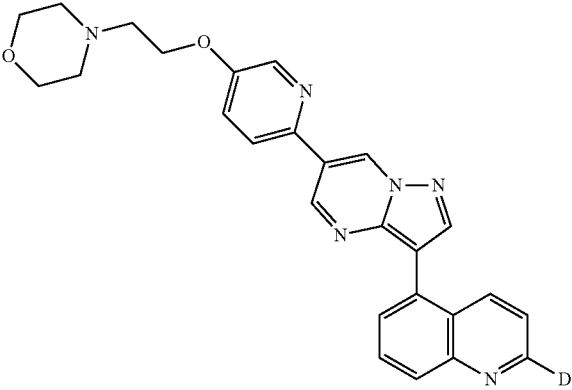 [SMILES: [2H]c1ccc2c(-c3cnn4cc(-c5ccc(OCCN6CCOCC6)cn5)cnc34)cccc2n1] | 413 | 120 | 3728 | | 46870 | |
| 56 | 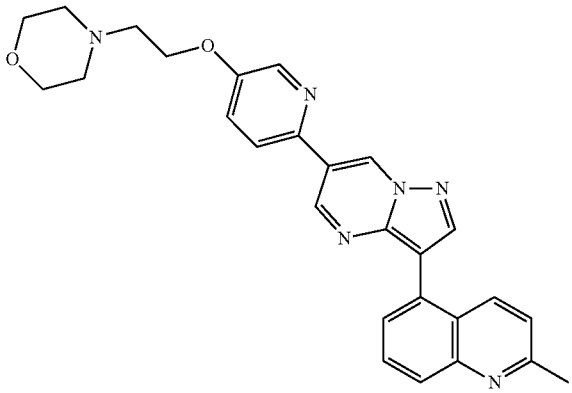 [SMILES: Cc1ccc2c(-c3cnn4cc(-c5ccc(OCCN6CCOCC6)cn5)cnc34)cccc2n1] | 632 | 562 | 2372 | | | |

TABLE 1-continued

FOP Enzymatic Assay Results

| | | IC$_{50}$ (nM) at 10 μM ATP | | | | | |
|---|---|---|---|---|---|---|---|
| CMPD | STRUCTURE | ALK1 | ALK2 | ALK3 | ALK4 | ALK5 | ALK6 |
| 57 | | 48 | 28 | | | | 4483 |
| 58 | | 602 | 107 | | 22290 | 19500 | |
| 59 | | 141 | 43 | 2698 | | | 18650 |

TABLE 1-continued

FOP Enzymatic Assay Results

| CMPD | STRUCTURE | IC$_{50}$ (nM) at 10 µM ATP | | | | | |
|------|-----------|------|------|------|------|------|------|
| | | ALK1 | ALK2 | ALK3 | ALK4 | ALK5 | ALK6 |
| 60 | | 766 | 155 | 11060 | 54180 | | 1112 |
| 61 | | 137 | 41 | 2345 | | | 18920 |
| 62 | | 719 | 180 | 14660 | 48280 | 1593 | 1854 |
| 63 | | 153 | 45 | 4605 | | | 42280 |

TABLE 1-continued
FOP Enzymatic Assay Results
| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 64 | 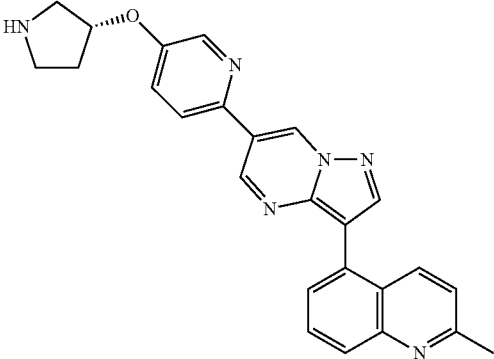 [SMILES: Cc1ccc2c(-c3cnn4cc(-c5ccc(O[C@@H]6CCNC6)cn5)cnc34)cccc2n1] | 1351 | 276 | | 46350 | | 6414 |
| 65 | 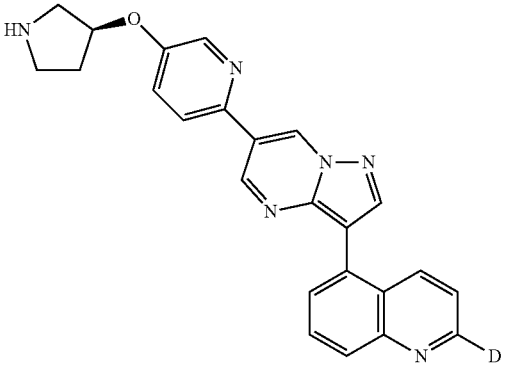 [SMILES: [2H]c1ccc2c(-c3cnn4cc(-c5ccc(O[C@H]6CCNC6)cn5)cnc34)cccc2n1] | 140 | 34 | 3208 | | | 50720 |
| 66 | 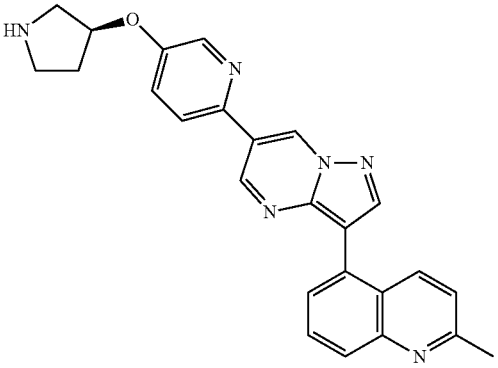 [SMILES: Cc1ccc2c(-c3cnn4cc(-c5ccc(O[C@H]6CCNC6)cn5)cnc34)cccc2n1] | 534 | 102 | | 44310 | 43020 | |

TABLE 1-continued

FOP Enzymatic Assay Results

| CMPD | STRUCTURE | IC$_{50}$ (nM) at 10 μM ATP | | | | | |
|---|---|---|---|---|---|---|---|
| | | ALK1 | ALK2 | ALK3 | ALK4 | ALK5 | ALK6 |
| 67 | | 618 | 157 | | | 22620 | 53560 |
| 68 | | 834 | 66 | | | 20660 | |

Example 3: Cell Luciferase Assay

C2C12 myofibroblasts cells stably transfected with BMP responsive element from the Id1 promoter fused to luciferase reporter gene (BRE-Luc) and human embryonic kidney 293T cells stably transfected with the TGF-β responsive element from the PAI-1 promoter fused to luciferase reporter gene (CAGA-Luc) were cultured in DMEM (Life Technologies) supplemented with 10% FBS, L-glutamine, and pen/strep at 37° C. and 10% $CO_2$. C2C12 Bre-Luc and 293T CAGA-Luc cells were seeded at 20,000 cells in 80 μL DMEM supplemented with 2% FBS per well in tissue culture treated 96-well plates (Costar® 3610; Corning). The cells were incubated for 1 hour at 37° C. and 10% $CO_2$ and allowed to settle and attach. The compounds of interest were diluted in DMEM at 10-fold the final concentrations ranging from 1 to 100 μM and added in 10 μL aliquots. Positive controls were generated by replacing the compound aliquot with just 10 μL of DMEM. The cells were then incubated for 30 min at 37° C. and 10% $CO_2$. Finally 10 μL aliquots of BMP6 and TGF-β1 ligand were added to achieve final concentrations of 50 ng $mL^{-1}$ and 5 ng $mL^{-1}$, respectively. The negative controls were generated by replacing both the compound and adenovirus aliquots with just 20 μL of DMEM. Plates were left to incubate overnight for 16 to 24 hours at 37° C. and 10% CO2. After determining cell viability using an MTT (3-(4,5-dimethylthiazol-2-yl)-2,5-diphenyl tetrazolium bromide) colorimetric assay (CellTiter 96®; Promega) per the manufacturer's instructions, the media was discarded, 30 μL of passive lysis buffer (Promega) added, and the plates allowed to incubate at RT on a shaker for 15 minutes. A multichannel pipette was used to add 15 μL of luciferase assay system (Promega) solution to each well and the plate was shaken gently for 15 seconds. Light output was measured using a Spectramax L luminometer (Molecular Devices) using the auto-range setting with an integration time of one second per well. Data was normalized to positive controls at 100% BMP or TGF-β signaling activity with negative controls being subtracted as background. GraphPad Prism® software was used for graphing and regression analysis by sigmoidal dose-response with variable Hill coefficient.

Results from the FOP SMAD1/SMAD3 cell based assay for several compounds of the invention are shown in Table 2. In certain instances where multiple tests were performed for a particular compound in a particular assay, the data shown in Table 2 represents an average of the individual results.

TABLE 2

FOP SMAD1/SMAD3 Cell Based Assay (Alpha) Results

| Compound | Cellular Assay IC50 (nM) | |
|---|---|---|
| | BMP | TGFβ |
| 1 | 158 | 8170 |
| 2 | 37 | 542 |
| 3 | 22 | 905 |
| 4 | 154 | 2697 |
| 5 | 560 | 40615 |
| 6 | 1406 | 39 |
| 7 | 430 | 3528 |
| 8 | | |
| 9 | 935 | 36079 |
| 10 | 36 | 96 |
| 11 | 21 | 30 |
| 12 | 125 | 463 |
| 13 | 52 | 198 |
| 14 | 346 | 2516 |
| 15 | 378 | 1303 |
| 16 | 157 | 4058 |
| 17 | 65 | 3450 |
| 18 | 305 | 4156 |
| 19 | 1219 | 13008 |
| 20 | 181 | 2957 |
| 21 | 14424 | 17091 |
| 22 | 100 | 100000 |
| 23 | 4509 | 37 |
| 24 | 251 | 7839 |
| 25 | 150 | 1484 |
| 26 | 287 | 5105 |
| 27 | 30 | 1959 |
| 28 | 26 | 4189 |
| 29 | 808 | 67883 |
| 30 | 2106 | 56798 |
| 31 | 516 | 21288 |
| 32 | 77 | 100000 |
| 33 | 69 | 928 |
| 34 | 528 | 3871 |
| 35 | 137 | 9619 |
| 36 | 434 | 11040 |
| 37 | 71 | 12052 |
| 38 | 472 | 12672 |
| 39 | 51 | 8038 |
| 40 | 176 | 12516 |
| 41 | 173 | 16717 |
| 42 | 1294 | 39042 |
| 43 | 233 | 8305 |
| 44 | 1786 | 58843 |
| 45 | 178 | 18260 |
| 46 | 976 | 53608 |
| 47 | 118 | 5252 |
| 48' | 587 | 1137 |
| 49 | 232 | 3206 |
| 50 | 1162 | 4304 |
| 51 | 144 | 11598 |
| 52 | 7 | 80 |
| 53 | 43 | 390 |
| 54 | 328 | 118 |
| 55 | 935 | 3956 |
| 56 | 9274 | 16529 |
| 57 | 88 | 1532 |
| 58 | 614 | 226 |
| 59 | 215 | 5859 |
| 60 | 757 | 801 |
| 61 | 200 | 5388 |
| 62 | 1505 | 1894 |
| 63 | 252 | 1542 |
| 64 | 1264 | 559 |
| 65 | 189 | 3074 |
| 66 | 843 | 583 |
| 67 | 2149 | 2796 |
| 68 | 187 | 5383 |

Example 4: In Vitro Metabolism of LDN-193189 in Mouse, Rat, Dog, Rabbit, Monkey, and Human Liver Microsomes and Cytosols Summary The metabolism of LDN-193189 was investigated in the presence of mouse, rat, dog, rabbit, monkey and human liver microsomes fortified with respective cytosols and supplemented with NADPH and UDPGA. To evaluate the formation of potential reactive intermediates, nucleophilic trapping agents, glutathione (GSH) and potassium cyanide (KCN), were added to the incubation mixtures fortified with NADPH. The formation of non-P450 mediated metabolite in the presence of cytosols from various species was also investigated. Metabolite profiles and metabolic soft spots of LDN-193189 were obtained using LC/UV and mass spectral techniques.

Following incubations for one hour, LDN-193189 was found to be extensively metabolized to an oxidized metabolite, M422c, especially in the presence of liver cytosols from all species except rats and dogs. The rank order for conversion of LDN-193189 to metabolite M422c in metabolizing systems containing liver cytosols was monkey>rabbit>human>mouse. The formation of M422c was inhibited in the presence of menadione, a specific inhibitor of aldehyde oxidase, suggesting that this cytosolic enzyme was responsible for the major route of metabolism for this compound. Furthermore, the structure of metabolite M422c was confirmed with the synthetic reference standard, NIH-Q55 (4-(6-(4-(piperazin-1-yl)phenyl)pyrazolo[1,5-a]pyrimidin-3-yl)quinolin-2(1H)-one), based on comparison of the HPLC retention time and the mass spectral fragmentation pattern. The structure of the metabolite suggested that the AO-mediated metabolism took place on the α-carbon of the quinoline nitrogen.

However, in the absence of cytosol, the compound was still found to be significantly metabolized in the presence of rabbit and dog liver microsomes, moderately in mouse, monkey and human and minimally in rat liver microsomes. The extent of microsomal metabolism could be ranked as dog>rabbit>mouse>human~monkey>rat. The structures of metabolites found in liver microsomal extracts were tentatively assigned based on mass spectral data. The aldehyde oxidase-mediated metabolite, M422c, is proposed to be produced by oxidation of the alpha-carbon of quinoline, while M422a and M422b are postulated to be formed by oxidation of basic nitrogens in the molecule. The mass spectral characterization of microsomal metabolites also suggested that LDN-193189 underwent extensive metabolism on the piperizine moiety, including a lactam derivative, M420; and piperazine-ring cleaved metabolites M337, M380, M381, M395; and M438. The scission of the piperazine moiety led to primary and secondary anilines which were found in all species. There were no glucuronide conjugates observed in any of the species.

In the presence of KCN, cyanide adducts M431 and M445, were observed in all species, suggesting the formation of reactive electrophilic intermediate. The reactive intermediate which can lead to such adducts, is proposed to be an iminium derivative of the piperazine moiety. Studies with GSH as a trapping agent failed to show the presence of any soft electrophile which would normally be trapped by a soft nucleophile such as glutathione.

In general, the metabolites produced by human liver microsomes and cyrosol were also observed in other species, i.e. there were no unique human metabolites observed in this study.

Introduction

This study was to investigate the metabolism of LDN-193189 in mouse, rat, dog, rabbit, monkey and human liver microsomes fortified with respective cytosols in the presence of NADPH and UDPGA. The formation of reactive intermediates was evaluated by addition of GSH or KCN to the incubation mixtures.

Materials and Methods

Materials

LDN-193189 hydrochloride and NIH-Q55 were stored at −20° C. until used. The structures of LDN-193189 and NIH-Q55 (synthetic reference standard of M422c) are as follows:

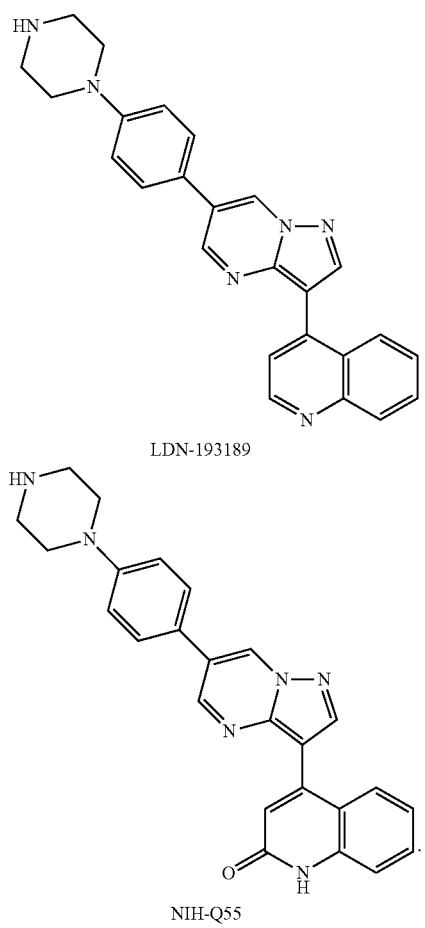

LDN-193189

NIH-Q55

Pooled liver microsomes and cytosol were obtained from commercial sources (Xenotech, Kans.), including the liver microsomes and cytosol from CD-1 mice (Lot #0310190 and Lot #0610024), rats (Lot #0710104 and Lot #0710103), dogs (Lot #452601 and Lot #0710436), rabbits (Lot #0810371 and Lot #0510023), monkeys (Lot #0510003 and Lot #0310071) and humans (Lot #452161 and Lot #01610370), respectively. The following reagents obtained from Sigma Aldrich (St Louis, Mo.) were used for in vitro studies: $MgCl_2$, NADPH-regenerating systems (NADP+, glucose-6-phosphate, and glucose-6-phosphate dehydrogenase), 0.1 M phosphate buffer (pH 7.4), GSH (glutathione, reduced), KCN, manadione (specific aldehyde oxidase inhibitor), allopurinol (xanthine oxidase inhibitor) and UDPGA. Solvents used for chromatographic analysis were HPLC or ACS reagent grade and purchased from EMD Chemicals (Gibbstown, N.J.) or other commercial suppliers. All other reagents were analytical or ACS reagent grade.

Methods

Preparation of Stock Solutions for Incubations

Stock solution (5 mM) of LDN-193189 HCl was made by adding 0.877 mL of DMSO/ACN (50/50, v/v) into a vial containing 1.78 mg of the compound. Further dilution was made by using 100% ACN to make 1 mM solution which was used for the incubations.

Incubations with Liver Microsomes and Cytosol from Different Species

LDN-193189 (10 μM) was incubated with mouse, rat, dog, rabbit, monkey and human liver microsomes (1 mg/mL) with/without cytosol (2 mg/mL) in the presence of NADPH-regenerating system {(glucose-6-phosphate (3.6 mM), NADP+ (1.3 mM), and glucose-6-phosphate dehdrogenase (0.4 units/mL)}, $MgCl_2$ (10 mM), and UDPGA (2 mM) in 0.1 M phosphate buffer (pH 7.4). Liver microsomes or cytosols containing appropriate cofactors were also fortified with KCN (0.1 mM) or GSH (2 mM), or menadione (1 mM) or allopurinol (0.1 mM). Various incubation conditions used to understand the metabolism of the compound are shown in Table 3 below. Total incubation volume was 1 mL. The metabolic reactions were initiated by the addition of cofactors, NADPH-regenerating system and UDPGA, after a pre-incubation at 37° C. for 5 min. The incubation mixtures were placed in a shaking water bath at 37° C. for 60 min. At the end of the reaction, three volumes of acetonitrile were added, followed by vortexing and centrifuging to remove proteins. The supernatants were transferred to clean tubes and dried completely under a stream of nitrogen at ambient temperature. The dried residues were reconstituted with 500 μL of 25% MeOH in water and transferred into HPLC vials for LC/UV/MS analysis.

TABLE 3

Incubation of LDN-193189 with liver microsomes and cytosols from various species.

| Incubation # | Substrate | NADPH[a] | Microsomes | Cytosol | $MgCl_2$ | GSH | KCN | UDPGA |
|---|---|---|---|---|---|---|---|---|
| 1 | ✓ | ✓ | ✓ | ✓ | ✓ | X | X | ✓ |
| 2 | ✓ | ✓ | ✓ | X | ✓ | ✓ | X | X |
| 3 | ✓ | ✓ | ✓ | X | ✓ | X | ✓ | X |
| 4 | ✓ | ✓ | ✓ | X | ✓ | X | X | ✓ |
| 5 | ✓ | X | ✓ | X | ✓ | X | X | X |

[a]NADPH or NADPH-regenerating system

Control incubations in the absence of co-factors were conducted under similar conditions. Testosterone at 100 µM was incubated with human liver microsomes as a positive control to demonstrate the viability of the microsomal preparations and the incubation conditions used for LDN-193189; however the incubation time was reduced to 20 minutes. Acetaminophen and nicotine were used as positive controls for GSH and KCN trapping studies, respectively.

LC/UV/MS Conditions for Metabolite Profiling and Identification

Metabolite profiling and characterization of metabolites in microsomal incubation extracts were performed using a LC/MS system consisting of a Surveyor HPLC system equipped with pump, autosampler and diode array detector interfaced to an LTQ ion trap mass spectrometer (Thermo Scientific, San Jose, Calif.). Chromatography was accomplished on a Phenomenex Luna, C8 (2) column, 3.0×250 mm, 5 µm (Torrance, Calif.). The column was kept at ambient temperature during sample analysis. The mobile phase gradient used is shown in Table 4. The first 4 minutes of the HPLC flow was diverted to waste prior to evaluation of metabolites. To facilitate distinction of carbon or heteroatom oxidations, hydrogen/deuterium (H/D) exchange experiments were performed by replacing the aqueous mobile phase (H2O) with $D_2O$ while keeping the rest of assay conditions unchanged. UV absorption spectra from 200-400 nm were recorded using the diode array detector.

ThermoFinnigan LTQ XL mass spectrometer (Thermo Scientific, San Jose, Calif.) was equipped with an electrospray ionization (ESI) interface and operated in positive ionization mode for metabolite profiling and identification. Mass spectra were acquired in full scan (MS) (m/z 200-1000) and data dependent scan (MS2, MS3, and MS4) modes. The parameter settings for the LTQ mass spectrometer used for the analysis are shown in Table 5.

TABLE 4

HPLC Gradient for LDN-193189 Analysis

| Time (min) | 0.05% TFA in Water[a] | 0.05% TFA in ACN | Flow Rate (µL/min) |
|---|---|---|---|
| 0 | 95 | 5 | 300 |
| 5 | 95 | 5 | 300 |
| 35 | 75 | 25 | 300 |
| 40 | 5 | 95 | 300 |
| 44 | 5 | 95 | 300 |
| 45 | 95 | 5 | 300 |
| 59 | 95 | 5 | 300 |

[a]$D_2O$ was used for H/D exchange study

TABLE 5

Settings for the LTQ Mass Spectrometer

| | |
|---|---|
| Spray voltage: | +5.0 kV |
| Capillary Temperature: | 300° C. |
| Sheath Gas: | 80 (arbitrary unit) |
| Auxiliary Gas: | 20 (arbitrary unit) |
| Activation Q: | 0.25 |
| Activation time: | 30 (ms) |
| Collision energy: | 40 eV |

Data Analysis

Xcalibur (version 2.07) was used to acquire and process mass spectral and UV absorption data. It was also used to control the various components of the LC/UV/MS system.

Results

Metabolite Profiles

Figure 7:
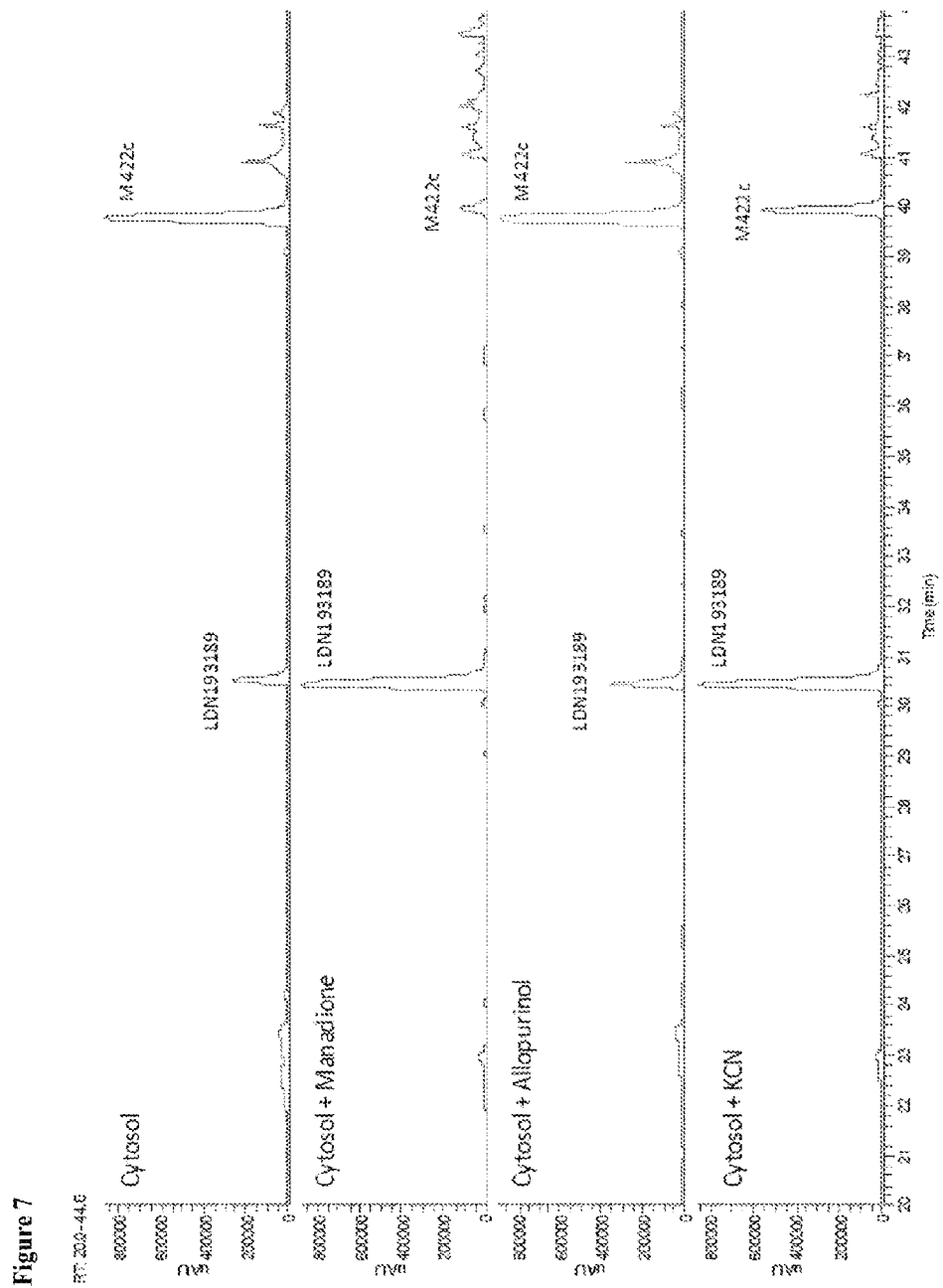
FIG. 7 shows inhibition of the formation of M422c by Menadione in mouse cytosol.
Figure 8:
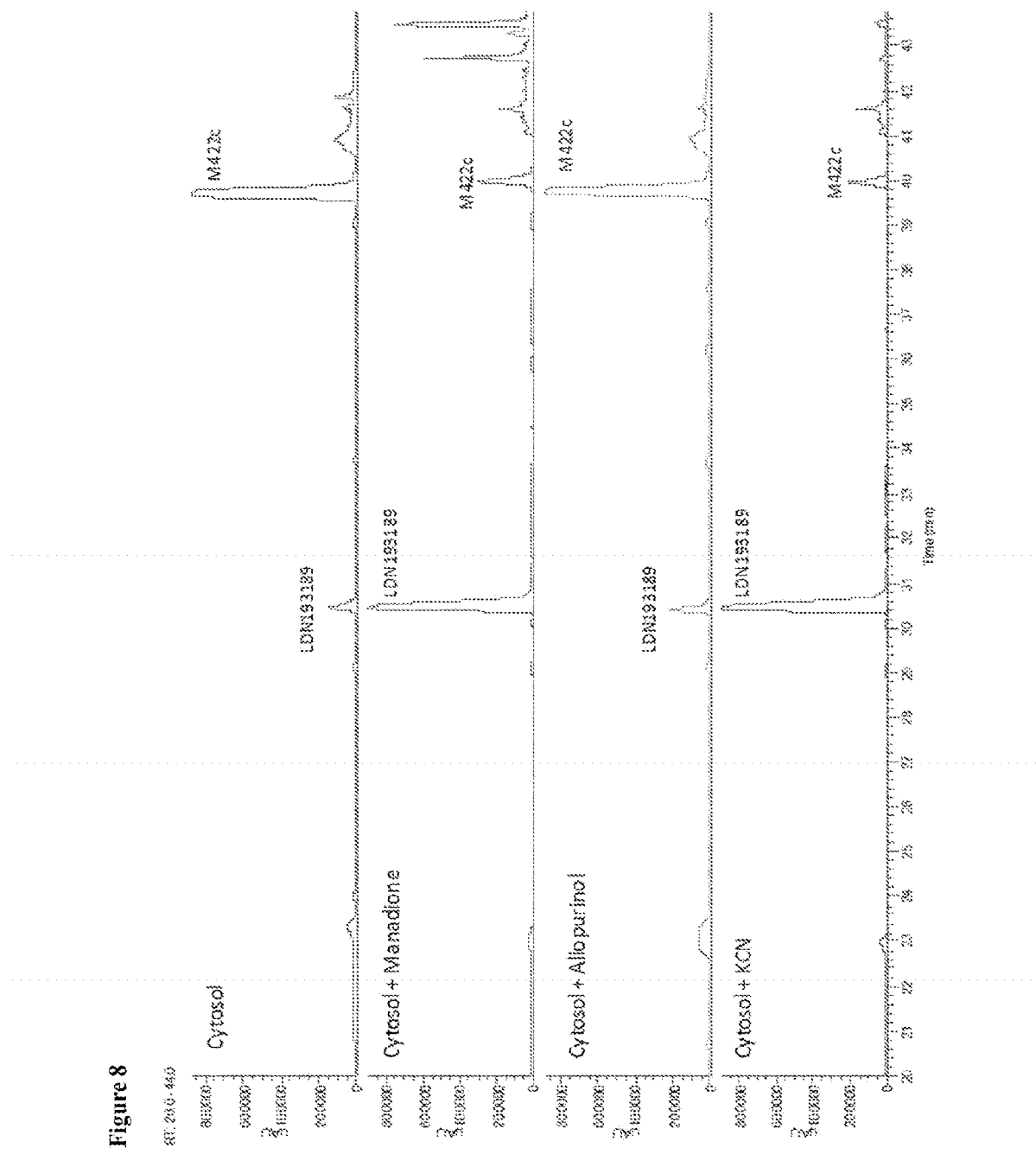
FIG. 8 shows inhibition of the formation of M422c by Menadione in human cytosol.

The metabolite profiles of LDN-193189 were obtained following incubations with mouse, rat, dog, rabbit, monkey and human liver microsomal preparations using LC/UV/MS analysis. Metabolite profiles (LC/UV, with λ 310-315 nm) of LDN-193189 obtained for various species are shown in FIG. 1 to FIG. 6. A significant metabolite, M422c, was observed in all species except rat and dog. The formation of M422c appeared to be mediated via cytosolic enzyme, suggesting that it was produced by either aldehyde oxidase (AO) or xanthine oxidase (XO). To confirm the identity of the enzyme responsible for the formation of M422c, LDN-193189 was incubated with mouse or human cytosol to which menadione (a specific inhibitor of aldehyde oxidase) or allopurinol (specific inhibitor of xanthine oxidase) was added. The results are shown in FIG. 7 and FIG. 8, respectively. Inhibition of the formation of M422c was observed in the presence of menadione, confirming that the metabolite production was mediated by aldehyde oxidase. A comparison of the LC/UV profiles across the species showed that LDN-193189 appeared to be rapidly converted to M422c when cytosol was added to the liver microsomes. The rate of metabolic conversion to M422c appeared to be monkey>rabbit>human>mouse with no conversion observed in rat and dog liver preparations. However, when cytosol was omitted from the incubation mixtures, the compound was essentially metabolized by CYP450 microsomal enzymes, such as NADPH dependent CYP450s. The rank ordering of the metabolic conversion in the presence of liver microsomes (no cytsosol added) was dog>rabbit>mouse>human~monkey>rat.

Figure 9:
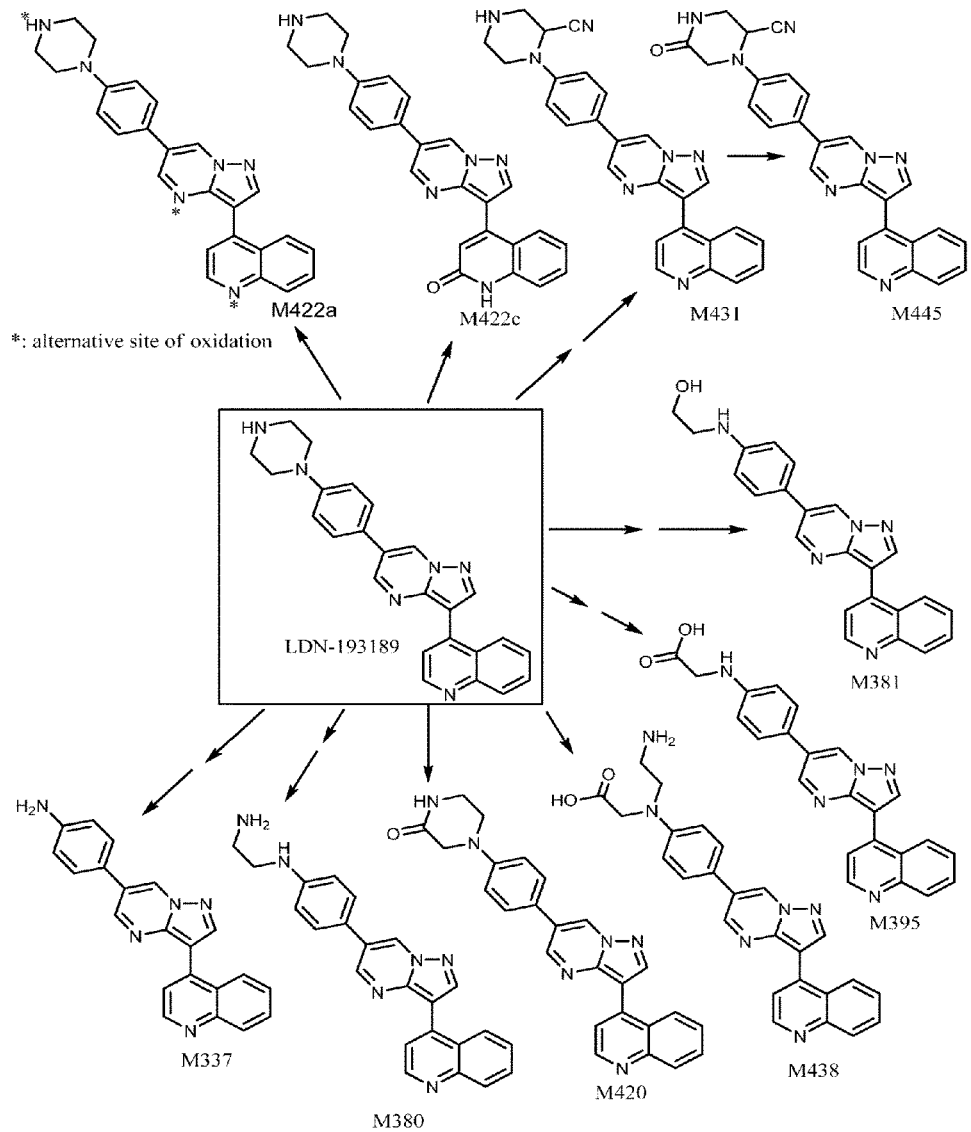
FIG. 9 shows the proposed metabolic pathways of LDN-193189 in liver microsomes and cytosols from mice, rats, rabbits, dogs, monkeys and humans.

The metabolic pathways for LDN-193189 was proposed on the identities of metabolites found under various incubation conditions (see FIG. 9). The identification of the metabolites was made based on the full scan and MS/MS spectral data.

Following incubations with liver microsomes, LDN-193189 was mainly metabolized on the piperazine moiety, producing various piperazine ring-cleaved derivatives including M337, M380, M381, M395, and M438. A piperazine ring-oxidized derivative (lactam), M420 was also demonstrated in all species. Two oxidative metabolites, M422a and M422b, are believed to be N-oxide/hydroxylamine analogues of LDN-193189 based on the mass spectral data obtained with H/D exchange study. Metabolite M422a and M422b showed the same number of exchangeable protons as the parent compound in the deuterium exchange study. In contrast, metabolite M422c, which is proposed to be formed by oxidation at a carbon, leads to an additional exchangeable proton (due to the hydroxyl group). Interestingly, there were no glucuronide conjugates observed in this study despite the formation of hydroxylated/oxidized metabolites.

Cyanide conjugate M431 and a further oxidized derivative, M445, were observed in all species when KCN was added to the incubation mixtures. This suggested that LDN-193189 could be bioactivated, forming a reactive intermediate that could be trapped by a hard nucleophile such as cyanide. Based on the mass spectral data, the bioactivation was localized on the piperazine moiety forming an iminium derivative. There is ample precedence in literature that describes the formation of iminium intermediates from alicyclic amines such as nicotine (Gorrod J W and Aislaitner G (1994): The metabolism of alicyclic amines to reactive iminium ion intermediates. European Journal of Drug metabolism and Pharmacokinetics, 19, 209-217; Murphy, P (1972): Enzymatic oxidation of nicotine to nicotine Δ1'(5')

iminium ion. Journal of Biological Chemistry, 248, 2796-2800.) Trapping studies conducted with GSH showed that there were no "soft electrophiles" produced from LDN-193189 in the presence of liver microsomes from all species.

The proposed metabolic pathways of LDN-193189 are presented in FIG. 9. It was observed that all metabolites observed in human liver preparations were also produced by other non-clinical species, i.e. there were no unique human metabolites observed in this study.

Metabolite Characterization by Mass Spectrometry

The metabolites of LDN-193189 produced in the presence of liver microsomes and cytosol from mice, rats, rabbits, dogs, monkeys and humans were tentatively identified by LC/MS/MS analysis. To facilitate the identification of oxidative metabolites, H/D exchange experiments were also conducted. The data from the deuterium exchange studies allowed us to distinguish between carbon-hydroxylated (C—OH) metabolites versus heteroatom oxidatized derivatives (e.g. N→O). An additional exchangeable proton in the mass spectrum of an oxidized metabolite would suggest hydroxylation on a carbon atom, while a heteroatom oxidation would not lead to an exchangeable proton.

The structures of the metabolites were tentatively assigned based on comparison of mass spectral fragmentation patterns with those produced by LDN-193189 under the same experimental conditions. In this study, the mass spectra of all metabolites were acquired in the positive ionization mode and up to MS4 tandem mass spectra were acquired to assist in the elucidation of structures. Nomenclature (metabolite names for identification/reference purposes) of the metabolites was based on the nominal molecular weights of the metabolites as determined from the pseudomolecular ions ([M+H]+) observed in the mass spectra of metabolites. For example, M422 corresponds to a metabolite with [M+H]+ at m/z 423.

Mass spectra of LDN-193189 showed a protonated molecular ion observed at m/z 407, consistent with the chemical formula C25H22N6 and structure of LDN-193189. The most intense fragment ions observed from the protonated molecular ions are produced by the cleavage of piperazine moiety, such as m/z 364, 350 and 337. In addition, a weak fragment ion at m/z 169 could be produced following several steps of fragmentations, such as the cleavage of piperazine combined with the cleavage of the pyrazole moiety.

The tentative structural elucidation of the metabolites shown in FIG. 9 was obtained through mass spectral analysis.

Figure 10:
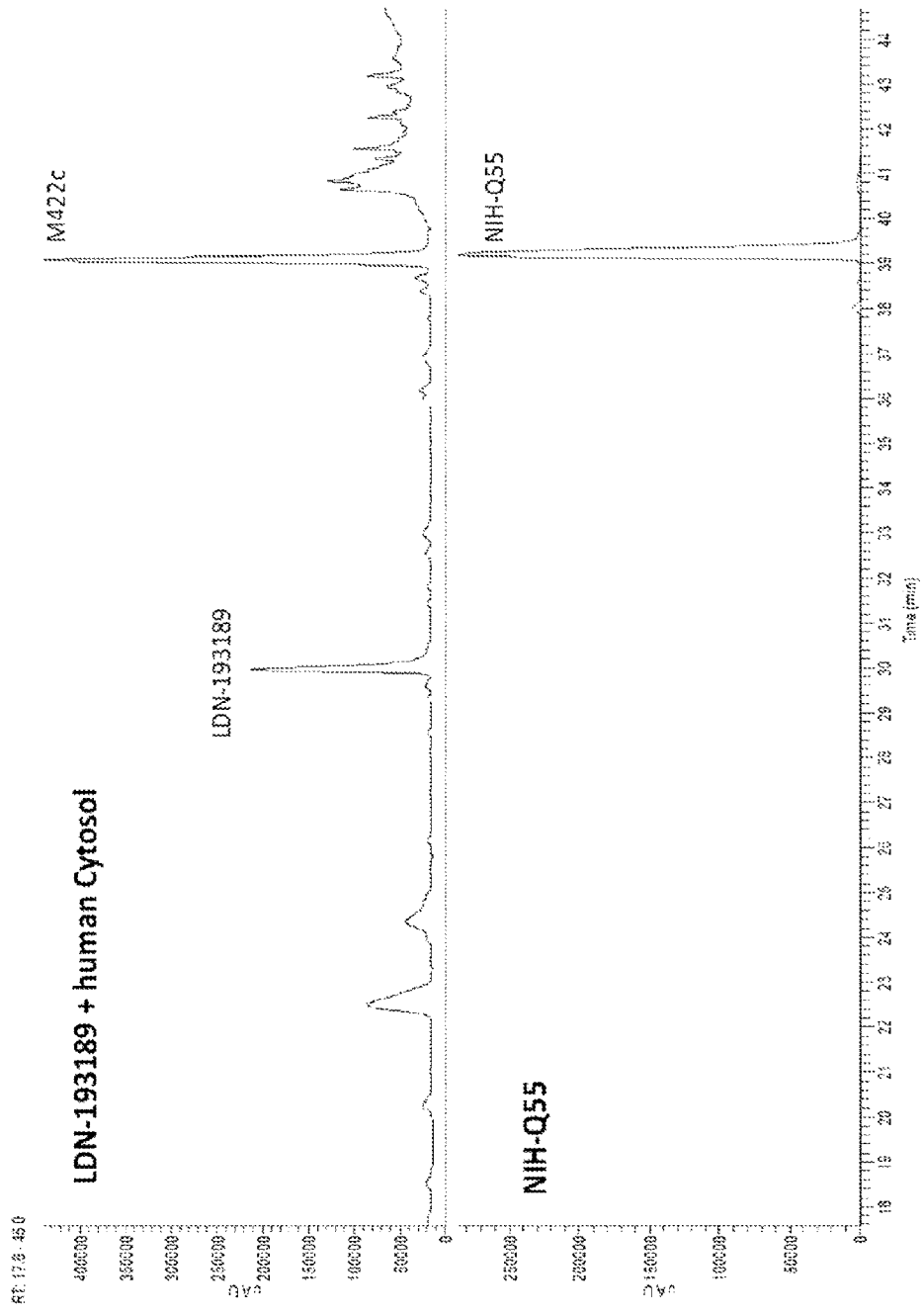
FIG. 10 shows the LC/UV chromatograms of NIH-Q55 and the incubation extract of LDN-193189 in the presence of human cytosol.

A confirmatory metabolite identification study was conducted with M422c. To confirm the identity of the major metabolite, M422c, a synthetic reference standard was analyzed using the same LC/MS conditions that was used for the analyses of in vitro metabolism extracts. The HPLC retention time and the mass spectral fragmentation pattern of M422c were compared with those of the synthetic standard. It was found that the mass spectral fragmentation patterns were identical between M422c and the synthetic reference standard. Furthermore, the HPLC retention times of M422c found in human cytosol incubation extract was identical to that produced by the synthetic standard (see FIG. 10). Hence the structure of M422c was confirmed to be (4-(6-(4-(piperazin-1-yl)phenyl)pyrazolo[1,5-a]pyrimidin-3-yl)quinolin-2(1H)-one).

Conclusions

The metabolism of LDN-193189 was studied using mouse, rat, dog, rabbit, monkey and human liver microsomes fortified with respective cytosols. The major route of metabolism was found to be via oxidation of the alpha-carbon of quinoline nitrogen, leading to M422c. The identity of M422c was unequivocally established by comparison with synthetic standard. This metabolite was formed in significant quantities in liver microsomes fortified with cytosol from mice, rabbits, monkeys and humans. Rats and dogs, which are known to be deficient in AO, did not produce this metabolite. In this study, no M422c was observed in rats, the species known to have low AO activities. The formation of this metabolite was proposed to be mediated by cytosolic enzyme, aldehyde oxidase (AO), which is expressed well in most species except rats and dogs. The since metabolite profiles were consistent with the natural abundance of AO in different species. Furthermore, a specific inhibitor of AO, menadione, was used to demonstrate the inhibition of M422c formation in the presence of mouse and human liver cytosol (see FIG. 7 and FIG. 8).

LDN-193189 was also found to be metabolized fairly extensively, in some species, when cytosol was omitted from the microsomal incubations. This was particularly evident in dog and rabbit liver microsomes which produced significant amounts of metabolites other than M422c. The major route of metabolism mediated by microsomal CYP450 enzymes appears to be via modification of the piperazine moiety. For example, in dog liver microsomes, M380 and M420 appear to be the major metabolites which are produced as a result of piperazine ring modification. Subsequent cleavage of the piperazine led to the formation of free anilines, M337 and M380 which were found in all species, except M337 was not found in rats. Interestingly, the metabolite profiles obtained in this study showed that the compound exhibited greatest metabolic stability in the presence of rat liver microsomes (with and without cytosol). Furthermore, the metabolite profile obtained from HLM showed a significant dependence on AO for its metabolism as the CYP450 mediated metabolism was minimal (see FIG. 6). Hence, this significant dependence upon AO for its metabolic clearance may have implications in studies conducted with this compound in humans. It is well known that AO is expressed differently in humans and if the clearance of this compound is dependent upon AO, significant variability in exposure values may be observed in subjects.

The formation of metabolites as a result of oxidation of heteroatoms (nitrogen in this case) was also evident, particularly in rabbits. The oxidation at heteroatoms was confirmed by deuterium exchange studies which often are very confirmatory of metabolism (insertion of oxygen) on nitrogen or sulfur. The enzymes responsible for these oxidations on nitrogen of LDN-193189 are not known at this stage, as it could be CYP and FMO-mediated.

Bioactivation of LDN-193189 to form a reactive intermediate was demonstrated by the presence of cyanide adducts in liver microsomal extracts from all species. It is proposed that an iminium derivative of the piperazine moiety was produced as the reactive intermediate, which subsequently was trapped by the cyanide.

Example 5: In Vitro Metabolism of Compound 1, Compound 2 and Compound 48 in Mouse and Human Liver Microsomes and Cytosols List of Abbreviations AO aldehyde oxidase
GLP Good Laboratory Practices
GSH glutathione
HLM human liver microsome HPLC high-performance liquid chromatography
KCN potassium cyanide
LC/UV/MS Liquid chromatography/ultraviolet/mass spectrometry
LSC liquid scintillation counter
m/z mass-to-charge ratio
MS mass spectrometry
NA Not available/Not applicable
NADPH nicotinamide adenine dinucleotide phosphate
PO Oral dose (by mouth)
QA Quality Assurance
QC Quality Control
SD Standard deviation
SOP standard operating procedure Summary The metabolism of compound 1, compound 2 and compound 48 was investigated in the presence of mouse and human liver microsomes fortified with respective cytosols and supplemented with NADPH and UDPGA. To evaluate the formation of potential reactive intermediates, nucleophilic trapping agents, glutathione (GSH) and potassium cyanide (KCN), were added to the incubation mixtures fortified with NADPH. The possible formation of non-P450 mediated metabolites in the presence of cytosols from various species was also investigated. Metabolite profiles and metabolic soft spots of the test compounds were obtained using liquid chromatography/ultraviolet (LC/UV) and mass spectral techniques.

Following incubations for one hour, compound 1 was found to be extensively metabolized to an oxidized metabolite, M423c in the presence of mouse and human liver cytosolic fractions. The formation of this metabolite is proposed to be aldehyde oxidase (AO)-mediated based on results from studies conducted with a structural analogue, LDN-193189, as described in Example 4. The site of oxidation was found to be the alpha-carbon of quinoline nitrogen of LDN-193189, as demonstrated by comparison of the AO-mediated metabolite M422c and the synthetic reference standard. In addition, compound 1 was found to be metabolized via N-hydroxylation and N-oxidation to produce M423a and M423b, respectively, in the presence of liver microsomes fortified with NADPH. A product formed by oxidation of the piperazine moiety (likely a lactam), M421, was observed in the liver microsomal extracts as well. There were no glucuronide conjugates observed with this compound. The compound was not metabolized as extensively as its analogue LDN-193189 by P450 enzymes. For example, the cleavage of piperazine ring, which was a significant metabolic pathway for LDN-193189, was not observed. Furthermore, secondary or primary aromatic amines (aniline analogues) which were observed with LDN-193189, were not detected in microsomal incubations with this compound. In the presence of KCN, a cyanide adduct, M432, was observed in both species, suggesting the formation of reactive electrophilic intermediate (iminium derivative). This observation also suggests that the formation of the reactive intermediate was not mitigated by replacing the phenyl moiety on LDN-193189 with a pyridine moiety (as in compound 1). Studies with GSH, a trapping agent for reactive intermediates, failed to show the presence of any soft electrophile in the microsomal incubations.

The major metabolic pathway of compound 2 in the presence of liver cytosol from mouse and humans was found to be via the oxidation of the alpha-carbon of quinoline nitrogen, leading to M450c. Again, the involvement of AO in mediating the formation of M450c in both species is invoked. In addition, the N-oxidation products, such as M450a, (hydroxylamine) and M450b (N-oxide), were found in the microsomal incubations fortified with NADPH. Trace quantities of an aniline product was found during the LC/MS analysis of the microsomal extracts. The structure of this compound was confirmed by comparison with a synthetic reference standard. Additional studies with a reference standard confirmed that this aniline was an impurity present in compound 2 and was not a metabolite. Potential reactive metabolites capable of being trapped by KCN were not detected by mass spectrometric techniques. This suggested that the introduction of the methyl groups adjacent to the nitrogen of piperazine moiety mitigated the formation of potential iminium reactive intermediate. Glucuronide and GSH conjugates were not observed with this compound.

Compound 48, similar in structure to the other two analogues, was metabolized mainly through the oxidation of the quinoline ring. It is speculated that the major metabolite, M421d, is also formed via AO. In the presence of microsomes fortified with NADPH, a metabolite formed by oxidation of the piperidine moiety, M421a, was observed. In addition, N-oxidation products, M421b and M421c, were also observed in microsomes fortified with NADPH. Reactive intermediates that could be trapped by KCN or GSH were not observed. The glucuronide conjugate was not observed as well.

In general, the metabolites produced by human liver microsomes and cytosol were also observed in mouse for all three compounds, i.e. there were no unique human metabolites observed in this study.

Introduction

These studies were conducted to investigate the metabolism of compound 1, compound 2 and compound 48 in mouse and human liver microsomes fortified with respective cytosols in the presence of NADPH and UDPGA. The formation of reactive intermediates was evaluated by addition of GSH or KCN to the incubation mixtures.

Materials and Methods

Materials

The test articles compound 1, compound 2 and compound 48, for in vitro metabolism studies were provided as their corresponding TFA salts and stored at −20° C. until used. The structures of the test articles are as follows:

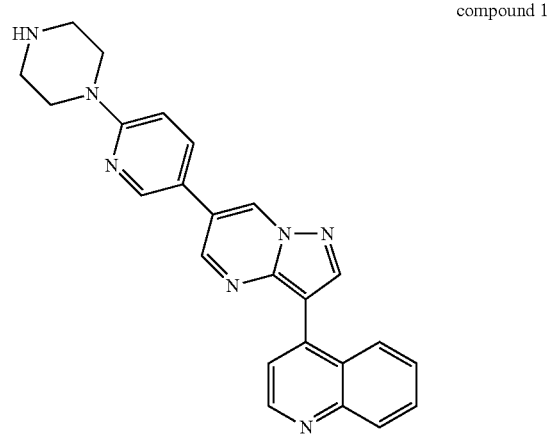

compound 1

-continued

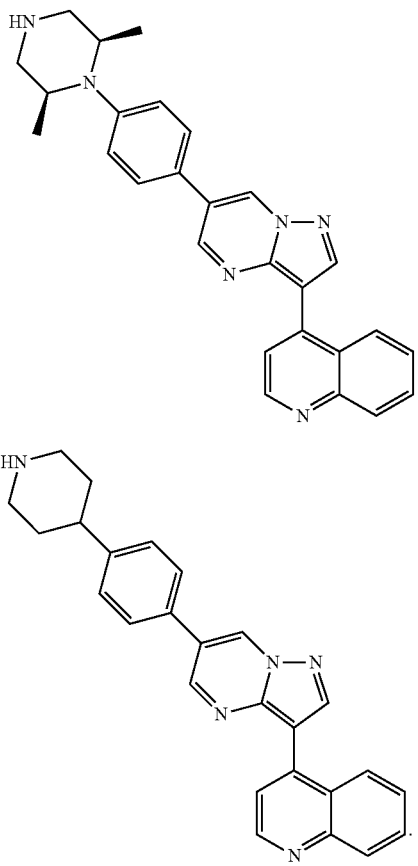

compound 2 compound 48

Methods

Preparation of Stock Solutions for Incubations

Stock solutions (10 mM) of compound 1, compound 2 and compound 48 were made by adding 0.224 mL, 0.191 mL and 0.235 mL of DMSO/ACN (50/50, v/v) into a vial containing 1.17 mg, 1.05 mg and 1.22 mg of compound 1, compound 2 and compound 48, respectively. Further dilution was made by using 1:1 v/v mixture of methanol:water to make 1 mM solution which was used for the incubations.

Incubations with Liver Microsomes and Cytosol from Mice and Humans

The test compounds, compound 1, compound 2 and compound 48, (10 µM) were incubated with mouse and human liver microsomes (1 mg/mL) with/without cytosol (2 mg/mL) in the presence of NADPH-regenerating system {(glucose-6-phosphate (3.6 mM), NADP+ (1.3 mM), and glucose-6-phosphate dehydrogenase (0.4 units/mL)}, $MgCl_2$ (10 mM), and UDPGA (2 mM) in 0.1 M phosphate buffer (pH 7.4). Liver microsomes or cytosols containing appropriate cofactors were also fortified with KCN (0.1 mM) or GSH (2 mM). Various incubation conditions used to understand the metabolism of the compounds are shown in Table 6. Total incubations volumes were 1 mL. The metabolic reactions were initiated by the addition of cofactors, NADPH-regenerating system and UDPGA, after a pre-incubation at 37° C. for 5 min. The incubation mixtures were placed in a shaking water bath at 37° C. for 60 min. At the end of the reaction, three volumes of acetonitrile were added, followed by vortexing and centrifuging to remove proteins. The supernatants were transferred to clean tubes and dried completely under a stream of nitrogen at ambient temperature. The dried residues were reconstituted with 500 µL of 25% MeOH in water and transferred into HPLC vials for LC/UV/MS analysis.

TABLE 6

Incubations of Compound 1, Compound 2 and Compound 48 with Liver Microsomes and Cytosols from Mice and Humans

| Incubation Number | Substrate | NADPH[a] | Microsomes | Cytosol | $MgCl_2$ | GSH | KCN | UDPGA |
|---|---|---|---|---|---|---|---|---|
| 1 | ✓ | X | ✓ | ✓ | ✓ | X | X | X |
| 2 | ✓ | ✓ | ✓ | ✓ | ✓ | X | X | ✓ |
| 3 | ✓ | ✓ | ✓ | X | ✓ | ✓ | X | X |
| 4 | ✓ | ✓ | ✓ | X | ✓ | X | ✓ | X |
| 5 | ✓ | ✓ | ✓ | ✓ | ✓ | X | ✓ | ✓ |

[a]NADPH or NADPH-regenerating system

Pooled liver microsomes and cytosol were obtained from commercial sources (Xenotech, Kans.), including the liver microsomes and cytosol from CD-1 mice (Lot #0310190 and Lot #0610024) and humans (Lot #452161 and Lot #01610370), respectively. The following reagents obtained from Sigma Aldrich (St Louis, Mo.) were used for in vitro studies: MgCl2, NADPH-regenerating systems (NADP+, glucose-6-phosphate, and glucose-6-phosphate dehydrogenase), 0.1 M phosphate buffer (pH 7.4), GSH (glutathione, reduced), KCN, and UDPGA. Solvents used for chromatographic analysis were HPLC or ACS reagent grade and purchased from EMD Chemicals (Gibbstown, N.J.) or other commercial suppliers. All other reagents were analytical or ACS reagent grade.

Testosterone at 100 µM was incubated for 20 minutes with human liver microsomes as a positive control to demonstrate the viability of the microsomal preparations. Acetaminophen and nicotine were used as positive controls for GSH and KCN trapping studies, respectively.

LC/UV/MS Conditions for Metabolite Profiling and Identification

Metabolite profiling and characterization of metabolites in the microsomal incubation extracts were performed using a LC/MS system consisting of a Surveyor HPLC system equipped with pump, autosampler and diode array detector interfaced to an LTQ ion trap mass spectrometer (Thermo Scientific, San Jose, Calif.). Chromatography was accomplished on a Phenomenex Luna, C8 (2) column (3.0×250 mm, 5 µm (Torrance, Calif.)). The column was kept at ambient temperature during sample analysis. The mobile phase gradient used is shown in Table 7. The first 4 minutes of the HPLC eluent was diverted to waste prior to evaluation of metabolites. To facilitate the identification of metabolites (distinction between oxidation on either carbon or heteroatom), H/D exchange experiments were performed by replacing the aqueous mobile phase with D2O while maintaining other conditions unchanged. The UV absorption spectra from 200-400 nm were recorded using the diode array detector.

ThermoFinnigan LTQ XL mass spectrometer (Thermo Scientific, San Jose, Calif.) was equipped with an electrospray ionization (ESI) interface and operated in the positive ionization mode for metabolite profiling and identification. Mass spectra were acquired in full scan (MS) (m/z 200-1000) and data dependent scan (MS2, MS3, and MS4) modes. The parameter settings for the LTQ mass spectrometer used for the analysis are shown in Table 8.

TABLE 7

HPLC Gradient Used to Obtain Metabolite Profiles of Compound 1, Compound 2 and Compound 48

| Time (min) | 0.05% TFA in Water[a] | 0.01% TFA in ACN | Flow rate (μL/min) |
|---|---|---|---|
| 0 | 95 | 5 | 300 |
| 5 | 95 | 5 | 300 |
| 35 | 85, 75, 80[b] | 15, 25, 20 | 300 |
| 40 | 5 | 95 | 300 |
| 44 | 5 | 95 | 300 |
| 45 | 95 | 5 | 300 |
| 50 | 95 | 5 | 300 |

[a]D2O for H/D exchange analysis
[b]for −3024, −3025 and −3246, respectively

TABLE 8

Settings for the LTQ Mass Spectrometer

| | |
|---|---|
| Spray voltage: | +5.0 kV |
| Capillary Temperature: | 300° C. |
| Sheath Gas: | 80 (arbitrary unit) |
| Auxiliary Gas: | 20 (arbitrary unit) |
| Activation Q: | 0.25 |
| Activation time: | 30 (ms) |
| Collision energy: | 50 eV |

Data Analysis

Xcalibur (version 2.07) was used to acquire and process mass spectral and UV absorption data. It was also used to control the various components of the LC/UV/MS system.

Results

Metabolite Profiles of Compound 1

Figure 11:
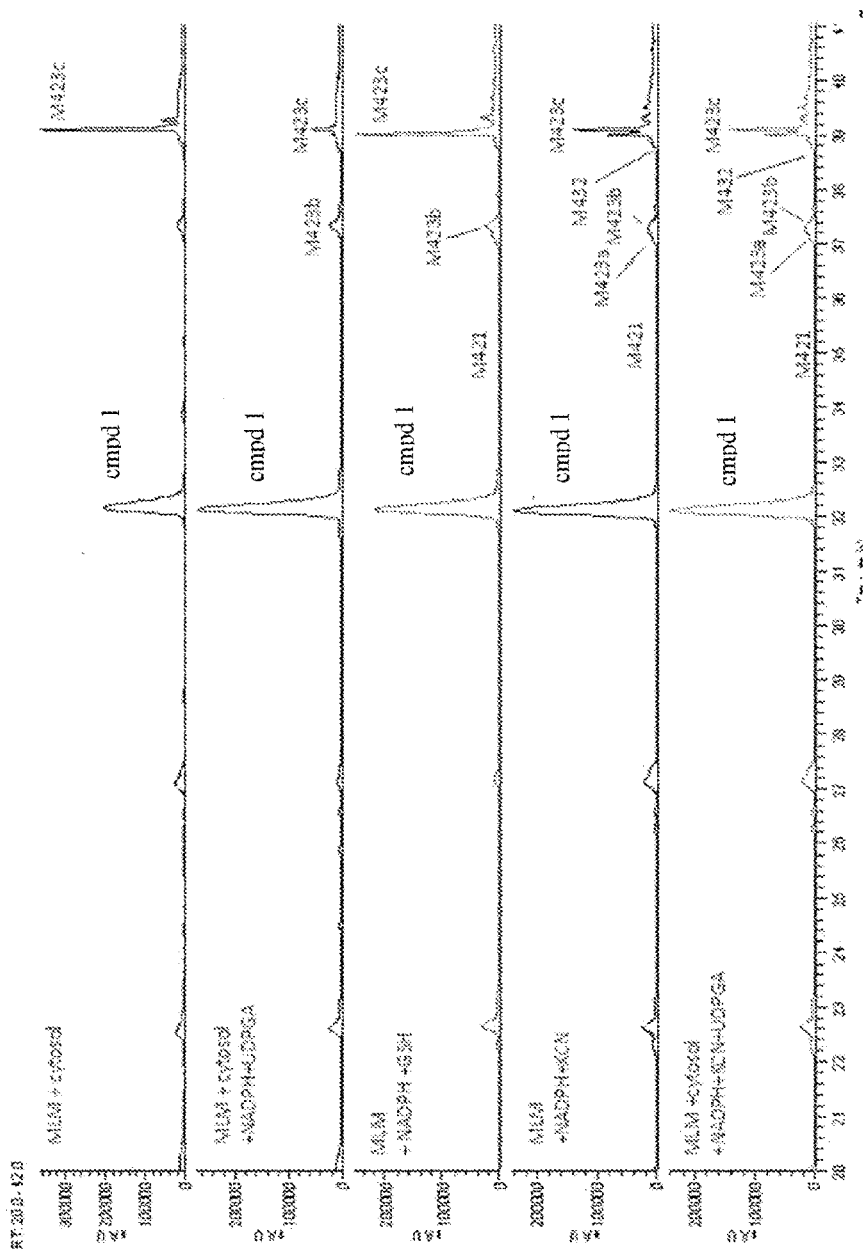
FIG. 11 shows the metabolite profiles (LC/UV) of compound 1 following incubations with mouse liver microsomes (MLM) and cytosol in the presence of NADPH, UDPGA, GSH, and KCN.
Figure 12:
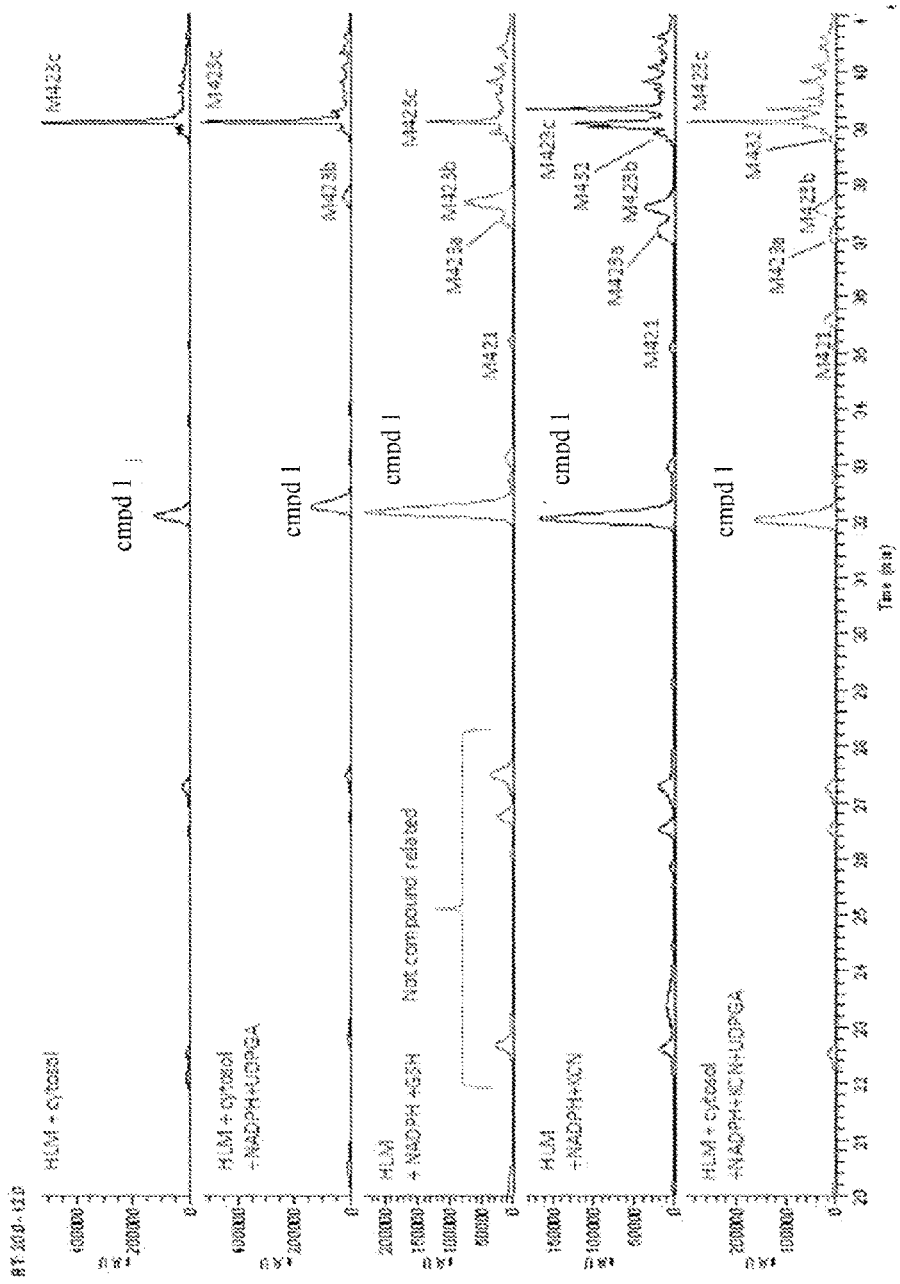
FIG. 12 shows metabolite profiles (LC/UV) of compound 1 following incubations with human liver microsomes (HLM) and cytosol in the presence of NADPH, UDPGA, GSH, and KCN.

The metabolite profiles of compound 1 were obtained following incubations with mouse and human liver microsomal preparations using LC/UV/MS analysis. Metabolite profiles (LC/UV, with λ 310-315 nm) of compound 1 obtained for both species are shown in FIG. 11 and FIG. 12, respectively. A significant metabolite, M423c, was observed in both species. The formation of M423c appears to have been mediated via the cytosolic enzyme, aldehyde oxidase (AO), based on results from previous studies performed with LDN-193189, as described in Example 4. Following incubations with liver microsomes, metabolic oxidations of the nitrogens of compound 1 was observed. Two oxidative metabolites, M423a and M423b, found in the microsomal extracts are believed to be the hydroxylamine and N-oxide analogues of compound 1 based on the mass spectral data obtained with H/D exchange studies Metabolite M423a and M423b showed the same number of exchangeable protons as the parent compound in the deuterium exchange study. This strongly suggested that these metabolites were formed by direct oxidations of the nitrogens (hence no additional exchangeable proton). In contrast, metabolite M423c, which is proposed to be formed by oxidation at a carbon, leads to an additional exchangeable proton (due to the hydroxyl group). A piperazine ring-oxidized derivative (lactam), M421 was also observed in both species. Interestingly, there were no glucuronide conjugates observed in this study despite the formation of hydroxylated/oxidized metabolites.

Cyanide conjugate M432 was observed in both species when KCN was added to the incubation mixtures. This suggested that compound 1 could be bioactivated, forming a reactive intermediate that could be trapped by a hard nucleophile such as cyanide. The mass spectral data supported the bioactivation of the piperazine moiety to an iminium derivative which was trapped as the cyanide adducts (M432 with [M+H] at m/z 433). There is ample precedence in literature that describes the formation of iminium intermediates from alicyclic amines such as nicotine. (Gorrod J W and Aislaitner G (1994): The metabolism of alicyclic amines to reactive iminium ion intermediates. European Journal of Drug metabolism and Pharmacokinetics, 19, 209-217; Murphy, P (1972): Enzymatic oxidation of nicotine to nicotine Δ1' (5') iminium ion. Journal of Biological Chemistry, 248, 2796-2800.) Trapping studies conducted with GSH showed that there were no "soft electrophiles" produced from compound 1 in the presence of liver microsomes from both species.

The metabolites observed in this study are summarized in Table 9. It was observed that all metabolites observed in human liver preparations were also produced by mouse, i.e. there were no unique human metabolites observed in this study. The proposed metabolic pathways of compound 1 are presented in FIG. 13.

TABLE 9

Summary of Metabolites of Compound 1 Following Incubations with Mouse and Human Liver Microsomes and Cytosol

| Metabolites | RT (min)[a] | MH+ | Biotransformation | Species |
|---|---|---|---|---|
| compound 1 | 32.4 | 408 | — | Mouse, Human |
| M421 | 35.4 | 422 | Oxidative (keto) | Mouse, Human |
| M423a | 37.6 | 424 | N-oxidation | Mouse, Human |
| M423b | 38 | 424 | N-oxidation | Mouse, Human |
| M432c | 38.9 | 433 | CN addition to reactive metabolite | Mouse, Human |
| M423c | 39.3 | 424 | Oxidation (AO-mediated) | Mouse, Human |

[a]RT based on LC/MS data of HLM + cytosol + NADPH + KCN

Structure Elucidation for Metabolites of Compound 1 by Mass Spectrometry

The metabolites of compound 1 produced in the presence of liver microsomes and cytosol from mice and humans were tentatively identified by LC/MS/MS analysis. To facilitate the identification of oxidative metabolites, H/D exchange experiments were conducted. The data from the deuterium exchange studies allowed us to distinguish carbon-hydroxylated (C—OH) metabolites versus oxidative derivatives of heteroatoms (e.g. N→O). An additional exchangeable proton in the mass spectrum of an oxidized metabolite would suggest hydroxylation on a carbon atom, while a heteroatom oxidation would not lead to an exchangeable proton.

The structures of the metabolites were tentatively assigned based on comparison of mass spectral fragmentation patterns with those produced by compound 1 under the same experimental conditions. In this study, the mass spectra of all metabolites were acquired in the positive ionization mode and up to MS4 tandem mass spectra were acquired to assist in the elucidation of structures. Nomenclature (metabolite names for identification/reference purposes) of the metabolites was based on the nominal molecular weights of the metabolites as determined from the pseudomolecular ions ([M+H]+) observed in the mass spectra of metabolites. For example, M423 corresponds to a metabolite with [M+H]+ at m/z 424.

Mass spectra of compound 1 showed the protonated molecular ion observed at m/z 408, consistent with the chemical formula C24H27N7 and structure of compound 1. The most intense fragment ions observed from the protonated molecular ions are produced by the cleavage of piperazine moiety, such as m/z 365, 351 and 338. In addition, a weak fragment ion at m/z 198 is believed to be due to multi-step fragmentations such as the cleavage of piperazine and the pyrazole moieties.

Metabolite Profiles of Compound 2

Figure 14:
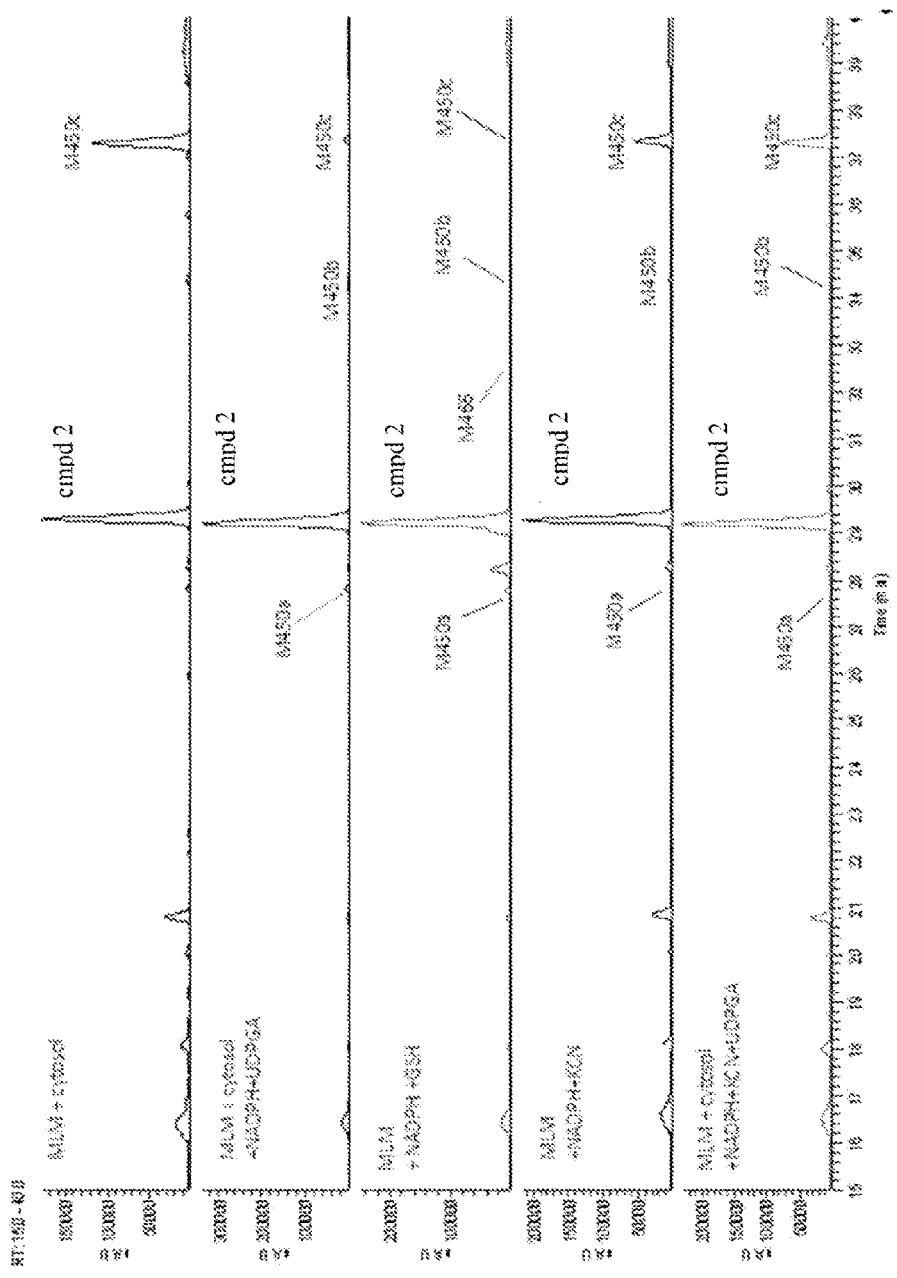
FIG. 14 shows the metabolite profiles (LC/UV) of compound 2 following incubations with mouse liver microsomes and cytosol in the presence of NADPH, UDPGA, GSH, and KCN.
Figure 15:
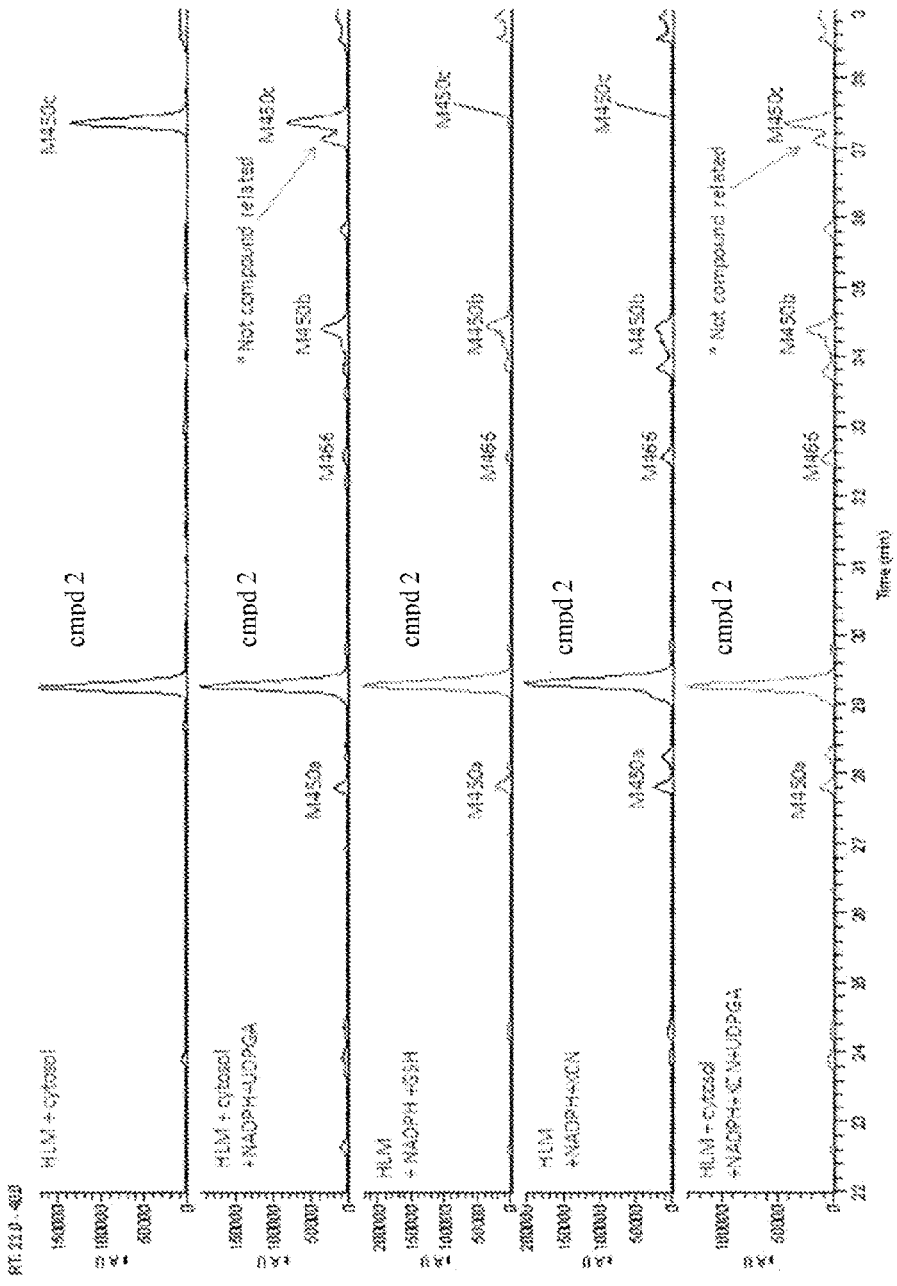
FIG. 15 shows the metabolite profiles (LC/UV) of compound 2 following incubations with human liver microsomes and cytosol in the presence of NADPH, UDPGA, GSH, and KCN.

The metabolite profiles of compound 2 were obtained following incubations with mouse and human liver microsomal preparations using LC/UV/MS analysis. Metabolite profiles (LC/UV, with λ 310-315 nm) of compound 2 obtained for both species are shown in FIG. 14 and FIG. 15, respectively. As observed with its analogue, compound 1, an aldehyde oxidase-mediated metabolite (M450c) was observed as the most significant product in both mouse and human liver cytosol fractions. Following incubations with liver microsomes, compound 2 was mainly metabolized via oxidation on the nitrogens of the molecule. Two oxidative metabolites, M450a and M450b, are proposed to be N-oxide/hydroxylamine analogues of compound 2 based on the mass spectral data obtained from the H/D exchange studies. A minor dihydroxylated metabolite was also observed in both species. There were no glucuronide conjugates observed in this study despite the formation of hydroxylated/oxidized metabolites. Compared to its structural analogue, LDN-193189, the piperazine moiety of compound 2 was found to be more stable as there were no ring-opened analogues detected in the microsomal extracts of both species. Interestingly, there were no cyanide adducts observed in either species. This suggests that the introduction of the methyl groups on the piperazine moiety protected the molecule from being metabolized to reactive iminium intermediate. The steric hindrance due to the presence of methyl groups may have effectively mitigated the reactive iminium metabolite formation. Trapping studies conducted with GSH showed that there were no "soft electrophiles" produced from compound 2 in the presence of liver microsomes from either species. Further analysis of the stock solution of compound 2 demonstrated the presence of low levels of an aniline impurity, whose identity was subsequently established by comparison with synthetic reference standard.

The metabolites observed in this study are summarized in Table 10. It was observed that all metabolites observed in human liver preparations were also produced by mouse, i.e. there were no unique human metabolites observed in this study. The proposed metabolic pathways of compound 2 are presented in FIG. 16.

TABLE 10

Summary of Metabolites of Compound 2 Following Incubations with Mouse and Human Liver Microsomes and Cytosol

| Metabolites | RT (min)$^a$ | MH$^+$ | Biotransformation | Species |
|---|---|---|---|---|
| compound 2 | 29.3 | 435 | — | Mouse, Human |
| M450a | 27.9 | 451 | N-Oxidation | Mouse, Human |
| M450b | 34.5 | 451 | N-oxidation | Mouse, Human |
| M450c | 37.5 | 451 | Oxidation (AO-mediated) | Mouse, Human |

$^a$RT based on LC/MS data of HLM + cytosol + NADPH + KCN

Structure Elucidation for Metabolites of Compound 2 by Mass Spectrometry

The metabolites of compound 2 produced in the presence of liver microsomes and cytosol from mice and humans were tentatively identified by LC/MS/MS analysis. As done previously with compound 1, the identification of oxidative metabolites was facilitated by H/D exchange experiments.

The structures of the metabolites were tentatively assigned based on comparison of mass spectral fragmentation patterns with those produced by compound 2 under the same experimental conditions.

Mass spectra of compound 2 showed the protonated molecular ion observed at m/z 435, consistent with the chemical formula C27H26N6 and structure of compound 2. The most intense fragment ions observed from the protonated molecular ions are produced by the cleavage of piperazine moiety, such as m/z 378, 364 and 337.

Metabolite Profiles of Compound 48

Figure 17:
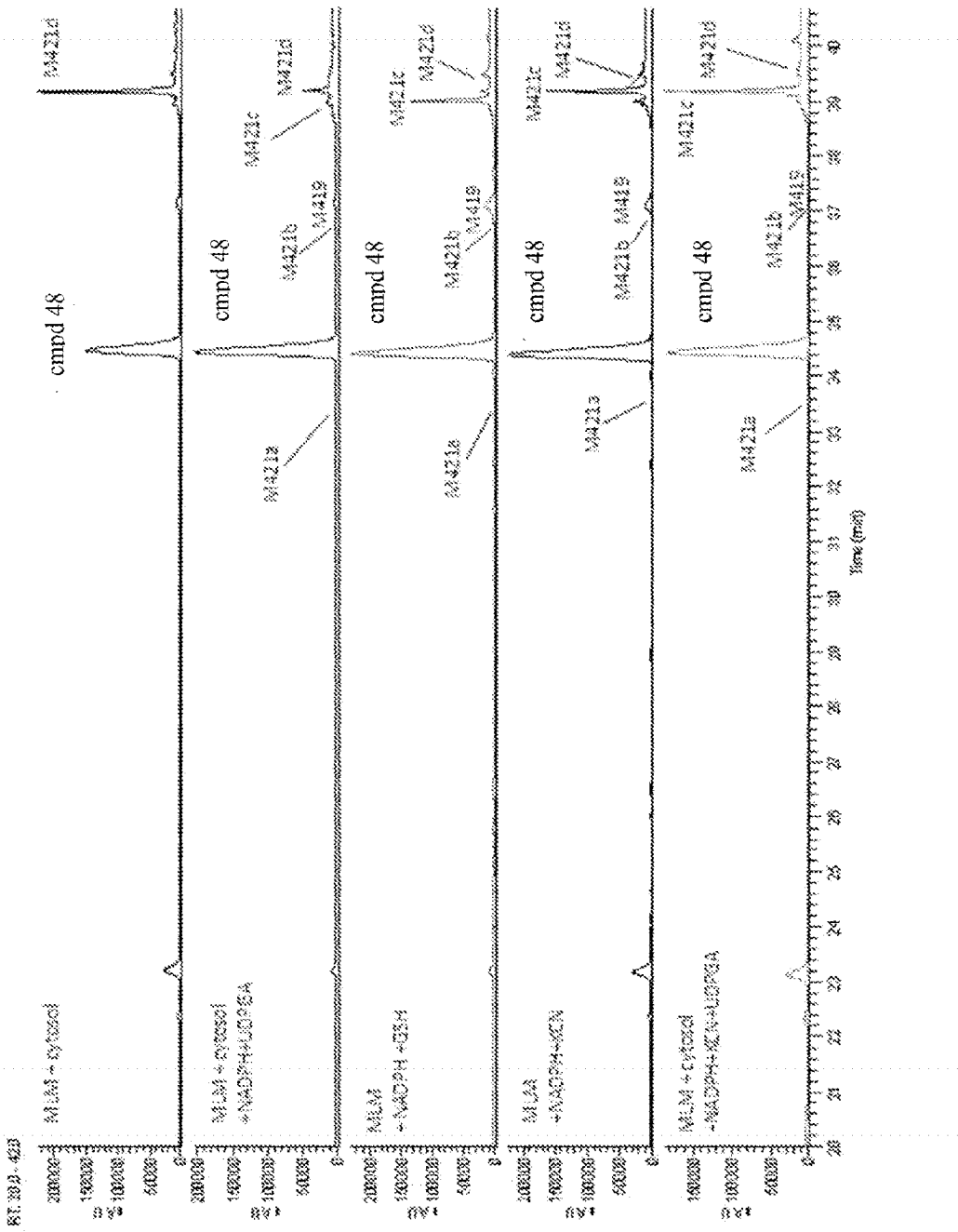
FIG. 17 shows the metabolite profiles (LC/UV) of compound 48 following incubations with mouse liver microsomes and cytosol in the presence of NADPH, UDPGA, GSH, and KCN.
Figure 18:
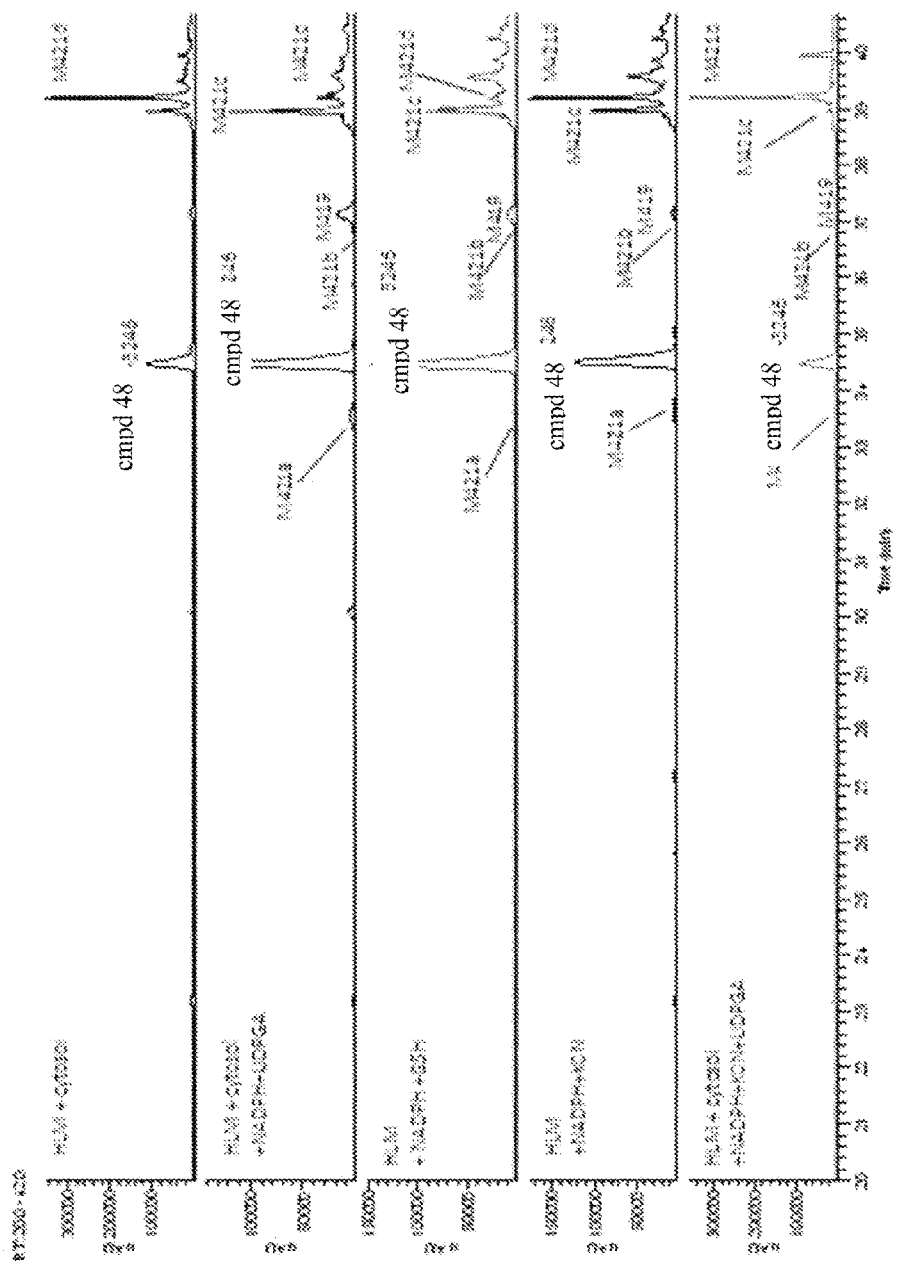
FIG. 18 shows the metabolite profiles (LC/UV) of compound 48 following incubations with human liver microsomes and cytosol in the presence of NADPH, UDPGA, GSH, and KCN.

The metabolite profiles of compound 48 were obtained following incubations with mouse and human liver microsomal preparations using LC/UV/MS analysis. Metabolite profiles (LC/UV, with λ 310-315 nm) of compound 48 obtained for both species are shown in FIG. 17 and FIG. 18, respectively. Similar to what was observed with other two analogues, an AO-mediated metabolite, M421d, was the most significant product of compound 48 found in both mouse and human liver cytosol incubation extracts. Following incubations with liver microsomes, compound 48 as metabolized by either carbon or nitrogen oxidation of the piperidine moiety. The C-oxidation led to formation of M421a while oxidation of the nitrogens produced the N-oxide or hydroxylamine analogues of compound 48 (M421b and M421c) based on the mass spectral data obtained with H/D exchange study. In addition, a metabolite, M419, was observed in both species. This was proposed to be a nitrone derivative of the molecule based on the H/D exchange data and tandem mass spectra of the metabolite. There were no glucuronide conjugates observed in this study despite the formation of hydroxylated/oxidized metabolites. There were no cyanide adducts observed with this compound in either species. This suggests that by the replacing the piperazine moiety (as present in LDN-193189) with a piperidine (as in compound 48) eliminated the metabolic bioactivation to form iminium intermediate. Again, like other two analogues, trapping studies conducted with GSH showed that there were no "soft electrophiles" produced from compound 48 in the presence of liver microsomes from both species.

The metabolites observed in this study are summarized in Table 11. It was observed that all metabolites observed in human liver preparations were also produced by mouse, i.e. there were no unique human metabolites observed in this study. The proposed metabolic pathways of compound 48 are presented in FIG. 19.

TABLE 11

Summary of Metabolites of Compound 48 following Incubations with Mouse and Human Liver Microsomes and Cytosol

| Metabolites | RT (min)$^a$ | MH$^+$ | Biotransformation | Species |
|---|---|---|---|---|
| compound 48 | 34.6 | 406 | — | Mouse, Human |
| M419 | 37.2 | 420 | Oxidation to nitrone | Mouse, Human |
| M421a | 33.6 | 422 | Oxidation on piperidine | Mouse, Human |
| M421b | 36.9 | 422 | N-oxidative | Mouse, Human |
| M421c | 39.0 | 422 | N-oxidative | Mouse, Human |
| M421d | 39.3 | 422 | Oxidation (AO-mediated) | Mouse, Human |

Structure Elucidation for Metabolites of Compound 48 by Mass Spectrometry

The metabolites of compound 48 produced in the presence of liver microsomes and cytosol from mice and humans were tentatively identified by LC/MS/MS analysis. Again, to facilitate the identification of oxidative metabolites, H/D exchange experiments were conducted.

The structures of the metabolites were tentatively assigned based on comparison of mass spectral fragmentation patterns with those produced by compound 48 under the same experimental conditions.

Mass spectra of compound 48 showed the protonated molecular ion observed at m/z 406, consistent with the chemical formula C26H23N5 and structure of compound 48. The most intense fragment ions observed from the protonated molecular ions are produced by the cleavage of piperidine moiety, such as m/z 361 and 336 and the cleavage of the piperidine moiety linked to the rest of the molecule, m/z 323. There were no diagnostic mass spectral ions corresponding to the cleavage of the aromatic rings observed.

Conclusions

The metabolism of compound 1, compound 2 and compound 48 were studied using mouse and human liver microsomes fortified with respective cytosols. In general, the major route of metabolism was found to be the aldehyde-oxidase mediated oxidation on the alpha-carbon of the quinoline nitrogen of all three compounds. These metabolites were formed in significant quantities from all 3 compounds in liver microsomes fortified with cytosol from mice and humans (without NADPH). The formation of these metabolites was proposed to be mediated by the cytosolic enzyme, aldehyde oxidase (AO). Previous studies with LDN-193189 showed that the major route of metabolism was via AO.

The formation of metabolites as a result of oxidation of heteroatoms (nitrogen in this case) was also evident. The oxidation at heteroatoms was confirmed by deuterium exchange studies which often are very confirmatory of metabolism (insertion of oxygen) on nitrogen or sulfur. The enzymes responsible for these heteroatom oxidations of the three test compounds are not known at this stage.

As demonstrated with LDN-193189, bioactivation to form a reactive intermediate was observed with compound 1 but not with compound 2 and compound 48. This finding is consistent with the proposed mechanism for the reactive iminium formation on the piperazine moiety. Such a reactive intermediate is trappable by a hard nucleophile such as cyanide ion. The bioactivation was inhibited by introduction of the methyl groups on the piperazine moiety on compound 2 or eliminated by replacement of the piperazine with piperidine on compound 48.

Compared to LDN-193189, structural modifications on the piperazine moiety did not alter the propensity of the test compounds compound 1, compound 2 and compound 48 to be metabolized by aldehyde oxidase (AO). This non-P450 metabolic pathway should be further investigated as this may have implications in clinic. Blocking the site of AO mediated metabolism may lead to a more stable compound, perhaps with the retention of pharmacological activity.

Figure 20A:
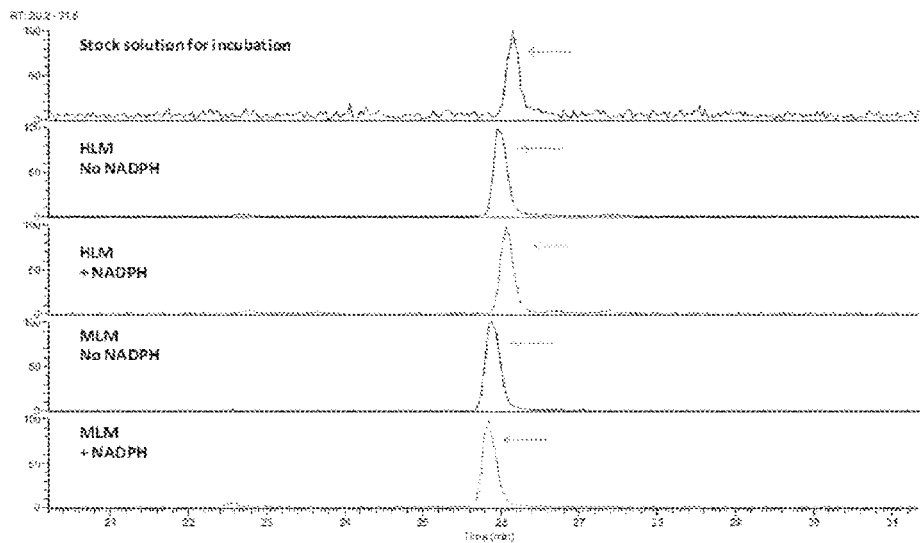
FIG. 20A shows the representative ion chromatograms of suspected aniline derivatives of compound 1 (m/z 339) and FIG. 20B shows the representative ion chromatogram of suspected aniline derivatives of compound 2 (m/z 338), as observed in stock solutions and incubation extracts.
Figure 20B:
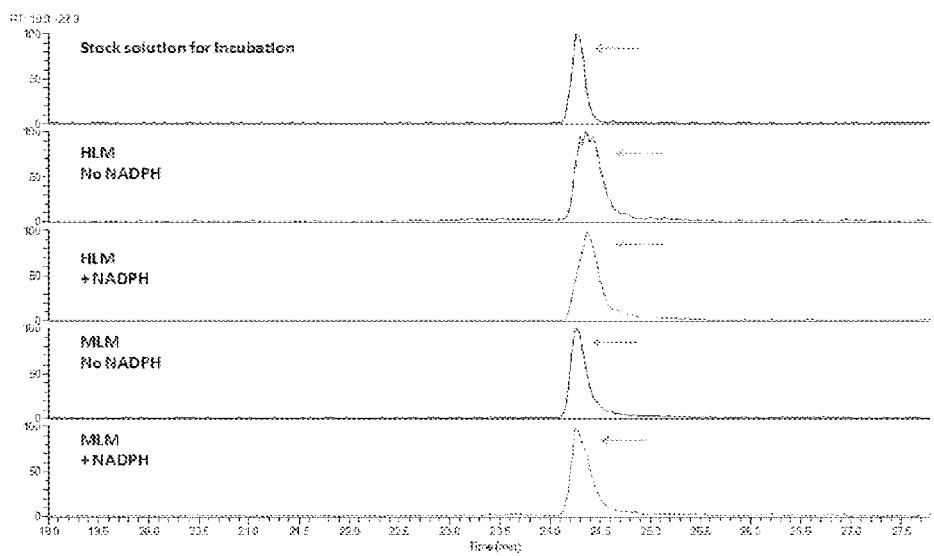

LC/MS analyses of both the stock solutions and incubation extracts of both compound 1 and compound 2 suggested the possibility of existence of aniline impurities, based on the LC/MS chromatograms (XIC, m/z 339 for compound 1 and m/z 338 for compound 2, see FIG. 20). Synthetic reference standard, compound 49, the aniline derivative of compound 2 was prepared. Based on the HPLC retention time and mass spectral data, the impurity present in compound 2 was confirmed to be the aniline compound 49. Based on this result, it is suggested that the impurity which was identified in the stock solution of compound 1 (with m/z 338, see FIG. 20) as well as in the microsomal extracts is most likely an aniline product as well. However, the origin of these aniline products as impurities in compound 1 and compound 2 is not currently known or understood. The amount of impurity did not change after incubation and therefore was not a result of metabolism; further studies are warranted to better understand the origin of these impurities in the reference standards. Furthermore, the presence of these impurities in the starting material has made it difficult to conclude if these anilines are also capable of being generated as metabolites in the presence of liver microsomes from mice and humans.

Example 6: In Vitro Metabolism of Compound 17 and Compound 12 in Human Liver Microsomes and Cytosols Introduction These studies were conducted to investigate the metabolism of compound 17 and compound 12 in human liver microsomes fortified with respective cytosols in the presence of NADPH and UDPGA. The formation of reactive intermediates was evaluated by addition of GSH or KCN to the incubation mixtures.

Methods

Incubations with Liver Microsomes and Cytosol from Humans

The study design was analogous to that described in Example 5 above, looking at human liver microsomes only, and was based on the following:

Substrate concentration: 10 μM

Human Liver Microsomes: 1 mg/mL

Human Cytosol: 2 mg/mL

NADPH: 100 uM

UDPGA: 4 mM

GSH: 4 mM

KCN: 1 mM

Incubation at 37° C. for 1 hr.

Various incubation conditions used to understand the metabolism of the compounds are shown in Table 12.

TABLE 12

Incubations of Compound 17 and Compound 12 with Liver Microsomes and Cytosols from Humans

| Incubation # | Substrate | NADPH* | Microsomes | Cytosol | MgCl$_2$ | GSH | KCN | UDPGA |
|---|---|---|---|---|---|---|---|---|
| 1 | ✓ | ✓ | ✓ | ✓ | ✓ | ✓ | ✓ | ✓ |
| 2 | ✓ | ✓ | ✓ | X | ✓ | ✓ | X | X |
| 3 | ✓ | ✓ | ✓ | X | ✓ | X | ✓ | X |
| 4 | ✓ | ✓ | ✓ | ✓ | ✓ | X | X | ✓ |
| 5 | ✓ | X | ✓ | ✓ | ✓ | X | X | X |

LC/UV/MS Conditions for Metabolite Profiling and Identification

Metabolite profiling and characterization of metabolites in the microsomal incubation extracts were performed in a manner analogous to Example 5 above, looking at human liver microsomes only, and was based on the following:

LC/UV/MS system: Agilent 1100 HPLC (pumps, autosampler and PDA) interfaced to LTQ-Orbitrap mass spectrometer (ThermoFinnigan);

HPLC column: Luna C18(2) column, 250×2.0 mm, 5 µm; and

LTQ Mass Spectrometer: Full scan (m/z 150-1000) and data dependent MSn (n=4) analysis.

The HPLC mobile phase gradient used for all test articles is shown in Table 13.

TABLE 13

HPLC Gradient Used to Obtain Metabolite Profiles of Compound 17 and Compound 12

| Time (min) | 0.05% TFA in Water* | 0.01% TFA in ACN | Flow rate (µL/min) |
|---|---|---|---|
| 0 | 95 | 5 | 300 |
| 5 | 95 | 5 | 300 |
| 35 | 70 | 30 | 300 |
| 40 | 5 | 95 | 300 |
| 41 | 5 | 95 | 300 |
| 42 | 95 | 5 | 300 |
| 50 | 95 | 5 | 300 |

Results

Metabolite Profiles of Compound 17

Figure 21:
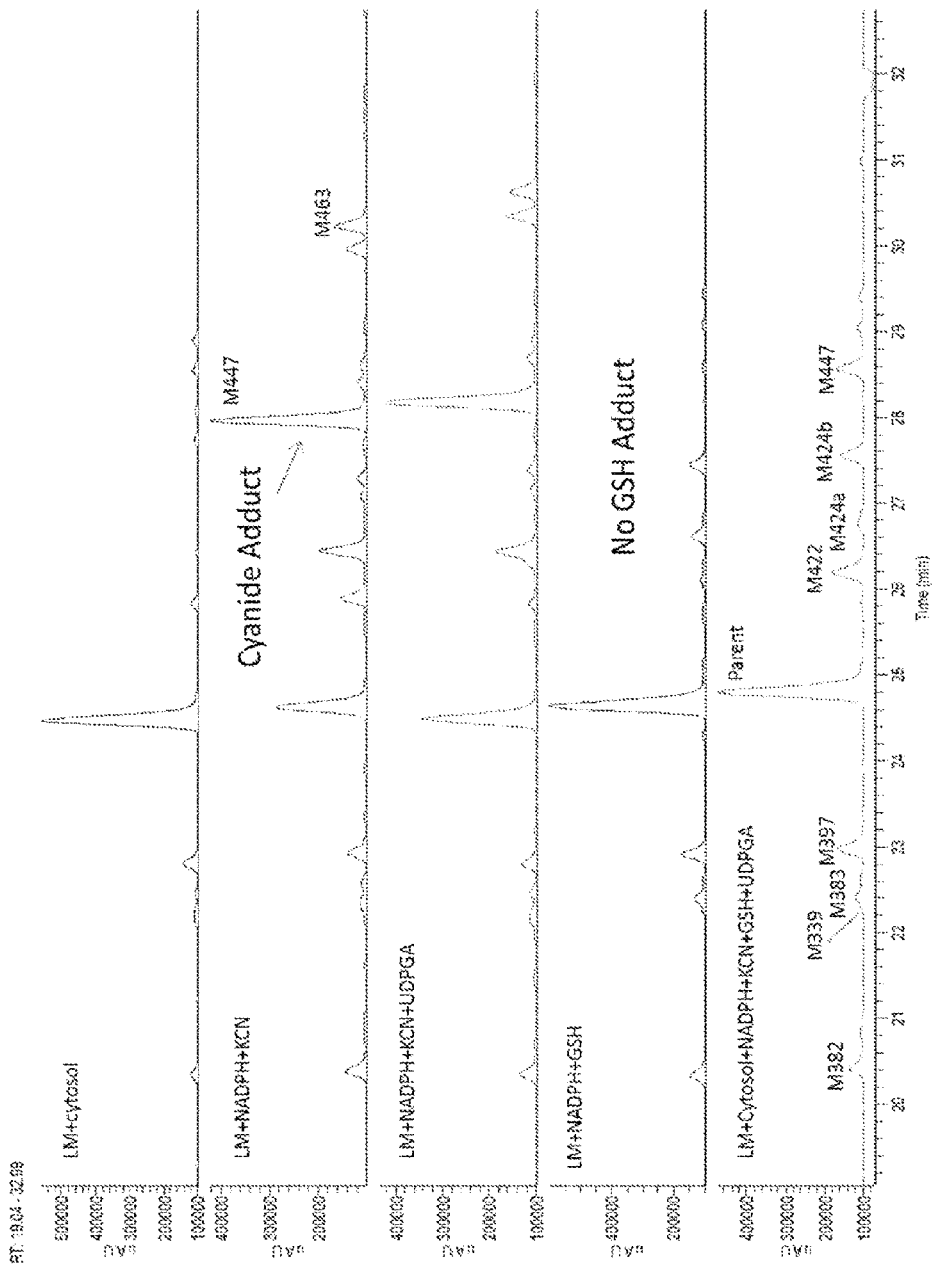
FIG. 21 shows the metabolite profiles (LC/UV, with λ 270-280 nm) of compound 17 following incubations with human liver microsomes and cytosol in the presence of NADPH, UDPGA, GSH, and KCN.

The metabolite profiles of compound 17 were obtained following incubations with human liver microsomal preparations using LC/UV/MS analysis. Metabolism was observed primarily on the piperazine moiety. An aniline derivative was observed. Oxidative metabolites were not observed in the incubation without NADPH, suggesting that AO mediated metabolism did not take place. A major cyanide adduct was observed, however, the mechanism of the formation is unknown. Glucuronide conjugates were not observed. The metabolite profiles of compound 17 were obtained following incubations with human liver microsomal preparations using LC/UV/MS analysis. Metabolite profiles (LC/UV, with λ 270-280 nm) of compound 17 are shown in FIG. 21.

Figure 22:
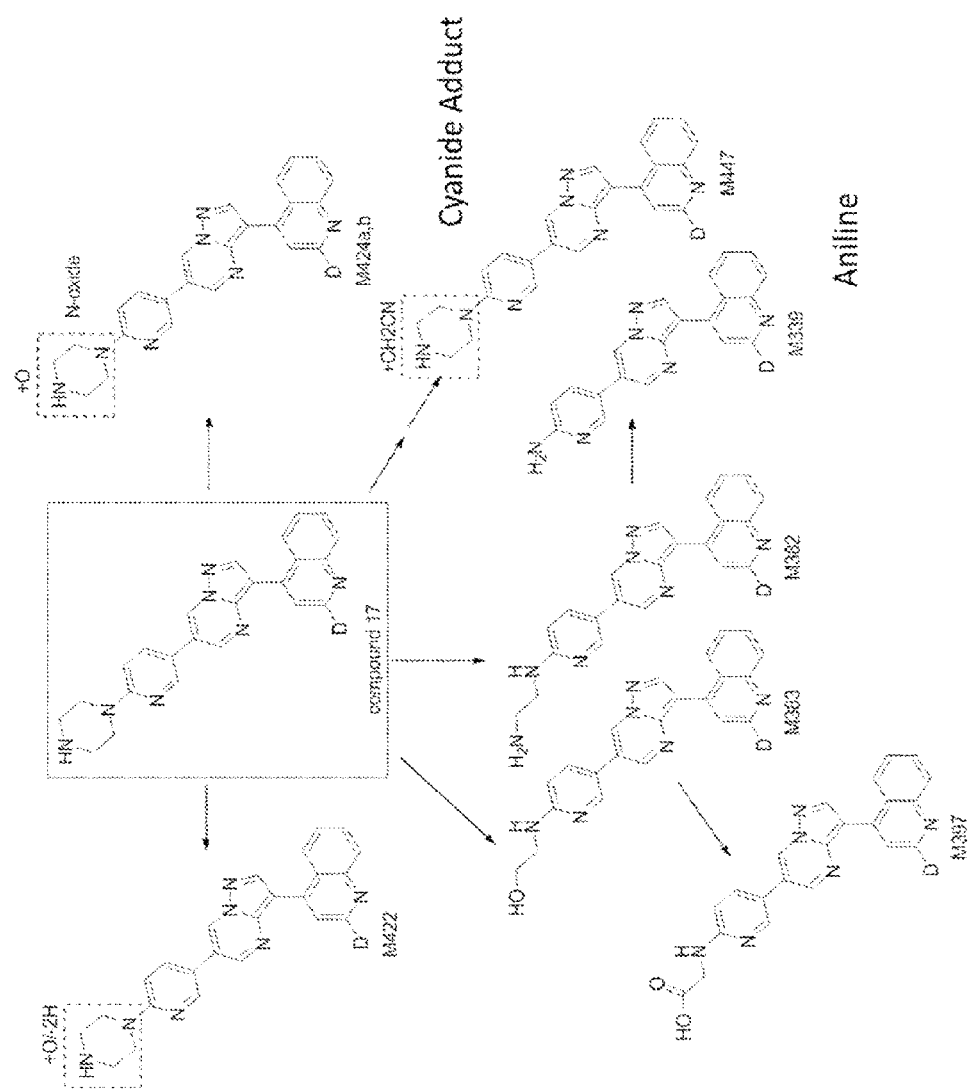
FIG. 22 shows the proposed metabolic pathways of compound 17 in liver microsomes and cytosols from humans.

The metabolites observed in this study are summarized in Table 14. The proposed metabolic pathways of compound 17 are presented in FIG. 22.

TABLE 14

Summary of Metabolites of Compound 17 Following Incubations with Human Liver Microsomes and Cytosol

| | | m/z (MH+) | | |
|---|---|---|---|---|
| Met | RT (min) | Measured | Calculated | Reaction |
| M339 | 22.3 | 340.1411 | 340.1415 | N,N-Didealkylation |
| M382 | 20.5 | 383.1836 | 383.1837 | N,N-Didealkylation |
| M383 | 22.5 | 384.1676 | 384.1678 | Oxidative deamination |
| M397 | 23 | 398.1468 | 398.1470 | Oxidative deamination |
| M422 | 26.2 | 423.1789 | 423.1787 | Dehydrogenation |
| M424a | 26.8 | 425.1946 | 425.1943 | Hydroxylation |
| M424b | 27.6 | 425.1944 | 425.1943 | Hydroxylation |
| M447 | 28.6 | 448.2105 | 448.2103 | Cyanide addition |
| Compound 17 | 24.9 | 409.1994 | 409.1994 | NA |

Based on the LC/UV of incubation extracts

Metabolite Profiles of Compound 12

Figure 23:
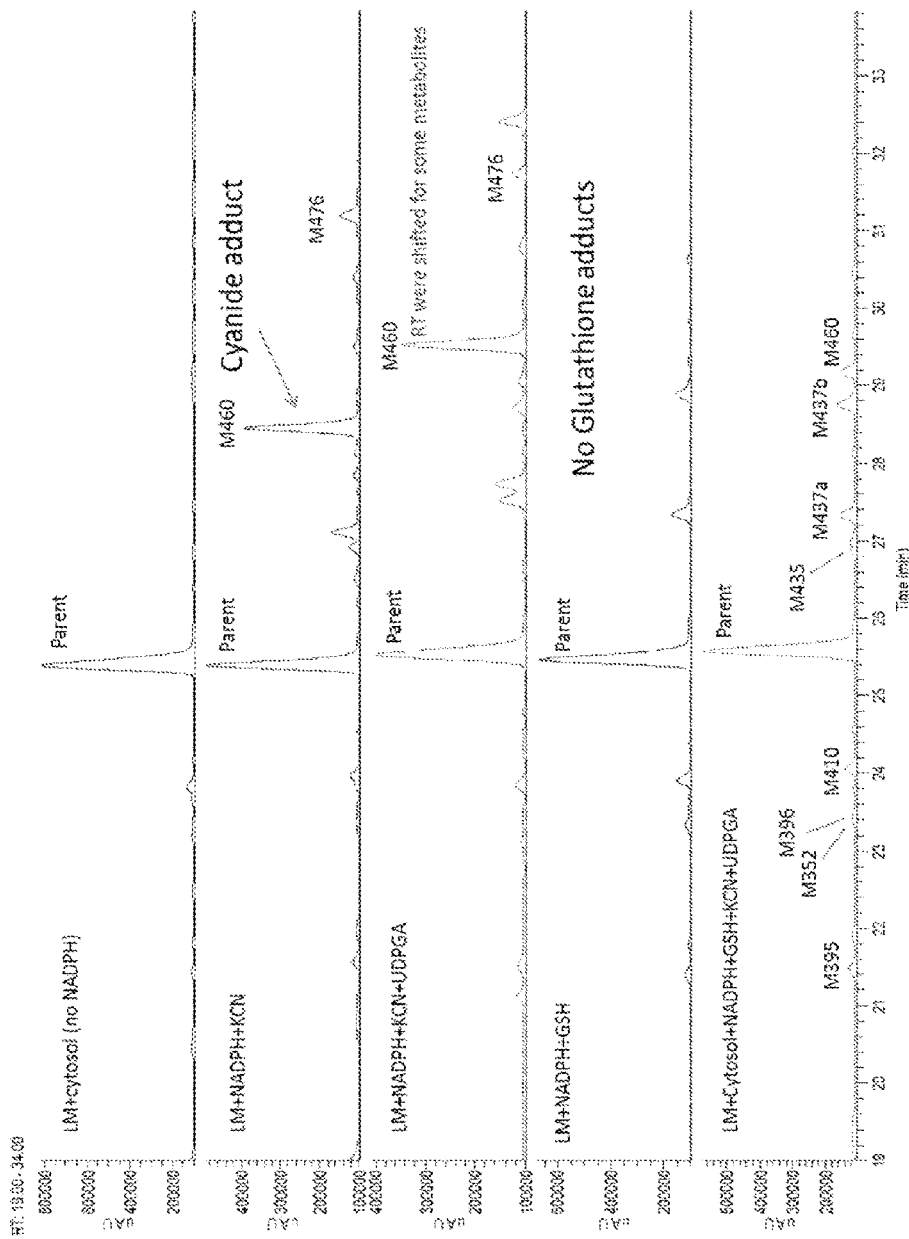
FIG. 23 shows the metabolite profiles (LC/UV, with λ 270-280 nm) of compound 12 following incubations with human liver microsomes and cytosol in the presence of NADPH, UDPGA, GSH, and KCN.

The metabolite profiles of compound 12 were obtained following incubations with human liver microsomal preparations using LC/UV/MS analysis. Metabolism was observed primarily on the piperazine moiety. An aniline derivative was observed. Oxidative metabolites were not observed in the incubation without NADPH, suggesting that AO mediated metabolism did not take place. A major cyanide adduct was observed, however, the mechanism of the formation is unknown. Glucuronide conjugates were not observed. The metabolite profiles of compound 12 were obtained following incubations with human liver microsomal preparations using LC/UV/MS analysis. Metabolite profiles (LC/UV, with λ 270-280 nm) of compound 12 are shown in FIG. 23.

Figure 24:
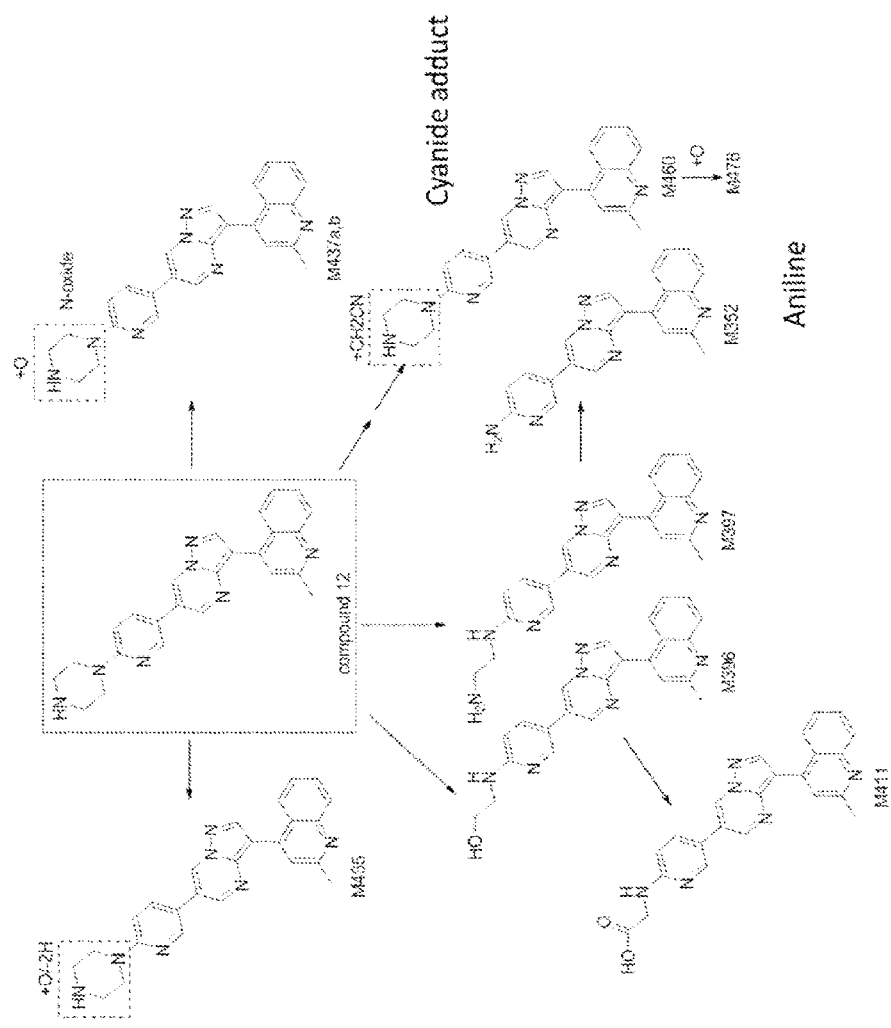
FIG. 24 shows the proposed metabolic pathways of compound 12 in liver microsomes and cytosols from humans.

The metabolites observed in this study are summarized in Table 15. The proposed metabolic pathways of compound 12 are presented in FIG. 24.

TABLE 15

Summary of Metabolites of Compound 12 Following Incubations with Human Liver Microsomes and Cytosol

| | | m/z (MH+) | | |
|---|---|---|---|---|
| Met | RT (min) | Measured | Calculated | Reaction |
| M352 | 23.5 | 353.1509 | 353.1509 | N,N-Didealkylation |
| M395 | 21.5 | 396.1922 | 396.1931 | N,N-Didealkylation |
| M396 | 23.6 | 397.1770 | 397.1771 | Oxidative deamination |
| M410 | 24.1 | 411.1571 | 411.1564 | Oxidative deamination |
| M435 | 26.9 | 436.1885 | 436.1880 | Hydroxylation Dehydrogenation |
| M437a | 27.3 | 438.2041 | 438.2037 | Hydroxylation |
| M437b | 28.8 | 438.2043 | 438.2037 | Hydroxylation |

TABLE 15-continued

Summary of Metabolites of Compound 12 Following Incubations with Human Liver Microsomes and Cytosol

| Met | RT (min) | m/z (MH+) Measured | Calculated | Reaction |
|---|---|---|---|---|
| M460 | 29.2 | 461.2202 | 461.2197 | Cyanide addition |
| M476 | 32.0 | 477.2161 | 477.2146 | Hydroxylated M460 |
| Compound 12 | 25.6 | 422.2091 | 422.2088 | NA |

Based on the LC/UV of incubation extracts

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

The invention claimed is:

1. A method of treating a disease or condition in a subject that would benefit from inhibition of Bone Morphogenetic Protein (BMP) signaling, comprising administering to the subject a compound having a structure of Formula I or a pharmaceutically acceptable salt, ester, or prodrug thereof,

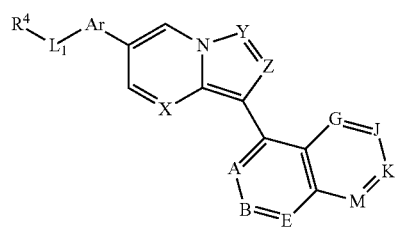

Formula I wherein
X and Y are independently selected from $CR^{15}$ and N;
Z is selected from $CR^3$ and N;
Ar is selected from substituted or unsubstituted aryl and heteroaryl;
$L_1$ is absent or selected from substituted or unsubstituted alkyl and heteroalkyl;
G, J, K, and M are all absent or, independently for each occurrence, are selected from $CR^{16}$ and N;
A, B, and E, independently for each occurrence, are selected from $CR^{16}$ and N;
provided that:
no more than three of A, B, E, G, J, K, and M are N, at least one of E and M is N, and
that if G, J, K, and M are absent, then the carbon atom drawn as connected to variable M is optionally substituted with $R^{16}$;
$R^3$ is selected from H, halogen, cyano, and substituted or unsubstituted alkyl, cycloalkyl, acylamino, carbamate, sulfonyl, sulfoxido, sulfamoyl, and sulfonamido;
$R^4$ is selected from hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, and sulfonamidol;
$R^{15}$, independently for each occurrence, is selected from H, halogen, cyano, and substituted or unsubstituted alkyl, cycloalkyl, heterocyclyl, cycloalkylalkyl, hetero-cyclylalkyl, acylamino, carbamate, sulfonyl, sulfoxido, sulfamoyl, and sulfonamido; and $R^{16}$, independently for each occurrence, is absent or is selected from H, OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide;

provided that:
i) if Ar is a phenyl ring, it is substituted with at least one non-protium ($^1$H) substituent;
ii) B is $C-R^{25}$ when E is N, or K is $C-R^{25}$ when M is N, or both, such that at least one of B and K is $C-R^{25}$, wherein
$R^{25}$ is selected from deuterium, halogen, hydroxyl, lower alkyl, and lower alkoxy; and/or
iii) $R^4$ is

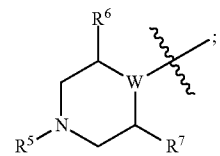

W is N, CH, or $CCH_3$;
$R^5$ is selected from H and substituted or unsubstituted alkyl, acyl, and ester; and
$R^6$ and $R^7$ are each independently H or alkyl, or
$R^6$ forms a one- or two-carbon bridge to the carbon atom adjacent to $R^7$ and $NR^5$;
wherein either W is CH or $CCH_3$, or $R^6$ and $R^7$ are not both H;
wherein the disease or condition is selected from pulmonary hypertension, hereditary hemorrhagic telangiectasia syndrome, cardiac valvular malformations, cardiac structural malformations, fibrodysplasia ossificans progressiva, juvenile familial polyposis syndrome, parathyroid disease, anemia, vascular calcification, atherosclerosis, valve calcification, renal osteodystrophy, ankylosing spondylitis, vascular inflammation, anemia of inflammation, inflammatory bowel disease, seronegative spondyloarthropathies, psoriasis, atherosclerosis, tuberculosis, infections with viruses, bacteria, fungi, and parasites, breast carcinoma, prostate carcinoma, renal cell carcinoma, bone metastasis, lung metastasis, osteosarcoma, and multiple myeloma.

2. The method of claim 1, wherein the disease or condition is selected from breast carcinoma, prostate carcinoma, renal cell carcinoma, bone metastasis, lung metastasis, osteosarcoma, and multiple myeloma.

3. The method of claim 1, wherein the disease or condition is ankylosing spondylitis.

4. The method of claim 1, where the disease or condition is fibrodysplasia ossificans progressiva or anemia.

5. A method of inhibiting Bone Morphogenetic Protein (BMP) signaling in a subject, comprising administering to the subject a compound having a structure of Formula I or a pharmaceutically acceptable salt, ester, or prodrug thereof,

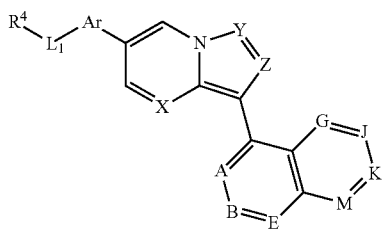

Formula I wherein
X and Y are independently selected from CR$^{15}$ and N;
Z is selected from CR$^3$ and N;
Ar is selected from substituted or unsubstituted aryl and heteroaryl;
L$_1$ is absent or selected from substituted or unsubstituted alkyl and heteroalkyl;
G, J, K, and M are all absent or, independently for each occurrence, are selected from CR$^{16}$ and N;
A, B, and E, independently for each occurrence, are selected from CR$^{16}$ and N;
provided that:
no more than three of A, B, E, G, J, K, and M are N, at least one of E and M is N, and
that if G, J, K, and M are absent, then the carbon atom drawn as connected to variable M is optionally substituted with R$^{16}$;
R$^3$ is selected from H, halogen, cyano, and substituted or unsubstituted alkyl, cycloalkyl, acylamino, carbamate, sulfonyl, sulfoxido, sulfamoyl, and sulfonamido;
R$^4$ is selected from hydroxyl, carboxyl, and substituted or unsubstituted alkenyl, alkynyl, cycloalkyl, heterocyclyl, aryl, heteroaryl, acyl, ester, alkoxyl, alkylthio, acyloxy, amino, acylamino, carbamate, amido, amidino, sulfonyl, sulfoxido, sulfamoyl, and sulfonamido;
R$^{15}$, independently for each occurrence, is selected from H, halogen, cyano, and substituted or unsubstituted alkyl, cycloalkyl, heterocyclyl, cycloalkylalkyl, heterocyclylalkyl, acylamino, carbamate, sulfonyl, sulfoxido, sulfamoyl, and sulfonamido; and
R$^{16}$, independently for each occurrence, is absent or is selected from H, OH, halogen, cyano, carboxyl, and substituted or unsubstituted alkyl, alkenyl, alkynyl, aralkyl, cycloalkyl, heterocyclyl, aryl, heteroaryl, heteroaralkyl, cycloalkylalkyl, heterocyclylalkyl, acyl, ester, alkoxy, alkylthio, acyloxy, amino, acylamino, carbamate, amido, amidino, sulfonyl, sulfoxido, sulfamoyl, and sulfonamide;
provided that:
i) if Ar is a phenyl ring, it is substituted with at least one non-protium ($^1$H) substituent;
ii) B is C—R$^{25}$ when E is N, or K is C—R$^{25}$ when M is N, or both, such that at least one of B and K is C—R$^{25}$, wherein
R$^{25}$ is selected from deuterium, halogen, hydroxyl, lower alkyl, and lower alkoxy; and/or
iii) R$^4$ is

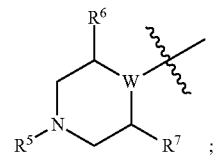

W is N, CH, or CCH$_3$;
R$^5$ is selected from H and substituted or unsubstituted alkyl, acyl, and ester; and
R$^6$ and R$^7$ are each independently H or alkyl, or
R$^6$ forms a one- or two-carbon bridge to the carbon atom adjacent to R$^7$ and NR$^5$;
wherein either W is CH or CCH$_3$, or R$^6$ and R$^7$ are not both H.

* * * * *